United States Patent [19]
Lambert, Jr. et al.

[11] Patent Number: 6,140,306
[45] Date of Patent: *Oct. 31, 2000

[54] METHOD OF TREATING GRAM-NEGATIVE BACTERIAL INFECTION BY ADMINISTRATION OF BACTERICIDAL/PERMEABILITY-INCREASING (BPI) PROTEIN PRODUCT AND ANTIBIOTIC

[75] Inventors: Lewis H. Lambert, Jr., Fremont; Roger G. Little, II, Benicia, both of Calif.

[73] Assignee: Xoma Corporation, Berkeley, Calif.

[*] Notice: This patent is subject to a terminal disclaimer.

[21] Appl. No.: 08/657,162

[22] Filed: Jun. 3, 1996

Related U.S. Application Data

[63] Continuation of application No. 08/311,611, Sep. 22, 1994, Pat. No. 5,523,288, which is a continuation-in-part of application No. 08/273,401, Jul. 11, 1994, abandoned, which is a continuation-in-part of application No. 08/125,651, Sep. 22, 1993, abandoned.

[51] Int. Cl.[7] .......................... A61K 38/17; C07G 11/00; C07H 15/234; C07K 14/47
[52] U.S. Cl. .......................... 514/12; 514/152; 514/192; 424/114; 530/319; 530/350; 536/136; 536/16.8
[58] Field of Search .......................... 514/12, 152, 192; 424/114, 405; 536/7.2, 13.1, 13.2, 13.3, 13.4, 13.5, 13.7, 13.9, 14, 13.6, 18.9, 8.8, 16.1, 16.2, 16.8; 530/319, 350; 540/226, 304, 314, 342, 335, 341; 552/202, 204, 205

[56] References Cited

U.S. PATENT DOCUMENTS

| | | | |
|---|---|---|---|
| 4,863,727 | 9/1989 | Zimmerman et al. | 424/85.2 |
| 5,000,958 | 3/1991 | Fountain et al. | 424/430 |
| 5,089,274 | 2/1992 | Marra et al. | 504/138 |
| 5,156,665 | 10/1992 | Sherba et al. | 514/12 |
| 5,171,739 | 12/1992 | Scott | 435/69.1 |
| 5,198,541 | 3/1993 | Elsbach et al. | 514/21 |
| 5,234,912 | 8/1993 | Marra et al. | 514/12 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |
| 5,523,288 | 6/1996 | Cohen et al. | 514/12 |

FOREIGN PATENT DOCUMENTS

| | | |
|---|---|---|
| WO 89/01486 | 2/1989 | WIPO . |
| 8912644 | 12/1989 | WIPO . |
| WO 89/12644 | 12/1989 | WIPO . |
| WO 92/03535 | 3/1992 | WIPO . |
| WO 92/09621 | 6/1992 | WIPO . |
| WO 93/05797 | 4/1993 | WIPO . |
| WO 93/06228 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |

OTHER PUBLICATIONS

Gross et al. "Choice of Bacteria in Animal Models of Sepsis" Infection & Immunity 61(7) 2741–2747, 1993.

Dictionary of Drugs 1990 p. 900 p 886 p 282.

Davies, "Inactivation of Antibiotics and the Dissemination of Resistance Genes", *Science*, 264:375–381 (Apr. 15, 1994).

(List continued on next page.)

*Primary Examiner*—Nancy Degen
*Attorney, Agent, or Firm*—Marshall, O'Toole, Gerstein, Murray & Borun

[57] ABSTRACT

The present invention relates to methods and compositions for treating gram-negative bacterial infections, using BPI protein products. Co-treatment, or concurrent administration, of BPI protein product with an antibiotic in treatment of gram-negative bacterial infections improves the therapeutic effectiveness of the antibiotic, including increasing antibiotic susceptibility of gram-negative bacteria and reversing resistance of the bacteria to antibiotics.

4 Claims, 22 Drawing Sheets

OTHER PUBLICATIONS

Eliopoulos and Moellering, "Antimicrobial Combinations", in *Antibiotics in Laboratory Medicine*, 3rd ed., pp. 432–492, (Lorian ed., Baltimore, MD) (1991).

Elsbach, "Antibiotics from Within: Antibacterials from Human and Animal Sources", *Trends. Biotech*, 8(1):26–30 (Jan. 1990).

Elsbach and Weiss, "Oxygen–Independent Bactericidal Systems of Polymorphonuclear Leukocytes", in *Advances in Inflammation Research*, vol. 2, pp. 95–113 (Weissmann ed., Raven Press, Ltd.) (1981).

Elsbach and Weiss, "Oxygen–Independent Antimicrobial Systems of Phagocytes," in *Inflammation: Basic Principles and Clinical Correlates*, pp. 603–636, (Gallin et al eds., Raven Press, Ltd.) (1992).

Elsbach et al., "Separation and Purification of a Potent Bactericidal/Permeability–Increasing Protein and a Closely Associated Phospholipase $A_2$ from Rabbit Polymorphonuclear Leukocytes", *J. Biol. Chem.*, 254(21):11000–11009 (Nov. 10, 1979).

Gabay, "Ubiquitous Natural Antibiotics", *Science*, 264:373–0374 (Apr. 15, 1994).

Gazzano–Santoro et al., "High–Affinity Binding of the Bactericidal/Permeability–Increasing Protein and a Recombinant Amino–Terminal Fragment to the Lipid A Region of Lipopolysaccharide", *Infect. Immun.*, 60(11):4754–4761 (Nov. 1992).

Gray et al., "Cloning of the cDNA of a Human Neutrophil Bactericidal Protein", *J. Biol. Chem.*, 264(16):9505–9509 (Jun. 5, 1989).

Kadurugamuwa et al., "Interaction of Gentamicin with the A Band and B Band Lipopolysaccharides of *Pseudomonas aeruginosa* and Its Possible Lethal Effect", *Antimicrobial Agents and Chemotherapy*, 37(4):715–721 (Apr. 1993).

Kingman, "Resistance a European Problem, Too", *Science*, 264:363–365 (Apr. 15, 1994).

Levy et al., "Antibacterial 15–kDa Protein Isoforms (p15s) are Members of a Novel Family of Leukocyte Proteins", *J. Biol. Chem.*, 268(8):6058–6068 (Mar. 16, 1993).

Mannion et al., "Preferential Binding of the Neutrophil Cytoplasmic Granule–Derived Bactericidal/Permeability Increasing Protein to Target Bacteria", *J. Clin. Invest.*, 142(8):2807–2812 (Apr. 15, 1989).

Mannion et al., "Separation of Sublethal and Lethal Effects of Polymorphonuclear Leukocytes on *Escherichia coli*", *J. Clin. Invest.*, 86:631–641 (Aug. 1990).

Mannion et al., "Separation of Sublethal and Lethal Effects of the Bactericidal/Permeability Increasing Protein on *Escherichia coli*", *J. Clin. Invest.*, 85:853–860 (Mar. 1990).

Nikaido, "Prevention of Drug Access to Bacterial Targets: Permeability Barriers and Active Efflux", *Science*, 264:382–387 (Apr. 15, 1994).

Ooi et al., "A 25–kDa $NH_2$–terminal Fragment Carries All the Antibacterial Activities of the Human Neutrophil 60–kDa Bactericidal/Permeability–Increasing Protein", *J. Biol. Chem.*, 262(31):14891–14894 (1987).

Ooi et al., Endotoxin–neutralizing Properties of the 25 kD N–Terminal Fragment and a Newly Isolated 30 kD C–Terminal Fragment of the 55–60 kD Bactericidal/Permeability–Increasing Protein of Human Neutrophils, *J. Exp. Med.*, 174:649–655 (Sep. 1991).

Ooi et al., "Isolation of Two Isoforms of a Novel 15–kDa Protein from Rabbit Polymorphonuclear Leukocytes that Modulate the Antibacterial Actions of Other Leukocyte Proteins", *J. Biol. Chem.*, 265(26):15956–15962 (Sep. 15, 1990).

Spratt, "Resistance to Antibiotics Mediated by Target Alterations", *Science*, 264:388–393 (Apr. 15, 1994).

Stratton, "In Vitro Testing: Correlations Between Bacterial Susceptibility, Body Fluid Levels and Effectiveness of Antibacterial Therapy", in *Antibiotics in Laboratory Medicine*, pp. 849–879 (Lorian ed. Williams & Wilkins) (1991).

Taber et al., "Bacterial Uptake of Aminoglycoside Antibiotics", *Microbiological Reviews*, 51(4):439–457 (Dec. 1987).

Travis, "Reviving the Antibiotic Miracle", *Science*, 264:360–362 (Apr. 15, 1994).

Vaara, "Agents that Increase the Permeability of the Outer Membrane", *Microbiological Reviews*, 56(3):395–411 (Sep. 1992).

Veld et al., "Effects of the Bactericidal/Permeability–Increasing Protein of Polymorphonuclear Leukocytes on Isolated Bacterial Cytoplasmic Membrane Vesicles", *Infect. Immun.*, 56(5):1203–1208 (May 1988).

Weiss and Olsson, "Cellular and Subcellular Localization of the Bactericidal/Permeability–Increasing Protein of Neutrophils", *Blood*, 69(2):652–659 (Feb. 1987).

Weiss et al., "Human Bactericidal/Permeability–Increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria", *J. Clin. Invest.*, 90:1122–1130 (Sep. 1992).

Weiss et al., "Resistance of Gram–negative Bacteria to Purified Bactericidal Leukocyte Proteins", *J. Clin. Invest.*, 65:619–628 (Mar. 1980).

Weiss et al., "The Role of Lipopolysaccharides in the Action of the Bactericidal/Permeability–Increasing Neutrophil Protein on the Bacterial Envelope", *J. Immunol.*, 132(6):3109–3115 (Jun. 1984).

Cross et al., "Choice of Bacteria in Animal Plodek of Sepsis", *Injection and Immunity.*, 61(7):2741–2747 (1993).

Dictionary of Drugs 1990 p. 900, p. 886, p. 282.

"Methods for Dilution Antimicrobial Susceptibility Tests for Bacteria that Grow Aerobically–Third Edition; Approved Standard", *National Committee for Clinical Laboratory Standards Document M7–A3*, vol. 13, No. 25 (1993).

Fig. 22 Piperacillin

Cefuroxime

METHOD OF TREATING GRAM-NEGATIVE BACTERIAL INFECTION BY ADMINISTRATION OF BACTERICIDAL/PERMEABILITY-INCREASING (BPI) PROTEIN PRODUCT AND ANTIBIOTIC

This is a Continuation of U.S. application Ser. No. 08/311,611, filed Sep. 22, 1994, now U.S. Pat. No. 5,523,288, which is a continuation-in-part of U.S. application Ser. No. 08/273,401 filed Jul. 11, 1994, now abandoned, which is a continuation-in-part of U.S. application Ser. No. 08/125,651 filed Sep. 22, 1993, now abandoned.

BACKGROUND OF THE INVENTION

The present invention relates generally to methods and compositions for treating gram-negative bacterial infections, and more specifically to the use of bactericidal/permeability-increasing protein (BPI) protein products for co-treatment of such infections with an antibiotic substance. Co-treatment with BPI protein products can improve the therapeutic effectiveness of antibiotics in gram-negative bacterial infections, increase the susceptibility of gram-negative organisms to antibiotics, and reverse resistance of gram-negative organisms to antibiotics.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. amino acid sequence is set out in SEQ ID NO: 69 hereto.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., *J. Bio. Chem.*, 262: 14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. Gazzano-Santoro et al., *Infect. Immun.* 60:4754–4761 (1992).

The bactericidal effect of BPI has been reported to be highly specific to gram-negative species, e.g., in Elsbach and Weiss, *Inflammation: Basic Principles and Clinical Correlates*, eds. Gallin et al., Chapter 30, Raven Press, Lld. (1992). BPI is commonly thought to be non-toxic for other microorganisms, including yeast, and for higher eukaryotic cells. Elsbach and Weiss (1992), supra, reported that BPI exhibits anti-bacterial activity towards a broad range of gram-negative bacteria at concentrations as low as $10^{-8}$ to $10^{-9}$ M, but that 100- to 1,000-fold higher concentrations of BPI were non-toxic to all of the gram-positive bacterial species, yeasts, and higher eukaryotic cells tested at that time. It was also reported that BPI at a concentration of $10^{-6}$ M or 160 μg/ml had no toxic effect, when tested at a pH of either 7.0 or 5.5, on the gram-positive organisms *Staphylococcus aureus* (four strains), *Staphylococcus epidermidis*, *Streptococcus faecalis*, *Bacillus subtilis*, *Micrococcus lysodeikticus*, and *Listeria monocytogenes*. BPI at $10^{-6}$ M reportedly had no toxic effect on the fungi *Candida albicans* and *Candida parapsilosis* at pH 7.0 or 5.5, and was non-toxic to higher eukaryotic cells such as human, rabbit and sheep red blood cells and several human tumor cell lines. See also Elsbach and Weiss, *Advances in Inflammation Research*, ed. G. Weissmann, Vol. 2, pages 95–113 Raven Press (1981). This reported target cell specificity was believed to be the result of the strong attraction of BPI for lipopolysaccharide (LPS), which is unique to the outer membrane (or envelope) of gram-negative organisms.

The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et al., *J. Clin. Invest.*, 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to LPS leads to organizational changes that probably result from binding to the anionic groups in the KDO region of LPS, which normally stabilize the outer membrane through binding of $Mg^{++}$ and $Ca^{++}$. Attachment of BPI to the outer membrane of gram-negative bacteria produces rapid permeabilization of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms [Weiss et al., *J. Clin. Invest.* 65: 619–628 (1980)]. This first stage of BPI action, permeabilization of the gram-negative outer envelope, is reversible upon dissociation of the BPI, a process requiring the presence of divalent cations and synthesis of new LPS [Weiss et al., *J. Immunol*. 132: 3109–3115 (1984)]. Loss of gram-negative bacterial viability, however, is not reversed by processes which restore the envelope integrity, suggesting that the bactericidal action is mediated by additional lesions induced in the target organism and which may be situated at the cytoplasmic membrane (Mannion et al., *J. Clin. Invest*. 86: 631–641 (1990)). Specific investigation of this possibility has shown that on a molar basis BPI is at least as inhibitory of cytoplasmic membrane vesicle function as polymyxin B (In't Veld et al., *Infection and Immunity* 56: 1203–1208 (1988)) but the exact mechanism as well as the relevance of such vesicles to studies of intact organisms has not yet been elucidated.

BPI is also capable of neutralizing the endotoxic properties of LPS to which it binds. Because of its bactericidal properties for gram-negative organisms and its ability to neutralize LPS, BPI can be utilized for the treatment of mammals suffering from diseases caused by gram-negative bacteria, such as bacteremia or sepsis.

U.S. Pat. No. 5,198,541 discloses recombinant genes encoding and methods for expression of BPI proteins, including BPI holoprotein and fragments of BPI. It also describes the use of N-terminal fragments of BPI protein for co-treatment with certain antibiotics, specifically penicillin, cephalosporins, rifampicin and actinomycin D.

Gram-negative bacteria include bacteria from the following species: Acidaminococcus, Acinetobacter, Aeromonas, Alcaligenes, Bacteroides, Bordetella, Branhamella, Brucella, Calymmatobacterium, Campylobacter, Cardiobacterium, Chromobactenum, Citrobacter, Edwardsiella, Enterobacter, Eschenchia, Flavobacterium, Francisella, Fusobacterium, Haemophilus, Klebsiella, Legionella, Moraxella, Morganella, Neisseria, Pasturella, Plesiomonas, Proteus, Providencia, Pseudomonas, Salmonella, Serratia, Shigella, Streptobacillus, Veillonella, Vibrio, and Yersinia species.

Antibiotics are natural chemical substances of relatively low molecular weight produced by various species of microorganisms, such as bacteria (including Bacillus species), actinomycetes (including Streptomyces) and fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are (1) the β-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

The penicillins have a characteristic double-ring system composed of a β-lactam ring, which provides the antibacterial activity, and a thiazolidene ring. The penicillins are differentiated by a single side chain that is unique for each penicillin. The compounds are bactericidal and act by inhibiting bacterial transpeptidase, an enzyme involved in synthesis of the bacterial cell wall. Because of their mechanism of action, penicillins are generally active against growing, but not resting, cells. Penicillins, especially penicillin G, have largely gram-positive activity; the relative insensitivity of gram-negative rods to penicillin G and several other penicillins is probably due to the permeability barrier of the outer membrane of gram-negative bacteria. Ampicillin, carbenicillin, ticarcillin, and some other penicillins are active against gram-negative bacteria because they can pass through this outer membrane. Penicillins have relatively few adverse effects, the most important of which are the hypersensitivity (allergic) reactions. These compounds are widely distributed in the body, but do not enter cells and do not usually accumulate in CSF.

Bacterial resistance to the penicillins is by production of the enzyme β-lactamase, which catalyzes hydrolysis of the β-lactam ring. The percentage of bacteria resistant to penicillin has risen to about 80%. Several penicillins, including methicillin, oxacillin, cloxacillin, dicloxacillin and nafcillin, are not affected by the β-lactamase of staphylococci. These antibiotics are useful against most β-lactamase-producing species of Staphylococcus. However, a small number of species are resistant even to these penicillins. Some penicillins, amoxicillin and ticarcillin, are marketed in combination with clavulanic acid, which is a β-lactamase inhibitor that covalently binds to the enzyme and prevents it from hydrolyzing the antibiotics. Another inhibitor, sulbactam, is marketed in combination with ampicillin.

The cephalosporins are characterized by a β-lactam ring, like the penicillins, but have an adjacent dihydrothiazine ring instead of a thiazolidene ring. For convenience, these compounds are generally classified by generations. The first generation includes cephalothin, cephapirin, cefazolin, cephalexin, cephradine and cefadroxil. These drugs generally have excellent gram-positive activity except for enterococci and methicillin-resistant staphylococci, and have only modest gram-negative coverage. The second generation includes cefamandole, cefoxitin, ceforanide, cefuroxime, cefuroxime axetil, cefaclor, cefonicid and cefotetan. This generation generally loses some gram-positive activity by weight and gains limited gram-negative coverage. The third generation includes cefotaxime, moxalactam, ceftizoxime, ceftriaxone, cefoperazone and ceftazidime. These compounds generally sacrifice further gram-positive activity by weight but gain substantial gram-negative coverage against Enterobacter and sometimes are active against Pseudomonas. The cephalosporins bind to penicillin-binding proteins with varying affinity. Once binding occurs, protein synthesis is inhibited. Cephalosporins are usually well tolerated; adverse effects include hypersensitivity reactions and gastrointestinal effects. Cephalosporins may interact with nephrotoxic drugs, particularly aminoglycosides, to increase toxicity. Resistance to cephalosporins is mediated by several mechanisms, including production of β-lactamase, although some strains that do not produce β-lactamase are nevertheless resistant.

Imipenem is a N-formimidoyl derivative of the mold product thienamycin. It contains a β-lactam ring and somewhat resembles penicillin except for differences in the second ring. It has activity against both gram-positive and gram-negative organisms and is resistant to most β-lactamases, although not those from Pseudomonas. It is marketed in combination with cilastin, a compound that inhibits inactivation of imipenem in the kidney by renal dihydropeptidase I enzyme. Cilastin increases the concentration of imipenem in urine, although not in blood.

Aztreonam is the first of a new group of antibiotics referred to as the monobactams. These agents have a β-lactam ring but lack the second ring characteristic of the penicillins and cephalosporins. It acts by binding to penicillin-binding proteins, and produces long, filamentous bacterial shapes that eventually lyse. Aztreonam is active only against aerobic gram-negative bacteria, is susceptible to inactivation by some β-lactamases, and has few adverse effects.

The aminoglycosides contain amino sugars linked to an aminocyclitol ring by glycosidic bonds. They have similar mechanisms of action and properties, but differ somewhat in spectrum of action, toxicity, and susceptibility to bacterial resistance. The compounds are bactericidal, with activity against both gram-positive and gram-negative organisms, and act by binding to proteins on the 30S ribosome of bacteria and inhibiting protein synthesis. The aminoglycosides also bind to isolated LPS and have a very weak outer membrane permeabilizing effect. [Taber et al., *Microbiological Reviews* 53: 439–457 (1987)); Kadurugamuwa et al., *Antimicrobial Agents and Chemotherapy*, 37: 715–721 (1993); Vaara, *Microbiological Reviews* 56: 395–411 (1992)]. This class of antibiotics includes amikacin, gentamicin, kanamycin, neomycin, netilmycin, paromomycin and tobramycin. The aminoglycosides are usually reserved for more serious infections because of severe adverse effects including ototoxicity and nephrotoxicity. There is a narrow therapeutic window between the concentration required to produce a therapeutic effect, e.g., 8 μg/ml for gentamicin, and the concentration that produces a toxic effect, e.g., 12 μg/ml for gentamicin. Neomycin in particular is highly toxic and is never administered parenterally.

Tetracyclines have a common four-ring structure and are closely congeneric derivatives of the polycyclic naphthacenecarboxamide. The compounds are bacteriostatic, and inhibit protein synthesis by binding to the 30S subunit of microbial ribosomes and interfering with attachment of aminoacyl tRNA. The compounds have some activity against both gram-positive and gram-negative bacteria; however, their use is limited because many species are now relatively resistant. Adverse effects include gastrointestinal effects, hepatotoxicity with large doses, and nephrotoxicity in some patients. This antibiotic class includes tetracycline, chlortetracycline, demeclocycline, doxycycline, methacycline, minocycline and oxytetracycline.

The sulfonamides are derivatives of sulfanilamide, a compound similar in structure to para-aminobenzoic acid (PABA), which is an essential precursor for bacterial synthesis of folic acid. The compounds are generally bacteriostatic, and act by competitively inhibiting incorporation of PABA into tetrahydrofolic acid, which is a required cofactor in the synthesis of thymidines, purines and DNA. Sulfonamides have a wide range of activity against gram-positive and gram-negative bacteria, but their usefulness has diminished with increasingly high prevalence of bacterial resistance. The sulfonamide class of antibiotics includes sulfacytine, sulfadiazine, sulfamethizole, sulfisoxazole, sulfamethoxazole, sulfabenzamide and sulfacetamide. Adverse effects include hypersensitivity reactions and occasional hematological toxicity.

Trimethoprim is an inhibitor of the dihydrofolate reductase enzyme, which converts dihydrofolic to tetrahydrofolic acid, a required factor for DNA synthesis. Adverse effects include gastrointestinal distress and rare hematological toxicity. Trimethoprim is also available in combination with sulfamethoxazole (also known as co-trimoxazole). The combination is usually bactericidal, although each agent singly is usually bacteriostatic. The combination is the drug of choice for Salmonella infections, some Shigella infections, *E. coli* traveler's diarrhea and *Pneumocystis carinii* pneumonia.

The fluoroquinolones and quinolones are derivatives of nalidixic acid, a naphthyridine derivative. These compounds are bactericidal, and impair DNA replication, transcription and repair by binding to the DNA and interfering with DNA gyrase, an enzyme which catalyzes negative supercoiling of DNA. The fluoroquinolones, which include norfloxacin, ciprofloxacin, and ofloxacin, and the quinolones, which include cinoxacin, have a broad spectrum of antimicrobial activity against gram-negative and gram-positive organisms. These compounds distribute widely through extravascular tissue sites, have a long serum half-life, and present few adverse effects. Because of their effect on DNA, the drugs are contraindicated in pregnant patients and in children whose skeletal growth is incomplete.

Vancomycin is a glycopeptide, with a molecular weight of about 1500, produced by a fungus. It is primarily active against gram-positive bacteria. The drug inhibits one of the final steps in synthesis of the bacterial cell wall, and is thus effective only against growing organisms. It is used to treat serious infections due to gram-positive cocci when penicillin G is not useful because of bacterial resistance or patient allergies. Vancomycin has two major adverse effects, ototoxicity and nephrotoxicity. These toxicities can be potentiated by concurrent administration of another drug with the same adverse effect, such as an aminoglycoside.

The macrolides are bacteriostatic and act by binding to the 50S subunit of 70S ribosomes, resulting in inhibition of protein synthesis. They have a broad spectrum of activity against gram-positive and gram-negative bacteria and may be bacteriostatic or bactericidal, depending on the concentration achieved at sites of infection. The compounds distribute widely in body fluids. Adverse effects include gastrointestinal distress and rare hypersensitivity reactions. The most common macrolide used is erythromycin, but the class includes other compounds such as clarithromycin and azithromycin.

The polymyxins are a group of closely related antibiotic substances produced by strains of *Bacillus polymyxa*. These drugs, which are cationic detergents, are relatively simple, basic peptides with molecular weights of about 1000. Their antimicrobial activity is restricted to gram-negative bacteria. They interact strongly with phospholipids and act by penetrating into and disrupting the structure of cell membranes.

Polymyxin B also binds to the lipid A portion of endotoxin and neutralizes the toxic effects of this molecule. Polymyxin B has severe adverse effects, including nephrotoxicity and neurotoxicity, and should not be administered concurrently with other nephrotoxic or neurotoxic drugs. The drug thus has limited use as a therapeutic agent because of high systemic toxicity, but may be used for severe infections, such as *Pseudomonas aeruginosa* meningitis, that respond poorly to other antibiotics.

Chloramphenicol inhibits protein synthesis by binding to the 50S ribosomal subunit and preventing binding of aminoacyl tRNA. It has a fairly wide spectrum of antimicrobial activity, but is only reserved for serious infections, such as meningitis, typhus, typhoid fever, and Rocky Mountain spotted fever, because of its severe and fatal adverse hematological effects. It is primarily bacteriostatic, although it may be bactericidal to certain species.

Lincomycin and clindamycin are lincosamide antimicrobials. They consist of an amino acid linked to an amino sugar. Both inhibit protein synthesis by binding to the 50S ribosomal subunit. They compete with erythromycin and chloramphenicol for the same binding site but in an overlapping fashion. They may be bacteriostatic or bactericidal, depending on relative concentration and susceptibility. Gastrointestinal distress is the most common side effect. Other adverse reactions include cutaneous hypersensitivity, transient hematological abnormalities, and minor elevations of hepatic enzymes. Clindamycin is often the drug of choice for infections caused by anaerobic bacteria or mixed aerobic/anaerobic infections, and can also be used for susceptible aerobic gram-positive cocci.

Some drugs, e.g. aminoglycosides, have a small therapeutic window. For example, 2 to 4 $\mu$g/ml of gentamicin or tobramycin may be required for inhibition of bacterial growth, but peak concentrations in plasma above 6 to 10 $\mu$g/ml may result in ototoxicity or nephrotoxicity. These agents are more difficult to administer because the ratio of toxic to therapeutic concentrations is very low. Antimicrobial agents that have toxic effects on the kidneys and that are also eliminated primarily by the kidneys, such as the aminoglycosides or vancomycin, require particular caution because reduced elimination can lead to increased plasma concentrations, which in turn may cause increased toxicity, Doses of antimicrobial agents that are eliminated by the kidneys must be reduced in patients with impaired renal function. Similarly, dosages of drugs that are metabolized or excreted by the liver, such as erythromycin, chloramphenicol, or clindamycin, must be reduced in patients with decreased hepatic function.

Antibiotic resistance in bacteria is an increasingly troublesome problem. The accelerating development of antibiotic-resistant bacteria, intensified by the widespread use of antibiotics in farm animals and overprescription of antibiotics by physicians, has been accompanied by declining research into new antibiotics with different modes of action. [*Science*, 264: 360–374 (1994).] Antibiotic resistance, once acquired, can be rapidly spread to other bacteria, including bacteria of a different species. There are some species of bacteria that are resistant to all but one antibiotic; it may be only a matter of time before the appearance of bacterial strains that are resistant to all antibiotics.

Bacteria acquire resistance to antibiotics through several mechanisms: (1) production of enzymes that destroy or inactivate the antibiotic [Davies, *Science*, 264:375–381 (1994)]; (2) synthesis of new or altered target sites on or within the cell that are not recognized by the antibiotic [Spratt, *Science*, 264:388–393 (1994)]; (3) low permeability to antibiotics, which can be reduced even further by altering cell wall proteins, thus restricting access of antibiotics to the bacterial cytoplasmic machinery; (4) reduced intracellular transport of the drug; and (5) increased removal of antibiotics from the cell via membrane-associated pumps [Nikaido, *Science*, 264:382–387 (1994)].

The susceptibility of a bacterial species to an antibiotic is generally determined by two microbiological methods. A rapid but crude procedure uses commercially available filter paper disks that have been impregnated with a specific quantity of the antibiotic drug. These disks are placed on the surface of agar plates that have been streaked with a culture of the organism being tested, and the plates are observed for zones of growth inhibition. A more accurate technique, the broth dilution susceptibility test, involves preparing test tubes containing serial dilutions of the drug in liquid culture media, then inoculating the organism being tested into the tubes. The lowest concentration of drug that inhibits growth of the bacteria after a suitable period of incubation is reported as the minimum inhibitory concentration.

The resistance or susceptibility of an organism to an antibiotic is determined on the basis of clinical outcome, i.e., whether administration of that antibiotic to a subject infected by that organism will successfully cure the subject. While an organism may literally be susceptible to a high concentration of an antibiotic in vitro, the organism may in fact be resistant to that antibiotic at physiologically realistic concentrations. If the concentration of drug required to inhibit growth of or kill the organism is greater than the concentration that can safely be achieved without toxicity to the subject, the microorganism is considered to be resistant to the antibiotic. To facilitate the identification of antibiotic resistance or susceptibility using in vitro test results, the National Committee for Clinical Laboratory Standards (NCCLS) has formulated standards for antibiotic susceptibility that correlate clinical outcome to in vitro determinations of the minimum inhibitory concentration of antibiotic.

Thus, there exists a desire in the art for agents that could act as adjuncts to conventional antibiotic therapy and that could act to improve the therapeutic effectiveness of antibiotics.

SUMMARY OF THE INVENTION

The present invention generally provides methods and compositions for prophylaxis or treatment of gram-negative bacterial infections, using BPI protein products. The methods and compositions, in addition to being useful for treatment, are useful for prophylaxis of patients at high risk of gram-negative bacterial infection, e.g., patients who will undergo abdominal or genitourinary surgery, or trauma victims. Specifically, the present invention provides, in a method for treating a gram-negative bacterial infection with an antibiotic, the improvement comprising the step of concurrently administering BPI protein product in an amount effective to improve the therapeutic effectiveness of the antibiotic.

The present invention is based upon the finding that BPI protein product is useful as adjunct therapy with conventional antibiotics, and specifically the finding that concurrent administration, or co-treatment, of a BPI protein product and an antibiotic or combination of antibiotics can improve the therapeutic effectiveness of the antibiotic or combination of antibiotics. BPI protein product may improve the therapeutic effectiveness of antibiotics in a variety of ways, including by increasing susceptibility of gram-negative bacteria to a reduced dosage of antibiotics, by effectively reversing resistance of gram-negative bacteria to antibiotics, by providing synergistic or potentiating effects beyond the individual or additive effects of the BPI protein product or antibiotic alone, or by neutralizing endotoxin released by bacteria killed by antibiotics. Concurrent administration of BPI protein product and antibiotic provides unexpectedly superior therapeutic effects in vivo than either agent provides when administered alone. Concurrent administration of BPI protein product according to this improved method of treatment is effective even when the gram-negative bacteria involved are considered to be resistant to the bactericidal effects of BPI protein product alone and/or antibiotic alone.

The present invention provides a use of a BPI protein product for the manufacture of a medicament for the co-treatment with an antibiotic of a gram-negative bacterial infection in mammals. This aspect of the invention contemplates co-treatment with any antibiotic or combinations of antibiotics, including β-lactam antibiotics with and without β-lactamase inhibitors, aminoglycosides, tetracyclines, sulfonamides and trimethoprim, vancomycin, macrolides, fluoroquinolones and quinolones, polymyxins and other antibiotics.

This aspect of the invention also provides the use of a BPI protein product for the manufacture of a medicament for improving the therapeutic effectiveness of antibiotics in a gram-negative bacterial infection, use of a BPI protein product for the manufacture of a medicament for increasing the susceptibility to an antibiotic of gram-negative bacteria involved in the gram-negative bacterial infection, and use of a BPI protein product for the manufacture of a medicament for reversing resistance to an antibiotic of gram-negative bacteria involved in the gram-negative bacterial infection.

The invention utilizes any of the large variety of BPI protein products known to the art including natural BPI protein, recombinant BPI protein, BPI fragments, BPI analogs, BPI variants, and BPI peptides. Concurrent administration of BPI protein product with any antibiotic or combination of antibiotics is contemplated, including β-lactam antibiotics with or without β-lactamase inhibitors, aminoglycosides, tetracyclines, sulfonamides and trimethoprim, vancomycin, macrolides, fluoroquinolones and quinolones, polymyxins, and other antibiotics.

Either the BPI protein product or the antibiotic may be administered systemically or topically to a subject suffering from a suspected or confirmed gram-negative bacterial infection. The BPI protein product and antibiotic may be administered by different routes and may be administered simultaneously or sequentially.

The invention also provides pharmaceutical compositions for treatment of gram-negative bacterial infections, comprising an antibiotic and a BPI protein product in an amount effective to improve the therapeutic effectiveness of the antibiotic. Such compositions optionally comprise pharmaceutically acceptable diluents, adjuvants or carriers. The compositions may be formulated for systemic or topical administration to subjects. In addition, compositions comprising BPI protein product and an antibiotic can be used in a variety of in vitro uses, such as use as a bactericide to decontaminate fluids and surfaces and to sterilize surgical and other medical equipment and implantable devices, including prosthetic joints.

Numerous additional aspects and advantages of the invention will become apparent to those skilled in the art upon consideration of the following detailed description of the invention which describes presently preferred embodiments thereof.

BRIEF DESCRIPTION OF THE DRAWINGS

FIG. 2 depicts survival data; FIG. 3 shows bacterial counts from peritoneal lavage fluid; and FIG. 4 shows bacterial counts in blood.

FIG. 6 depicts survival data; FIG. 7 shows bacterial count in blood, which FIG. 8 displays as percentage of bacterial dose; FIG. 9 shows blood endotoxin levels; FIG. 10 shows mean arterial blood pressure; FIG. 11, cardiac index; FIG. 12, total peripheral resistance; FIG. 13, arterial oxygen tension; FIG. 14, alveolar-arterial oxygen gradient; FIG. 15, respiration rate; and FIG. 16, arterial blood pH.

FIG. 19 shows the bactericidal effect of $rBPI_{21}$ alone. FIG. 20 shows the effect of $rBPI_{21}$ in combination with trimethoprim/sulfamethoxazole; FIG. 21, $rBPI_{21}$ with ciprofloxacin; FIG. 22, $rBPI_{21}$ with piperacillin; FIG. 23, $rBPI_{21}$ with cefotaxime; FIG. 24, $rBPI_{21}$ with cefuroxime; and FIG. 25, $rBPI_{21}$ with amikacin.

DETAILED DESCRIPTION

Figure 1:
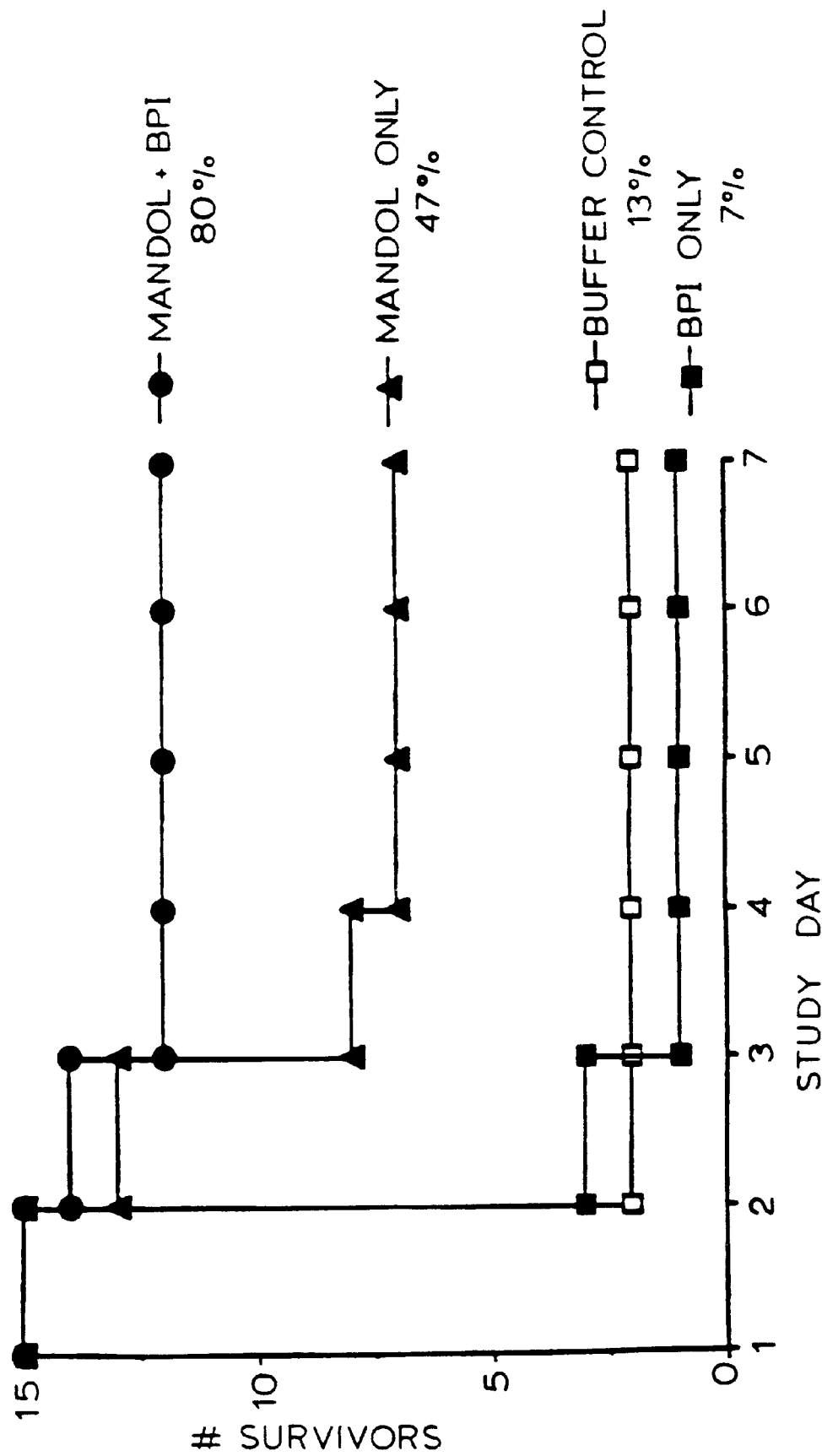
FIG. 1 depicts survival data after treatment with $rBPI_{21}$ and cefamandole, separately or in combination, in an *E. coli* 0111:B4 mouse peritonitis assay.

The present invention relates to methods and compositions for treating a gram-negative bacterial infection, using a BPI protein product. The invention is based on the unexpected discovery that, when treating a gram-negative bacterial infection with an antibiotic, the concurrent administration of BPI protein product with the antibiotic improves the therapeutic effectiveness of the antibiotic, even at doses at which the BPI protein product alone or antibiotic alone may be inactive. BPI protein product by itself typically has an antibacterial potency less than that of conventional antibiotics. However, because its administration unexpectedly improves the therapeutic effectiveness of conventional antibiotic therapy, BPI protein product is useful as adjunct therapy with conventional antibiotic therapy for the treatment of gram-negative bacterial infections.

"Gram-negative bacterial infection," as used herein, encompasses conditions associated with or resulting from gram-negative bacterial infection (e.g., sequelae). These conditions include gram-negative sepsis, endotoxin-related hypotension and shock, and one or more of the conditions associated therewith, including fever, metabolic acidosis, disseminated intravascular coagulation and related clotting disorders, anemia, thrombocytopenia, leukopenia, adult respiratory distress syndrome and related pulmonary disorders, renal failure and related renal disorders, hepatobiliary disease and central nervous system disorders. These conditions also include translocation of bacteria from the intestines and concomitant release of endotoxin.

BPI protein product may improve the therapeutic effectiveness of the antibiotic in a variety of ways, including by increasing susceptibility of gram-negative bacteria to a reduced dosage of antibiotics, by effectively reversing resistance of gram-negative bacteria to antibiotics, by providing synergistic or potentiating effects beyond the individual or additive effects of the BPI protein product or antibiotic alone, or by neutralizing endotoxin released by bacteria killed by antibiotics. Concurrent administration of BPI protein product and antibiotic is expected to provide more effective treatment of gram-negative bacterial infection. Concurrent administration of the two agents may provide greater therapeutic effects in vivo than either agent provides when administered singly. It may permit a reduction in the dosage of one or both agents with achievement of a similar therapeutic effect. Alternatively, the concurrent administration may produce a more rapid or complete bactericidal/bacteriostatic effect than could be achieved with either agent alone.

Therapeutic effectiveness is based on a successful clinical outcome, and does not require that the antimicrobial agent or agents kill 100% of the organisms involved in the infection. Success depends on achieving a level of antibacterial activity at the site of infection that is sufficient to inhibit the bacteria in a manner that tips the balance in favor of the host. When host defenses are maximally effective, the antibacterial effect required may be minimal. Reducing organism load by even one log (a factor of 10) may permit the host's own defenses to control the infection. In addition, augmenting an early bactericidal/bacteriostatic effect can be more important than long-term bactericidal/bacteriostatic effect. These early events are a significant and critical part of therapeutic success, because they allow time for host defense mechanisms to activate. Increasing the bactericidal rate may be particularly important for infections such as meningitis, bone or joint infections. [Stratton, *Antibiotics in Laboratory Medicine*, 3rd ed. (Lorian, V., Ed.) pp. 849–879, Williams and Wikins, Baltimore Md. (1991)].

The effect of BPI protein product to improve the therapeutic effectiveness of antibiotics in vivo may be demonstrated in in vivo animal models, or may be predicted on the basis of a variety of in vitro tests, including (1) determinations of the minimum inhibitory concentration (MIC) of an antibiotic required to inhibit growth of a gram-negative organism for 24 hours, (2) determinations of the effect of an antibiotic on the kinetic growth curve of a gram-negative organism, and (3) checkerboard assays of the MIC of serial dilutions of antibiotic alone or in combination with serial dilutions of BPI protein product. Exemplary models or tests are described in Eliopoulos and Moellering In *Antibiotics in Laboratory Medicine*, 3rd ed. (Lorian, V., Ed.) pp. 432–492, Williams and Wilkins, Baltimore Md. (1991).

Using in vitro determinations of antibiotic MIC at 24 hours, a BPI protein product may be shown to reduce the MIC of the antibiotic. With this result, it is expected that concurrent administration of the BPI protein product in vivo will increase susceptibility of the gram-negative organism to the antibiotic. A BPI protein product may also be shown to reduce the MIC of an antibiotic from the range in which the organism is considered clinically resistant to a range in which the organism is considered clinically susceptible. With this result, it is expected that concurrent administration in vivo of the BPI protein product with the antibiotic win reverse resistance and effectively convert the antibiotic-resistant organism into an antibiotic-susceptible organism.

By measuring the effect of antibiotics on the in vitro growth curves of gram-negative organisms, in the presence or absence of a BPI protein product, the BPI protein product may be shown to enhance the early antibacterial effect of antibiotics at 0–24 hours. Enhancement of early bactericidal/growth inhibitory effects is important in determining therapeutic outcome.

The BPI protein product and antibiotic may also be shown to have synergistic or potentiating effects beyond the individual effects of each agent alone or the additive effects of the agents together. In a checkerboard assay, the combination of BPI protein product with antibiotics may be shown to result in a "synergistic" fractional inhibitory concentration index (FIC). The checkerboard method is based on additivity, which assumes that the result observed with multiple drugs is the sum of the separate effects of the drugs being tested; according to this system a FIC of less than 0.5 is scored as synergy, 1 is scored as additive, and greater than 1 but less than 2 is scored as indifferent. In contrast, kinetic assays are based on the idea that only one metabolic pathway at a time can be growth rate-limiting for an organism; according to this system, the combined effect of drugs that do not interact with one another (autonomous or indifferent) is simply the effect of the most active drug alone.

Concurrent administration of BPI protein products and antibiotics is shown herein to lower MICs of a variety of antibiotics for a variety of gram-negative organisms. It is also shown to reverse resistance of a variety of gram-negative organisms to antibiotics. In some cases where BPI protein product does not affect the MIC of antibiotic at 24 hours, BPI protein product is shown herein to enhance the early bactericidal effect of antibiotics on growth curves at 0–7 or 7–24 hours. The BPI protein products exert these effects even on gram-negative organisms that are not considered susceptible to the direct bactericidal or growth inhibitory effects of BPI protein product alone. It is also shown herein that the concurrent administration of BPI protein products with antibiotics in vivo allows a reduction in the dosages of both agents to amounts that, if administered alone, would be insufficient to exert the same clinical effect.

Either the BPI protein product or the antibiotic, or both, may be administered at levels at which neither would alone be therapeutically effective against a gram-negative bacterial infection. Alternatively, according to a preferred method, the antibiotic and BPI protein product can be administered in amounts where each would alone be therapeutically effective against a gram-negative bacterial infection but wherein the combination of the two antibiotics provides even more potent effects. The BPI protein product may be administered in an amount which increases susceptibility of gram-negative bacteria to reduced antibiotic dosage, or in an amount which reverses resistance of the gram-negative bacteria to an antibiotic.

BPI protein product is thought to interact with a variety of host defense elements present in whole blood or serum, including complement, p15 and LBP, and other cells and components of the immune system. Such interactions may result in potentiation of the activities of BPI protein product. Because of these interactions, BPI protein products can be expected to exert even greater activity in vivo than in vitro. Thus, while in vitro tests are predictive of in vivo utility, absence of activity in vitro does not necessarily indicate absence of activity in vivo. For example, BPI has been observed to display a greater bactericidal effect on gram-negative bacteria in whole blood or plasma assays than in assays using conventional media. [Weiss et al., *J. Clin. Invest.* 90:1122–1130 (1992)]. This may be because conventional in vitro systems lack the blood elements that facilitate or potentiate BPI's function in vivo, or because conventional media contain higher than physiological concentrations of magnesium and calcium, which are typically inhibitors of the antibacterial activity of BPI protein products. Furthermore, in the host, BPI protein product is available to neutralize endotoxin released during antibiotic killing of bacteria, a further clinical benefit not seen in or predicted by in vitro tests.

It is also contemplated that the BPI protein product be administered with other products that potentiate the bactericidal activity of BPI protein products. For example, serum complement potentiates the gram-negative bactericidal activity of BPI protein products; the combination of BPI protein product and serum complement provides synergistic bactericidal/growth inhibitory effects. See, e.g., Ooi et al. *J. Biol Chem.*, 265: 15956 (1990) and Levy et al. *J. Biol Chem.*, 268: 6038–6083 (1993) which address naturally-occurring 15 kD proteins potentiating BPI antibacterial activity. See also co-owned, co-pending PCT Application No. US94/07834 filed Jul. 13, 1994, which corresponds to U.S. patent application Ser. No. 08/274,303 filed Jul. 11, 1994 as a continuation-in-part of U.S. patent application Ser. No. 08/093,201 filed Jul. 14, 1993. These applications, which are all incorporated herein by reference, describe methods for potentiating gram-negative bactericidal activity of BPI protein products by administering lipopolysaccharide binding protein (LBP) and LBP protein products. LBP protein derivatives and derivative hybrids which lack CD-14 immunostimulatory properties are described in PCT Application No. US94/06931 filed Jun. 17, 1994, which corresponds to co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of all of which are hereby incorporated by reference.

An advantage provided by the present invention is the ability to provide more effective treatment of gram-negative bacterial infection by virtue of the improved therapeutic effectiveness of the antibiotic treatment. Another advantage is the ability to treat gram-negative organisms that are normally resistant to one or more antibiotics. Yet another advantage is the ability to accelerate the killing of gram-negative organisms by antibiotics. An additional advantage is the ability to neutralize endotoxin released during antibiotic killing of bacteria. A further advantage is the ability to use lower concentrations of toxic antibiotics such as gentamicin and polymyxin B, or expensive antibiotics such as vancomycin. Because the use of some antibiotics is limited by their systemic toxicity or prohibitive cost, lowering the concentration of antibiotic required for therapeutic effectiveness reduces toxicity and/or cost of treatment, and thus allows wider use of the antibiotic. The present invention may also provide quality of life benefits due to, e.g., decreased duration of therapy, reduced stay in intensive care units or overall in the hospital, with the concomitant reduced risk of serious nosocomial (hospital-acquired) infections.

The invention further provides pharmaceutical compositions for treatment of gram-negative bacterial infections, comprising an antibiotic and a BPI protein product in an amount effective to improve the therapeutic effectiveness of the antibiotic. Such compositions optionally comprise pharmaceutically acceptable diluents, adjuvants or carriers. The compositions may be formulated for systemic or topical administration to subjects. In addition, antiseptic compositions comprising BPI protein product and an antibiotic can be used in a variety of in vitro uses such as use as a bactericide to decontaminate fluids and surfaces and to sterilize surgical and other medical equipment and implantable devices, including prosthetic joints. The invention also provides improved methods of in vitro decontamination of fluids and surfaces comprising administering a BPI protein product in combination with an antibiotic.

Either the BPI protein product or the antibiotics may be administered systemically or topically. Systemic routes of administration include oral, intravenous, intramuscular or subcutaneous injection, intrathecal, intraperitoneal (e.g. by intraperitoneal ravage), transpulmonary using aerosolized or nebulized drug, or transdermal. Topical routes include administration in the form of salves, ophthalmic drops, ear drops, or irrigation fluids (for, e.g., irrigation of wounds).

"Concurrent administration," or co-treatment, as used herein includes administration of the agents together, or before or after each other. The BPI protein product and antibiotics may be administered by different routes. For example, the BPI protein product may be administered intravenously while the antibiotics are administered intramuscularly, intravenously, subcutaneously, orally or intraperitoneally. Alternatively, the BPI protein product may be administered intraperitoneally while the antibiotics are administered intraperitoneally or intravenously, or the BPI protein product may be administered in an aerosolized or nebulized form while the antibiotics are administered, e.g., intravenously. The BPI protein product and antibiotics are preferably both administered intravenously. The BPI protein product and antibiotics may be given sequentially in the same intravenous line, after an intermediate flush, or may be given in different intravenous lines. The BPI protein product and antibiotics may be administered simultaneously or sequentially, as long as they are given in a manner sufficient to allow both agents to achieve effective concentrations at the site of infection.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; and biologically active polypeptide analogs of BPI protein or fragments or variants thereof, including cysteine-substituted analogs. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as rBPI$_{50}$ and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as rBPI$_{23}$. In that publication, an expression vector was used as a source of DNA encoding a recombinant expression product (rBPI$_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 145 and 146) set out in FIG. 1 of Gray et al., supra, with the exceptions noted for rBPI$_{23}$ and with the exception that residue 417 is alanine (specified by GCT) rather than valine (specified by GTT). Other examples include dimeric forms of BPI fragments, as described in co-owned and co-pending U.S. patent application Ser. No. 08/212,132, filed Mar. 11, 1994, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated rBPI$_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064,693 filed May 19, 1993 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}$ΔAcys or rBPI$_2$,. Other examples include dimeric forms of BPI analogs; e.g. co-owned and co-pending U.S. patent application Ser. No. 08/212,132 filed Mar. 11, 1994, and corresponding PCT 1995, the disclosures of which are incorporated herein by reference.

Other BPI protein products useful according to the methods of the invention are peptides derived from or based on BPI produced by recombinant or synthetic means (BPI-derived peptides), such as those described in co-owned and copending PCT Application No. PCT/US94/10427 filed Sep. 15,1994, which corresponds to U.S. patent application Ser. No. 08/306,473, now U.S. Pat. No. 5,652,332 filed Sep. 15, 1994, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference.

Presently preferred BPI protein products include recombinantly-produced N-terminal fragments of BPI, especially those having a molecular weight of approximately between 21 to 25 kD such as rBPI$_{23}$ or rBPI$_{21}$, or dimeric forms of these N-terminal fragments (e.g., rBPI$_{42}$ dimer). Additionally, preferred BPI protein products include rBPI$_{50}$ and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-microbial agents. A preferred pharmaceutical composition containing BPI protein products (e.g., rBPI$_{50}$, rBPI$_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another preferred pharmaceutical composition containing BPI protein products (e.g., rBPI$_{21}$) comprises the BPI protein product at a concentration of 2 mg/ml in 5 mM citrate, 150 mM NaCl, 0.2% poloxamer 188 and 0.002% polysorbate 80. Such preferred combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

Suitable antibiotics, and therapeutically effective concentrations thereof when administered with BPI protein products, may be determined in in vivo models or according to in vitro tests, for example, the in vitro minimum inhibitory concentration (MIC) and in vivo mouse peritonitis or rabbit bacteremia assays taught herein. Suitable antibiotics are antibiotics that act on the bacterial cell wall, cell membrane, protein metabolism or nucleic acid metabolism. These would include antibiotics or combinations of antibiotics from the following classes: β-lactam antibiotics with or without β-lactamase inhibitors, aminoglycosides, tetracyclines, sulfonamides and trimethoprim, vancomycin, macrolides, fluoroquinolones and quinolones, polymyxins, and other antibiotics. Dosage and administration of suitable antibiotics are known in the art, and briefly summarized below.

PENICILLINS

When a BPI protein product is concurrently administered with a penicillin, for treatment of a gram-negative bacterial infection, the BPI protein product is generally given parenterally in doses ranging from 1 μg/kg to 100 mg/kg daily, and preferably at doses ranging from 1 μg/kg to 20 mg/kg daily. The penicillin is generally given in doses ranging from 1 μg/kg to 750 mg/kg daily, preferably not to exceed 24 grams daily for adults (or 600 mg/kg daily for children), and is preferably administered as follows:

Penicillin G is preferably administered parenterally to adults in doses ranging from 600,000 to 1,000,000 units per day. In conventional administration, it is effective largely against gram-positive organisms. For treatment of pneumococcal meningitis, penicillin G is administered in doses of 20–24 million units daily, in divided doses every 2 or 3 hours. For children, the preferred parenteral dose of penicillin G is 300,000 to 1,000,000 units per day. One unit of penicillin G contains 0.6 μg of pure sodium penicillin G (i.e., 1 mg is 1667 units).

Amoxicillin may be administered parenterally to adults in doses ranging from 750 mg to 1.5 grams per day, in 3 equally divided doses. For children, preferred parenteral doses of amoxicillin range from 20 to 40 mg/kg per day in 3 equally divided doses. Amoxicillin is also available in combination with clavulanic acid, a β-lactamase inhibitor. A 250 mg dose of the combination drug amoxicillin/clavulanate will contain 250 mg of amoxicillin and either 125 or 62.5 mg of clavulanic acid. The combination is preferably administered to adults orally in doses of 750 mg per day divided into 3 equal doses every 8 hours, with a preferred dose of 1.5 grams per day for severe infections, given in 3 equally divided doses. In children, the preferred oral dose is 20 to 40 mg/kg per day in 3 equally divided doses.

Ampicillin is preferably administered parenterally to adults in doses of 6 to 12 grams per day for severe infections, in 3 to 4 equally divided doses. In children, the preferred parenteral dose of ampicillin is 50 to 200 mg/kg per day in 3 to 4 equally divided doses. Larger doses of up to 400 mg/kg per day, for children, or 12 grams per day, for adults, may be administered parenterally for treatment of meningitis. Ampicillin is also available in combination with sulbactam, a β-lactamase inhibitor. Each 1.5 gram dose of ampicilin/sulbactam contains 1 gram of ampicillin and 0.5 grams of sulbactam. The combination is preferably administered parenterally to adults in doses of 6 to 12 grams per day divided into 4 equal doses every 6 hours, not to exceed a total of 12 grams per day.

Azlocillin is preferably administered parenterally to adults in doses of 8 to 18 grams per day, given in 4 to 6 equally divided doses.

Carbenicillin is preferably administered parenterally to adults in doses of 30 to 40 grams per day, given by continuous infusion or in 4 to 6 equally divided doses. Daily doses of up to 600 mg/kg have been used to treat children with life-threatening infections.

Mezlocillin is preferably administered to adults parenterally in doses of 100 to 300 mg/kg per day, given in 4 to 6 equally divided doses. The usual dose is 16 to 18 grams per day; for life threatening infections, 350 mg/kg per day may be administered, but in doses not to exceed 24 grams per day given in 6 equally divided doses every 4 hours. For children, the preferred parenteral dose of mezlocillin is 150 to 300 mg/kg per day.

Nafcillin is preferably administered intravenously to adults in doses of 3 grams per day, given in 6 equally divided doses every 4 hours, with doubled doses for very severe infections. In conventional administration, it is effective largely against gram-positive organisms. In children, the preferred parenteral dose is 20 to 50 mg/kg per day, in 2 equally divided doses every 12 hours. The preferred oral dose for nafcillin ranges from 1 gram per day to 6 grams per day in 4 to 6 divided doses.

Oxacillin is preferably administered parenterally to adults in doses of 2 to 12 grams per day, in 4 to 6 equally divided doses. In conventional administration, it is effective largely against gram-positive organisms. In children, oxacillin is preferably administered in doses of 100 to 300 mg/kg per day.

Piperacillin is preferably administered parenterally to adults in doses ranging from 100 mg/kg, or 6 grams per day, in 2 to 4 equally divided doses, up to a maximum of 24 grams per day, in 4 to 6 equally divided doses. Higher doses have been used without serious adverse effects.

Ticarcillin is preferably administered parenterally to adults in doses ranging from 4 grams per day to 18 grams per day administered in 4 to 6 equally divided doses. The usual dose is 200 to 300 mg/kg per day. For children, the preferred parenteral dose of ticarcillin ranges from 50 mg/kg per day to 300 mg/kg per day, given in 3, 4 or 6 equally divided doses. The combination ticarcillin/clavulanate is preferably administered parenterally to adults in doses of 200 to 300 mg/kg per day (based on ticarcillin content), in 4 to 6 equally divided doses. For adults, the usual dose is 3.1 grams (which contains 3 grams of ticarcillin and 100 mg of clavulanic acid) every 4 to 6 hours. The combination is also available in a dose of 3.2 grams, which contains 3 grams of ticarcillin and 200 mg of clavulanic acid.

In general, it is desirable to limit each intramuscular injection of a penicillin or cephalosporin to 2 grams; larger doses should be administered by multiple injections in different large muscle masses.

CEPHALOSPORINS

When a BPI protein product is concurrently administered with a cephalosporin, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The cephalosporin is generally given in doses ranging from 1 μg/kg to 500 mg/kg daily, preferably not to exceed 16 grams daily, and is preferably administered as follows:

Cefamandole is preferably administered parenterally to adults in doses ranging from 1.5 grams per day, given in 3 equally divided doses every 8 hours, to 12 grams per day for life-threatening infections, given in 6 equally divided doses every 4 hours. In children, cefamandole is preferably administered in doses ranging from 50 to 150 mg/kg per day, in 3 to 6 equally divided doses, not to exceed a total of 12 grams per day.

Cefazolin is preferably administered parenterally to adults in doses of 750 mg per day, given in 3 equally divided doses every 8 hours. In severe, life-threatening infections, it may be administered at doses of 6 grams per day divided into 4 equal doses every 6 hours; in rare instances, up to 12 grams per day have been used. In children, the preferred parenteral dose of cefazolin is 20 to 50 mg/kg per day, divided into 3 or 4 equal doses, with 100 mg/kg per day administered for severe infections.

Cefonicid is preferably administered parenterally to adults in doses ranging from 500 mg once daily, to 2 grams once daily for life-threatening infections. For intramuscular administration, a 2 gram dose should be divided into two 1-gram injections.

Cefoperazone is preferably administered parenterally to adults in doses ranging from 2 grams per day, given in 2 equally divided doses every 12 hours, to 12 grams per day for severe infections, given in 2, 3 or 4 equally divided doses. Doses up to 16 grams per day have been administered without complications.

Cefotetan is preferably administered parenterally to adults in doses of 1 to 4 grams per day, in 2 equally divided doses every 12 hours. Cefotetan may be administered in higher doses for life-threatening infections, not to exceed a total dose of 6 grams per day.

Cefotaxime is preferably administered parenterally to adults in doses ranging from 1 to 12 grams per day, not to exceed 12 grams per day (2 grams every 4 hours) for life-threatening infections. In children, the parenteral dose of cefotaxime is preferably 50 to 180 mg/kg, divided into 4 to 6 equal doses.

Cefoxitin is preferably administered parenterally to adults in doses ranging from 3 to 12 grams per day, given in 3, 4, or 6 equally divided doses. In children, cefoxitin is preferably administered parenterally in doses of 80 to 160 mg/kg per day, given in 4 or 6 equally divided doses, not to exceed a total dose of 12 grams per day.

Ceftazidime is preferably administered parenterally to adults in doses ranging from 500 mg per day, given in 2 to 3 equally divided doses (every 8 or 12 hours), up to a maximum of 6 grams per day. In children, ceftazidime is preferably administered intravenously in doses of 30 to 50 mg/kg, to a maximum of 6 grams per day.

Ceftizoxime is preferably administered parenterally to adults in doses ranging from 1 gram per day, given in 2 equally divided doses every 12 hours, to 12 grams per day for life-threatening infections, given in 3 equally divided doses every 8 hours. The usual adult dose is 1 to 2 grams every 8 or 12 hours. For children, the preferred parenteral dose is 50 mg/kg every 6 or 8 hours, for a total daily dose of 200 mg/kg.

Ceftriaxone is preferably administered parenterally to adults in doses ranging from 1 to 2 grams per day, given in 2 equally divided doses every 12 hours. It may be given in higher doses, not to exceed a total of 4 grams per day. In children, the preferred parenteral dose of ceftriaxone is 50 to 75 mg/kg per day, not to exceed 2 grams per day. In meningitis, ceftriaxone may be administered in doses of 100 mg/kg per day, not to exceed 4 grams per day.

Cefuroxime is preferably administered parenterally to adults in doses ranging from 2.25 to 4.5 grams per day, in 3 equally divided doses every 8 hours. For life-threatening infections, 6 grams per day may be administered in 4 equally divided doses every 6 hours, and for meningitis, 9 grams per day may be administered in 3 equally divided doses every 8 hours. For children, the preferred parenteral dose of cefuroxime is 50 to 150 mg/kg per day in 3 to 4 equally divided doses, or 240 mg/kg per day for meningitis.

Cephalexin is formulated for oral administration, and is preferably administered orally to adults in doses ranging from 1 to 4 grams per day in 2 to 4 equally divided doses. For children, the preferred dose is 20 to 50 mg/kg per day in divided doses, with doses being doubled for severe infections.

Cephalothin is usually administered parenterally to adults in doses of 8 to 12 grams per day.

OTHER BETA-LACTAMS

When a BPI protein product is concurrently administered with an imipenem antibiotic, for treatment of a gram-negative bacterial infection, the BPI protein product is generally given parenterally in doses ranging from 1 $\mu$g/kg to 100 mg/kg daily, and preferably at doses ranging from 1 mg/kg to 20 mg/kg daily. The imipenem is generally given in doses ranging from 1 $\mu$g/kg to 100 mg/kg daily, and is preferably administered as follows:

Imipenem is available in combination with cilastatin, an inhibitor of the renal dipeptidase enzyme that rapidly inactivates imipenem. The combination is preferably administered intramuscularly to adults in doses of 1 to 1.5 grams per day, given in 2 equally divided doses every 12 hours. Intramuscular doses exceeding 1.5 grams per day are not recommended. The combination is preferably administered intravenously in doses ranging from 1 to 4 grams per day, in 4 equally divided doses every 6 hours; doses exceeding 50 mg/kg per day, or 4 grams per day, are not recommended.

When a BPI protein product is concurrently administered with a monobactam antibiotic, for treatment of a gram-negative bacterial infection, the BPI protein product is generally given parenterally in doses ranging from 1 $\mu$g/kg to 100 mg/kg daily, and preferably at doses ranging from 1 mg/kg to 20 mg/kg daily. The monobactam is generally given in doses ranging from 1 $\mu$g/kg to 200 mg/kg daily, and is preferably administered as follows:

Aztreonam is preferably administered parenterally to adults in doses ranging from 1 gram per day, given in 2 equally divided doses every 12 hours, up to a maximum recommended dose of 8 grams per day in cases of life-threatening infection, given in 3 or 4 equally divided doses.

AMINOGLYCOSIDES

When a BPI protein product is concurrently administered with an aminoglycoside, for treatment of a gram-negative bacterial infection, the BPI protein product is generally given parenterally in doses ranging from 1 $\mu$g/kg to 100 mg/kg daily, and preferably at doses ranging from 1 mg/kg to 20 mg/kg daily. The aminoglycoside is generally given in doses ranging from 1 $\mu$g/kg to 20 mg/kg daily, preferably not to exceed 15 mg/kg daily, and is preferably administered as follows:

When administering aminoglycosides, it is desirable to measure serum peak and trough concentrations to ensure the adequacy and safety of the dosage. Dosages should generally be adjusted to avoid toxic peak and trough concentrations. Amikacin is preferably administered parenterally to adults and children in doses of 15 mg/kg per day, divided into two or three equal doses every 8 or 12 hours, and not to exceed a total dose of 1.5 grams per day. For uncomplicated infections, a dose of 500 mg amikacin per day, in 2 equally divided doses, may be administered. Dosages should be adjusted to avoid prolonged serum peak concentrations of amikacin above 35 $\mu$g/ml and prolonged trough concentrations greater than 10 $\mu$g/ml.

Gentamicin is preferably administered parenterally to adults in doses of 3 mg/kg per day, in three equally divided doses every 8 hours. For life-threatening infections, up to 5 mg/kg per day in 3 to 4 equally divided doses may be administered, but this dosage should be reduced to 3 mg/kg per day as soon as clinically indicated. For children, gentamicin is preferably administered parenterally in doses of 6 to 7.5 mg/kg per day. Dosages should be adjusted to avoid prolonged serum peak concentrations of gentamicin above 12 $\mu$g/ml and prolonged trough concentrations greater than 2 $\mu$g/ml.

Netilmicin may be administered parenterally to adults in doses ranging from 3 mg/kg per day, in 2 equally divided doses every 12 hours, to 6.5 mg/kg per day for serious systemic infection, in 2 or 3 equally divided doses. In children, the preferred parenteral dose is 5.5 to 8 mg/kg per day, in 2 or 3 equally divided doses. Dosages should be adjusted to avoid prolonged serum peak concentrations of netilmicin above 16 $\mu$g/ml and prolonged serum trough concentrations above 4 $\mu$g/ml.

Tobramycin is preferably administered parenterally to adults in doses of 3 mg/kg per day, given in three equally divided doses every 8 hours. For life-threatening infections, tobramycin may be administered in doses up to 5 mg/kg per day, in 3 or 4 equally divided doses, but this dosage should be reduced to 3 mg/kg per day as soon as clinically indicated. In children, tobramycin is preferably administered parenterally in doses of 6 to 7.5 mg/kg per day. Prolonged serum concentrations of tobramycin above 12 μg/ml should be avoided, and rising trough levels above 2 μg/ml may indicate tissue accumulation, which may contribute to toxicity.

Concurrent administration of BPI protein product with the aminoglycosides, including amikacin, gentamicin, netilmicin and tobramycin, may permit a lowering of the dose of these toxic antibiotics necessary to achieve a therapeutic effect.

TETRACYCLINES

When a BPI protein product is concurrently administered with a tetracycline, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The tetracycline is generally given in doses ranging from 1 μg/kg to 50 mg/kg daily, and is preferably administered as follows:

The tetracycline antibiotics are generally administered to adults in doses of 1 to 2 grams per day. An exception is doxycycline, which is preferably administered intravenously to adults in doses of 100 to 200 mg per day, and to children in doses of 2 mg/lb per day. Tetracycline may be administered parenterally to adults in doses of 0.5 to 2 grams per day, in 2 equally divided doses, and to children in doses of 10 to 20 mg/kg per day.

SUFLONAMIDES

When a BPI protein product is concurrently administered with a sulfonamide or trimethoprim, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The sulfonamide or trimethoprim is generally given in doses ranging from 1 μg/kg to 150 mg/kg daily, preferably not to exceed a combination dose of 960 mg trimethoprim/4.8g sulfamethoxazole daily, and is preferably administered as follows:

The combination trimethoprim/sulfamethoxazole is available in a formulation containing a 1:5 ratio of trimethoprim and sulfamethoxazole (e.g., 16 mg trimethoprim and 80 mg sulfamethoxazole). The combination is preferably administered intravenously to adults or children in doses of 8 to 10 mg/kg (based on the weight of the trimethoprim component) per day, in 2 to 4 equally divided doses. For *Pneumocystis carinii* infection, the combination can be administered in doses of 20 mg/kg (based on the weight of the trimethoprim component) per day, in 3–4 equally divided doses, to a maximum recommended dose of 960 mg trimethoprim/4.8 g sulfamethoxazole per day. Trimethoprim alone is preferably administered orally to adults in doses of 200 mg per day. Sulfamethoxazole alone is preferably administered orally to adults in doses of 2 to 3 grams per day, and to children orally in doses of 50 to 60 mg/kg per day.

FLUOROQUINOLONES

When a BPI protein product is concurrently administered with a fluoroquinolone or quinolone, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The fluoroquinolone or quinolone is generally given in doses ranging from 1 μg/kg to 50 mg/kg daily, preferably not to exceed 1 gram daily, and is preferably administered as follows:

Norfloxacin is preferably administered orally to adults in doses from 400 to 800 mg daily, divided into two doses every 12 hours. Cinoxacin is preferably administered orally to adults in doses of 1 gram per day, given in 2 or 4 equally divided doses. Ciprofloxacin is preferably administered to adults intravenously in doses from 400 to 800 mg daily, or orally in doses from 500 to 1500 mg daily, divided into two doses every 12 hours. Ofloxacin is preferably administered to adults intravenously in doses from 400 to 800 mg daily, or orally in doses from 400 to 800 mg daily, divided into two doses every 12 hours.

VANCOMYCIN

When a BPI protein product is concurrently administered with vancomycin, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The vancomycin is generally given in doses ranging from 1 mg/kg to 50 mg/kg daily, and is preferably administered parenterally to adults in doses of 2 grams per day, divided into 2 or 4 doses every 6 or 12 hours. In children it is preferably administered in doses of 40 mg/kg, given in 4 equally divided doses every 6 hours. In conventional administration, vancomycin is effective largely against gram-positive organisms.

MACROLIDES

When a BPI protein product is concurrently administered with a macrolide, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily. The macrolide is generally given in doses ranging from 1 μg/kg to 100 mg/kg daily, and is preferably administered as follows:

Erythromycin is preferably administered intravenously to adults and children in doses of 15 to 20 mg/kg per day, given by continuous infusion or in 4 equally divided doses every 6 hours. Erythromycin can be administered at doses up to 4 grams per day in cases of very severe infection.

Clarithromycin is preferably administered orally to adults in doses of 500 mg to 1 gram daily, in equally divided doses every 12 hours.

Azithromycin is preferably administered orally to adults at a dose of 500 mg on the first day of treatment followed by 250 mg once daily for 4 days, for a total dose of 1.5 grams.

OTHERS

When a BPI protein product is concurrently administered with other antibiotics, for treatment of a gram-negative bacterial infection, the BPI protein product is generally given parenterally in doses ranging from 1 μg/kg to 100 mg/kg daily, and preferably at doses ranging from 1 mg/kg to 20 mg/kg daily.

Polymyxin B is generally given in doses ranging from 1 unit/kg to 45,000 units/kg daily, and is preferably administered intravenously to adults and children in doses of 15,000 to 25,000 units/kg per day, divided into 2 equal doses every 12 hours. It may be administered intramuscularly in doses of 25,000 to 30,000 units/kg per day, although these injections are very painful. Doses of polymyxin B as high as 45,000 units/kg per day have been used in limited clinical studies to treat neonates for *Pseudomonas aeruginosa* sepsis. Polymyxin B is the treatment of choice for *P. aeruginosa* meningitis, and is preferably administered intrathecally to adults and older children in doses of 50,000 units once daily for 3 to 4 days, followed by 50,000 units every other day; in children under two years old, it is administered intrathecally in doses of 20,000 daily for 3 to 4 days, followed by 25,000 units every other day.

Chloramphenicol is preferably administered intravenously to adults in doses of 50 mg/kg per day, in 4 equally divided doses; in exceptional cases, it can be administered in doses up to 100 mg/kg per day. In children, chloramphenicol is preferably administered intravenously in doses of 25 mg/kg per day, although up to 100 mg/kg per day can be administered in cases of severe infection.

Clindamycin is preferably administered parenterally to adults in doses ranging from 600 mg to 4.8 grams per day, given in 2, 3 or 4 equally divided doses. It is recommended that the dose in each intramuscular injection not exceed 600 mg. For children, clindamycin is preferably administered parenterally in doses of 15–40 mg/kg per day, given in 3 or 4 equally divided doses.

Dosages of all antimicrobial agents should be adjusted in patients with renal impairment or hepatic insufficiency, due to the reduced metabolism and/or excretion of the drugs in patients with these conditions. Doses in children should also be reduced, generally according to body weight. Those slilled in the art can readily optimize effective dosages and administration regimens for the BPI protein product and the antibiotics in concurrent administration.

Other aspects and advantages of the present invention will be understood upon consideration of the following illustrative examples. Example 1 addresses the bactericidal effect of gentamicin and BPI when administered to two different strains of *E. coli*. Example 2 addresses the bactericidal effect of gentamicin and BPI for a number of other gram-negative strains. Example 3 addresses the bactericidal effect of polymyxin B and BPI when administered to two different strains of *E. coli*. Example 4 addresses the bactericidal effect of polymyxin B and BPI for a number of other gram-negative strains. Example 5 addresses the effect of a BPI protein product with a cephalosporin antibiotic in an in vivo mouse peritonitis *E. coli* 0111:B4 challenge model. Example 6 also relates to the effect of a BPI protein product with a cephalosporin antibiotic in an in vivo mouse peritonitis *E. coli* 0111:B4 challenge model. Example 7 relates to the effect of a BPI protein product with a cephalosporin antibiotic in an in vivo mouse peritonitis *E. coli* 07:K1 challenge model. Example 8 addresses the effect of a BPI protein product with a cephalosporin antibiotic in an in vivo rabbit bacteremia *E. coli* 07:K1 challenge model. Example 9 addresses the effect of a BPI protein product with an aminoglycoside antibiotic in an in vivo mouse peritonitis *E. coli* 07:K1 challenge model. Example 10 relates to the effect of a BPI protein product in vitro on the antibiotic susceptibility of ceftriaxone-resistant gram-negative organisms. Examples 11–19 address large-scale screening of the antibiotic susceptibility-increasing effect of a BPI protein product on a variety of gram-negative organisms: *Pseudomonas aeruginosa* and other Pseudomonas species (Example 11), *E. coli* (Example 12), Citrobacter (Example 13), Klebsiella (Example 14), Enterobacter (Example 15), Serratia (Example 16), Proteus (Example 17), Providencia (Example 18), Morganella (Example 19), Acinetobacter (Example 20), and Salmonella and Shigella (Example 21). Example 22 examines the early in vitro bactericidal effect of BPI protein product and selected antibiotics on *E. coli* J5, *E. coli* 07:K1, *Enterobacter cloacae* and *Klebsiella pneumoniae*. Example 23 examines the effect of a variety of BPI protein products on several representative organisms, *Acinetobacter anitratus, Enterobacter cloacae*, and two strains of *E. coli*. Example 24 relates to the screening of BPI peptides for antibacterial activity against *E. coli*. Example 25 addresses the effect on *E. coli* 0111:B4 of concurrent administration of BPI protein product with tetracycline or gentamicin.

EXAMPLE 1

SYNERGISTIC BACTERICIDAL EFFECTS OF GENTAMICIN AND BPI: ADMINISTRATION TO *E. COLI* AND *E. COLI* 0111:B4 GRAM-NEGATIVE ORGANISMS

In this example, a micro dilution plate minimum inhibitory concentration (MIC) assay was conducted to determine the sensitivity of *E. coli* organisms to the bactericidal effects of BPI protein products concurrently administered with the antibiotic gentamicin. The assays were conducted against the BPI sensitive organism *E. coli* J5 (an Rc rough mutant of *E. coli* 0111:B4), and a BPI resistant organism *E. coli* 0111:B4.

Specifically, organisms were grown overnight on blood agar plates at 37° C. in air, single colonies were then sub-cultured in 100 mL of nutrient broth No. 2 (Oxoid CM67) and incubated with gentle agitation on an orbital shaker for 5¼ hours until in log phase. Fifty mL of the bacterial suspension was then spun down in a Denley BR401 bench centrifuge at 4000 rpm for 15 minutes and the pellet was resuspended and washed twice using sterile normal saline. Bacteria were then resuspended in saline such that a 1:10 dilution had an optical density of 0.9 (+/−0.01) at 325 nm (corresponding to approximately $4 \times 10^9$ cells per mL) and diluted to give a final concentration of $4 \times 10^6$ cells per mL in "BPI media" (described below).

All assays and dilutions of BPI protein products and gentamicin were performed using "BPI media" consisting of 50% peptone water (Oxoid L137, Lot: 25851279) with 0.1 M MOPS (Sigma M-1254) buffered to pH 6.00 with sodium hydroxide. This provides a nutritive media with a low protein and divalent cation concentration adjusted to a pH which is not inhibitory to bacterial growth and allows for readily measurable (though not optimal) BPI activity.

$rBPI_{23}$ and gentamicin (Sigma G-1264, Lot: 91H00325) were diluted in BPI media such that 100 μL of diluted BPI, 50 μL of diluted gentamicin and 50 μL of bacterial suspension in the final volume of 200 μL per well, gave concentrations in serial dilutions from 1000 nM (25 μg per mL) BPI and 32 μg per mL of gentamicin with a fixed concentration of $10^6$ cells/mL. Checkerboards were then constructed in round bottomed 96 well microtitre plates (Greiner No.

650180) and incubated with non-sealing lids at 37° C. in air for 18 hours. Plates were then read by eye and in an automatic plate reader (Titretek Multiscan plus) at 580 nm with visible growth corresponding to an optical density of approximately 0.1 (see Table 1 for *E. coli* j5, and Table 3 for *E. coli* 0111:B4). Viable counts were made from the wells adjacent to the cutoff of visible growth for the two *E. coli* plates (see Table 2 for *E. coli* J5, and Table 4 for *E. coli* 0111:B4) by dilution of 10 μL in 990 μL of Nutrient Broth No. 2 and spread plates were prepared with 25 μL on blood agar. The inhibitory activity of BPI protein product with antibiotic was evaluated by the method of Eliopoulos and Moellering In *Antibiotics in Laboratory Medicine*, 3rd ed. (Lorian, V., Ed.) pp. 432–492, Williams and Wilkins, Baltimore Md. (1991), wherein a fractional inhibitory concentration index (FIC) of less than 0.5 was scored as synergy, 1 was scored as additive and greater than 1 but less than 2 was scored as indifferent.

A positive synergistic interaction was demonstrated between $rBPI_{23}$ and gentamicin using the BPI sensitive *E. coli* J5 with gentamicin at a concentration of 0.25 μg per mL, reducing the MIC of BPI by approximately eight-fold from 500 nM (12.5 μg per mL) to 62.5 nM (1.56 μg per mL) with similar reductions of the minimum bactericidal concentration (MBC).

TABLE 1

Visible Growth (bold line) of *E. coli* J5 and ODS (580 nm)

| BPI (nM): | Gentamicin (μg per ml) | | | | | | | | | | | |
|---|---|---|---|---|---|---|---|---|---|---|---|---|
| | 32 | 16 | 8 | 4 | 2 | 1 | 0.5 | 0.25 | 1.25 | .06 | .03 | 0 |
| 1000 | .071 | .067 | .069 | .067 | .068 | .071 | .073 | .072 | .065 | .068 | .062 | .065 |
| 500 | .055 | .050 | .052 | .055 | .053 | .056 | .054 | .059 | .106 | .054 | .056 | .054 |
| 250 | .056 | .055 | .053 | .057 | .058 | .057 | .055 | .060 | .055 | .054 | .194 | .201 |
| 125 | .058 | .053 | .051 | .053 | .055 | .062 | .064 | .061 | .060 | .215 | .258 | .236 |
| 62.5 | .052 | .053 | .056 | .054 | .054 | .053 | .062 | .056 | .172 | .196 | .262 | .261 |
| 31 | .057 | .058 | .052 | .055 | .056 | .058 | .063 | .135 | .206 | .251 | .259 | .286 |
| 16 | .057 | .059 | .057 | .058 | .059 | .062 | .081 | .148 | .240 | .262 | .297 | .327 |
| 0 | .060 | .053 | .060 | .057 | .054 | .058 | .071 | .151 | .252 | .285 | .330 | .326 |

TABLE 2

Visible Growth (bold line) of *E. coli* J5 and Viable Counts

| BPI (nM): | Gentamicin (μg per ml) | | | | | | | | | | | |
|---|---|---|---|---|---|---|---|---|---|---|---|---|
| | 32 | 16 | 8 | 4 | 2 | 1 | 0.5 | 0.25 | .125 | .06 | .03 | 0 |
| 1000 | NC | NC | NC | NC | NC | NC | NC | 0 | 0 | 0 | 0 | 0 |
| 500 | NC | NC | NC | NC | NC | NC | 0 | 0 | 147 | 2 | 0 | 0 |
| 250 | NC | NC | NC | NC | NC | 0 | 0 | 0 | 0 | 0 | 0 | NC |
| 125 | NC | NC | NC | NC | 0 | 0 | 0 | 0 | 0 | ++ | NC | NC |
| 62.5 | NC | NC | NC | NC | 0 | 0 | 121 | 1 | ++ | NC | NC | NC |
| 31 | NC | NC | NC | NC | 0 | 0 | 555 | ++ | NC | NC | NC | NC |
| 16 | NC | NC | NC | NC | 0 | 0 | 438 | 438 | NC | NC | NC | NC |
| 0 | NC | NC | NC | NC | 0 | 0 | 267 | ++ | NC | NC | NC | NC |

Counts expressed as counts per ml, NC = not counted, ++ = too numerous to count.

TABLE 3

Visible Growth (bold line) of *E. coli* 0111:B4 and ODs (580 nm)

| BPI (nM): | Gentamicin (μg per ml) | | | | | | | | | | | |
|---|---|---|---|---|---|---|---|---|---|---|---|---|
| | 32 | 16 | 8 | 4 | 2 | 1 | 0.5 | 0.25 | .125 | .06 | .03 | 0 |
| 1000 | .067 | .064 | .057 | .057 | .055 | .067 | .062 | .191 | .275 | .328 | .308 | .370 |
| 500 | .054 | .051 | .049 | .052 | .050 | .050 | .048 | .179 | .245 | .282 | .276 | .342 |
| 250 | .054 | .053 | .053 | .053 | .058 | .061 | .054 | .161 | .245 | .282 | .269 | .345 |
| 125 | .048 | .051 | .049 | .047 | .049 | .050 | .109 | .198 | .239 | .267 | .261 | .328 |
| 62.5 | .062 | .058 | .054 | .051 | .053 | .052 | .059 | .176 | .252 | .283 | .287 | .353 |
| 31 | .059 | .054 | .054 | .052 | .051 | .051 | .054 | .192 | .250 | .287 | .278 | .357 |
| 16 | .061 | .054 | .058 | .063 | .052 | .054 | .048 | .158 | .261 | .285 | .284 | .349 |
| 0 | .054 | .058 | .055 | .049 | .050 | .053 | .079 | .155 | .280 | .309 | .322 | .374 |

TABLE 4

Visible Growth (bold line) of *E. coli* 0111:B4 and viable counts

| BPI (nM): | Gentamicin (μg per ml) | | | | | | | | | | | |
|---|---|---|---|---|---|---|---|---|---|---|---|---|
| | 32 | 16 | 8 | 4 | 2 | 1 | 0.5 | 0.25 | .125 | .06 | .03 | 0 |
| 1000 | NC | NC | NC | NC | 0 | 0 | 6 | ++ | NC | NC | NC | NC |
| 500 | NC | NC | NC | NC | 0 | 0 | 0 | +++ | NC | NC | NC | NC |
| 250 | NC | NC | NC | NC | 0 | 0 | 0 | +++ | NC | NC | NC | NC |
| 125 | NC | NC | NC | NC | 0 | 0 | 0 | +++ | NC | NC | NC | NC |
| 62.5 | NC | NC | NC | NC | 0 | 0 | 0 | +++ | NC | NC | NC | NC |
| 31 | NC | NC | NC | NC | 0 | 0 | 1 | +++ | NC | NC | NC | NC |
| 16 | NC | NC | NC | NC | 0 | 0 | 0 | +++ | NC | NC | NC | NC |
| 0 | NC | NC | NC | NC | 0 | 0 | 287 | +++ | NC | NC | NC | NC |

Counts expressed as count per ml, NC = not counted, ++ = too numerous to count.

EXAMPLE 2

SYNERGISTIC BACTERICIDAL EFFECTS OF GENTAMICIN AND BPI: ADMINISTRATION TO ADDITIONAL GRAM-NEGATIVE ORGANISMS

In this example, micro dilution plate MIC assays were conducted according to the method of Example 1 to determine the sensitivity of a variety of gram-negative organisms to the cytotoxic effects of BPI protein products concurrently administered with gentamicin antibiotic. The results of those assays are shown in Table 5 below. Positive synergistic bactericidal interactions were observed against *E. coli* J5, *E. coli* 01:K1, *E. coli* (S2252), *K. oxytoca*, *E. tarda*, *Salmonella typhimurium* (S2136) and *Salmonella arizonae*. Possible synergistic bactericidal interactions (indicated as "additive (+)") were observed against *E. cloacae* (10005), *E. gergoviae* (11434), *P. aeruginosa* (10332) and *P. aeruginosa* (10662). The concurrent administration of gentamicin and $rBPI_{23}$ had only additive, indifferent or indeterminate effects against the other tested gram-negative bacteria.

TABLE 5

MIC Values and Results of Checkerboard Susceptibility Testing With BPI and Gentamicin

| Organism (NCTC) | MIC of Single Agent BPI$_{23}$ (nM) | MIC of Single Agent Gentamicin (μg/ml) | Lowest MIC of the Agents Together rBPI$_{23}$/Gentamicin | Interpretation (Gentamicin) |
|---|---|---|---|---|
| E. coli J5 | 250 | 1.0 | 62.5/0.125 | synergy |
| E. coli 0l:K1 | >2000 | 2.0 | 31/0.5 | synergy |
| E. coli (S2252) NCTC 10418 | 500 | 0.5 | 250/0.25 | additive/synergy |
| E. coli 0111:B4 | >2000 | 1.0 | >2000/1.0 | indifferent |
| E. coli (S2216) | >500 | 1.0 | >500/1.0 | indifferent |
| E. coli H262 | >500 | — | — | indifferent |
| E. dispar (S2162) | >500 | — | — | indifferent |
| E. alcalescens (S2196) | >2000 | — | — | indifferent |
| K. oxytoca | >2000 | 1.0 | 1000/0.25 | synergy |
| K. pneumoniae | >2000 | 0.5 | >2000/0.5 | indifferent |
| E. cloacae (10005) | >2000 | 1.0 | 1000/0.5 | additive (+) |
| E. gergoviae (11434) | >2000 | 2.0 | 2000/0.5 | additive (+) |
| S. marcescens (10211) | >2000 | 4.0 | >2000/4.0 | indifferent |
| P. rettgeri (S2253) | >500 | 2.0 | 1000/1.0 | indifferent |
| P. vulgaris (4175) | 500 | 0.25 | 250/0.125 | additive |
| P. morganii (S2161) | >2000 | 2.0 | 2000/2.0 | indifferent |
| P. aeruginosa (10332) | >2000 | 0.5 | 31/0.25 | additive (+) |
| P. aeruginosa (840P) | >2000 | 1.0 | >2000/1.0 | indifferent |
| P. aeruginosa (10662) | >2000 | 0.25 | 2000/0.125 | additive (+) |
| P. aeruginosa (U600) | >2000 | 0.5 | 62.5/0.25 | indifferent |
| K. aerogenes NCTC 9496 | >2000 | 1.0 | 2000/0.5 | indifferent |
| Shigella dysenteriae NCTC 4837 | >2000 | 1.0 | >2000/1.0 | indifferent |
| E. tarda | 500 | 1.0 | 31/0.125 | synergy |
| K. rhinoscleromatis | >500 | 1.0 | >500/1.0 | indifferent |
| Salmonella choleresuis | >2000 | — | — | indifferent |
| Salmonella typhimurium (S2185) | >500 | 0.25 | >500/0.25 | indifferent |
| Salmonella typhimurium (S2136) | >2000 | >4.0 | 31/4.0 | synergy |
| Salmonella arizonae | >500 | 1.0 | — | synergy |
| E. aerogenes (S2164) | >2000 | 1.0 | 62.5/1.0 | indifferent |
| C. freundi | >2000 | — | — | indifferent |

(+) possibility of synergy but FIC incalculable because rBPI$_{23}$ MIC outside tested concentration range.

EXAMPLE 3

SYNERGISTIC BACTERICIDAL EFFECTS OF POLYMYXIN B AND BPI: ADMINISTRATION TO E. COLI J5 AND E. COLI 0111: B4 GRAM-NEGATIVE ORGANISMS

In this example, micro dilution plate MIC assays were conducted according to the method of Example 1 to determine the sensitivity of E. coli J5 and E. coli 0111:B4 to the cytotoxic effects of BPI protein products concurrently administered with the antibiotic polymyxin B. Polymyxin B solution with an activity of 10240 units/mL was prepared by preparing a solution of 1.595 mg of polymyxin B sulfate stock powder per mL, and diluting it in sterile water for injection as 20 μg in 12.54 mL.

A positive synergistic interaction was demonstrated between rBPI$_{23}$ and polymyxin B using E. coli 0111:B4 (see Tables 8 and 9) but the administration of polymyxin B with BPI did not have synergistic bactericidal effects with BPI when applied to E. coli J5 as illustrated by the results shown in Tables 6 and 7.

TABLE 6

Visible Growth (bold line) of E. coli J5 and ODs (580 nm) Polymyxin B (μg/ml)

| BPI (nM): | Gentamicin (μg per ml) | | | | | | | | |
|---|---|---|---|---|---|---|---|---|---|
| | 5 | 2.5 | 1.25 | .6 | .3 | .15 | .075 | .075 | 0 |
| 2000 | .071 | .006 | .001 | .001 | .002 | .001 | .011 | .002 | .006 |
| 1000 | .069 | .003 | .002 | .004 | .003 | .001 | .001 | .009 | .007 |
| 500 | .055 | .000 | .018 | .001 | .001 | .007 | .012 | .012 | .006 |
| 250 | .049 | .000 | .001 | .001 | .012 | .026 | .025 | .013 | .006 |
| 125 | .047 | .002 | .095 | .123 | .114 | .107 | .130 | .093 | .157 |
| 62.5 | .047 | .002 | .047 | .131 | .144 | .164 | .141 | .124 | .185 |
| 31 | .044 | .001 | .094 | .160 | .163 | .184 | .183 | .168 | .238 |
| 0 | .046 | .002 | .128 | .230 | .254 | .282 | .270 | .245 | .307 |

TABLE 7

Visible Growth (bold line) of *E. coli* and Viable Counts Polymyxin B (μg/ml)

| BPI (nM): | Gentamicin (μg per ml) | | | | | | | | |
|---|---|---|---|---|---|---|---|---|---|
| | 5 | 2.5 | 1.25 | .6 | .3 | .15 | .075 | .075 | 0 |
| 2000 | NC | NC | 0 | 0 | 0 | 0 | 0 | 0 | 0 |
| 1000 | NC | NC | 0 | 5 | 1 | 0 | 0 | 0 | 0 |
| 500 | NC | NC | 12 | 15 | ++ | ++ | 264 | 379 | 0 |
| 250 | NC | 81 | ++ | ++ | +++ | +++ | +++ | +++ | 496 |
| 125 | 0 | 0 | NC | NC | NC | NC | NC | NC | NC |
| 62.5 | 0 | 0 | NC | NC | NC | NC | NC | NC | NC |
| 31 | 0 | 0 | NC | NC | NC | NC | NC | NC | NC |
| 0 | 0 | 0 | NC | NC | NC | NC | NC | NC | NC |

Counts expressed as counts per ml, NC = not counted, ++ = too numerous to count.

TABLE 8

Visible Growth (bold line) of *E. coli* 0111:B4 and ODS (580 nM)

| BPI (nM): | Polymyxin B (μg/ml) | | | | | | | | |
|---|---|---|---|---|---|---|---|---|---|
| | 10 | 5 | 2.5 | 1.25 | .6 | .3 | .15 | .075 | 0 |
| 2000 | 0 | .015 | .009 | .01 | .011 | .011 | .295 | .379 | .360 |
| 1000 | 0 | .003 | .035 | .109 | .148 | .217 | .261 | .305 | .286 |
| 500 | 0 | .006 | .008 | .145 | .166 | .280 | .238 | .292 | .282 |
| 250 | 0 | .006 | .012 | .146 | .216 | .265 | .254 | .294 | .260 |
| 125 | 0 | .016 | .101 | .193 | .228 | .269 | .233 | .298 | .269 |
| 62.5 | 0 | .050 | .012 | .212 | .201 | .277 | .246 | .288 | .281 |
| 31 | 0 | .002 | .054 | .245 | .223 | .260 | .234 | .291 | .271 |
| 0 | 0 | .001 | .144 | .267 | .265 | .295 | .272 | .309 | .290 |

TABLE 9

Visible Growth (bold line) of *E. coli* 0111:B4 and Viable Counts

| BPI (nM): | Polymyxin B (μg/ml) | | | | | | | | |
|---|---|---|---|---|---|---|---|---|---|
| | 10 | 5 | 2.5 | 1.25 | .6 | .3 | .15 | .075 | 0 |
| 2000 | NC | 0 | 0 | 0 | 0 | 1 | +++ | NC | NC |
| 1000 | 0 | 0 | NC | ++ | +++ | +++ | NC | NC | NC |
| 500 | 0 | 0 | 0 | +++ | NC | NC | NC | NC | NC |
| 250 | 0 | 0 | 89 | +++ | NC | NC | NC | NC | NC |
| 125 | 0 | 7 | +++ | +++ | NC | NC | NC | NC | NC |
| 62.5 | 0 | 80 | 5 | +++ | NC | NC | NC | NC | NC |
| 31 | 0 | 0 | +++ | NC | NC | NC | NC | NC | NC |
| 0 | 0 | 0 | +++ | NC | NC | NC | NC | NC | NC |

Counts expressed as counts per ml, NC = not counted, ++ = too numerous to count.

EXAMPLE 4

SYNERGISTIC BACTERICIDAL EFFECTS OF POLYMYXIN B AND BPI: ADMINISTRATION TO ADDITIONAL GRAM-NEGATIVE ORGANISMS

In this example, micro dilution MIC assays were conducted according to the method of Example 1 to determine the sensitivity of a variety of gram-negative organisms to the cytotoxic effects of BPI protein products concurrently administered with polymyxin B antibiotic. The results of those assays are shown in Table 10 below.

These assay results show additive or synergistic effects with the use of polymyxin B at concentrations of 0.3 μg/mL, a level of which is 10–20 times lower than when that antibiotic is used conventionally.

TABLE 10

MIC Values and Results of Checkerboard Susceptibility Testing With BPI and Polymyxin B (PB)

| Organism (NCTC) | MIC of Single Agent $BPI_{23}$ (nM) | MIC of Single Agent PB (μg/ml) | Lowest MIC of the Agents Together $rBPI_{23}$/PB | Interpretation (Polymyxin B) |
|---|---|---|---|---|
| *E. coli* J5 | 250 | 2.5 | 250/2.5 | indifferent |
| *E. coli* (S2252) NCTC 10418 | 500 | 5.0 | 250/2.5 | indifferent |
| *E. coli* 0111:B4 | >2000 | 5.0 | 250/2.5 | synergy |
| *E. cloacae* (10005) | >500 | 0.5 | 500/0.5 | indifferent |
| *E. gergoviae* (11434) | >2000 | 5.0 | 125/2.5 | additive (+) |
| *S. marcescens* (10211) | >2000 | >10.0 | >2000/10.0 | indifferent |
| *P. rettgeri* (S2253) | >2000 | 2.5 | 125/1.25 | synergy |
| *P. aeruginosa* (10332) | >2000 | 1.25 | 250/0.6 | synergy |
| *P. aeruginosa* (840P) | >2000 | 1.25 | 1000/0.6 | synergy |
| *P. aeruginosa* (10662) | >2000 | 1.25 | 125/0.6 | synergy |
| *P. aeruginosa* (U600) | >2000 | 1.25 | 2000/0.3 | synergy |
| *E. aerogenes* (S2164) | >2000 | >10.0 | >2000/10.0 | indifferent |

EXAMPLE 5

SYNERGISTIC EFFECTS OF CEFAMANDOLE AND BPI PROTEIN PRODUCT IN VIVO IN MICE CHALLENGED INTRAPERITONEALLY WITH LIVE *E. COLI* 0111:B4 BACTERIA: EFFECT ON SURVIVAL

In this example, the protective effect of cefamandole nafate antibiotic (MANDOL®, Lilly) a semisynthetic broad-spectrum cephalosporin antibiotic with and without a BPI protein product was evaluated by means of challenging ICR mice with an $LD_{90-100}$ dose level of live *E. coli* 0111:B4 bacteria, a strain that is not susceptible to the bactericidal/growth inhibitory effects of BPI protein product. Specifically, four groups of 15 ICR mice were treated such that each ICR mouse received an injection of bacteria ($1.8 \times 10^9$ CFU/mouse) intraperitoneally; an intraperitoneal injection of cefamandole nafate (MANDOL®, 100 mg/kg) or saline; and then an intraperitoneal injection of $rBPI_{21}$ (500 μg/mouse) or BPI buffer. Survival of the mice was then evaluated over a period of 7 days with the results illustrated in FIG. 1.

Concurrent administration of BPI protein product with cefamandole, or administration of cefamandole alone, showed significant protection in mice challenged with *E. coli* 0111:B4 when compared to the buffer control ($p \leq 0.001$ and $p \leq 0.05$ respectively). The protective effect of the BPI protein product when administered without cefamandole was not evident. When compared to treatment with cefamandole alone, concurrent administration of BPI protein product with cefamandole showed improved protection at $p \leq 0.1$. These results indicate that the concurrent administration of cefamandole and a BPI protein product has synergistic therapeutic effects against *E. coli* 0111:B4.

EXAMPLE 6

SYNERGISTIC EFFECTS OF CEFAMANDOLE AND BPI PROTEIN PRODUCT IN VIVO IN MICE CHALLENGED INTRAPERITONEALLY WITH LIVE *E. COLI* 0111:B4 BACTERIA: EFFECT ON SURVIVAL AND ON BACTERIAL CLEARANCE FROM BLOOD AND PERITONEAL LAVAGE FLUID

The protective effects of a cephalosporin antibiotic and a BPI protein product were evaluated in mice challenged intraperitoneally with *E. coli* 0111:B4, a strain that is resistant to the bactericidal effects of BPI protein product. The assay was conducted using the following procedure. Male ICR mice (Simonsen Laboratories, Gilroy Calif.), 5–7 weeks old, were housed under controlled climate and dark/light cycles and were allowed free access to food and water. Mice received an intraperitoneal injection of 0.5 ml of bacteria in doses near an $LD_{90}$ ($2 \times 10^9$ CFU/mouse). Immediately after bacterial challenge the animals received an intraperitoneal injection of (1) vehicle only, (2) 500 μg/mouse $rBPI_{21}$ and vehicle, (3) 100 mg/kg cefamandole nafate (Mandol® in phosphate buffered saline; Eli Lilly, Indianapolis, Ind.) and vehicle, or (4) 500 μg $rBPI_{21}$ and 100 mg/kg cefamandole.

Survival of the four groups was monitored for 7 days. Survival data was statistically analyzed using the Chi-square test. In a separate experiment using a bacterial challenge of $2.5 \times 10^9$ CFU *E. coli* 0111:B4, blood and peritoneal lavage fluid were collected for culture at different time points following bacterial challenge. Blood was obtained from the retro-orbital sinus. At least 1 ml of peritoneal lavage fluid was obtained after intraperitoneal injection of 3 ml of phosphate buffered saline. Bacterial counts (expressed as CFU/ml) were determined by inoculating trypticase soy agar plates with 10-fold dilutions of blood or peritoneal lavage samples, incubating the plates overnight at 37° C., and counting the colonies. Statistical comparisons of this data were performed with the analysis of variance.

Figure 2:
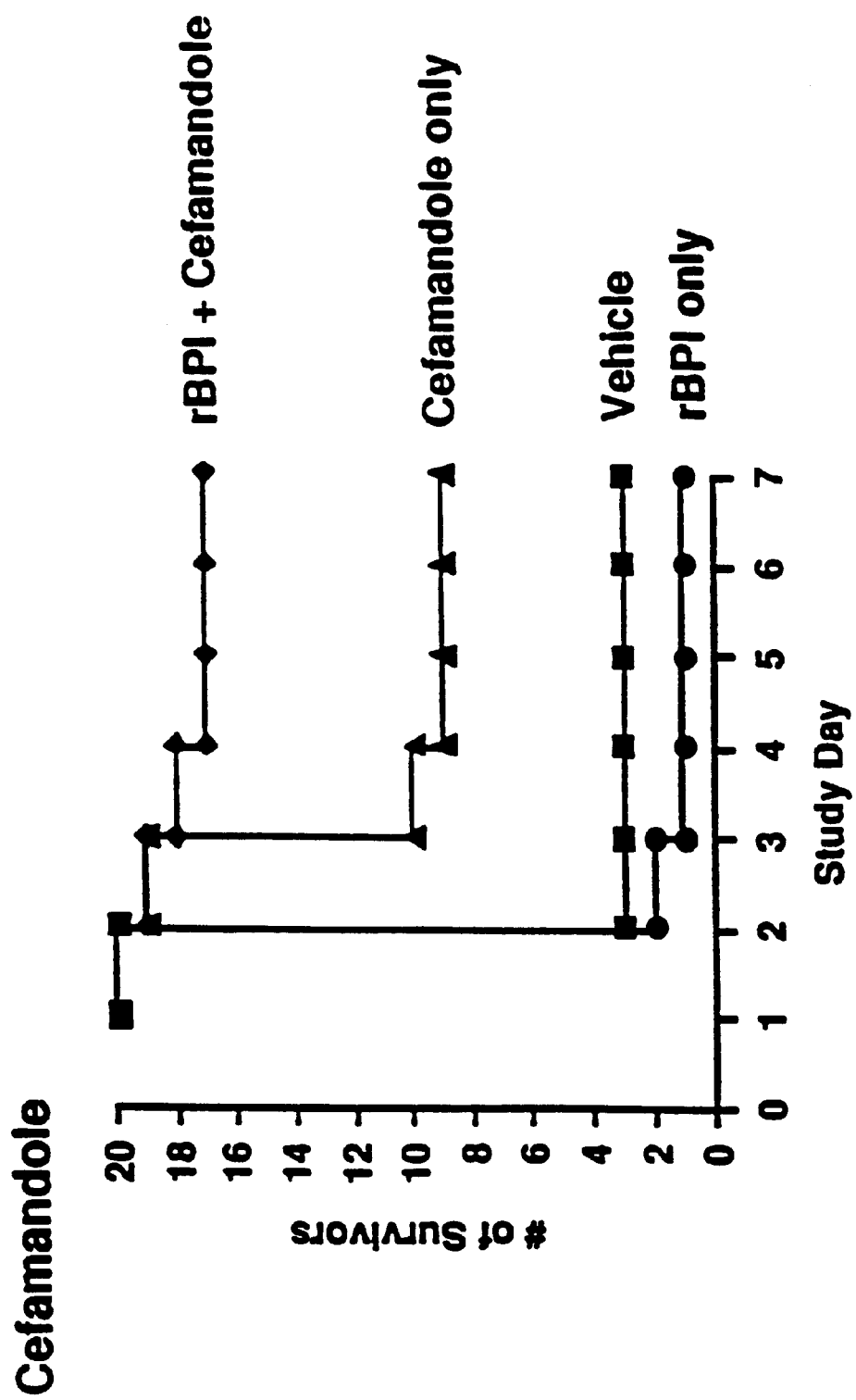
FIGS. 2–4 relate to results from an *E. coli* 0111:B4 mouse peritonitis assay with $rBPI_{21}$ and cefamandole, separately or in combination.
Figure 4:
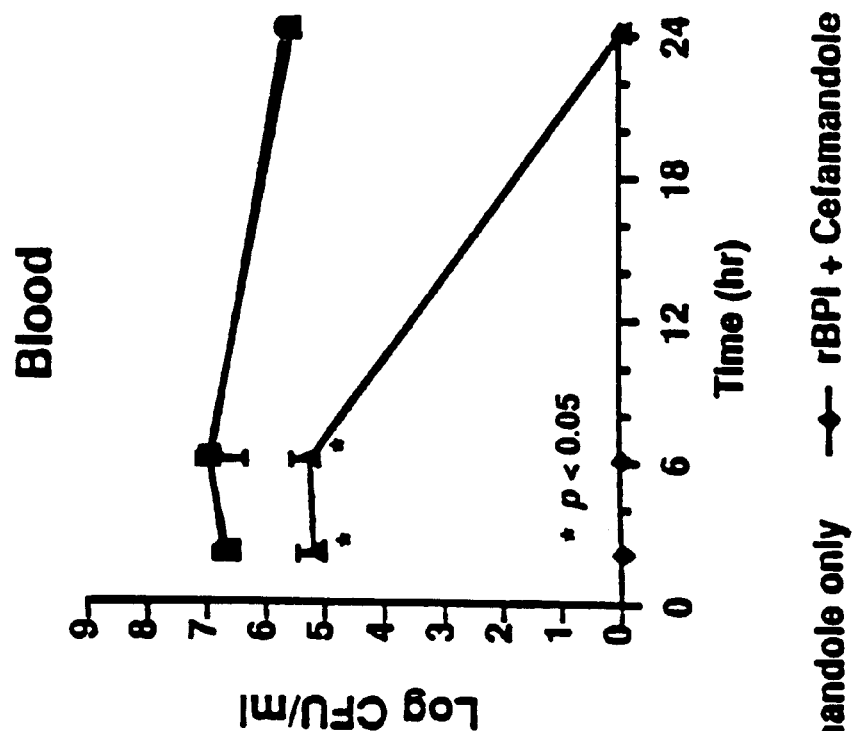
Figure 3:
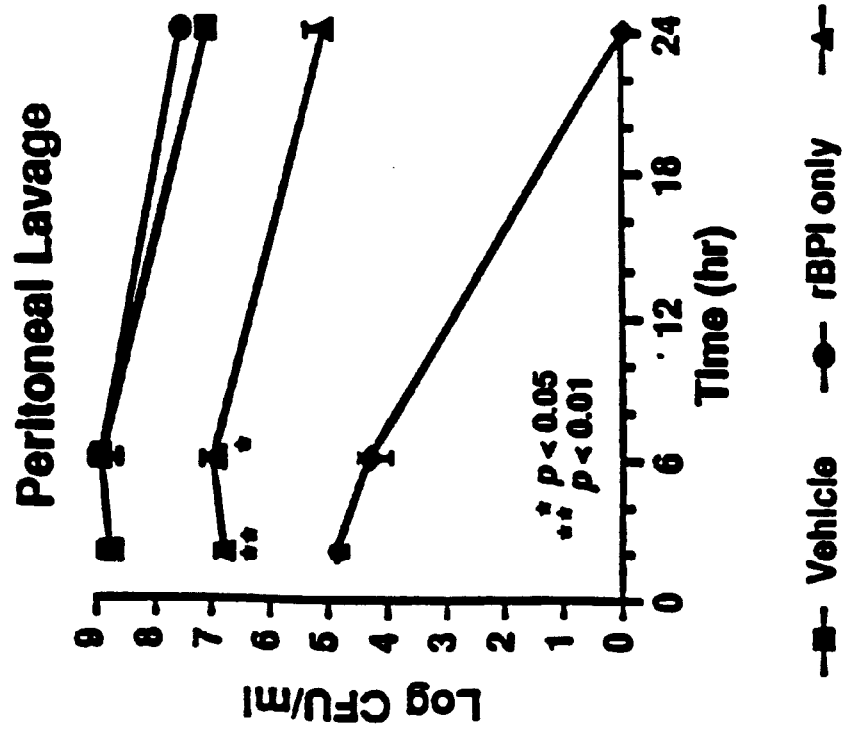

FIG. 2 shows effects on survival of cefamandole (100 mg/kg), $rBPI_{21}$ (500 μg) or the concurrent administration of the two agents. The BPI protein product alone had no effect, while cefamandole treatment alone increased survival, although not significantly. In contrast, the concurrent administration of $rBPI_{21}$ with cefamandole resulted in a significant increase in survival ($p<0.05$) above that achieved by either treatment alone. FIGS. 3 and 4 show that $rBPI_{21}$ alone failed to reduce counts in either peritoneal lavage fluid or blood after challenge with bacteria, while cefamandole treatment alone significantly reduced counts in both ($p<0.01$ vs. vehicle). However, the concurrent administration of $rBPI_{21}$ and cefamandole reduced bacterial counts in the peritoneal lavage fluid by more than two orders of magnitude below that achieved by cefamandole alone ($p<0.01$ of concurrent administration vs. cefamandole only) at the 2 and 6 hour time points, and entirely eliminated counts after 24 hours. Blood of mice that received concurrent administration of $rBPI_{21}$ and cefamandole was completely free of bacteria at all time points.

Thus, the concurrent administration of a BPI protein product, $rBPI_{21}$, with a suboptimal dose of a cephalosporin antibiotic, cefamandole, resulted in a superior therapeutic effect. The data indicates that BPI protein products and cephalosporin antibiotics produce a synergistic therapeutic effect. Since cefamandole alone reduced counts by approximately two orders of magnitude compared to vehicle-treated animals, another experiment was conducted to determine if $rBPI_{21}$ alone reduced bacterial counts when the inoculum was reduced to $10^7$ CFU. Data from this experiment showed that $rBPI_{21}$ (500 μg) did not significantly reduce bacterial counts in blood or peritoneal lavage fluid after a challenge of $10^7$ CFU. This suggests that an antibiotic-mediated reduction in the magnitude of the bacterial count cannot, in itself, explain the protection associated with concurrent administration of BPI protein product and antibiotic.

EXAMPLE 7

SYNERGISTIC EFFECTS OF CEFAMANDOLE AND BPI PROTEIN PRODUCT IN VIVO IN MICE CHALLENGED INTRAPERITONEALLY WITH LIVE *E. COLI* 07:K1 BACTERIA: EFFECT ON SURVIVAL

Figure 5A:
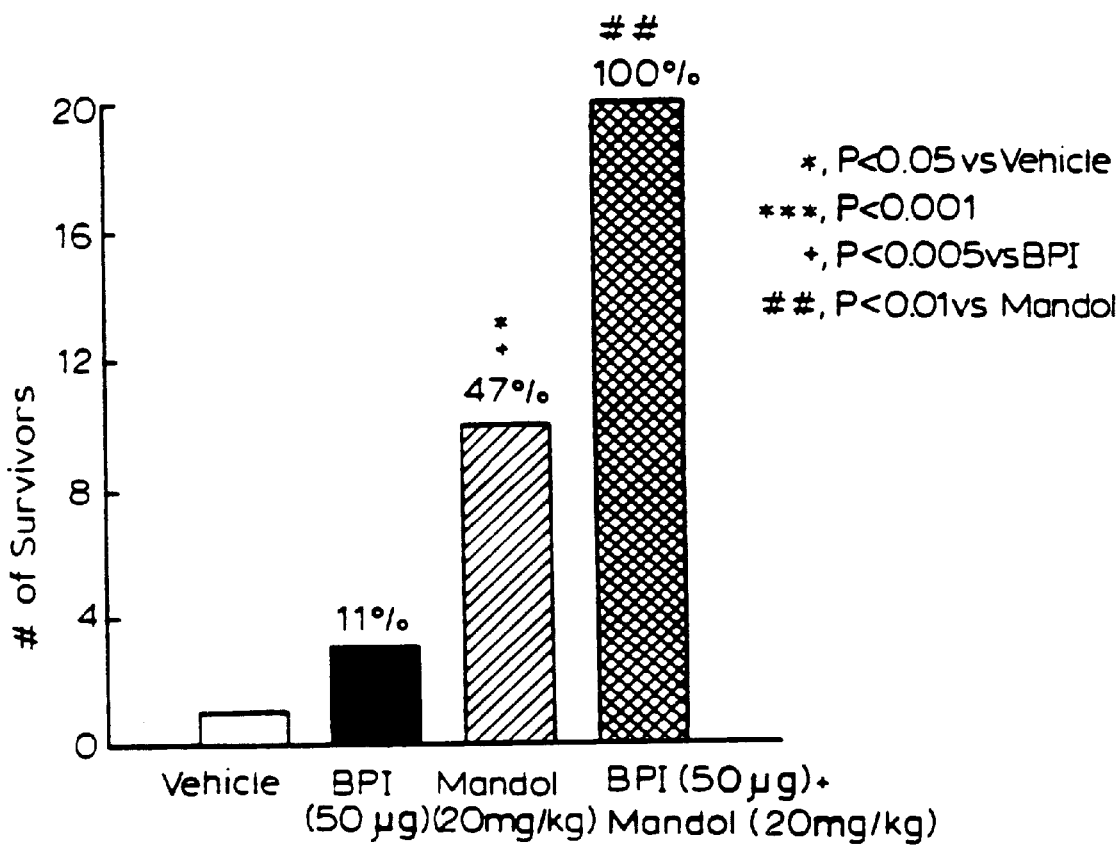
FIGS. 5A and 5B display results from two trials of treatment with $rBPI_{21}$ and cefamandole, separately or in combination, in an *E. coli* 07:K1 mouse peritonitis assay.
Figure 5B:
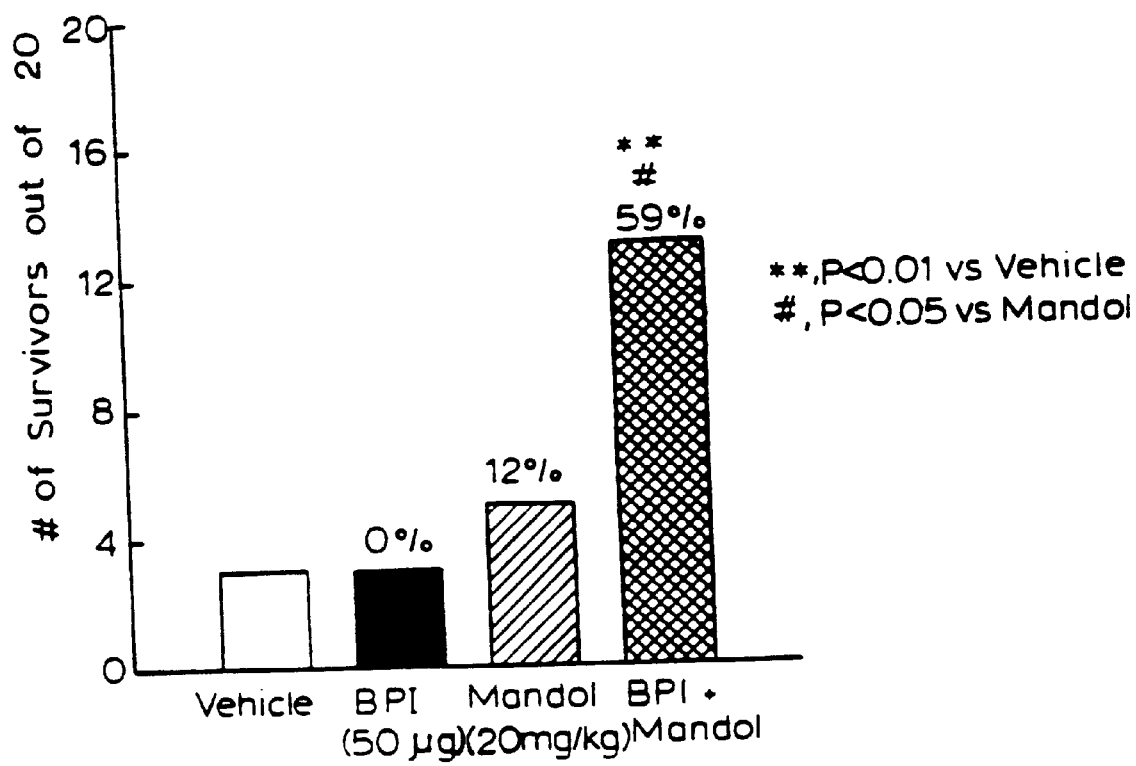

The protective effects of a cephalosporin antibiotic and a BPI protein product were evaluated in mice challenged intraperitoneally with *E. coli* 07: K1 (ATCC Accession No. 23503), a strain that is susceptible to the bactericidal effects of BPI protein product. The general procedure described above in Example 5 was followed. Four groups of 20 mice were challenged intraperitoneally with $2 \times 10^7$ *E. coli* 07: K1 bacteria and then treated with (1) vehicle, (2) 50 μg $rBPI_{21}$ only, (3) 20 mg/kg cefamandole only, or (4) both 50 μg $rBPI_{21}$ and 20 mg/kg cefamandole. Survival of the mice was followed over a period of 7 days; results of two trials are displayed in FIGS. 5A and 5B.

In one trial, $rBPI_{21}$ alone protected 11% of the survivors compared to vehicle controls, cefamandole protected 47% of the survivors compared to vehicle controls (p<0.05 vs. vehicle), and the concurrent administration of $rBPI_{21}$ and cefamandole protected 100% of the survivors compared to vehicle controls (p<0.001 vs. vehicle, p<0.01 vs. cefamandole alone). In the second trial, $rBPI_{21}$ alone protected 0% of the survivors compared to vehicle, cefamandole protected 12% compared to vehicle, and the concurrent administration of $rBPI_{21}$ and cefamandole protected 59% compared to vehicle (p<0.01 vs. vehicle, p<0.05 vs. cefamandole alone). In both trials, the increase in survival associated with the concurrent administration of $rBPI_{21}$ and cefamandole was greater than the sum of the increases in survival due to the individual therapies. Thus, there appears to be synergy (a greater than additive effect) between cefamandole and BPI protein product in this model.

EXAMPLE 8

SYNERGISTIC EFFECTS OF CEFAMANDOLE AND BPI PROTEIN PRODUCT IN VIVO IN RABBITS CHALLENGED INTRAVENOUSLY WITH LIVE E. COLI 07:K1 BACTERIA: EFFECT ON BACTERIAL CLEARANCE AND ON CARDIOVASCULAR, RESPIRATORY AND METABOLIC PARAMETERS

Adult male New Zealand White rabbits (Charles River Laboratories, St. Constant, Canada) weighing between 1.8 and 2.3 kilograms were fasted for 24 hours before the experiment. Each rabbit was anesthetized with an intramuscular injection of 80/4 mg/kg Ketamine/xylazine. The left femoral artery was catheterized for blood pressure determinations and blood sample collection. A catheter was placed adjacent the right atrium via the right jugular vein and a thermistor-tipped catheter was placed in the aortic arch via the right carotid artery. The rabbits were allowed to stabilize for 90–120 minutes following catheterization to normalize hemodynamic and blood gas parameters.

The rabbits were divided into four treatment groups with 4 animals per group: (1) vehicle alone, (2) cefamandole and vehicle, (3) $rBPI_{21}$ and vehicle, and (4) cefamandole and $rBPI_{21}$. The rabbits were administered cefamandole Mandol®; Eli Lilly, Indianapolis, Ind.) or vehicle intravenously 5 minutes before the start of the bacterial infusion (considered to be T=0). At T=0, $2 \times 10^{10}$ CFU/rabbit of E. coli 07:K1 was infused intravenously over 10 minutes into the ear vein. Simultaneously (at T=0), 10 mg/kg $rBPI_{21}$ or vehicle was infused over 10 minutes via the right jugular catheter. After the ten minute infusion, $rBPI_{21}$ was slowly infused at 10 mg/kg/hr for 2 hours (resulting in a total dose of 30 mg/kg $rBPI_{21}$).

Arterial blood samples for determination of bacterial counts and endotoxin levels were collected at the end of the 10 minute bacterial infusion and at 30 minutes, 1, 2, 3 and 4 hours. The whole blood was 10-fold serially diluted in sterile PBS and aliquots were plated onto tryptic soy agar plates, incubated at 37° C. overnight, and the plates were counted for colony forming units (CFU). The results were expressed as CFU/ml blood and percent bacteria dose per ml blood. The remaining portion of the blood was centrifuged, the plasma removed and passed through a 0.2 micron Whatman syringe filter to remove the bacteria. The endotoxin levels were determined using a modified limulus amoebocyte lysate assay (Pyrochrome LAL Assay, Associates of Cape Cod, Woods Hole, Mass.). These results were expressed as ng LPS per ml plasma.

Cardiovascular, respiratory and metabolic parameters were measured every 30 minutes. Mean arterial blood pressure (MABP) and heart rate were monitored continuously throughout the experiments and displayed on a cardiac output computer (Columbus Instruments Cardiomax II) or on a chart recorder. Heart rate was derived from the arterial pressure wave. Cardiac output was determined in duplicate with the thermodilution technique: Changes in blood temperature resulting from injection of 900 μl of room temperature PBS were recorded with the thermistor-tipped catheter in the aortic arch. The cardiac output computer then generated thermodilution curves that were visualized on the chart recorder, and derived cardiac output from the temperature-time curves. Cardiac index (CI) was then calculated as cardiac output per kg body weight. In addition, total peripheral resistance (TPR) was determined by dividing blood pressure by cardiac output.

Blood samples for blood gas determinations were drawn from the femoral artery catheter every 30 minutes throughout the study. Blood gases were measured with a Ciba-Corning Blood Gas System, Model 278 (Ciba-Corning Diagnostics Corp., Medfield, Mass.). The blood gas system directly measures blood pH, partial pressure of $pCO_2$, and partal pressure of $pO_2$. Other parameters including the alveolar-arterial oxygen gradient, arterial oxygen content, estimated oxygen saturation, standard bicarbonate, and in vivo base excess were calculated using the formulas provided by Ciba-Corning Diagnostic Corp. Plasma levels of glucose and lactate were determined using a Glucose/L-lactate Analyzer (2300 STAT, YSI, Yellow Springs, Ohio).

Figure 6:
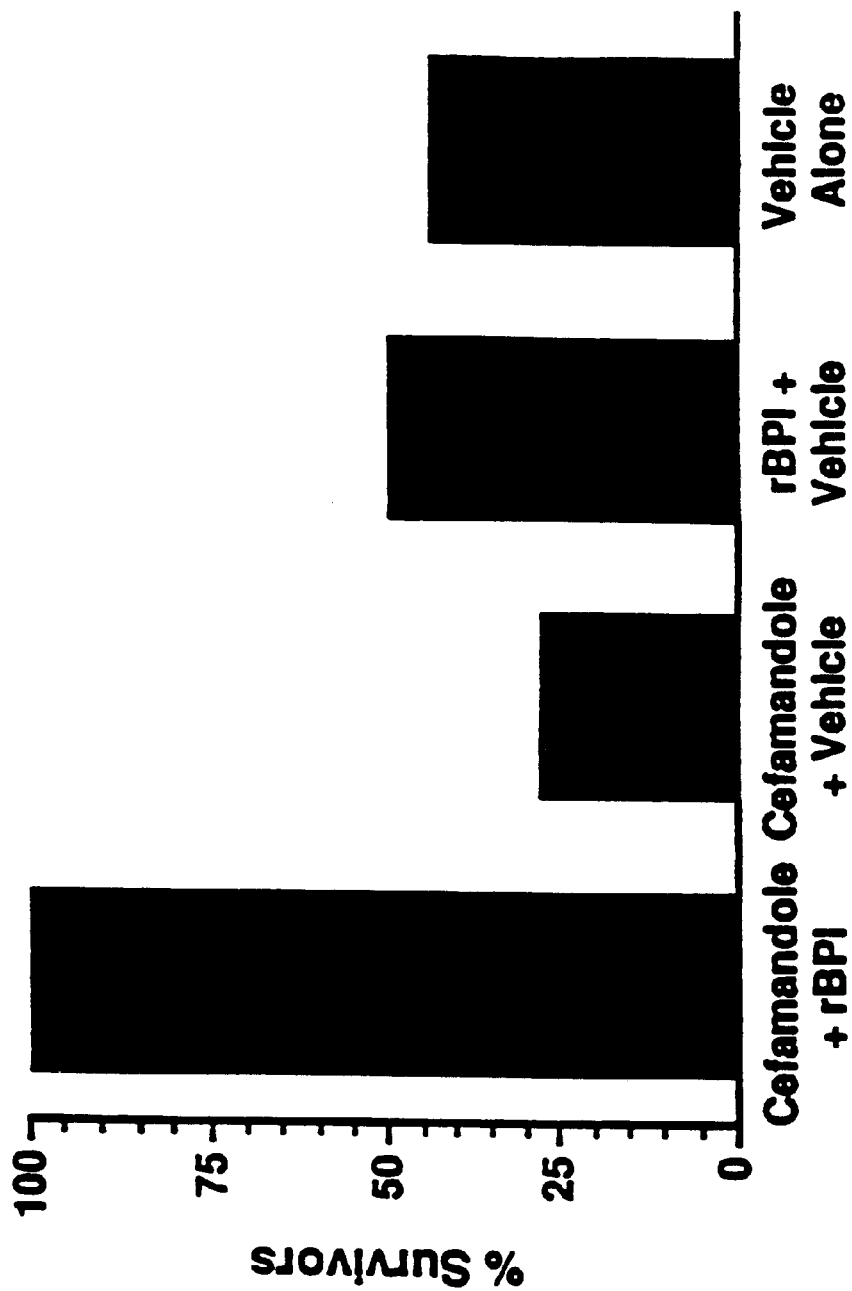
FIGS. 6–16 relate to results, including cardiovascular and metabolic findings, from an *E. coli* 07:K1 rabbit bacteremia assay with $rBPI_{21}$ and cefamandole, separately or in combination.
Figure 7:
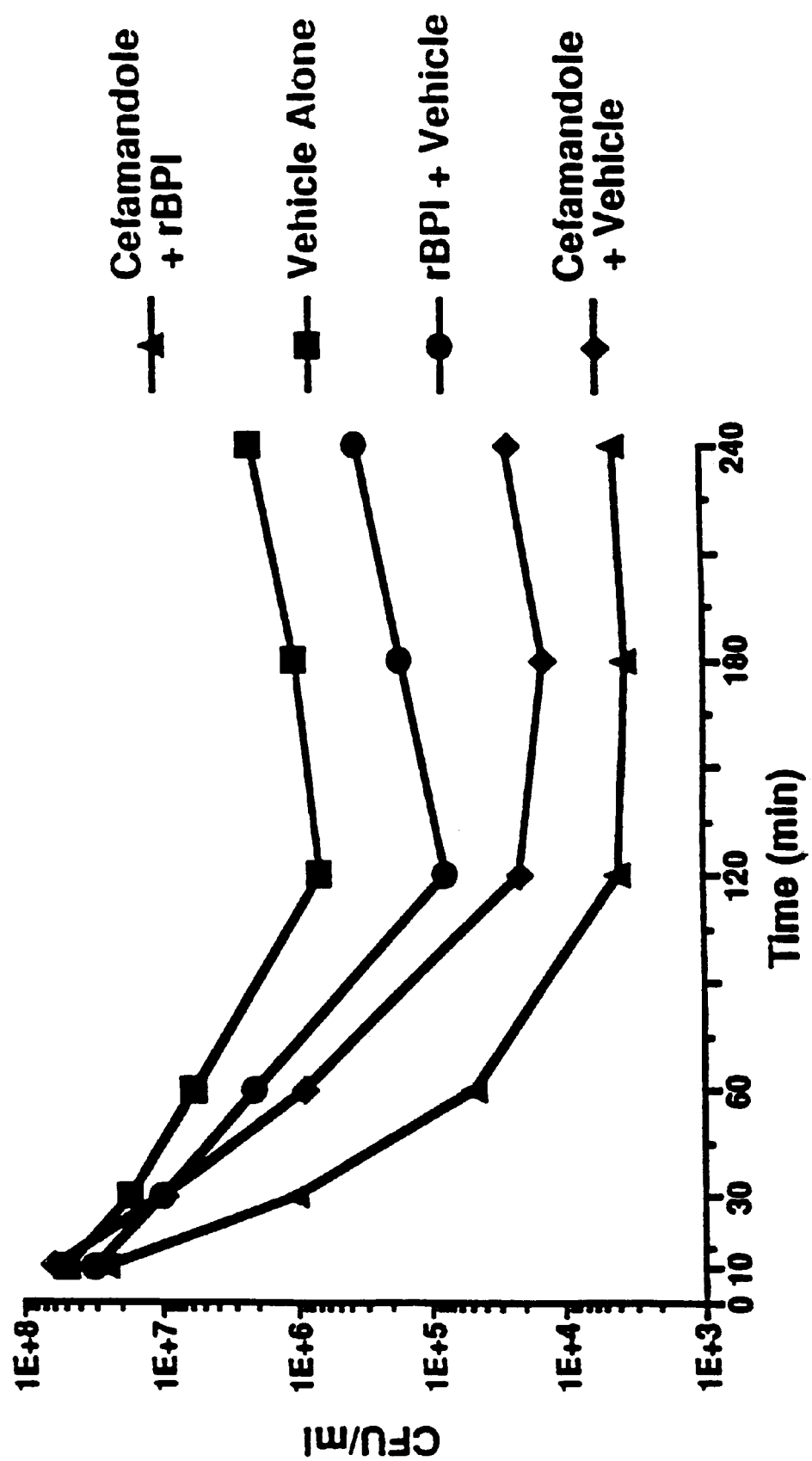
Figure 8:
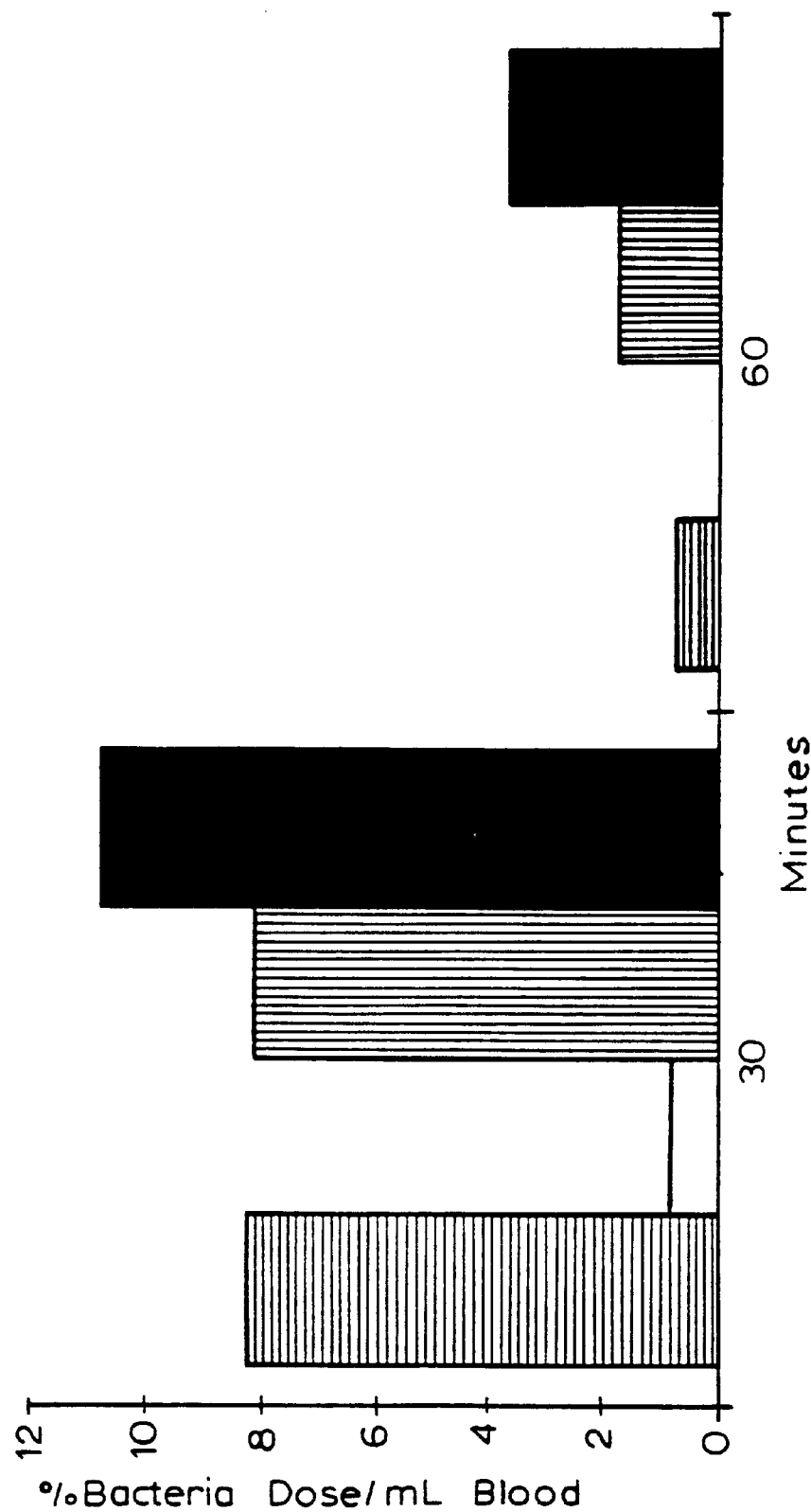

Survival data is shown in FIG. 6. Two of the four animals (50%) treated with vehicle alone died before the end of the experiment. None of the animals concurrently treated with $rBPI_{21}$ and cefamandole died. Bacterial counts in blood, expressed as CFU/ml or percent bacteria dose/ml, are shown in FIGS. 7 and 8, respectively. In FIG. 7, the squares represent treatment with vehicle alone, the diamonds represent cefamandole alone, the circles represent $rBPI_{21}$ alone, and the triangles represent the concurrent administration of $rBPI_{21}$ and cefamandole. In FIG. 8, the bar with horizontal hatching indicates treatment with cefamandole alone, the hollow bar indicates the concurrent administration of $rBPI_{21}$ and cefamandole, the bar with vertical hatching indicates $rBPI_{21}$ alone, and the solid bar indicates buffer alone. The group concurrently treated with $rBPI_{21}$ and cefamandole demonstrated a higher clearance of bacteria compared to the groups treated with either $rBPI_{21}$ alone or cefamandole alone. There appears to be a synergistic effect at 30 and 60 minutes; at 30 minutes, the concurrent administration of $rBPI_{21}$ and cefamandole resulted in a higher percentage clearance of bacteria than the sum of the separate treatments.

Figure 9:
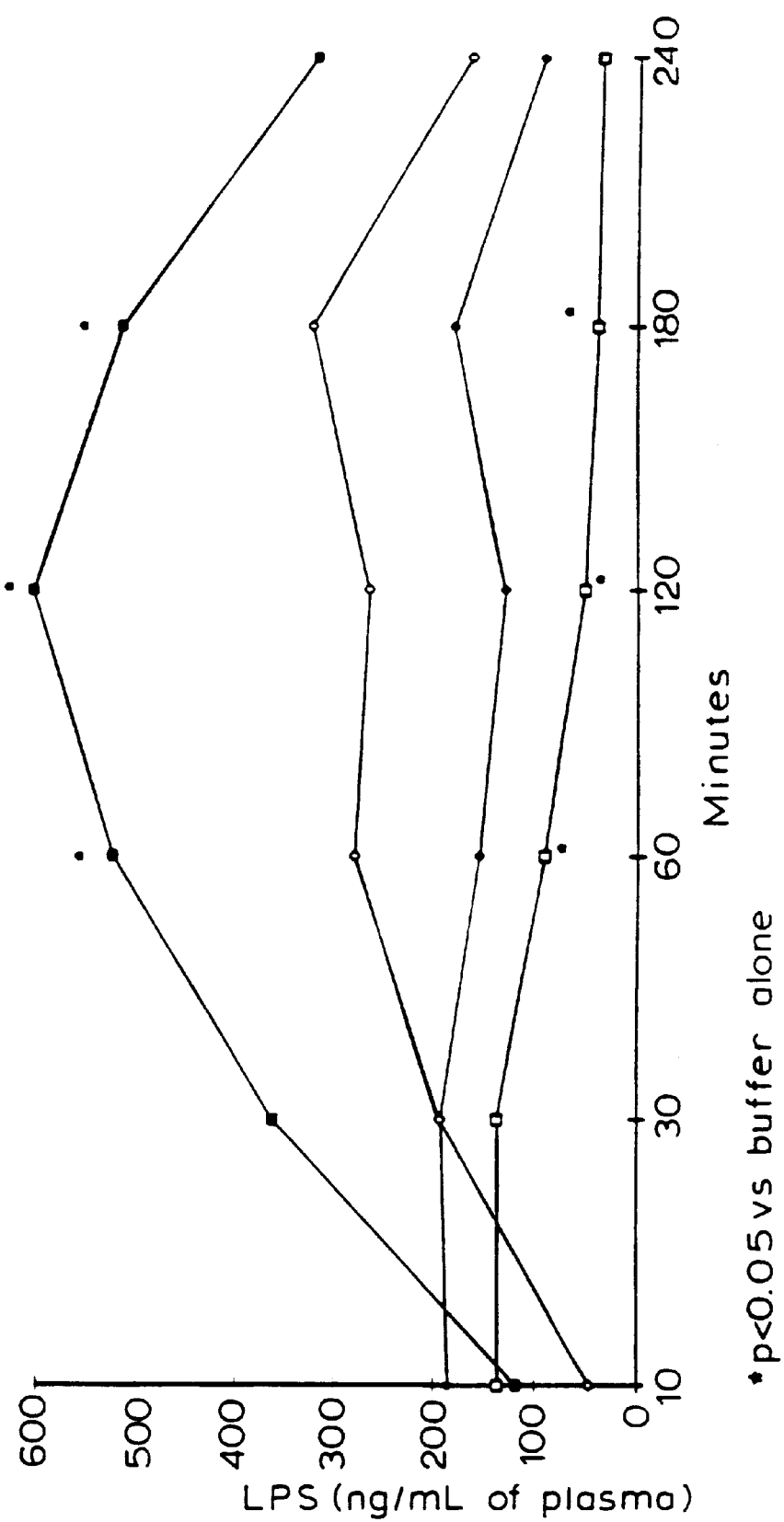
Figure 10:
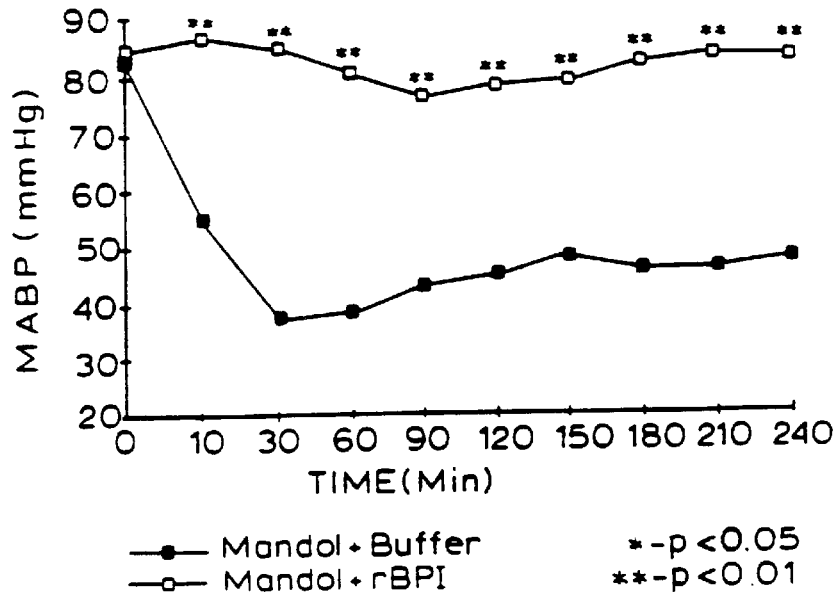
Figure 11:
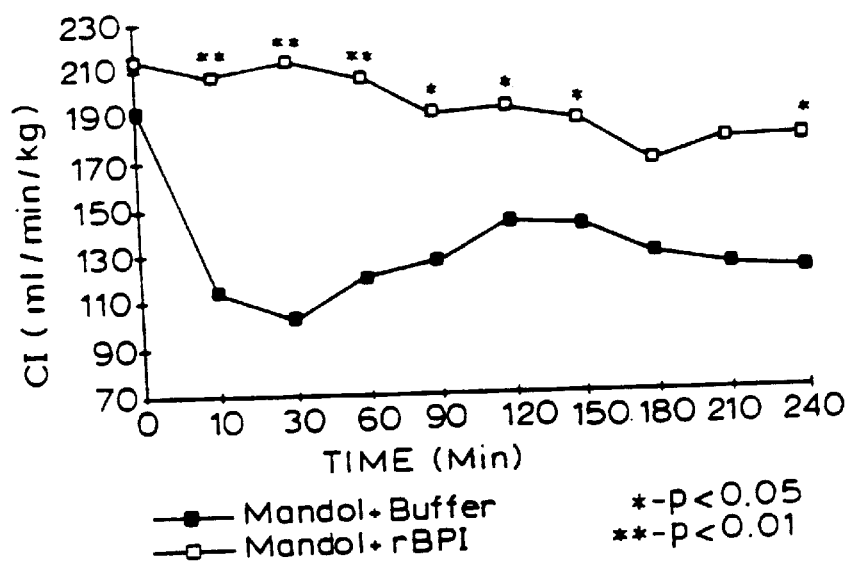
Figure 12:
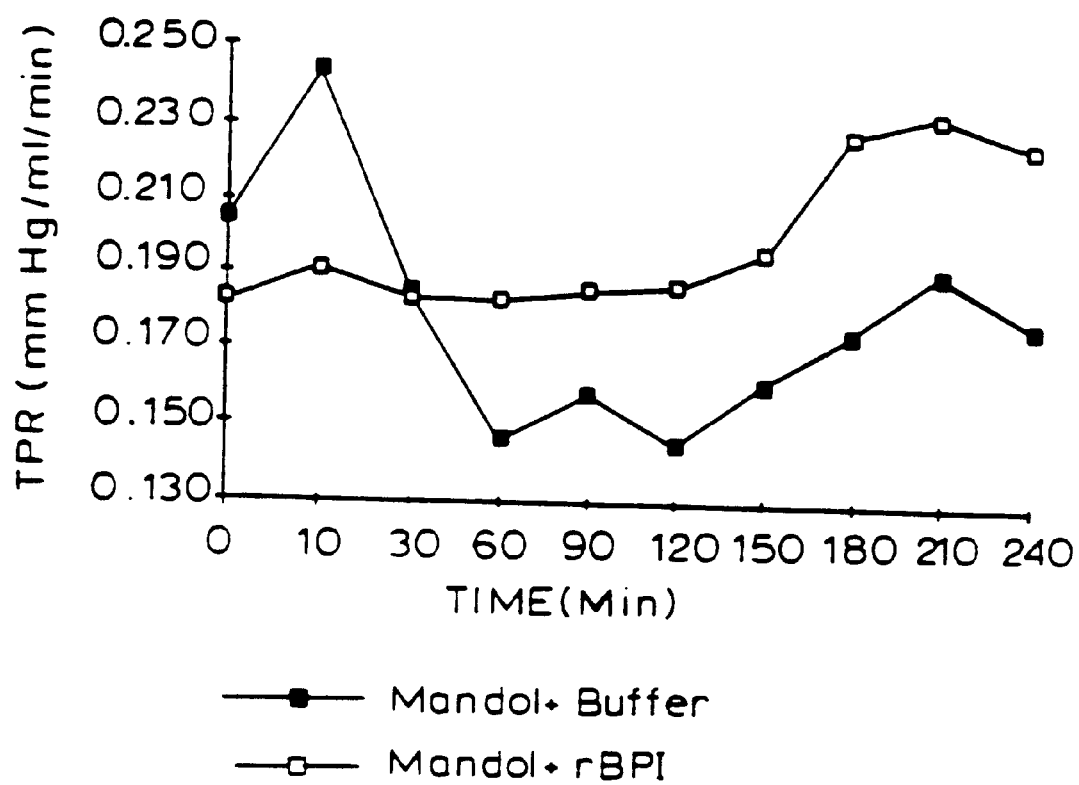
Figure 13:
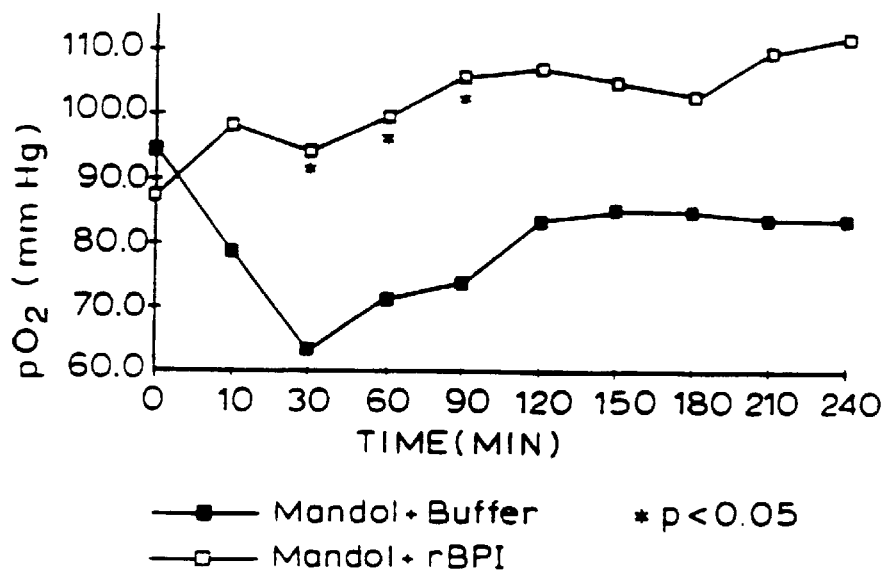
Figure 14:
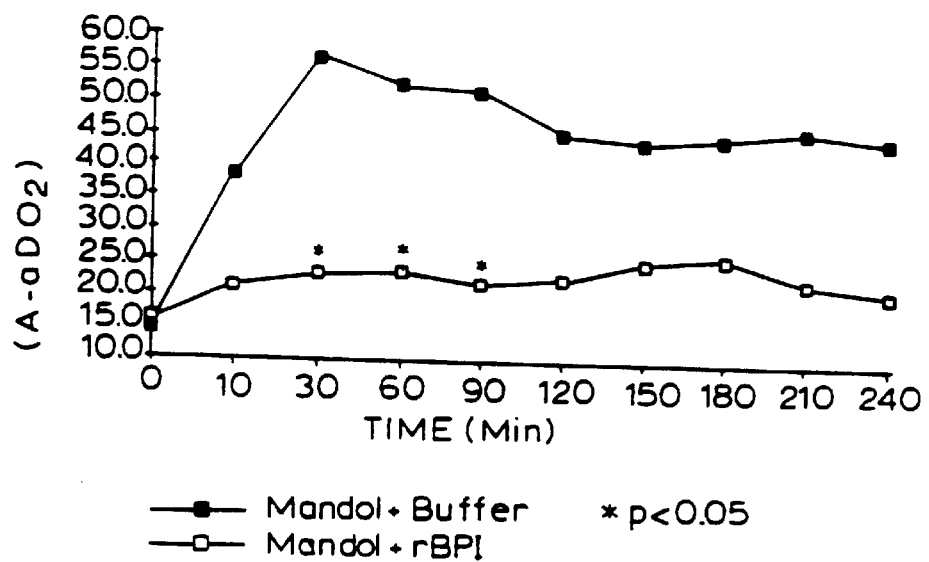
Figure 15:
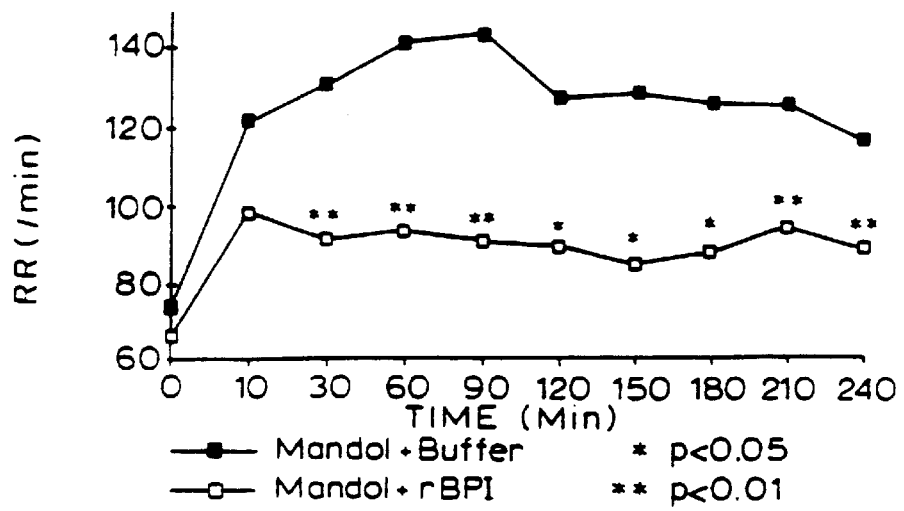
Figure 16:
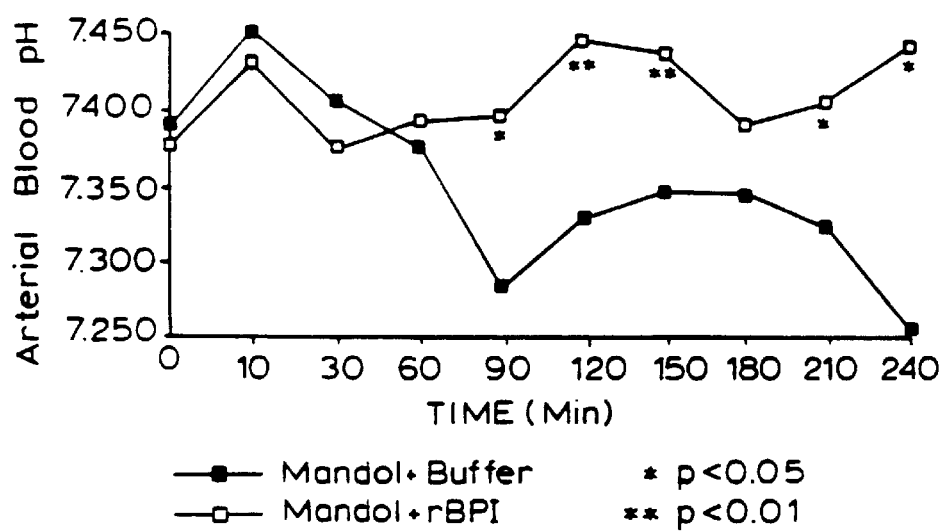

Endotoxin levels are displayed in FIG. 9. The open diamonds indicate treatment with vehicle alone, filled diamonds indicate $rBPI_{21}$ alone, the filled squares indicate cefamandole alone, and the open squares indicate concurrent administration of $rBPI_{21}$ and cefamandole. Animals administered cefamandole alone have a much higher LPS level than animals treated with vehicle alone, due to release of LPS as cefamandole kills bacteria. The concurrent administration of $rBPI_{21}$ and cefamandole produced a dramatic decrease in LPS levels compared to cefamandole therapy alone.

Cardiovascular/pulmonary parameters (MABP, CI, TPR, arterial oxygen tension, alveolar-arterial $O_2$ gradient, respiration rate, and arterial blood pH) are shown in FIGS. 10–16, respectively. These figures only display results for the groups treated with cefamandole alone (indicated by open squares) and concurrent treatment with $rBPI_{21}$ and cefamandole (indicated by filled squares). Single stars indicate that the concurrent administration of both agents provided statistically significant (p<0.05) improvement over antibiotic alone, while two stars indicate p<0.01. Cefamandole alone or rBPI$_{21}$ alone failed to protect the animals; cardiovascular and respiratory dysfunction began during the bacterial infusion and the animals were in circulatory shock by the end of the infusion. Cardiovascular shock lasted for the rest of the experiment. Arterial blood pH began to decrease at 60 minutes in the group treated with cefamandole alone, and was at its lowest level by the end of the experiment. In contrast, concurrent administration of rBPI$_{21}$ and cefamandole preserved cardiopulmonary function and prevented septic shock. Thus, the concurrent administration of BPI protein product with antibiotic protected the animals against the lethal effect of bacteremia and preserved cardiopulmonary function when antibiotic alone failed to do so.

EXAMPLE 9

SYNERGISTIC EFFECTS OF GENTAMICIN AND

BPI PROTEIN PRODUCT IN VIVO IN MICE CHALLENGED INTRAPERITONEALLY WITH LIVE E. COLI 07:K1 BACTERIA: EFFECT ON SURVIVAL

Figure 17:
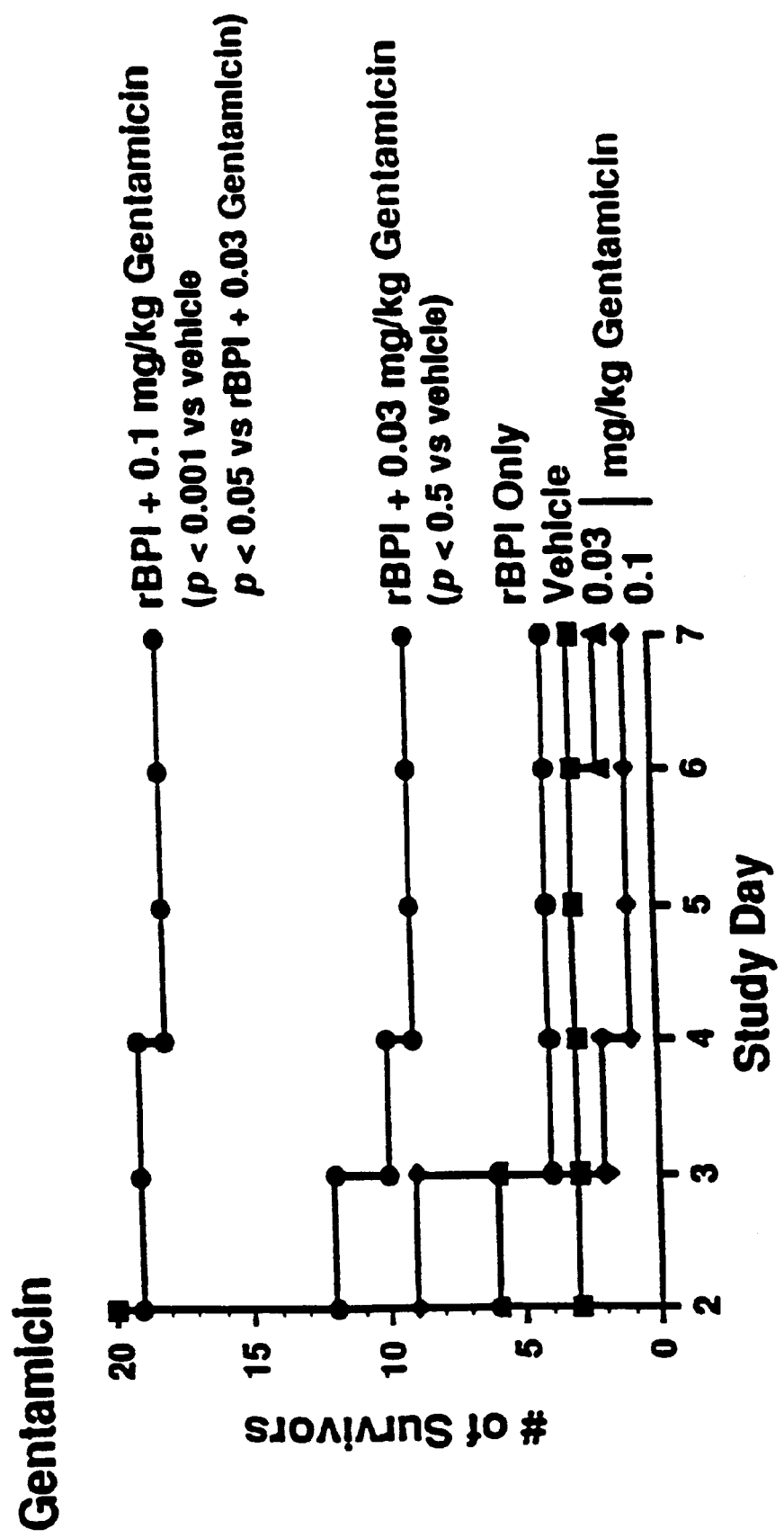
FIG. 17 depicts survival data after treatment with $rBPI_{21}$, and gentamicin, separately or in combination, in an *E. coli* 07:K1 mouse peritonitis assay.

The synergistic effects of an aminoglycoside antibiotic and a BPI protein product were evaluated in mice challenged intraperitoneally with E. coli 07:K1 (ATCC Accession No. 23503), a smooth encapsulated strain that is susceptible to the bactericidal effects of BPI protein product. The general procedure described above in Example 4 was followed. Six groups of 20 mice were challenged intraperitoneally with $2 \times 10^7$ E. coli 07:K1 bacteria and treated immediately with (1) vehicle, (2) 0.03 mg/kg gentamicin, (3) 0.1 mg/kg of gentamicin, (4) 50 µg of rBPI$_{21}$, (5) 0.03 mg/kg gentamicin followed by 50 µg of rBPI$_{21}$, or (6) 0.1 mg/kg of gentamicin followed by 50 µg of rBPI$_{21}$. Survival was followed over 7 days. Results are shown in FIG. 17. Neither antibiotic alone nor rBPI$_{21}$ alone had any effect on mortality other than to slightly retard the death rate. However, the concurrent administration of rBPI$_{21}$ with low-dose gentamicin significantly increased survival (p<0.5 vs. vehicle). Concurrent administration of rBPI$_{21}$ with high-dose gentamicin dramatically increased survival (p<0.001 vs. vehicle, and p<0.05 vs. 0.03 mg/kg gentamicin with rBPI$_{21}$), protecting all but two of the mice from the lethal effects of bacterial challenge. The results clearly indicate synergism between gentamicin and BPI protein product. The greater synergistic effect of the concurrent administration of BPI protein product with gentamicin, compared to the effect of the concurrent administration of BPI protein product with cefamandole, may be related to the fact that aminoglycosides, which inhibit protein synthesis, have a different mechanism of action than BPI protein product.

EXAMPLE 10

EFFECT OF BPI PROTEIN PRODUCT IN VITRO ON ANTIBIOTIC SUSCEPTIBILITY OF CEFTRIAXONE-RESISTANT GRAM-NEGATIVE ORGANISMS

The ability of BPI protein product, BPI$_{21}$, to reverse the resistance of a variety of gram-negative organisms to ceftriaxone (Roche Laboratories) was evaluated in vitro.

The strain of gram-negative bacteria to be tested was grown overnight at 37° C. on Trypticase soy agar (TSA) plates. Colonies from the plate were then inoculated into nutrient broth (or triethanolamine-buffered minimal salts medium), grown overnight to stationary growth phase, diluted 1:10 in fresh medium, and grown to mid-late logarithmic growth phase (3 to 4 hours at 37° C.) to an approximate concentration of 6 to $10 \times 10^8$ organisms/mL. Organism counts were performed by making serial dilutions, plating in triplicate on TSA plates, incubating at 37° C. overnight, and counting colonies by visual inspection. Following development of a standard curve, counts were made by measuring OD$_{540}$ and confirming by plating. The bacteria were sedimented by centrifugation at 6,000 g for 10 min. and resuspended in sterile saline to the desired concentration.

Ceftriaxone solutions were prepared from standard powder (Roche Laboratories). Solutions of BPI protein product were prepared from rBPI$_{21}$, Hanks solution, vitamin-free casamino acid, and TRIS-HCl buffer, pH 7.0. Broth MIC studies were performed as follows: U-bottom, disposable, microtiter array plates (Dynatech) containing 100 µL/well of broth and serial dilutions of 1:1 proportion rBPI$_{21}$ and ceftriaxone were prepared using a multichannel pipetting instrument, inoculated with organisms diluted to approximately $2.5 \times 10^5$ CFU/ml, and incubated overnight at 37° C. Media controls containing no organism and growth controls containing organisms but no ceftriaxone or rBPI$_{21}$ were also prepared. The MIC was determined as the lowest drug concentration (µg/mL) that inhibited bacterial growth. Agar MIC studies were performed as follows: The organism was grown in Mueller-Hinton broth (Difco Laboratories) overnight at 37° C., transferred and grown to logarithmic phase, counted by optical densitometry, diluted with buffer and rBPI$_{21}$ and ceftriaxone, and incubated for 30 minutes at 37° C. After the 30 minutes of incubation, samples were serially diluted in sterile saline and plated onto TSA agar for bacterial counts after overnight incubation at 37° C.

A variety of different bacterial species were tested, including Pseudomonas, Enterobacter, Citrobacter, Klebsiella, and Escherichia species. A summary of the results is displayed in Table 11 below, which reports the minimum inhibitory concentration (MIC) of BPI protein product alone, the MIC of ceftriaxone alone, and the MIC of both agents together (in a fixed 1:1 proportion of rBPI$_{21}$ and ceftiaxone). The experiments were replicated, and each number given in the table represents the highest, or worst-case, MIC for the group.

TABLE 11

Synergistic Effect of rBPI$_{21}$ and Ceftriaxone on Ceftriaxone-Resistant Organisms

| Organism | MIC of BPI alone (µg/mL) | MIC of Ceftriaxone alone (µg/mL) | MIC of BPI + Ceftriaxone (µg/mL) |
|---|---|---|---|
| PA 589 | 64 | >64 | 4 |
| PA 631 | >64 | >64 | 4 |
| PA 672 | 32 | 32 | 2 |
| PA 677 | >64 | >64 | 4 |
| EA 658 | >64 | >64 | 4 |
| CF 595 | 4 | >64 | 1 |
| CF 596 | 4 | >64 | 1 |
| CF 597 | >64 | >64 | 8 |
| CF 598 | 8 | 32 | 2 |
| CF 642 | 4 | 16 | 8 |
| CF 661 | 32 | 16 | 1 |
| KP 601 | 64 | >64 | 8 |
| EC 004 | >64 | >64 | <0.1 |
| EC 600 | >64 | 32 | 8 |
| EC 664 | 64 | >64 | 32 |
| ECL 03 | 16 | >64 | 16 |
| ECL 05 | 16 | >64 | 16 |

TABLE 11-continued

Synergistic Effect of rBPI$_{21}$ and Ceftriaxone on Ceftriaxone-Resistant Organisms

| Organism | MIC of BPI alone (μg/mL) | MIC of Ceftriaxone alone (μg/mL) | MIC of BPI + Ceftriaxone (μg/mL) |
|---|---|---|---|
| ECL 07 | >64 | 64 | 16 |
| ECL 13 | >64 | >64 | 16 |
| ECL 14 | 16 | >64 | 32 |
| ECL 15 | >64 | >64 | 32 |
| ECL 19 | >64 | >64 | 32 |
| PA 001 | >64 | >64 | 8 |
| PA 003 | >64 | >64 | 8 |
| PA 004 | >64 | 64 | 16 |
| PA 005 | >64 | >64 | 64 |
| PA 012 | >64 | >64 | 16 |
| PA 014 | >64 | >64 | 8 |
| PA 017 | >64 | >64 | 32 |
| PA 023 | >64 | >64 | 32 |
| PA 026 | 64 | 64 | 8 |
| PA 027 | 64 | 64 | 8 |
| PA 028 | >64 | >64 | 16 |

PA = *Pseudomonas aeruginosa*
EA = *Enterobacter aerogenes*
CF = *Citrobacter freundii*
KP = *Klebsiella pneumoniae*
EC = *Escherichia coli*
ECL = *Enterobacter cloacae*

Checkerboard synergy studies on selected strains were performed as follows. Microplates were prepared using the following organization: Column 1, control organisms (growth control); Columns 2 through 9, serial dilutions of ceftriaxone; Column 10, ceftriaxone alone; Column 11, rBPI$_{21}$ alone; Column 12, control media; Rows 1 through 8, serial dilutions of rBPI$_{21}$. Columns 2 through 9 thus contained a serial array of various proportions of ceftriaxone and BPI concentrations. All wells, except the media control, were inoculated with suspended organisms and incubated overnight at 37° C. Turbidity was recorded at 24 and 48 hours.

Results of a representative synergy study of the effects of the concurrent administration of rBPI$_{21}$ and ceftriaxone on ceftriaxone-resistant *E. coli* are shown in the checkerboard in Table 12 below. In this checkerboard assay, rBPI$_{21}$ and ceftriaxone were each serially diluted to concentrations ranging from 100 μg/ml to 0.8 μg/ml. These results show that the concurrent administration of both agents is synergistic. There was uniform growth in all growth control wells (containing bacteria, no rBPI$_{21}$ and no antibiotic), while there was no growth in the media control wells (containing no bacteria). There was uniform growth in all ceftriaxone control wells (bacteria with ceftriaxone alone). In the BPI control wells (bacteria with rBPI$_{21}$ alone) there was growth in the wells with a concentration of 6.2 μg/ml rBPI$_{21}$ or less, and no growth at higher concentrations of BPI protein product.

Survival (or kill) curve studies were performed as follows. Tubes containing (1) media alone, (2) media plus ceftriaxone, (3) media plus rBPI$_{21}$, and (4) media plus ceftriaxone and rBPI$_{21}$, were prepared, inoculated with the desired organism, and incubated as described above. At 0, 1, 2, 4, 8 and 24 hours, diluted aliquots from each tube were plated, incubated and counted as described above. Growth curves over 24 hours (plots of log$_{10}$ CFU/mL versus time) were constructed to demonstrate the dynamics of antibiotic-BPI protein product interactions on bacterial growth and survival.

Figure 18:
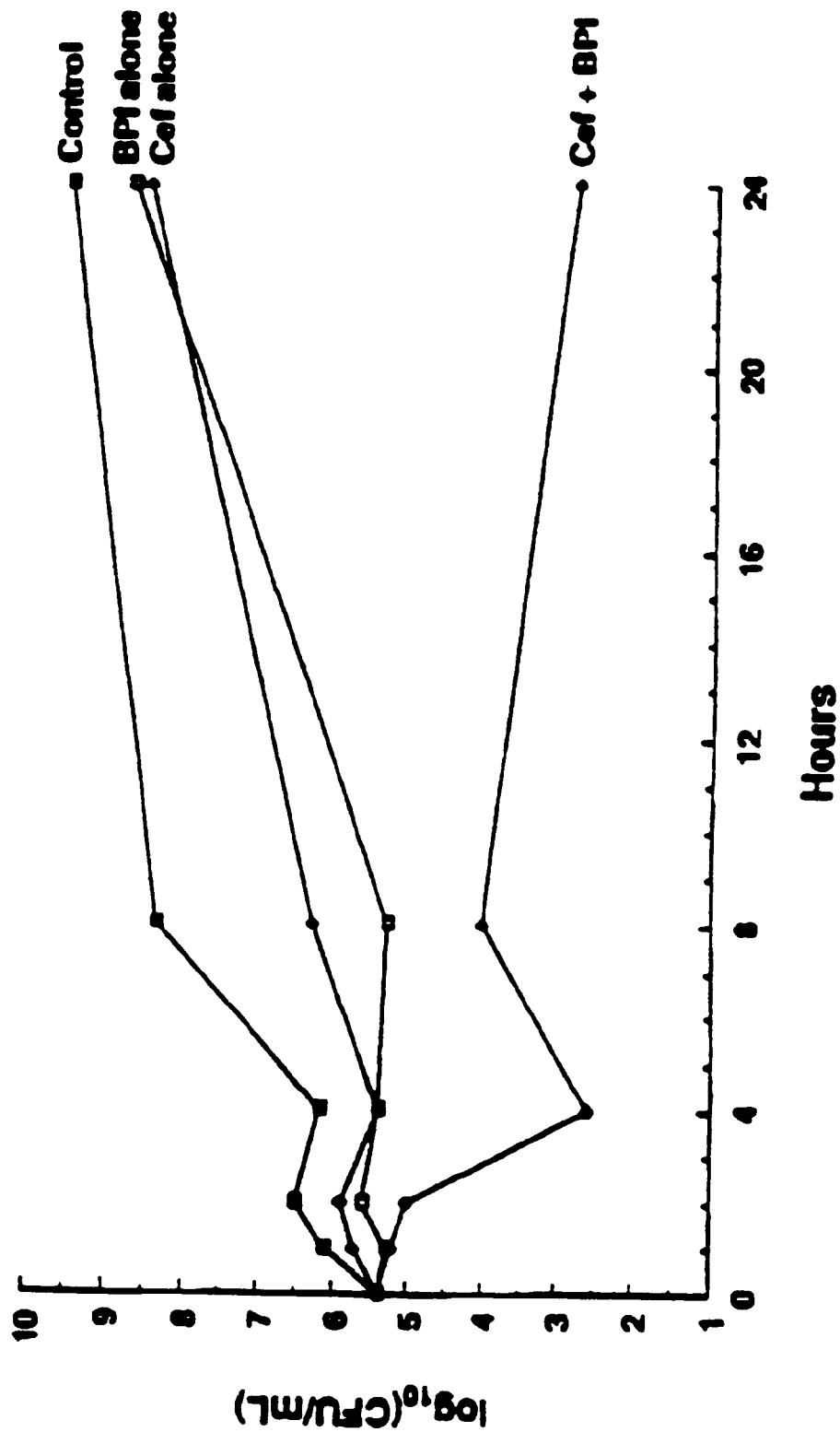
FIG. 18 shows the bactericidal effect of $rBPI_{21}$ and ceftriaxone, separately or in combination, on growth of ceftriaxone-resistant *E. coli*.

Results of a representative killing curve study of the effects of the concurrent administration of rBPI$_{21}$ and ceftriaxone on ceftriaxone-resistant *E. coli* are shown in FIG. 18. The filled square is the control (neither rBPI$_{21}$ nor ceftriaxone), the open square is rBPI$_{21}$ alone, the filled diamond is ceftriaxone alone, and the open diamond is the concurrent administration of ceftriaxone and rBPI$_{21}$. Ceftriaxone or rBPI$_{21}$ alone have some early bactericidal effect at 4–8 hours, but organism growth for both almost reaches that of the control curve by 24 hours (about a 1 log difference from control). In contrast, the concurrent administration of rBPI$_{21}$ and ceftriaxone produces a significantly greater bactericidal effect that is sustained at 24 hours (a more than 6 log difference from control).

TABLE 12

Checkerboard Synergy Study for Ceftriaxone-Resistant *E. coli* Using Ceftriaxone and rBPI$_{21}$

| | 0.8 μg/mL Ceftriaxone | 1.5 μg/mL Ceftriaxone | 3.1 μg/mL Ceftriaxone | 6.2 μg/mL Ceftriaxone | 12.5 μg/mL Ceftriaxone | 25 μg/mL Ceftriaxone | 50 μg/mL Ceftriaxone | 100 μg/mL Ceftriaxone |
|---|---|---|---|---|---|---|---|---|
| 0.8 μg/mL BPI | + | + | 0 | 0 | 0 | 0 | 0 | 0 |
| 1.5 μg/mL BPI | + | 0 | 0 | 0 | 0 | 0 | 0 | 0 |
| 3.1 μg/mL BPI | 0 | 0 | 0 | 0 | 0 | 0 | 0 | 0 |
| 6.2 μg/mL BPI | 0 | 0 | 0 | 0 | 0 | 0 | 0 | 0 |
| 12.5 μg/mL BPI | 0 | 0 | 0 | 0 | 0 | 0 | 0 | 0 |
| 25 μg/mL BPI | 0 | 0 | 0 | 0 | 0 | 0 | 0 | 0 |
| 50 μg/mL BPI | 0 | 0 | 0 | 0 | 0 | 0 | 0 | 0 |
| 100 μg/mL BPI | 0 | 0 | 0 | 0 | 0 | 0 | 0 | 0 |

KEY:
+ Growth
0 No Growth

EXAMPLE 11

EFFECTS OF BPI PROTEIN PRODUCT AND ANTIBIOTICS IN VITRO ON PSEUDOMONAS SPECIES

The effects of a BPI protein product, rBPI$_{21}$, on the antibiotic susceptibility of clinical isolates of *Pseudomonas aeruginosa* and other Pseudomonas species (from Baxter Microscan® library, Sacramento, Calif.) was evaluated using Microscan® panel plates (Baxter Diagnostics, Inc., Deerfield, Ill.) that allow simultaneous determination of minimum inhibitory concentrations for a number of different antibiotics. Control assays confined that the formulation buffer for rBPI$_{21}$ had no effect on the antibiotic susceptibility of various organisms.

The antimicrobial susceptibility tests performed on the Microscan® panel plates are miniaturizations of the broth dilution susceptibility test. Antimicrobial agents are serially diluted in Mueller-Hinton broth (supplemented with calcium and magnesium, or with sodium chloride for oxacillin, or with thymidine phosphorylase for trimethoprim, sulfamethoxazole and trimethoprim/sulfamethoxazole) to concentrations bridging the range of clinical interest. One well on the 96-well Microscan® plate is a growth control well that contains dehydrated broth only. The remaining wells contain dehydrated broth and antibiotic (or broth and biochemical reagent indicator), which is rehydrated to the desired concentration by inoculation of a standardized suspension of test organism. The chromogenic biochemical agent indicators are used to identify and characterize the species of bacteria based on detection of pH changes and substrate utilization. After incubation overnight, the minimum inhibitory concentration (MIC) of an antibiotic for the test organism is determined by observing the well with the lowest concentration of the antibiotic that shows inhibition of growth. Gram-negative organisms were tested using Neg Combo Type 16, MIC Plus Type 2, or Neg Breakpoint Combo Type 9 panel plates (Microscan®, Baxter Diagnostics, Inc., Deerfield, Ill.). The concentrations of antibiotics tested in these panel plates are shown below in Tables 13, 14 and 15, respectively. The antibiotic susceptibility standards (interpretation of an MIC as resistant, intermediate or susceptible according to Microscan®'s NCCLS-derived standards) applicable to the gram-negative organisms tested in each panel plate appear in Tables 13A, 14A and 15A, respectively.

TABLE 13

ANTIBIOTIC CONCENTRATIONS TESTED IN NEG COMBO TYPE 16 PANEL PLATE

| Antibiotic | Two-Fold Serial Dilutions Tested µg/ml |
|---|---|
| Amikacin | 2–16 |
| Ampicillin | 2–16 |
| Ampicillin/Sulbactam | 8/4–16/8 |
| Aztreonam | 8–16 |
| Cefazolin | 2–16 |
| Cefotaxime | 4–32 |
| Cefoxitin | 2–16 |
| Ceftazidime | 2–16 |
| Ceftriaxone | 4–32 |
| Cefuroxime | 2–16 |
| Ciprofloxacin | 1–2 |
| Gentamicin | 1–4, 6 |
| Imipenem | 4–8 |
| Ofloxacin | 2–4 |
| Piperacillin | 8–64 |
| Ticarcillin | 8–64 |
| Tobramycin | 1–4, 6 |
| Trimethoprim/Sulfamethoxazole | 0.5/9.5, 2/38 |

TABLE 13A

MICROSCAN NEG COMBO PANEL 16 ANTIBIOTIC SUSCEPTIBILITY RANGES FOR GRAM-NEGATIVE BACTERIA

| | MIC (µg/ml) | | |
|---|---|---|---|
| Antibiotic | Resistant | Intermediate | Susceptible |
| Amikacin | >16 | | ≦16 |
| Ampicillin[E] | >16 | 16 | ≦8 |
| Ampicillin/Sulbactam[E] | >16/8 | 16/8 | ≦8/4 |
| Aztreonam | >16 | 16 | ≦8 |

TABLE 13A-continued

MICROSCAN NEG COMBO PANEL 16 ANTIBIOTIC SUSCEPTIBILITY RANGES FOR GRAM-NEGATIVE BACTERIA

| | MIC (µg/ml) | | |
|---|---|---|---|
| Antibiotic | Resistant | Intermediate | Susceptible |
| Cefazolin | >16 | 16 | ≦8 |
| Cefotaxime | >32 | 16–32 | ≦8 |
| Cefoxitin | >16 | 16 | ≦8 |
| Ceftazidime | >16 | 16 | ≦8 |
| Ceftriaxone | >32 | 16–32 | ≦8 |
| Cefuroxime | >16 | 16 | ≦8 |
| Ciprofloxacin | >2 | 2 | ≦1 |
| Gentamicin | >6 | 6 | ≦4 |
| Imipenem | >8 | 8 | ≦4 |
| Ofloxacin | >4 | 4 | ≦2 |
| Piperacillin[E] | >64 | 32–64 | ≦16 |
| Piperacillin[P] | >64 | | ≦64 |
| Ticarcillin[E] | >64 | 32–64 | ≦16 |
| Ticarcillin[P] | >64 | | ≦64 |
| Tobramycin | >6 | 6 | ≦4 |
| Trimethoprim/Sulfamethoxazole | >2/38 | | ≦2/38 |

[E]Enterobacteriaceae only
[P]Pseudomonas only

TABLE 14

ANTIBIOTIC CONCENTRATIONS TESTED IN MIC PLUS TYPE 2 PANEL PLATE

| Antibiotic | Two-Fold Serial Dilutions Tested (µg/ml) |
|---|---|
| Amoxicillin/K Clavulanate | 1/0.5–32/16 |
| Ampicillin/Sulbactam | 1/0.5–32/16 |
| Azlocillin | 64 |
| Aztreonam | 1–32 |
| Carbenicillin | 16–128 |
| Cefamandole | 4–32 |
| Cefonicid | 2–16 |
| Cefoperazone | 4–32 |
| Cefotaxime | 2–64 |
| Cefotetan | 4–32 |
| Ceftazidime | 1–32 |
| Ceftizoxime | 2–32 |
| Ceftriaxone | 2–64 |
| Chloramphenicol | 2–16 |
| Ciprofloxacin | 0.25–4 |
| Imipenem | 0.5–16 |
| Mezlocillin | 16–128 |
| Netilmicin | 2–16 |
| Ticarcillin | 16–128 |
| Ticarcillin/K Clavulanate | 16–128 |

TABLE 14A

MICROSCAN MIC PLUS TYPE 2 ANTIBIOTIC SUSCEPTIBILITY RANGES FOR GRAM-NEGATIVE BACTERIA

| | MIC (µg/ml) | | |
|---|---|---|---|
| Antibiotic | Resistant | Intermediate | Susceptible |
| Amoxicillin/K Clavulanate | ≧32/16 | 16/8 | ≦8/4 |
| Ampicillin/Sulbactam | ≧32/16 | 16/8 | ≦8/4 |
| Azlocillin[P] | >64 | | ≦64 |
| Aztreonam | ≧32 | 16 | ≦8 |
| Carbenicillin[E] | ≧64 | 32 | ≦16 |
| Carbenicillin[P] | >128 | | ≦128 |
| Cefamandole | ≧32 | 16 | ≦8 |
| Cefonicid | >16 | 16 | ≦8 |
| Cefoperazone | >32 | 32 | ≦16 |
| Cefotaxime | ≧64 | 16–32 | ≦8 |
| Cefotetan | >32 | 32 | ≦16 |

TABLE 14A-continued

MICROSCAN MIC PLUS TYPE 2 ANTIBIOTIC SUSCEPTIBILITY
RANGES FOR GRAM-NEGATIVE BACTERIA

| | MIC (µg/ml) | | |
|---|---|---|---|
| Antibiotic | Resistant | Intermediate | Susceptible |
| Ceftazidime | ≧32 | 16 | ≦8 |
| Ceftizoxime | >32 | 16–32 | ≦8 |
| Ceftriaxone | ≧64 | 16–32 | ≦8 |
| Chloramphenicol | >16 | 16 | ≦8 |
| Ciprofloxacin | ≧4 | 2 | ≦1 |
| Imipenem | ≧16 | 8 | ≦4 |
| Mezlocillin[E] | ≧128 | 32–64 | ≦16 |
| Mezlocillin[P] | ≧128 | | ≦64 |
| Netilmicin | >16 | 16 | ≦8 |
| Ticarcillin[E] | ≧128 | 32–64 | ≦16 |
| Ticarcillin[P] | ≧128 | | ≦64 |
| Ticarcillin/K Clavulanate[E] | ≧128 | 32–64 | ≦16 |
| Ticarcillin/K Clavulanate[P] | ≧128 | | ≦64 |

[E]Enterobacteriaceae only
[P]Pseudomonas only

TABLE 15

ANTIBIOTIC CONCENTRATIONS TESTED IN NEG BREAKPOINT
COMBO TYPE 9 PANEL PLATE

| Antibiotic | Dilutions Tested (µg/ml) |
|---|---|
| Nitrofurantoin | 32 & 64 |
| Cephalothin | 8 & 16 |
| Ampicillin | 8 & 16 |
| Ofloxacin | 2 & 4 |
| Ticarcillin | 16 & 64 |
| Piperacillin | 16 & 64 |
| Mezlocillin | 16 & 64 |
| Tetracycline | 4 & 8 |
| Ampicillin/Sulbactam | 8/4 & 16/8 |
| Amoxicillin/K Clavulanate | 8/4 & 16/8 |
| Ticarcillin/K Clavulanate | 16 & 64 |
| Gentamicin | 4 & 8 |
| Tobramycin | 4 & 8 |
| Amikacin | 16 & 32 |
| Ciprofloxacin | 1 & 2 |
| Imipenem | 4 & 8 |
| Cefazolin | 8 & 16 |
| Cefamandole | 8 & 16 |
| Cefuroxime | 8 & 16 |
| Cefotetan | 16 & 32 |
| Cefoxitin | 8 & 16 |
| Aztreonam | 8 & 16 |
| Ceftriaxone | 8 & 32 |
| Ceftazidime | 8 & 16 |
| Cefoperazone | 16 & 32 |
| Cefotaxime | 8 & 32 |
| Chloramphenicol | 8 & 16 |
| Trimethoprim/Sulfamethoxazole | 2/38 & 8/152 |
| Norfloxacin | 4 & 8 |
| Cinoxacin | 16 |
| Trimethoprim | 8 |
| Sulfamethoxazole | 256 |

TABLE 15A

MICROSCAN NEG BREAKPOINT COMBO TYPE 9 ANTIBIOTIC
SUSCEPTIBILITY RANGES FOR GRAM-NEGATIVE BACTERIA

| | MIC (µg/ml) | | |
|---|---|---|---|
| Antibiotic | Resistant | Intermediate | Susceptible |
| Nitrofurantoin | >64 | 64 | ≦32 |
| Cephalothin | >16 | 16 | ≦8 |

TABLE 15A-continued

MICROSCAN NEG BREAKPOINT COMBO TYPE 9 ANTIBIOTIC
SUSCEPTIBILITY RANGES FOR GRAM-NEGATIVE BACTERIA

| | MIC (µg/ml) | | |
|---|---|---|---|
| Antibiotic | Resistant | Intermediate | Susceptible |
| Ampicillin[E] | >16 | 16 | ≦8 |
| Ofloxacin | >4 | 4 | ≦2 |
| Ticarcillin[E] | >64 | 64 | ≦16 |
| Ticarcillin[P] | >64 | | ≦64 |
| Piperacillin[E] | >64 | 64 | ≦16 |
| Piperacillin[P] | >64 | | ≦64 |
| Mezlocillin[E] | >64 | 64 | 16 |
| Mezlocillin[P] | >64 | | ≦64 |
| Tetracycline | >8 | 8 | ≦4 |
| Ampicillin/Sulbactam[E] | >16/8 | 16/8 | ≦8/4 |
| Amoxicillin/K Clavulanate | >16/8 | 16/8 | ≦8/4 |
| Ticarcillin/K Clavulanate[E] | >64 | 64 | ≦16 |
| Ticarcillin/K Clavulanate[P] | >64 | | ≦64 |
| Gentamicin | >8 | 8 | ≦4 |
| Tobramycin | >8 | 8 | ≦4 |
| Amikacin | >32 | 32 | ≦16 |
| Ciprofloxacin | >2 | 2 | ≦1 |
| Imipenem | >8 | 8 | ≦4 |
| Cefazolin | >16 | 16 | ≦8 |
| Cefamandole | >16 | 16 | ≦8 |
| Cefuroxime | >16 | 16 | ≦8 |
| Cefotetan | >32 | 32 | ≦16 |
| Cefoxitin | >16 | 16 | ≦8 |
| Aztreonam | >16 | 16 | ≦8 |
| Ceftriaxone | >32 | 32 | ≦8 |
| Ceftazidime | >16 | 16 | ≦8 |
| Cefoperazone | >32 | 32 | ≦16 |
| Cefotaxime | >32 | 32 | ≦8 |
| Chloramphenicol | >16 | 16 | ≦8 |
| Trimethoprim/Sulfamethoxazole | >8/152 | 8/152 | ≦2/38 |
| Norfloxacin | >8 | 8 | ≦4 |
| Cinoxacin | >16 | | ≦16 |
| Trimethoprim | >8 | | ≦8 |
| Sulfamethoxazole | >256 | | ≦256 |

[E]Enterobacteriaceae only
[P]Pseudomonas only

For each experimental run, the following procedure was performed: The organism was streaked onto 5% sheep blood agar plates (Remel, Lenexa, Kansas) and incubated for 18–24 hours overnight. Well-isolated colonies from the plates were emulsified in 3 ml of sterile Inoculum Water (catalog no. B1015-2, MicroScan® system, Baxter Diagnostics, Inc., Deerfield, Ill.) to a final turbidity equivalent to 0.5 McFarland Barium Sulfate standard. This cell suspension was vortexed for 2 to 3 seconds and 100 µl was transferred to glass tubes containing 25 ml of Inoculum Water with Pluronic-D (catalog no. B1015-7, MicroScan® system, Baxter Diagnostics, Inc., Deerfield, Ill.) (hereinafter "Pluronic Inoculum Water"), or 25 ml of Pluronic Inoculum Water into which rBPI$_{21}$ (in formulation buffer) had been diluted to the desired concentration between 0.5 to 64 µg/ml rBPI$_{21}$.

The 25 ml of this inoculum containing rBPI$_{21}$ was mixed by inversion and poured into a tray. The inoculum was drawn up into a manual 96-well pipetting system (RENOK® rehydrator-inoculator system, Baxter Health Care Corporation, West Sacramento, Calif.) designed for use with the Microscan® panel plates, and 110 µl of the inoculum was delivered to each well of a Microscan® Neg Combo Type 16 panel plate. When added to the wells, this inoculum achieves a final bacterial concentration of 4×10$^5$ to 7×10$^5$ CFU/ml. The panel plates were then incubated at 35° C. for 15–24 hours and read visually for cell growth.

No growth was defined as a slight whiteness in the well or a clear broth. Growth appeared as turbidity which could take the form of a white haze throughout the well, a white button in the center of the well, or a fine granule growth throughout the well. All wells were read against a black indirectly lighted background. Visual results of the biochemical reactions were read into a database for bacterial identification. The MICs for each antibiotic tested were determined by identifying the lowest concentration of antibiotic which inhibited visible growth.

The clinical isolates of Pseudomonas aeruginosa and other Pseudomonas species were tested using the Neg Combo Type 16 panel plate. Tables 16, 17 and 18 below display a summary of the results of the antibiotic screening panels, reported for each strain tested as the MIC of the tested antibiotics at the various concentrations of $rBPI_{21}$ indicated. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Table 13A. Stars after the antibiotic name in the "antibiotic tested" column indicate whether $rBPI_{21}$ reversed the resistance of that organism to the antibiotic tested (two stars) or converted an indifferent MIC into a susceptible MIC (one star). These data show that BPI protein product reversed resistance to ticarcillin, cefazolin, cefoxitin, cefuroxime, ofloxacin, aztreonam, piperacillin, and amikacin for some strains of P. aeruginosa and increased the susceptibility of some P. aeruginosa strains to ticarcillin, aztreonam, imipenem, piperacillin, ofloxacin, ceftazidime, amikacin, ceftriaxone, cefotaxime, cefuroxime, tobramycin, ciprofloxacin, trimethoprim/sulfamethoxazole, gentamicin, and cefazolin. BPI protein product reversed resistance of some P. cepacia strains to cefazolin, cefoxitin, cefuroxime, ceftriaxone, ticarcillin, and increased the susceptibility of some P. cepacia strains to ampicillin, ticarcillin, piperacillin, cefazolin, cefoxitin, cefuroxime, ceftriaxone, ampicillin/sulbactam, cefotaxime, gentamicin, tobramycin, and amikacin. BPI protein product reversed resistance of Xanthamonas maltophilia to trimethoprimlsulfamethoxazole, piperacillin and amikacin, and increased susceptibility to ciprofloxacin.

Tables 16, 17 and 18 also show the presence or absence of bacterial growth in the growth control wells, which contained varying concentrations of $rBPI_{21}$ alone without antibiotic. "G" indicates growth, while "NG" indicates no growth. These results indicate that $rBPI_{21}$ at a concentration of 32 μg/ml has direct bactericidal/growth inhibitory effects on some of the tested Pseudomonas isolates.

TABLE 16

EFFECTS OF $rBPI_{21}$ ± ANTIBIOTICS ON Pseudomonas aeruginosa

| Microscan Library ID No. | Antibiotic Tested | Minimum Inhibitory Concentration of Antibiotic (μg/mL) | | |
|---|---|---|---|---|
| | | With 0 μg/mL $rBPI^{21}$ | With 8 μg/mL $rBPI^{21}$ | With 32 μg/mL $rBPI_{21}$ |
| 19610 | BPI | G | G | G |
| | Ticarcillin** | >64 | 64 | 64 |
| | Aztreonam* | 16 | <8 | <8 |
| | Piperacillin | 32 | 16 | <8 |
| | Ofloxacin** | >4 | 4 | <2 |
| | Ceftazidime | 8 | 8 | 4 |
| | Amikacin | 16 | 8 | 8 |

TABLE 16-continued

EFFECTS OF $rBPI_{21}$ ± ANTIBIOTICS ON Pseudomonas aeruginosa

| Microscan Library ID No. | Antibiotic Tested | Minimum Inhibitory Concentration of Antibiotic (μg/mL) | | |
|---|---|---|---|---|
| | | With 0 μg/mL $rBPI^{21}$ | With 8 μg/mL $rBPI^{21}$ | With 32 μg/mL $rBPI_{21}$ |
| 18433 | BPI | G | G | NG |
| | Aztreonam* | 16 | <8 | — |
| | Ceftriaxone | >32 | 32 | — |
| | Cefotaxime | >32 | 32 | — |
| | Cefuroxime* | 16 | 4 | — |
| | Tobramycin | 2 | <1 | — |
| | Amikacin | 16 | 8 | — |
| 12892 | BPI | G | G | G |
| | Ciprofloxacin | >2 | >2 | 2 |
| | Ofloxacin | >4 | >4 | 4 |
| | Ceftazidime | 4 | 4 | <2 |
| | Cefotaxime | >32 | >32 | 32 |
| | Amikacin | 16 | 16 | 8 |
| 19054 | BPI | G | G | G |
| | Trimethoprim/Sulfamethoxazole | >2 | >2 | 2 |
| | Ticarcillin | 64 | 16 | 16 |
| | Ceftriaxone* | 16 | 32 | 8 |
| | Gentamicin | 4 | 4 | 2 |
| | Amikacin | 16 | 8 | 4 |
| | Cefazolin | >16 | >16 | 16 |
| 19672 | BPI | G | G | G |
| | Tobramycin | >6 | >6 | 6 |
| 19551 | BPI | G | G | G |
| | Aztreonam** | >16 | <8 | <8 |
| | Piperacillin** | >64 | <8 | <8 |
| | Ceftriaxone | 32 | 16 | 16 |
| | Gentamicin | 4 | <1 | <1 |
| | Tobramycin | 2 | <1 | <1 |
| | Amikacin** | >16 | <2 | <2 |
| 19660 | BPI | G | G | NG |
| | Trimethoprim/Sulfamethoxazole | >2 | 2 | — |
| | Ceftriaxone* | 16 | 8 | — |
| | Cefotaxime | 16 | 16 | — |
| Opal[b] | BPI | G | G | G |
| | Ampicillin[a] | >16 | >16 | 4 |
| | Trimethoprim/Sulfamethoxazole | >2 | >2 | 2 |
| | Ticarcillin | 16 | 16 | <8 |
| | Cefazolin** | >16 | >16 | <2 |
| | Cefoxitin** | >16 | >16 | <2 |
| | Cefuroxime** | >16 | >16 | <2 |
| | Ceftriaxone* | 16 | 8 | <4 |
| | Ampicillin/Sulbactam[a] | >16 | >16 | <8 |
| | Cefotaxime* | 16 | 8 | <4 |

[a]The Microscan ® worksheet did not supply antibiotic susceptibility ranges, but there was reversal of antibiotic indifference according to NCCLS standards, Publication M7-A3, Table 2 (1993).
[b]Strain 12.4.4, provided by S. M. Opal, Brown University, Providence, RI.

TABLE 17

EFFECTS OF $rBPI_{21}$ ± ANTIBIOTICS ON Pseudomonas aeruginosa

| Microscan Library ID No. | Antibiotic Tested | Minimum Inhibitory Concentration of Antibiotic (μg/mL) | | |
|---|---|---|---|---|
| | | With 0 μg/mL $rBPI^{21}$ | With 4 μg/mL $rBPI_{21}$ | With 16 μg/mL $rBPI_{21}$ |
| N113-100 | BPI | G | G | G |
| | Ofloxacin* | 4 | 4 | <2 |
| | Gentamicin | >6 | 6 | 6 |
| | Tobramycin | 2 | 2 | <1 |

TABLE 17-continued

EFFECTS OF rBPI$_{21}$ ± ANTIBIOTICS ON *Pseudomonas aeruginosa*

| | | Minimum Inhibitory Concentration of Antibiotic (µg/mL) | | |
|---|---|---|---|---|
| Microscan Library ID No. | Antibiotic Tested | With 0 µg/mL rBPI$^{21}$ | With 4 µg/mL rBPI$_{21}$ | With 16 µg/mL rBPI$_{21}$ |
| N113-101 | BPI | G | G | G |
| | Aztreonam | >16 | >16 | <8 |
| | Ofloxacin* | 4 | 4 | <2 |
| | Gentamicin | >6 | 6 | 6 |
| | Tobramycin | 4 | 2 | <1 |
| N113-102 | BPI | G | G | G |
| | Piperacillin | 64 | <8 | <8 |
| | Ceftriaxone* | 32 | 16 | 8 |
| | Cefotaxime | 32 | 16 | 16 |
| | Gentamicin | 4 | 4 | <1 |
| | Amikacin | 8 | 8 | <2 |
| N113-103 | BPI | G | G | G |
| | Ticarcillin | 16 | 16 | 32 |
| | Amikacin | 4 | 8 | 4 |
| N113-104 | BPI | G | G | G |
| | Ceftazidime | <2 | <2 | 4 |
| | Ceftriaxone* | 16 | 8 | 8 |
| N113-105 | BPI | G | G | G |
| | Ticarcillin | 64 | 32 | 32 |
| | Aztreonam* | 16 | <8 | <8 |
| | Ceftriaxone | 32 | 32 | 16 |
| | Cefotaxime | 32 | 32 | 16 |
| | Gentamicin | 2 | 2 | <1 |
| N113-106 | BPI | G | G | G |
| | Ticarcillin | 16 | 16 | <8 |
| | Ceftriaxone* | 32 | 16 | 8 |
| | Cefotaxime* | 16 | 16 | 8 |
| | Gentamicin | 4 | 2 | 2 |
| | Amikacin | 8 | 4 | 4 |
| N113-107 | BPI | G | G | G |
| | Ticarcillin | >64 | >64 | 64 |
| | Ciprofloxacin* | 2 | 2 | <1 |
| | Ceftazidime | 8 | 4 | 4 |
| | Ceftriaxone | 32 | 32 | >32 |
| | Imipenem | >8 | 8 | >8 |

TABLE 18

EFFECTS OF rBPI$_{21}$ ± ANTIBIOTICS ON Pseudomonas SPECIES

| | | Minimum Inhibitory Concentration of Antibiotic (µg/mL) | | |
|---|---|---|---|---|
| Microscan Library ID No. | Antibiotic Tested | With 0 µg/mL rBPI$^{21}$ | With 8 µg/mL rBPI$_{21}$ | With 32 µg/mL rBPI$_{21}$ |
| 31142 (*P. cepacia*) | BPI | G | G | NG |
| | Ampicillin | >16 | 16 | — |
| | Ticarcillin | 32 | <8 | — |
| | Piperacillin | 32 | <8 | — |
| | Cefazolin** | >16 | 8 | — |
| | Cefoxitin** | >16 | <2 | — |
| | Cefuroxime** | >16 | <2 | — |
| | Ceftriaxone** | >32 | 8 | — |
| | Ampicillin/Sulbactam$^a$ | 16 | <8 | — |
| | Cefotaxime* | 32 | <4 | — |
| | Gentamicin* | 6 | <1 | — |
| | Tobramycin | 2 | <1 | — |
| | Amikacin | 8 | <2 | — |
| 12122 (*P. cepacia*) | BPI | G | G | G |
| | Ticarcillin** | >64 | 64 | 32 |
| | Piperacillin | 16 | <8 | <8 |
| | Cefuroxime | 4 | <2 | <2 |
| | Amikacin | 4 | 4 | <2 |
| 17211 (*Xanthamonas maltophilia*) | BPI | G | G | NG |
| | Trimethoprim/Sulfamethoxazole** | >2 | 2 | — |
| | Piperacillin** | >64 | 16 | — |
| | Amikacin** | >16 | 16 | — |
| | Ciprofloxacin | 2 | 2 | — |

$^a$The Microscan® worksheet did not supply antibiotic susceptibility ranges for this organism, but there was reversal of antibiotic indifference according to NCCLS standards, Publication M7-A3, Table 2 (1993).

EXAMPLE 12

EFFECTS OF BPI PROTEIN PRODUCT AND ANTIBIOTICS IN VITRO ON STRAINS OF *E. COLI*

The effect of a BPI protein product, rBPI$_{21}$, on the antibiotic susceptibility of various strains of *E. coli* was evaluated in the Microscan® antibiotic susceptibility screening assay of Example 11 using the Neg Combo Type 16 panel plate. The direct growth inhibitory effect of rBPI$_{21}$ on these strains was also evaluated in the same assay. Assays were conducted on clinical isolates of *E. coli* (from Baxter Microscan® library, Sacramento, Calif.).

A summary of the results of the antibiotic screening panels, reported as MICs (µg/ml) of the antibiotic tested, is shown in Table 19 below. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Table 13A. These results show that BPI protein product reversed the resistance of some strains to cefazolin and increased the susceptibility of other strains to ampicillin, cefuroxime, cefazolin, amikacin, and cefoxitin.

TABLE 19

EFFECTS OF rBPI$_{21}$ ± ANTIBIOTICS ON *Escherichia coli*

| | | Minimum Inhibitory Concentration of Antibiotic (µg/mL) | | |
|---|---|---|---|---|
| Microscan Library ID No. | Antibiotic Tested | With 0 µg/mL rBPI$^{21}$ | With 4 µg/mL rBPI$_{21}$ | With 16 µg/mL rBPI$_{21}$ |
| 19536 | Ampicillin$^a$ | 16 | 16 | 8 |
| | Cefuroxime | 4 | 8 | 4 |
| F101-309 | Cefoxitin | 4 | <2 | 4 |
| | Cefuroxime | 8 | 4 | 4 |
| 19612 | Cefazolin** | >16 | >16 | 8 |
| | Amikacin | 16 | 8 | 8 |
| | Cefoxitin | <2 | 4 | <2 |
| 17164 | Ampicillin | 8 | 8 | 4 |
| | Cefoxitin | 8 | 8 | 4 |

TABLE 19-continued

EFFECTS OF rBPI$_{21}$ ± ANTIBIOTICS ON *Escherichia coli*

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 4 μg/mL rBPI$_{21}$ | With 16 μg/mL rBPI$_{21}$ |
| 19522 | Cefazolin | 8 | 8 | 4 |
| | Cefoxitin | >16 | >16 | 16 |

[a]The Microscan ® worksheet did not supply antibiotic susceptibility ranges for this organism, but there was reversal of antibiotic indifference according to NCCLS standards, Publication M7-A3, Table 2 (1993).

EXAMPLE 13

EFFECTS OF BPI PROTEIN PRODUCT AND ANTIBIOTICS IN VITRO ON CITROBACTER SPECIES

The effect of a BPI protein product, rBPI$_{21}$, on the antibiotic susceptibility of various Citrobacter species was evaluated in the Microscan® antibiotic susceptibility screening assay of Example 11 using the Neg Combo Type 16 panel plate. The direct growth inhibitory effect of rBPI$_{21}$ on these strains was also evaluated in the same assay. Assays were conducted on clinical isolates of Citrobacter species (from Baxter Microscan® library, Sacramento, Calif.).

A summary of the results of the antibiotic screening panels, reported as MICs (μg/ml) of the antibiotic tested, is shown in Table 20 below. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Table 13A. These results show that BPI protein product increased the susceptibility of the tested Citrobacter species to aztreonam, cefotaxime, tobramycin, amikacin, cefuroxime, ampicillin, ticarcillin, piperacillin, and cefuroxime.

TABLE 20

EFFECTS OF rBPI$_{21}$ ± ANTIBIOTICS ON Citrobacter SPECIES

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 4 μg/mL rBPI$_{21}$ | With 16 μg/mL rBPI$_{21}$ |
| 18419 | Aztreonam | >16 | >16 | 16 |
| (*C. freundii*) | Cefotaxime | >32 | 32 | 32 |
| | Tobramycin | 4 | 2 | <1 |
| | Amikacin | 4 | <2 | 4 |
| 18420 | Cefuroxime | >16 | >16 | 16 |
| (*C. freundii*) | Amikacin | >2 | >2 | >2 |
| F052-007 | Ampicillin | >16 | >16 | 16 |
| (*C. diversus*) | Ticarcillin | >64 | >64 | 64 |
| | Piperacillin[a] | 32 | 16 | <8 |
| | Cefuroxime | 8 | 4 | 4 |

[a]The Microscan ® worksheet did not supply antibiotic susceptibility ranges for this organism, but there was reversal of antibiotic indifference according to NCCLS standards, Publication M7-A3, Table 2 (1993).

EXAMPLE 14

EFFECTS OF BPI PROTEIN PRODUCT AND ANTIBIOTICS IN VITRO ON KLEBSIELLA SPECIES

The effect of a BPI protein product, rBPI$_{21}$, on the antibiotic susceptibility of various Klebsiella species was evaluated in the Microscan® antibiotic susceptibility screening assay of Example 11 using the Neg Combo Type 16 panel plate. The direct growth inhibitory effect of rBPI$_{21}$ on these strains was also evaluated in the same assay. Assays were conducted on clinical isolates of Klebsiella species (from Baxter Microscan® library, Sacramento, Calif.).

A summary of the results of the antibiotic screening panels, reported as MICs (μg/ml) of the antibiotic tested, is shown in Table 21 below. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Table 13A. These results show that BPI protein product reversed the resistance of one strain of *K. pneumoniae* to trimethoprim/sulfamethoxazole and increased the susceptibility of the tested species to cefoxitin, ampicillin/sulbactam, trimethoprim/sulfamethoxazole, cefazolin, and cefuroxime.

TABLE 21

EFFECTS OF rBPI$_{21}$ ± ANTIBIOTICS ON Klebsiella SPECIES

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 4 μg/mL rBPI$_{21}$ | With 16 μg/mL rBPI$_{21}$ |
| 19645 | Cefoxitin | 8 | <2 | 4 |
| (*K. pneumoniae*) | Ampicillin/Sulbactam | >16 | >16 | >16 |
| 18427 | Cefazolin | <2 | 4 | <2 |
| (*K. pneumoniae*) | Ampicillin/Sulbactam[a] | 16 | 16 | <8 |
| 16135 | Trimethoprim/Sulfa-methoxazole** | >2 | >2 | <0.5 |
| (*K. pneumoniae*) | Cefazolin* | 16 | 16 | 8 |
| 30434 | Cefazolin* | 16 | 16 | 8 |
| (*K. oxytoca*) | Cefoxitin | 4 | <2 | 4 |
| | Cefuroxime | 8 | 4 | 8 |
| | Ampicillin/Sulbactam | <8 | 16 | <8 |

[a]The Microscan ® worksheet did not supply antibiotic susceptibility ranges for this organism, but there was reversal of antibiotic indifference according to NCCLS standards, Publication M7-A3, Table 2 (1993).

EXAMPLE 15

EFFECTS OF BPI PROTEIN PRODUCT AND ANTIBIOTICS IN VITRO ON ENTEROBACTER SPECIES

The effect of a BPI protein product, rBPI$_{21}$, on the antibiotic susceptibility of various Enterobacter species was evaluated in the Microscan® antibiotic susceptibility screening assay of Example 11 using the Neg Combo Type 16 panel plate. The direct growth inhibitory effect of rBPI$_{21}$ on these strains was also evaluated in the same assay. Assays were conducted on clinical isolates of Enterobacter species (from Baxter Microscan® library, Sacramento, Calif.).

A summary of the results of the antibiotic screening panels, reported as MICs (μg/ml) of the antibiotic tested, is shown in Table 22 below. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Table 13A. These results show that BPI protein product reversed the resistance of one strain of *E. cloacae* to ticarcillin, cefuroxime, ceftazidime and cefotaxime. BPI protein product also increased the susceptibility of some Enterobacter species to ticarcillin, aztreonam, piperacillin, ciprofloxacin, cefotaxime, trimethoprim/sulfamethoxazole, cefuroxime, ceftazidime, ceftriaxone, and ampicillin/sulbactam.

TABLE 22

EFFECTS OF rBPI$_{21}$ ± ANTIBIOTICS ON Enterobacter SPECIES

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 4 μg/mL rBPI$_{21}$ | With 16 μg/mL rBPI$_{21}$ |
| 19565 (E. aerogenes) | Ticarcillin | 64 | >64 | 64 |
| | Aztreonam* | 16 | <8 | <8 |
| | Piperacillin | >64 | >64 | 64 |
| | Ciprofloxacin* | 2 | <1 | <1 |
| | Cefotaxime* | 16 | 8 | 8 |
| 19626 (E. aerogenes) | Piperacillin | >64 | 64 | 64 |
| | Ticarcillin | >64 | >64 | >64 |
| 19625 (E. aerogenes) | Trimethoprim/ Sulfa- methoxazole* | 2 | <0.5 | <0.5 |
| | Piperacillin | >64 | >64 | >64 |
| 19680 (E. cloacae) | Ticarcillin** | >64 | >64 | <8 |
| | Aztreonam | >16 | 16 | <8 |
| | Piperacillin* | 64 | 32 | <8 |
| | Cefuroxime** | >16 | >16 | 8 |
| | Ceftazidime** | >32 | 32 | <4 |
| | Ceftriaxone | >16 | >16 | 16 |
| | Ampicillin/ Sulbactam | >16 | >16 | 16 |
| | Cefotaxime** | >32 | >32 | <4 |
| 19686 (E. cloacae) | Ceftriaxone | 32 | 32 | 16 |
| | Piperacillin | >64 | >64 | >64 |

EXAMPLE 16

EFFECTS OF BPI PROTEIN PRODUCT AND ANTIBIOTICS IN VITRO ON *SERRATIA MARCESCENS*

The effect of a BPI protein product, rBPI$_{21}$, on the antibiotic susceptibility of *Serratia marcescens* was evaluated in the Microscan® antibiotic susceptibility screening assay of Example 11 using the Neg Combo Type 16 panel plate. The direct growth inhibitory effect of rBPI$_{21}$ on these strains was also evaluated in the same assay. Assays were conducted on clinical isolates of *Serratia marcescens* (from Baxter Microscan® library, Sacramento, Calif.).

A summary of the results of the antibiotic screening panels, reported as MICs (μg/ml) of the antibiotic tested, is shown in Table 23 below. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Table 13A. These results show that BPI protein product reversed the resistance of some strains to ceftazidime and cefotaxime, and increased the susceptibility of other strains to piperacillin, cefoxitin, ceftazidime, ceftriaxone, cefotaxime, tobramycin, ampicillin/sulbactam, and ampicillin.

TABLE 23

EFFECTS OF rBPI$_{21}$ ± ANTIBIOTICS ON *Serratia marcescens*

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 4 μg/mL rBPI$_{21}$ | With 16 μg/mL rBPI$_{21}$ |
| 19646 | Piperacillin | >64 | >64 | 32 |
| | Cefoxitin | 16 | >16 | 8 |
| | Ceftazidime** | >16 | >16 | 8 |
| | Ceftriaxone* | 32 | 16 | 8 |
| | Cefotaxime** | >32 | 32 | <4 |
| | Tobramycin* | 6 | 6 | 4 |
| 19647 | Piperacillin$^a$ | >64 | 64 | 16 |
| | Cefoxitin | 8 | 8 | 4 |
| | Ceftazidime* | 16 | 16 | 4 |
| | Ceftriaxone | 8 | <4 | <4 |
| | Ampicillin/Sulbactam | >16 | >16 | 16 |
| | Cefotaxime | 8 | <4 | <4 |
| | Tobramycin | 2 | 2 | <1 |
| 18443 | Ampicillin$^a$ | 16 | 16 | 8 |
| | Ampicillin/Sulbactam | >16 | >16 | 16 |

$^a$The Microscan ® worksheet did not supply antibiotic susceptibility ranges for this organism, but there was reversal of antibiotic indifference according to NCCLS standards, Publication M7-A3, Table 2 (1993).

EXAMPLE 17

EFFECTS OF BPI PROTEIN PRODUCT AND ANTIBIOTICS IN VITRO ON *PROTEUS MIRABILIS*

The effect of a BPI protein product, rBPI$_{21}$, on the antibiotic susceptibility of *Proteus mirabilis* was evaluated in the Microscan® antibiotic susceptibility screening assay of Example 11 using the Neg Combo Type 16 panel plate. The direct growth inhibitory effect of rBPI$_{21}$ on these strains was also evaluated in the same assay. Assays were conducted on clinical isolates of Proteus mirabilis (from Baxter Microscan® library, Sacramento, Calif.).

A summary of the results of the antibiotic screening panels, reported as MICs (μg/ml) of the antibiotic tested, is shown in Table 24 below. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Table 13A. These results show that BPI protein product increased the susceptibility of some strains to trimethoprim/sulfamethoxazole, cefazolin, cefoxitin, imipenem, tobramycin, and amikacin.

TABLE 24

**EFFECTS OF rBPI$_{21}$ ± ANTIBIOTICS ON *Proteus mirabilis***

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 8 μg/mL rBPI$_{21}$ | With 32 μg/mL rBPI$_{21}$ |
| 19593 | Trimethoprim/ Sulfamethoxazole* | 2 | <0.5 | <0.5 |
| | Cefazolin | 4 | <2 | 4 |
| | Cefoxitin | 8 | <2 | <2 |
| | Imipenem* | 8 | <4 | <4 |
| | Tobramycin | 2 | 2 | <1 |
| | Amikacin | 8 | 4 | 4 |
| F231-129 | Cefoxitin | 4 | <2 | 4 |
| | Imipenem* | 8 | <4 | <4 |
| | Amikacin | 4 | <2 | <2 |

EXAMPLE 18

EFFECTS OF BPI PROTEIN PRODUCT AND ANTIBIOTICS IN VITRO ON PROVIDENCIA SPECIES

The effect of a BPI protein product, rBPI$_{21}$, on the antibiotic susceptibility of various Providencia species was evaluated in the Microscan® antibiotic susceptibility screening assay of Example 11 using the Neg Combo Type 16 panel plate. The direct growth inhibitory effect of rBPI$_{21}$ on these strains was also evaluated in the same assay. Assays were conducted on clinical isolates of Providencia species (from Baxter Microscan® library, Sacramento, Calif.).

A summary of the results of the antibiotic screening panels, reported as MICs (μg/ml) of the antibiotic tested, is shown in Table 25 below. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Table 13A. These results show that BPI protein product reversed the resistance of *P. stuartii* to cefazolin and cefuroxime, and increased its susceptibility to piperacillin, ceftazidime, ampicillin/sulbactam, imipenem, and amikacin. BPI protein product also increased susceptibility of *P. rettgeri* to cefoxitin and cefuroxime.

TABLE 25

EFFECTS OF rBPI$_{21}$ ± ANTIBIOTICS ON Providencia SPECIES

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 8 μg/mL rBPI$_{21}$ | With 32 μg/mL rBPI$_{21}$ |
| 19614 (*P. rettgeri*) | Cefoxitin | >16 | 8 | >16 |
| | Cefuroxime* | 16 | 8 | <2 |
| | Amikacin | 16 | 16 | 16 |
| 18435 (*P. stuartii*) | Piperacillin[a] | >64 | 32 | 16 |
| | Cefazolin** | >16 | >16 | 8 |
| | Cefuroxime** | >16 | >16 | 8 |
| | Ceftazidime | 4 | <2 | <2 |
| | Ampicillin/ Sulbactam | >16 | 16 | 16 |
| | Imipenem* | 8 | <4 | <4 |
| | Amikacin | 16 | 16 | 8 |

[a]The Microscan® worksheet did not supply antibiotic susceptibility ranges for this organism, but there was reversal of antibiotic indifference according to NCCLS standards, Publication M7-A3, Table 2 (1993).

EXAMPLE 19

EFFECTS OF BPI PROTEIN PRODUCT AND ANTIBIOTICS IN VITRO ON *MORGANELLA MORGANII*

The effect of a BPI protein product, rBPI$_{21}$, on the antibiotic susceptibility of *Morganella morganii* was evaluated in the Microscan® antibiotic susceptibility screening assay of Example 11 using the Neg Combo Type 16 panel plate. The direct growth inhibitory effect of rBPI$_{21}$ on these strains was also evaluated in the same assay. Assays were conducted on clinical isolates of *Morganella morganii* (from Baxter Microscan® library, Sacramento, Calif.).

A summary of the results of the antibiotic screening panels, reported as MICs (μ/ml) of the antibiotic tested, is shown in Table 26 below. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Table 13A. These results show that BPI protein product increased the susceptibility of the tested strains to ampicillin/sulbactam, amikacin and piperacillin.

TABLE 26

**EFFECTS OF rBPI$_{21}$ ± ANTIBIOTICS ON *Morganella morganii***

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 8 μg/mL rBPI$_{21}$ | With 32 μg/mL rBPI$_{21}$ |
| F19-004 | Ampicillin/ Sulbactam | >16 | 16 | 16 |
| | Amikacin | 4 | <2 | 4 |
| F19-005 | Ampicillin/ Sulbactam[a] | >16 | <8 | <8 |
| | Amikacin | 4 | <2 | <2 |
| F19-006 | Piperacillin | >64 | 64 | 64 |
| | Amikacin | <2 | <2 | 4 |

[a]The Microscan® worksheet did not supply antibiotic susceptibility ranges for this organism, but there was reversal of antibiotic indifference according to NCCLS standards, Publication M7-A3, Table 2 (1993).

EXAMPLE 20

EFFECTS OF BPI PROTEIN PRODUCT AND ANTIBIOTICS IN VITRO ON ACINETOBACTER SPECIES

The effect of a BPI protein product, rBPI$_{21}$, on the antibiotic susceptibility of various Acinetobacter species was evaluated in the Microscan® antibiotic susceptibility screening assay of Example 11 using the Neg Combo Type 16 and MIC Plus Type 2 panel plate. The direct growth inhibitory effect of $rBPI_{21}$ on these strains was also evaluated in the same assay. Assays were conducted on clinical isolates of Acinetobacter species (from Baxter Microscan® library, Sacramento, Calif.). Different production lots of $rBPI_{21}$ that had been formulated with surfactant or unformulated (without surfactant) were tested, but no difference was seen in results for formulated or unformulated $rBPI_{21}$.

A summary of the results of the antibiotic screening panels, reported as MICs (μg/ml) of the antibiotic tested, is shown in Tables 27 and 28 below. Results are reported for each strain tested, but susceptibility data is listed for only those antibiotics for which BPI protein product altered susceptibility. The antibiotic susceptibility standards (interpretation of an MIC as resistant, intermediate or susceptible according to Microscan®'s NCCLS-derived standards) applicable to the organism tested appear in Tables 13A and 14A. For interpretation purposes, when antibiotic susceptibility standards were given only for Enterobacter or Pseudomonas, the standards for Acinetobacter were considered to be the same as for Enterobacter.

These results show that BPI protein product reversed resistance of *A. anitratus* strains to amoxicillin/K clavulanate, ampicillin/sulbactam, aztreonam, carbenicillin, cefamandole, cefazolin, cefonicid, cefoperazone, cefotaxime, cefotetan, cefoxitin, ceftazidime, ceftizoxime, ceftriaxone, chloramphenicol, ciprofloxacin, gentamicin, mezlocillin, netilmicin, ticarcillin, ticarcillin/K clavulanate, and trimethoprim/sulfamethoxazole, and increased susceptibility of some *A. anitratus* strains to amikacin, amoxicillin/K clavulanate, ampicillin, ampicillin/sulbactam, azlocillin, aztreonam, carbenicillin, cefamandole, cefazolin, cefonicid, cefoperazone, cefotaxime, cefotetan, cefoxitin, ceftazidime, ceftizoxime, ceftriaxone, cefuroxime, chloramphenicol, ciprofloxacin, gentamicin, imipenem, mezlocillin, netilmicin, ofloxacin, piperacillin, ticarcillin, ticarcillin/K clavulanate, tobramycin and trimethoprim/sulfamethoxazole.

BPI protein product reversed resistance of *A. lwoffii* strains to aztreonam, cefazolin, cefuroxime, ceftazidime, cefoxitin, trimethoprim/sulfamethoxazole and piperacillin, and increased susceptibility of *A. lwoffii* strains to ampicillin; ampicillin/sulbactam, aztreonam, cefazolin, cefotaxime, cefoxitin, ceftazidime, ceftriaxone, cefuroxime, piperacillin, ticarcillin and trimethoprinm/sulfamethoxazole.

These results also show that $rBPI_{21}$ at a concentration of 16 μg/ml has direct bactericidal/growth inhibitory effects on some of the tested Acinetobacter isolates.

TABLE 27

EFFECTS OF $rBPI_{21}$ ± ANTIBIOTICS ON Acinetobacter SPECIES

| Microscan Library ID No. | Antibiotic Tested | Minimum Inhibitory Concentration of Antibiotic (μg/mL) | | |
|---|---|---|---|---|
| | | With 0 μg/mL $rBPI^{21}$ | With 4 μg/mL $rBPI_{21}$ | With 16 μg/mL $rBPI_{21}$ |
| N011-002 (*A. anitratus*) | BPI | G | G | G |
| | Ampicillin | >16 | 16 | 16 |
| | Amikacin | 4 | <2 | <2 |
| N011-003 (*A. anitratus*) | BPI | G | G | G |
| | Ampicillin | 4 | <2 | 4 |
| | Ticarcillin | 16 | <8 | <8 |

TABLE 27-continued

EFFECTS OF $rBPI_{21}$ ± ANTIBIOTICS ON Acinetobacter SPECIES

| Microscan Library ID No. | Antibiotic Tested | Minimum Inhibitory Concentration of Antibiotic (μg/mL) | | |
|---|---|---|---|---|
| | | With 0 μg/mL $rBPI^{21}$ | With 4 μg/mL $rBPI_{21}$ | With 16 μg/mL $rBPI_{21}$ |
| | Cefazolin** | >16 | >16 | 8 |
| | Cefoxitin** | >16 | 8 | 8 |
| | Cefuroxime | 8 | 4 | 8 |
| N011-070 (*A. anitratus*) | BPI | G | Reduced | NG |
| | Ampicillin | 8 | 8 | <2 |
| | Trimeth/Sulfa** | >2 | 2 | <0.5 |
| | Cefazolin** | >16 | >16 | <2 |
| | Cefoxitin* | 16 | 16 | <2 |
| | Cefuroxime* | 16 | 8 | <2 |
| | Ceftazidime | 4 | <2 | <2 |
| N011-071 (*A. anitratus*) | BPI | G | G | Very reduced |
| | Ticarcillin* | 32 | <8 | <8 |
| | Aztreonam | >16 | 16 | 16 |
| | Piperacillin* | 32 | 16 | <8 |
| | Ciprofloxacin** | >2 | 2 | <1 |
| | Ofloxacin* | 4 | <2 | <2 |
| | Ceftazidime | 8 | 8 | 4 |
| | Ceftriaxone | 32 | 16 | 16 |
| | Cefotaxime | 32 | 16 | 16 |
| | Gentamicin** | >6 | >6 | 2 |
| | Tobramycin* | 6 | 4 | 4 |
| | Amikacin** | >16 | 16 | 8 |
| N011-072 (*A. anitratus*) | BPI | G | Reduced | NG |
| | Ampicillin* | 16 | 16 | <2 |
| | Trimeth/Sulfa** | >2 | >2 | <0.5 |
| | Cefazolin** | >16 | >16 | <2 |
| | Cefoxitin* | 16 | 16 | <2 |
| | Cefuroxime | 8 | 8 | <2 |
| | Gentamicin* | 6 | 4 | <1 |
| | Tobramycin | 2 | <1 | <1 |
| | Amikacin | 8 | 4 | <2 |
| N012-001 (*A. lwoffii*) | BPI | G | G | G |
| | Aztreonam** | >16 | >16 | <8 |
| | Cefazolin** | >16 | 8 | <2 |
| | Cefuroxime** | >16 | 4 | <2 |
| | Ceftazidime** | >16 | 4 | <2 |
| | Ampicill/Sulbact | >16 | >16 | 16 |
| | Cefotaxime | 8 | <4 | <4 |
| N012-002 (*A. lwoffii*) | BPI | G | NG | NG |
| | Ampicillin | 4 | <2 | <2 |
| | Trimeth/Sulfa** | >2 | 2 | <0.5 |
| | Aztreonam** | >16 | <8 | <8 |
| | Cefazolin** | >16 | <2 | <2 |
| | Cefoxitin** | >16 | <2 | <2 |
| | Cefuroxime | 8 | <2 | <2 |
| | Ceftazidime | 4 | <2 | <2 |
| N012-003 (*A. lwoffii*) | BPI | G | G | NG |
| | Ampicillin* | >16 | 4 | <2 |
| | Trimeth/Sulfa* | 2 | <0.5 | <0.5 |
| | Ticarcillin* | 64 | <8 | <8 |
| | Aztreonam** | >16 | <8 | <8 |
| | Piperacillin** | >64 | <8 | <8 |
| | Cefazolin** | >16 | >16 | <2 |
| | Cefoxitin** | >16 | 8 | <2 |
| | Cefuroxime** | >16 | <2 | <2 |
| | Ceftazidime* | 16 | <2 | <2 |
| | Ceftriaxone* | 16 | <4 | <4 |
| | Cefotaxime | 8 | <4 | <4 |
| N012-004 (*A. lwoffii*) | BPI | G | G | G |
| | Ampicillin | 4 | <2 | 4 |
| | Trimeth/Sulfa* | 2 | 2 | <0.5 |
| | Cefazolin | >16 | 16 | 16 |
| | Cefoxitin* | 16 | <2 | 4 |
| | Cefuroxime | 4 | <2 | <2 |
| N012-005 (*A. lwoffii*) | BPI | G | G | NG |
| | Ampicillin | 4 | <2 | <2 |
| | Trimeth/Sulfa* | 2 | <0.5 | <0.5 |

TABLE 27-continued

EFFECTS OF rBPI$_{21}$ ± ANTIBIOTICS ON Acinetobacter SPECIES

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 4 μg/mL rBPI$_{21}$ | With 16 μg/mL rBPI$_{21}$ |
| | Cefazolin** | >16 | >16 | 4 |
| | Cefoxitin* | 16 | 8 | 4 |
| | Cefuroxime | 4 | 4 | <2 |

TABLE 28

EFFECTS OF rBPI$_{21}$ ± ANTIBIOTICS ON Acinetobacter SPECIES

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 4 μg/mL rBPI$_{21}$ | With 16 μg/mL rBPI$_{21}$ |
| 12292 (A. anitratus) | Ceftizoxime** | >32 | <2 | <2 |
| | Ceftazidime** | >32 | 32 | <1 |
| | Cefotaxime** | >64 | 8 | <2 |
| | Ceftriaxone** | >64 | <2 | <2 |
| | Cefoperazone** | >32 | 8 | <4 |
| | Cefonicid** | >16 | 16 | <2 |
| | Cefotetan** | >32 | 32 | <4 |
| | Netilmicin** | >16 | <2 | <2 |
| | Cefamandole** | >32 | <4 | <4 |
| | Chloramphenicol** | >16 | <2 | <2 |
| | Ticarcillin* | 64 | 32 | <16 |
| | Azlocillin | >64 | <64 | <64 |
| | Imipenem | 4 | <0.5 | <0.5 |
| | Amp/Sulbact** | 32 | 4 | <1 |
| | Aztreonam** | 32 | 4 | <1 |
| | Amox/K Clavulanate* | 16 | <1 | <1 |
| | Ciprofloxacin** | >4 | 1 | <25 |
| | Ticar/K Clavulanate** | 64 | <16 | <16 |
| | Mezlocillin** | >128 | <16 | <16 |
| | Carbenicillin** | >128 | <16 | <16 |
| 12300 (A. anitratus) | Ceftizoxime** | >32 | >32 | <8 |
| | Ceftazidime | 8 | 8 | 2 |
| | Cefotaxime** | 64 | 64 | <2 |
| | Ceftriaxone* | 32 | 32 | <2 |
| | Cefoperazone | >32 | >32 | 32 |
| | Cefonicid | >16 | >16 | >16 |
| | Cefotetan | >32 | >32 | >32 |
| | Netilmicin | >16 | 16 | 16 |
| | Cefamandole** | >32 | >32 | <4 |
| | Chloramphenicol** | >16 | >16 | 8 |
| | Ticarcillin | <16 | <16 | <16 |
| | Azlocillin | >64 | <64 | <64 |
| | Imipenem | <0.5 | <0.5 | <0.5 |
| | Amp/Sulbact | 2 | 2 | <1 |
| | Aztreonam | 8 | 8 | 4 |
| | Amox/K Clavulanate* | 16 | 16 | <1 |
| | Ciprofloxacin** | >4 | >4 | 1 |
| | Ticar/K Clavulanate | <16 | <16 | <16 |
| | Mezlocillin** | 128 | 128 | <16 |
| | Carbenicillin | <16 | <16 | <16 |
| 12487 (A. anitratus) | Ceftizoxime** | >32 | >32 | <2 |
| | Ceftazidime** | >32 | 2 | 8 |
| | Cefotaxime** | >64 | 64 | 4 |
| | Ceftriaxone** | >64 | >64 | <2 |
| | Cefoperazone** | >32 | >32 | <4 |
| | Cefonicid | >16 | >16 | >16 |
| | Cefotetan | >32 | >32 | 32 |
| | Netilmicin** | >16 | <2 | <2 |
| | Cefamandole** | >32 | <4 | <4 |
| | Chloramphenicol** | >16 | 8 | <2 |
| | Ticarcillin** | 128 | 32 | <16 |
| | Azlocillin | >64 | <64 | <64 |

TABLE 28-continued

EFFECTS OF rBPI$_{21}$ ± ANTIBIOTICS ON Acinetobacter SPECIES

| Microscan Library ID No. | Antibiotic Tested | Minimum Inhibitory Concentration of Antibiotic (μg/mL) | | |
|---|---|---|---|---|
| | | With 0 μg/mL rBPI$^{21}$ | With 4 μg/mL rBPI$_{21}$ | With 16 μg/mL rBPI$_{21}$ |
| | Imipenem | 2 | <0.5 | <0.5 |
| | Amp/Sulbact* | 16 | 2 | <1 |
| | Aztreonam** | 32 | 16 | <1 |
| | Amox/K Clavulanate | 8 | <1 | 2 |
| | Ciprofloxacin* | 2 | 1 | <0.25 |
| | Ticar/K Clavulanate | 32 | <16 | <16 |
| | Mezlocillin** | >128 | 32 | <16 |
| | Carbenicillin** | 128 | <16 | <16 |
| 19687 (A. anitratus) | Ceftizoxime | >32 | >32 | >32 |
| | Ceftazidime | >32 | >32 | >32 |
| | Cefotaxime | >64 | >64 | >64 |
| | Ceftriaxone | >64 | >64 | >64 |
| | Cefoperazone | >32 | >32 | >32 |
| | Cefonicid | >16 | >16 | >16 |
| | Cefotetan | >32 | >32 | >32 |
| | Netilmicin* | 16 | 8 | <2 |
| | Cefamandole | >32 | >32 | >32 |
| | Chloramphenicol** | >16 | 16 | 8 |
| | Ticarcillin | >128 | <16 | 128 |
| | Azlocillin | >64 | >64 | >64 |
| | Imipenem | 4 | 2 | <0.5 |
| | Amp/Sulbact** | 32 | 8 | 2 |
| | Aztreonam | >32 | >32 | >32 |
| | Amox/K Clavulanate** | 32 | 16 | 8 |
| | Ciprofloxacin** | >4 | >4 | 0.5 |
| | Ticar/K Clavalanate | >128 | 128 | <16 |
| | Mezlocillin | >128 | 64 | 32 |
| | Carbenicillin** | >128 | 64 | <16 |
| 19693 (A. anitratus) | Ceftizoxime** | >32 | >32 | 4 |
| | Ceftazidime | >32 | >32 | >32 |
| | Cefotaxime | >64 | 64 | 32 |
| | Ceftriaxone | >64 | 64 | 16 |
| | Cefoperazone** | >32 | >32 | 8 |
| | Cefonicid** | >16 | >16 | <2 |
| | Cefotetan** | >32 | >32 | <4 |
| | Netilmicin | >16 | >16 | >16 |
| | Cefamandole | >32 | >32 | 16 |
| | Chloramphenicol** | >16 | >16 | <2 |
| | Ticarcillin** | >128 | >128 | <16 |
| | Azlocillin | >64 | >64 | <64 |
| | Imipenem | 2 | 2 | <0.5 |
| | Amp/Sulbact** | 32 | 32 | 2 |
| | Aztreonam** | 32 | 16 | <1 |
| | Amox/K Clavulanate* | 16 | 8 | 4 |
| | Ciprofloxacin | >4 | >4 | >4 |
| | Ticar/K Clavulanate** | >128 | 32 | <16 |
| | Mezlocillin** | >128 | 128 | <16 |
| | Carbenicillin** | >128 | >128 | <16 |
| 19694 (A. anitratus) | Ceftizoxime | >32 | >32 | 32 |
| | Ceftazidime* | 16 | 16 | 8 |
| | Cefotaxime | 64 | 64 | 64 |
| | Ceftriaxone | 64 | 64 | 32 |
| | Cefoperazone | >32 | >32 | >32 |
| | Cefonicid** | >16 | >16 | 8 |
| | Cefotetan** | >32 | >32 | 8 |
| | Netilmicin** | >16 | >16 | 4 |
| | Cefamandole | >32 | >32 | >32 |
| | Chloramphenicol | >16 | >16 | 16 |
| | Ticarcillin | >128 | >128 | 32 |
| | Azlocillin | >64 | >64 | >64 |
| | Imipenem | 1 | 1 | <0.5 |
| | Amp/Sulbact | 32 | 32 | 16 |
| | Aztreonam | 8 | 8 | 8 |
| | Amox/K Clavulanate** | 32 | 8 | 4 |
| | Ciprofloxacin | >4 | >4 | >4 |

TABLE 28-continued

EFFECTS OF rBPI$_{21}$ ± ANTIBIOTICS ON Acinetobacter SPECIES

| Microscan Library ID No. | Antibiotic Tested | Minimum Inhibitory Concentration of Antibiotic (µg/mL) | | |
| --- | --- | --- | --- | --- |
| | | With 0 µg/mL rBPI$^{21}$ | With 4 µg/mL rBPI$_{21}$ | With 16 µg/mL rBPI$_{21}$ |
| | Ticar/K Clavulanate** | >128 | <16 | <16 |
| | Mezlocillin | >128 | >128 | 64 |
| | Carbenicillin** | >128 | >128 | <16 |

EXAMPLE 21

EFFECTS OF BPI PROTEIN PRODUCT AND ANTIBIOTICS IN VITRO ON SALMONELLA AND SHIGELLA SPECIES

Ten clinical isolates of Salmonella (F270-001 through -010) and 10 clinical isolates of Shigella (F321-010 and F325-002 through -010) (all isolates from Baxter Microscan® library, Sacramento, Calif.), were evaluated in the Microscan® antibiotic susceptibility screening assay of Example 11 using the Neg Breakpoint Combo Type 9 panel plate. Essentially no effect was seen at rBPI$_{21}$ concentrations of 0, 4 and 16 µg/mL.

EXAMPLE 22

EFFECTS OF BPI PROTEIN PRODUCT ON ANTIBIOTIC KILLING CURVES FOR E. COLI J5, E. COLI 07:K1, ENTEROBACTER CLOACAE, AND KLEBSIELLA PNEUMONIAE

The effect of a BPI protein product, rBPI$_{21}$, on the killing curves of selected antibiotics was determined for selected organisms. Microscan® panel plates were prepared for E. coli J5l, E. coli 07:K1, Enterobacter cloacae (Microscan library ID no. 19680) and Klebsiella pnemnoniae (Microscan library ID no. 16135), according to Example 11. Cell suspensions were added to 25 ml Pluronic Inoculum Water containing 0 or 16 µg/ml rBPI$_{21}$. After inoculation, the panel plates were incubated at 35° C. for 24 hours. At 0, 4, 7 and 24 hours after inoculation, 5 µl samples were removed from each growth control well (containing culture media without antibiotic) and from each well containing: 2/38 µg/ml trimethoprim/sulfamethoxazole, 2 µg/ml ciprofloxacin, 64 µg/ml piperacillin, 32 µg/ml cefotaxime, 6 µg/ml cefuroxime, and 16 µg/ml amikacin. These 5 µl samples were diluted in sterile water and inoculated onto Trypticase Soy agar plates (Remel, Lenexa, Kans.). After 48 hours of incubation at 35° C., the plates were counted and the number of colony forming units of bacteria in the well was calculated.

The results are shown below in FIGS. 19–25. In all of the figures the growth, in the presence of antibiotic but without rBPI$_{21}$, is indicated for: E. coli J5 (a filled square); E. coli 07:K1 (a filled diamond); E. cloacae (a filled triangle); and K. pneumoniae (an "X"). Also, in all figures, the growth in the presence of antibiotic with rBPI$_{21}$ is indicated for E. coli J5 (an open square); E. coli 07:K1 (an open diamond); E. cloacae (an open triangle); and K. pneumoniae (a star).

Figure 19:
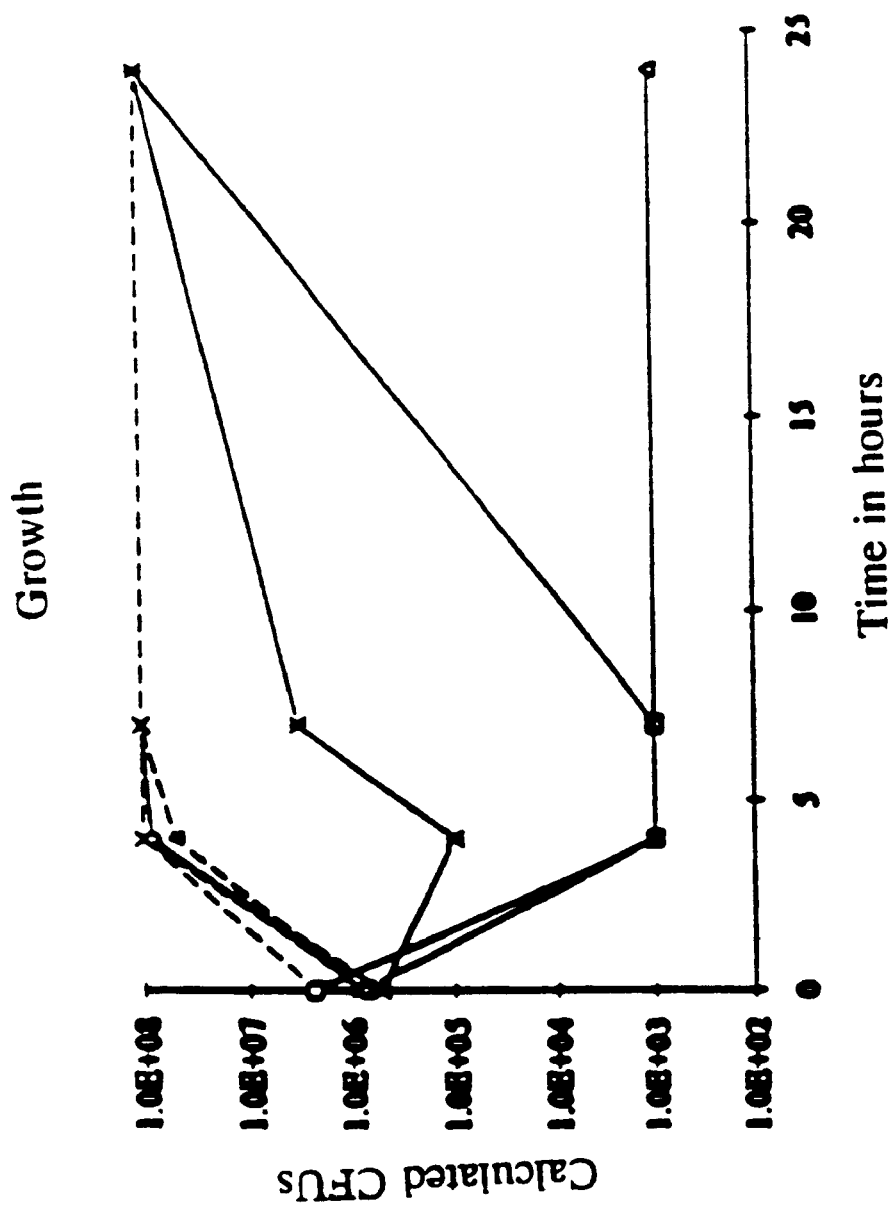
FIGS. 19–25 relate to the synergistic effect of $rBPI_{21}$ on antibiotic killing curves for selected gram-negative organisms.

FIG. 19 shows the kinetic growth curve of organisms with rBPI$_{21}$ (and without antibiotic) and without rBPI$_{21}$ (and without antibiotic). In FIG. 19, the growth curves for E. coli J5 without rBPI$_{21}$ (filled squares), E. coli 07:K1 with rBPI$_{21}$ (open diamonds), E. coli 07:K1 without rBPI$_{21}$ (filled diamonds), and K. pneumoniae without rBPI$_{21}$ ("X"s) overlap substantially, while the growth curves for E. coli J5 with rBPI$_{21}$ (open squares) and E. cloacae with rBPI$_{21}$ (open triangles) overlap at 0–7 hours but diverge by 24 hours. FIG. 19 demonstrates that BPI protein product alone has a bactericidal effect at 0–7 hours on E. coli J5 and K. pneumoniae, and a bactericidal effect on E. cloacae throughout the 24 hour period studied.

Figure 20:
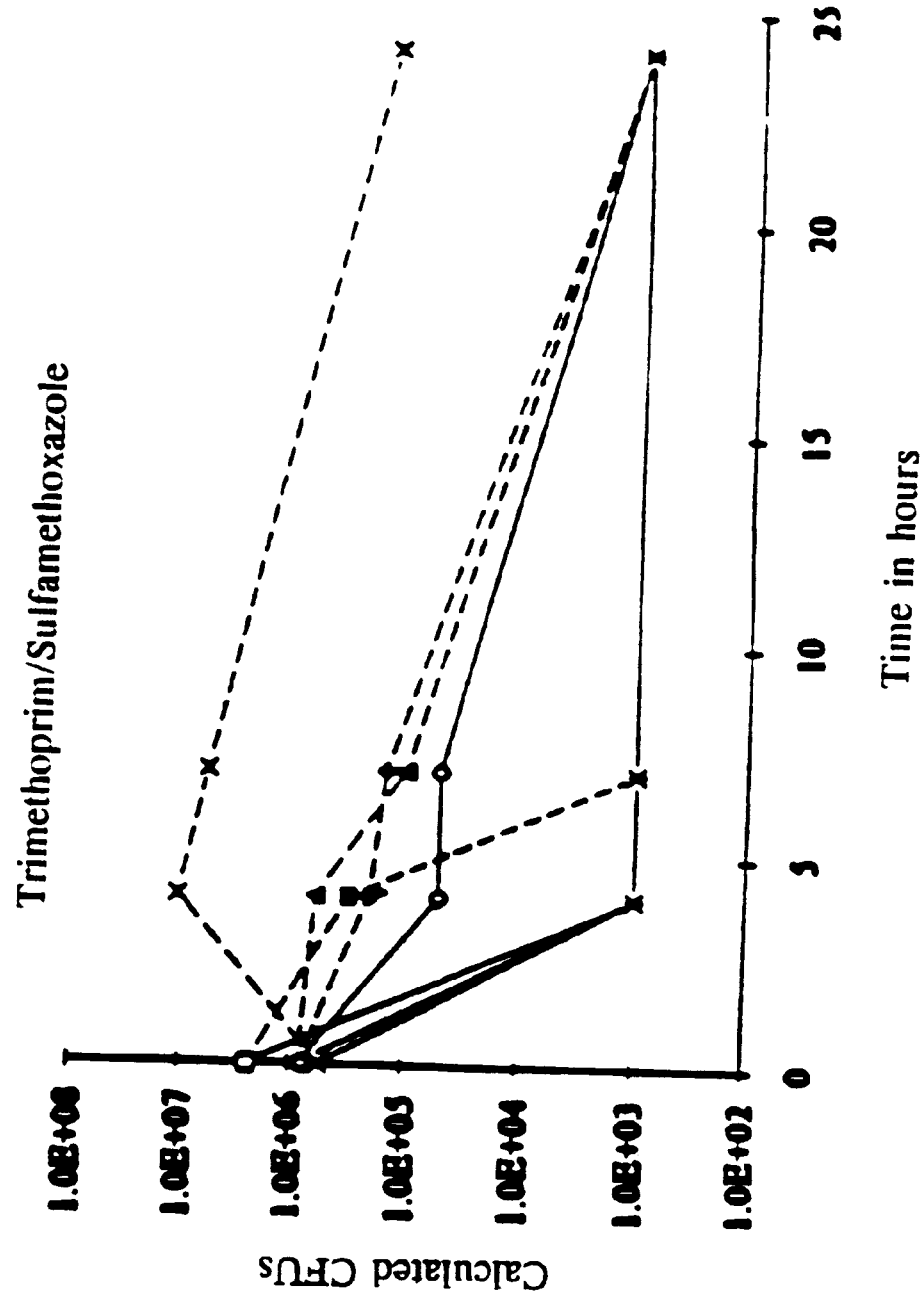

In FIG. 20, the growth curves for E. coli J5 with rBPI$_{21}$ (open squares), E. cloacae with rBPI$_{21}$ (open triangles) and K. pneumoniae with rBPI$_{21}$ (stars) overlap. FIG. 20 shows that rBPI$_{21}$ enhanced the bactericidal effect of trimethoprim/sulfamethoxazole on E. cloacae and K. pneumoniae at 0–24 hours, and slightly enhanced the antibiotics' effect on E. coli J5 and E. coli 07:K1.

Figure 21:
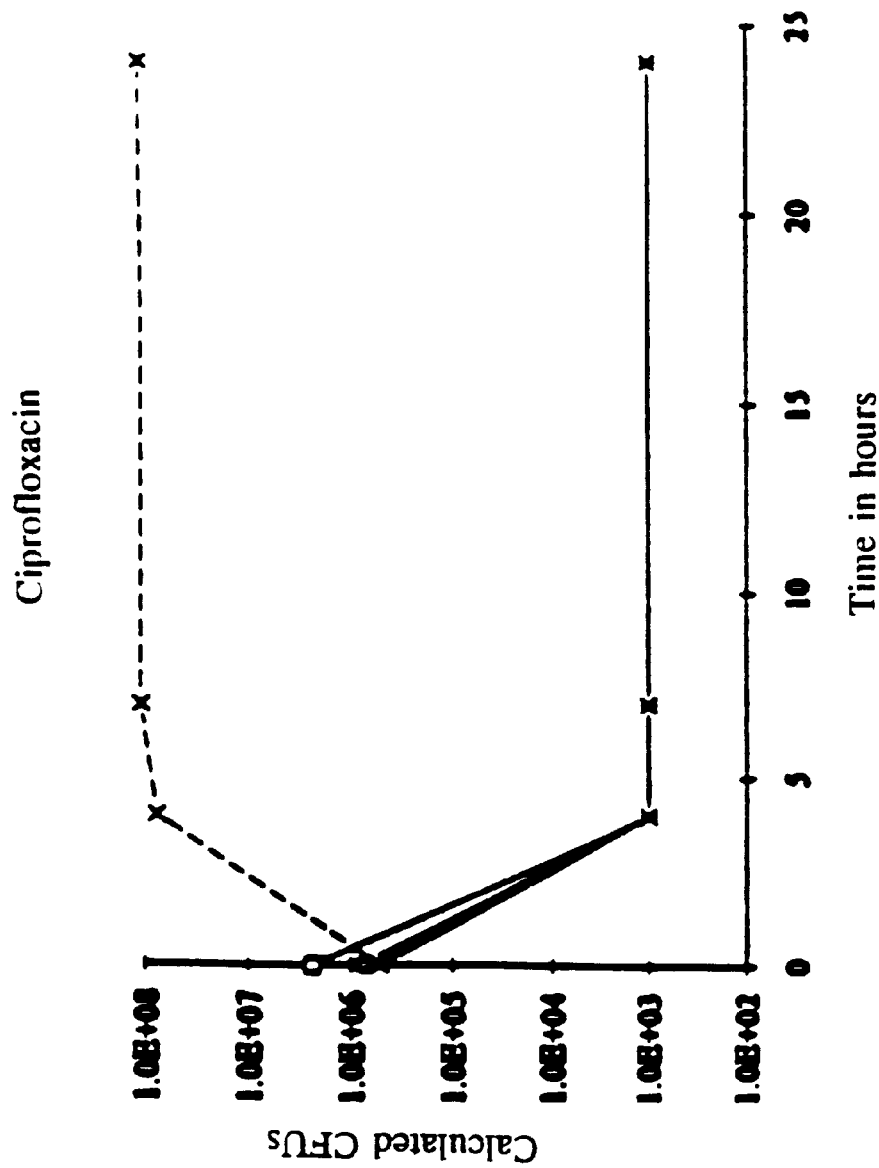

In FIG. 21, the growth curves for E. coli J5 with rBPI$_{21}$ (open squares), E. coli J5 without rBPI$_{21}$ (filled squares), E. coli 07:K1 with rBPI$_{21}$ (open diamonds), E. coli 07:K1 without rBPI$_{21}$ (filled diamonds), E. cloacae with rBPI$_{21}$ (open triangles), E. cloacae without rBPI$_{21}$ (filled triangles), and K. pneumoniae with rBPI$_{21}$ (stars) overlap. FIG. 21 shows that rBPI$_{21}$ reversed resistance of K. pneumoniae to ciprofloxacin at 0–24 hours; the other organisms were already very susceptible to ciprofloxacin.

Figure 22:
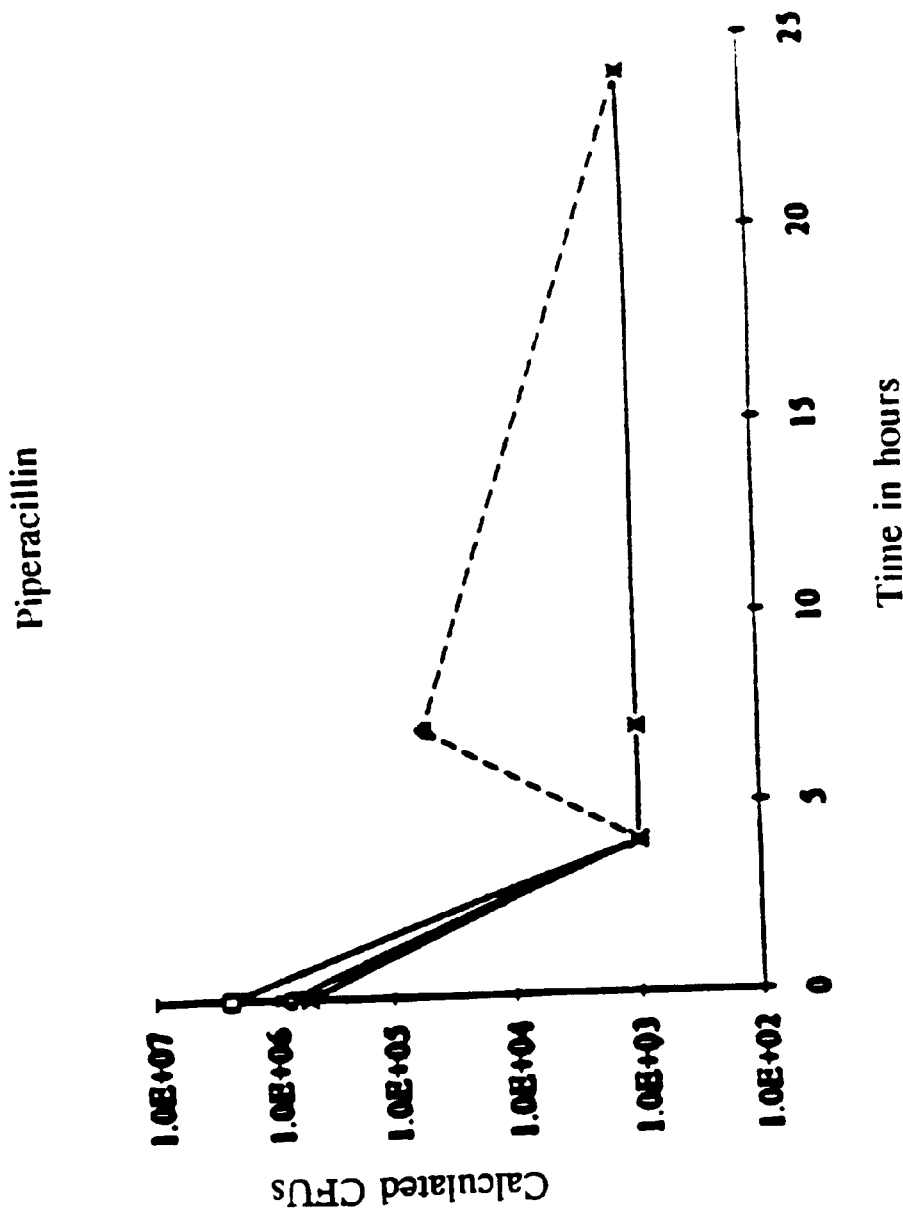

In FIG. 22, the growth curves for E. coli 07:K1 without rBPI$_{21}$ (filled diamonds) and E. cloacae without rBPI$_{21}$ (filled triangles) overlap, while the growth curves for E. coli J5 with rBPI$_{21}$ (open squares), E. coli J5 without rBPI$_{21}$ (filled squares), E. coli 07:K1 with rBPI$_{21}$ (open diamonds), E. cloacae with rBPI$_{21}$ (open triangles), K. pneumoniae without rBPI$_{21}$ ("X"s) and K. pneumoniae with rBPI$_{21}$ (stars) overlap. FIG. 22 shows that rBPI$_{21}$ enhanced the bactericidal effect of piperacillin on E. coli 07:K1 and E. cloacae; the other organisms were already susceptible to the drug.

Figure 23:
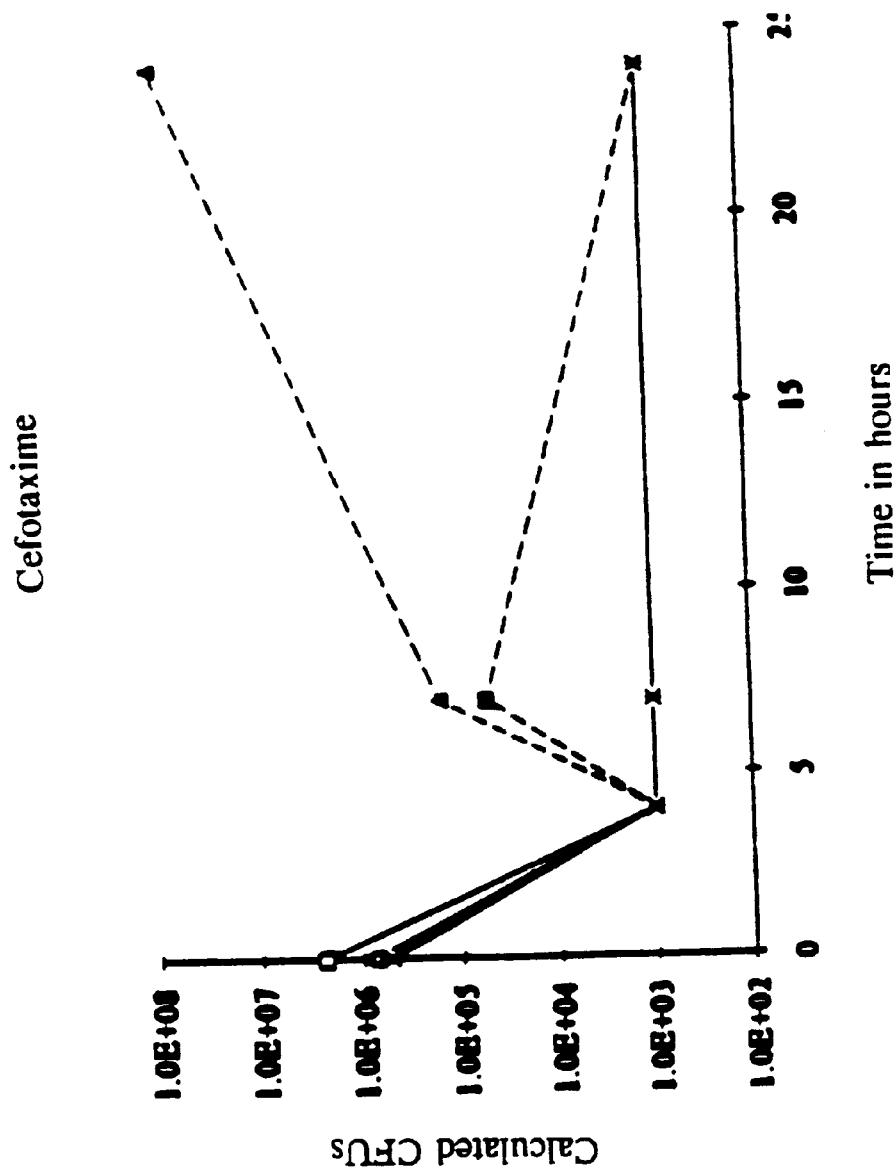

In FIG. 23, the growth curves for E. coli J5 with rBPI$_{21}$ (open squares), E. coli 07:K1 with rBPI$_{21}$ (open diamonds), E. coli 07:K1 without rBPI$_{21}$ (filled diamonds), K. pneumoniae without rBPI$_{21}$ ("X"s) and K. pneumoniae with rBPI$_{21}$ (stars) overlap. FIG. 23 shows that rBPI$_{21}$ enhanced the bactericidal effect of cefotaxime on J5 and E. cloacae; the other organisms were susceptible to the drug.

Figure 24:
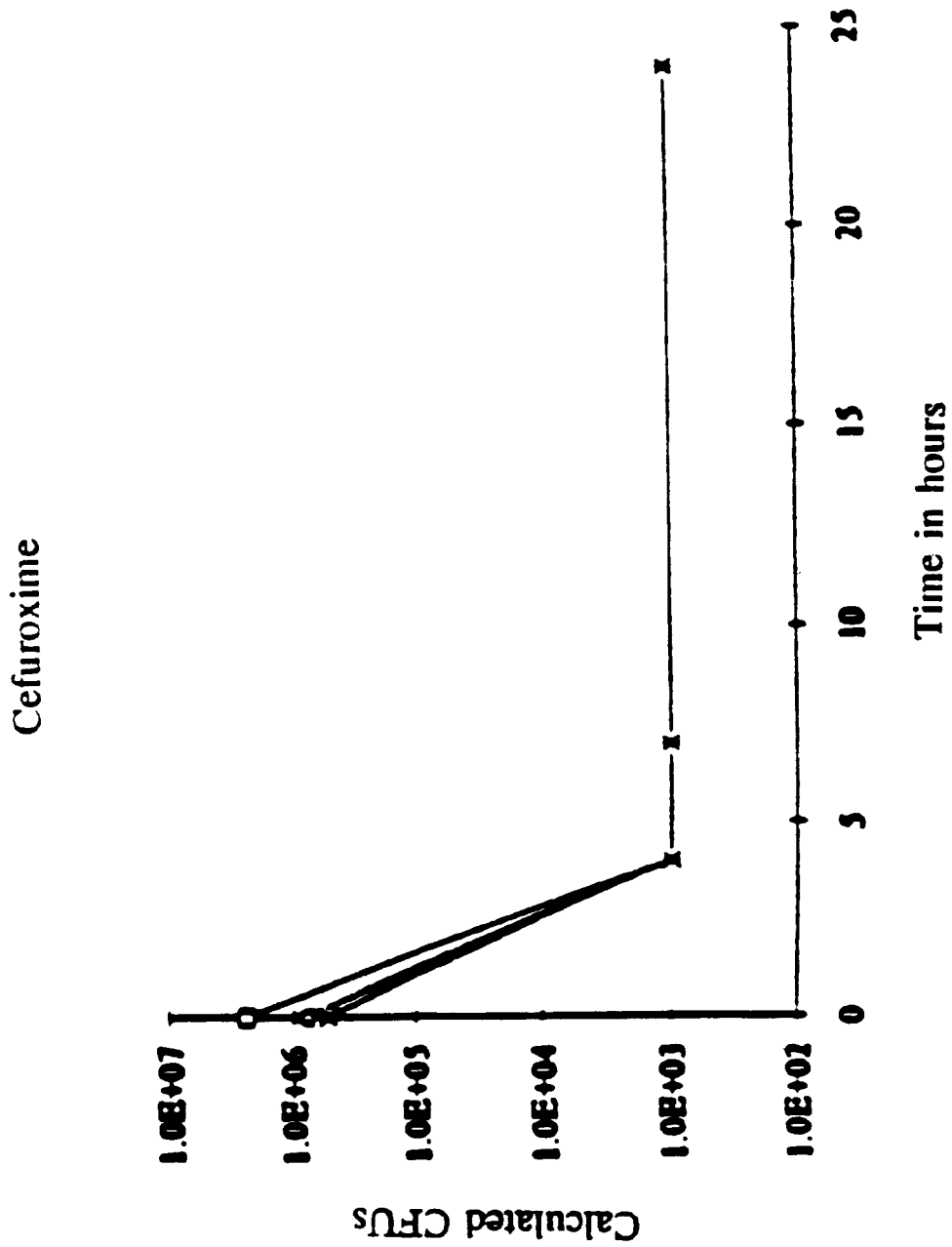

In FIG. 24, all of the curves overlap. FIG. 24 shows the effect of rBPI$_{21}$ and cefuroxime; addition of rBPI$_{21}$ had no effect on the killing curves because all of the tested species were very susceptible to the antibiotic.

Figure 25:
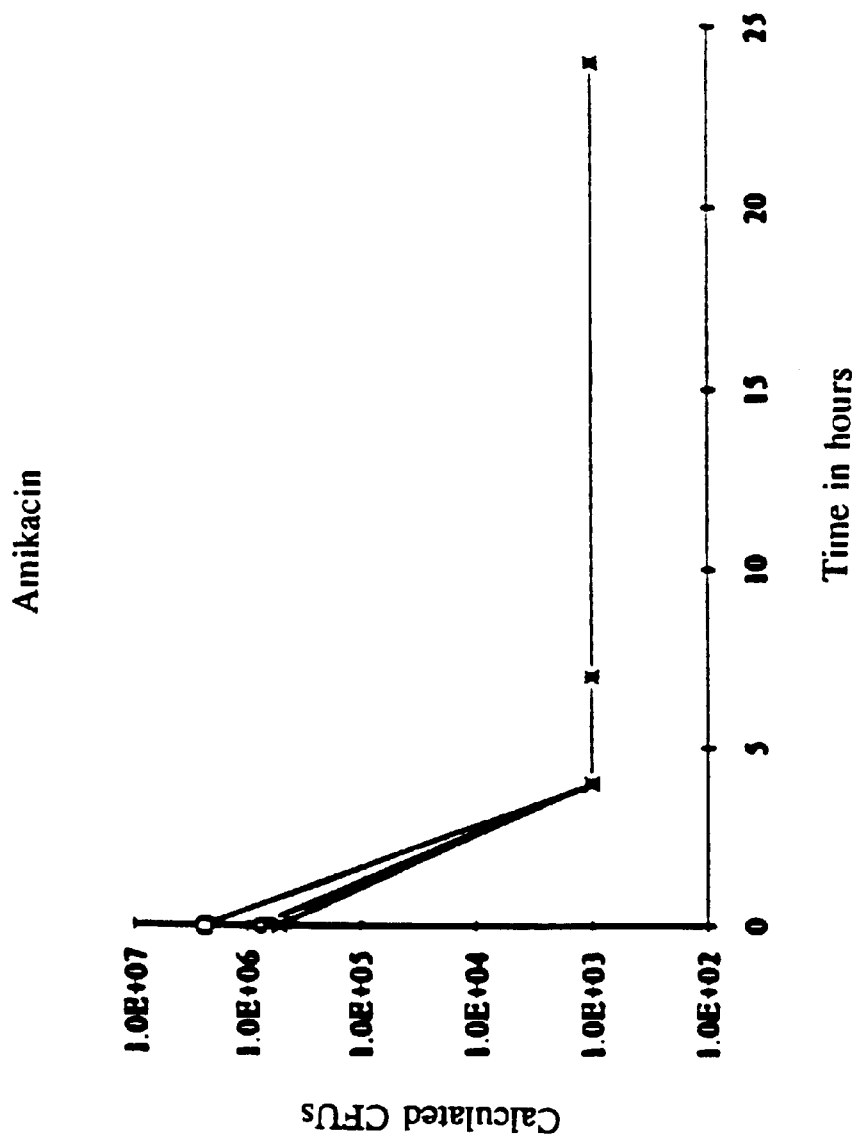

In FIG. 25, all of the curves overlap. FIG. 25 shows the effect of rBPI$_{21}$ and amikacin; again, all tested species were very susceptible to the antibiotic.

EXAMPLE 23

EFFECTS OF A VARIETY OF BPI PROTEIN PRODUCTS AND ANTIBIOTICS IN VITRO ON REPRESENTATIVE GRAM-NEGATIVE ORGANISMS

The effects of a variety of BPI protein products, rBPI$_{21}$, rBPI$_{23}$, rBPI$_{50}$ and rBPI$_{42}$ dimer on the antibiotic susceptibility of various representative gram-negative organisms was evaluated in the Microscan® antibiotic susceptibility screening assay of Example 11 using the MIC Plus Type 2 panel plate. Assays were conducted on clinical isolates of Acinetobacter anitratus and Enterobacter cloacae (from Baxter Microscan® library, Sacramento, Calif.), and on E. coli J5-L and 07:K1.

The results, reported as MICs (µg/ml) of the antibiotic tested at the various concentrations of BPI protein product indicated, are shown in Tables 29, 30, 31 and 32 below.

TABLE 29

EFFECTS OF BPI PROTEIN PRODUCTS ± ANTIBIOTICS ON *A. anitratus* (Microscan ID No. 12292)

Minimum Inhibitory Concentration of Antibiotic (μg/ml) With:

| ANTIBIOTIC TESTED | 0 μg/mL BPI | 4 μg/mL $BPI_{21}$ | 4 μg/mL $BPI_{23}$ | 4 μg/mL $BPI_{50}$ | 4 μg/mL $BPI_{42}$ dimer | 16 μg/mL $BPI_{21}$ | 16 μg/mL $BPI_{23}$ | 16 μg/mL $BPI_{50}$ | 16 μg/mL $BPI_{42}$ dimer |
|---|---|---|---|---|---|---|---|---|---|
| Ceftizoxime | >32 | >32 | >32 | >32 | >32 | >32 | >32 | >32 | >32 |
| Ceftazidime | >32 | 16 | >32 | >32 | >32 | 32 | >32 | >32 | 32 |
| Cefotaxime | >64 | >64 | >64 | >64 | >64 | 16 | >64 | >64 | >64 |
| Ceftriaxone | >64 | 8 | >64 | >64 | >64 | 4 | >64 | >64 | >64 |
| Cefopetazone | >32 | >32 | >32 | >32 | >32 | 32 | >32 | >32 | >32 |
| Cefonicid | >16 | >16 | >16 | >16 | >16 | 8 | >16 | >16 | >16 |
| Cefotetan | >32 | 32 | >32 | >32 | >32 | <4 | >32 | >32 | >32 |
| Netilmicin | >16 | <2 | >16 | >16 | >16 | >16 | >16 | >16 | >16 |
| Cefamandole | >32 | 8 | >32 | >32 | >32 | <4 | >32 | >32 | >32 |
| Chloramphenicol | >16 | <2 | >16 | 16 | >16 | <2 | 16 | 16 | 16 |
| Ticarcillin | 128 | <16 | 128 | 64 | 64 | <16 | 64 | 32 | 64 |
| Azlocillin | >64 | >64 | >64 | >64 | >64 | <64 | >64 | >64 | >64 |
| Imipenem | 4 | <0.5 | 2 | 2 | 2 | <0.5 | 2 | 2 | 2 |
| Ampicillin/Sulbactam | 32 | 4 | 16 | 32 | 16 | <1 | 8 | 16 | 8 |
| Aztreonam | 32 | 16 | 32 | 32 | 32 | 4 | 32 | 32 | 32 |
| Amoxicillin/K Clavulanate | 16 | 2 | 16 | 16 | 8 | 4 | 8 | 8 | 4 |
| Ciprofloxacin | 4 | 2 | 4 | 4 | 4 | 2 | 4 | 4 | 2 |
| Ticarcillin/K Clavulanate | 64 | <16 | 64 | 64 | 32 | 32 | 32 | 32 | 32 |
| Mezlocillin | >128 | 128 | >128 | >128 | >128 | <16 | >128 | >128 | >128 |
| Carbeniclliin | 128 | <16 | 128 | 128 | 64 | <16 | 64 | 64 | 64 |

TABLE 30

EFFECTS OF BPI PROTEIN PRODUCTS ± ANTIBIOTICS ON *E. cloacae* (Microscan ID No. 19680)

Minimum Inhibitory Concentration of Antibiotic (μg/ml) With:

| ANTIBIOTIC TESTED | 0 μg/mL BPI | 4 μg/mL $BPI_{21}$ | 4 μg/mL $BPI_{23}$ | 4 μg/mL $BPI_{50}$ | 4 μg/mL $BPI_{42}$ dimer | 16 μg/mL $BPI_{21}$ | 16 μg/mL $BPI_{23}$ | 16 μg/mL $BPI_{50}$ | 16 μg/mL $BPI_{42}$ dimer |
|---|---|---|---|---|---|---|---|---|---|
| Ceftizoxime | 32 | 32 | 32 | 16 | 32 | <2 | <2 | <2 | 8 |
| Ceftazidime | 32 | 16 | 16 | 32 | 16 | <1 | <1 | <1 | 4 |
| Cefotaxime | 64 | 32 | 32 | 32 | 32 | <2 | <2 | <2 | 16 |
| Ceftriaxone | 32 | 4 | 32 | 32 | 32 | <2 | <2 | <2 | 16 |
| Cefoperazone | 32 | 16 | 16 | 16 | 32 | <4 | <4 | <4 | <4 |
| Cefonicid | >16 | >16 | >16 | >16 | >16 | <2 | <2 | 8 | >16 |
| Cefotetan | 32 | >32 | >32 | >32 | >32 | <4 | <4 | <4 | >32 |
| Netilmicin | <2 | <2 | <2 | <2 | <2 | <2 | <2 | <2 | <2 |
| Cefamandole | >32 | >32 | 32 | >32 | >32 | <4 | <4 | <4 | 16 |
| Chloramphenicol | 8 | 4 | 4 | 4 | 4 | <2 | <2 | <2 | <2 |
| Ticarcillin | >128 | 64 | 64 | 128 | 128 | <16 | <16 | <16 | 64 |
| Azlocillin | >64 | >64 | <64 | >64 | >64 | <64 | <64 | <64 | <64 |
| Imipenem | 1 | <0.5 | <0.5 | <0.5 | <0.5 | <0.5 | <0.5 | <0.5 | <0.5 |
| Ampicillin/Sulbactam | >32 | >32 | >32 | 32 | >32 | 2 | 2 | 4 | 32 |
| Aztreonam | 32 | 8 | 4 | 32 | 16 | <1 | <1 | <1 | 16 |
| Amoxicillin/K Clavulanate | 32 | 32 | 32 | 32 | 32 | 8 | 8 | 16 | >32 |
| Ciprofloxacin | <.25 | <.25 | <.25 | <.25 | <.25 | <.25 | <.25 | <.25 | <.25 |
| Ticarcillin/K Clavulanate | >128 | 64 | 128 | 128 | 128 | <16 | <16 | <16 | 32 |
| Mezlocillin | <16 | <16 | <16 | <16 | <16 | <16 | <16 | <16 | <16 |
| Carbenicillin | >128 | 128 | 64 | 128 | 128 | <16 | <16 | <16 | 128 |

TABLE 31

EFFECTS OF BPI PROTEIN PRODUCTS ± ANTIBIOTICS ON  E. coli  J5-L

Minimum Inhibitory Concentration of Antibiotic (μg/ml) With:

| ANTIBIOTIC TESTED | 0 μg/mL BPI | 4 μg/mL $BPI_{21}$ | 4 μg/mL $BPI_{23}$ | 4 μg/mL $BPI_{50}$ | 4 μg/mL $BPI_{42}$ dimer | 16 μg/mL $BPI_{21}$ | 16 μg/mL $BPI_{23}$ | 16 μg/mL $BPI_{50}$ | 16 μg/mL $BPI_{42}$ dimer |
|---|---|---|---|---|---|---|---|---|---|
| Ceftizoxime | <2 | <2 | <2 | <2 | <2 | <2 | <2 | <2 | <2 |
| Ceftazidime | <1 | <1 | <1 | <1 | <1 | <1 | <1 | <1 | <1 |
| Cefotaxime | <2 | <2 | <2 | <2 | <2 | <2 | <2 | <2 | <2 |
| Ceftriaxone | <2 | <2 | <2 | <2 | <2 | <2 | <2 | <2 | <2 |
| Cefoperazone | <4 | <4 | <4 | <4 | <4 | <4 | <4 | <4 | <4 |
| Cefonicid | <2 | <2 | <2 | <2 | <2 | <2 | <2 | <2 | <2 |
| Cefotetan | <4 | <4 | <4 | <4 | <4 | <4 | <4 | <4 | <4 |
| Neilmicin | <2 | <2 | <2 | <2 | <2 | <2 | <2 | <2 | <2 |
| Cefamandole | <4 | <4 | <4 | <4 | <4 | <4 | <4 | <4 | <4 |
| Chloramphenicol | <2 | <2 | <2 | <2 | <2 | <2 | <2 | <2 | <2 |
| Ticarcillin | <16 | <16 | <16 | <16 | <16 | <16 | <16 | <16 | <16 |
| Azlocillin | <64 | <64 | <64 | <64 | <64 | <64 | <64 | <64 | <64 |
| Imipenem | <0.5 | <0.5 | <0.5 | <0.5 | <0.5 | <0.5 | <0.5 | <0.5 | <0.5 |
| Ampicillin/ Sulbactam | 2 | 2 | 2 | 2 | 2 | <1 | <1 | <1 | 2 |
| Aztreonam | <1 | <1 | <1 | <1 | <1 | <1 | <1 | <1 | |
| Amoxicillin/K Clavulanate | 4 | <1 | 2 | 4 | 2 | <1 | <1 | 2 | 2 |
| Ciprofloxacin | <.25 | <.25 | <.25 | <.25 | <.25 | <.25 | <.25 | <.25 | <.25 |
| Ticarcillin/K Clavulanate | <16 | <16 | <16 | <16 | <16 | <16 | <16 | <16 | <16 |
| Mezlocillin | <16 | <16 | <16 | <16 | <16 | <16 | <16 | <16 | <16 |
| Carbenicillin | <16 | <16 | <16 | <16 | <16 | <16 | <16 | <16 | <16 |

TABLE 32

EFFECTS OF BPI PROTEIN PRODUCTS ± ANTIBIOTICS ON  E. coli  O7:K1

Minimum Inhibitory Concentration of Antibiotic (μg/ml) With:

| ANTIBIOTIC TESTED | 0 μg/mL BPI | 4 μg/mL $BPI_{21}$ | 4 μg/mL $BPI_{23}$ | 4 μg/mL $BPI_{50}$ | 4 μg/mL $BPI_{42}$ dimer | 16 μg/mL $BPI_{21}$ | 16 μg/mL $BPI_{23}$ | 16 μg/mL $BPI_{50}$ | 16 μg/mL $BPI_{42}$ dimer |
|---|---|---|---|---|---|---|---|---|---|
| Ceftizoxime | <2 | <2 | <2 | <2 | <2 | <2 | <2 | <2 | <2 |
| Ceftazidime | <1 | <1 | <1 | <1 | <1 | <1 | <1 | <1 | <1 |
| Cefotaxime | <2 | <2 | <2 | <2 | <2 | <2 | <2 | <2 | <2 |
| Ceftriaxone | <2 | <2 | <2 | <2 | <2 | <2 | <2 | <2 | <2 |
| Cefoperazone | <4 | <4 | <4 | <4 | <4 | <4 | <4 | <4 | <4 |
| Cefonicid | <2 | <2 | <2 | <2 | <2 | <2 | <2 | <2 | <2 |
| Cefotetan | <4 | <4 | <4 | <4 | <4 | <4 | <4 | <4 | <4 |
| Netilmicin | <2 | <2 | <2 | <2 | <2 | <2 | <2 | <2 | <2 |
| Cefamandole | <4 | <4 | <4 | <4 | <4 | <4 | <4 | <4 | <4 |
| Chloramphenicol | <2 | <2 | <2 | <2 | <2 | <2 | <2 | <2 | <2 |
| Ticarcillin | <16 | <16 | <16 | <16 | <16 | <16 | <16 | <16 | <16 |
| Azlocillin | <64 | <64 | <64 | <64 | <64 | <64 | <64 | <64 | <64 |
| Imipenem | <0.5 | <0.5 | <0.5 | <0.5 | <0.5 | <0.5 | <0.5 | <0.5 | <0.5 |
| Ampicillin/ Sulbactam | <1 | <1 | <1 | <1 | <1 | <1 | <1 | <1 | <1 |
| Aztreonam | <1 | <1 | <1 | <1 | <1 | <1 | <1 | <1 | < |
| Amoxicillin/K Clavulanate | <1 | <1 | <1 | <1 | <1 | <1 | <1 | <1 | <1 |
| Ciprofloxacin | <.25 | <.25 | <.25 | <.25 | <.25 | <.25 | <.25 | <.25 | <.25 |
| Ticarcillin/K Clavulanate | <16 | <16 | <16 | <16 | <16 | <16 | <16 | <16 | <16 |
| Mezlocillin | <16 | <16 | <16 | <16 | <16 | <16 | <16 | <16 | <16 |
| Carbenicillin | <16 | <16 | <16 | <16 | <16 | <16 | <16 | <16 | <16 |

EXAMPLE 24

GRAM-NEGATIVE BACTERICIDAL ACTIVITY OF BPI PEPTIDES

BPI peptides were produced according to co-owned and copending PCT Application No. PCT/US94/10427 filed Sep. 15, 1994, which corresponds to U.S. patent application Ser. No. 08/306,473 filed Sep. 15, 1994 now U.S. Pat. No. 5,652,332, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul.

15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference.

The BPI peptides were screened for bactericidal effects on *E. coli* J5 and *E. Coli* 0111:B4 bacteria in a radial diffusion assay. Specifically, an overnight culture of the bacteria was diluted 1:50 into fresh tryptic soy broth and incubated for 3 hours at 37° C. to attain log phase growth of the culture. Bacteria were then pelleted at 3,000 rpm for 5 minutes in a Sorvall RT600B centrifuge (Sorvall Instruments, Newton, TC). 5 mL of 10 mM sodium phosphate buffer (pH 7.4) was added and the preparation was re-pelleted. The supernatant was decanted and 5 mL of fresh buffer was added, the bacteria were resuspended and their concentration was determined by measurement of absorbance at 590 nm (an Absorbance value of 1.00 at this wavelength equals a concentration of about $1.25 \times 10^9$ CFU/mL in suspension). The bacteria were diluted to $4 \times 10^6$ CFU/mL in 10 mL of molten underlayer agarose (at approximately 45° C.) and inverted repeatedly to mix in 15 mL polypropylene tubes conventionally used for this purpose.

The entire contents of such tubes were then poured into a level square petri dish and distributed evenly by rocking the dish side-to-side. The agarose hardened in less than 30 seconds and had a uniform thickness of about 1 mm. A series of wells were then punched into the hardened agarose using a sterile 3 mm punch attached to a vacuum apparatus. The punch was sterilized with 100% alcohol and allowed to air dry prior to use to avoid contaminating the bacterial culture.

5 or 10 μL of each of the BPI peptides were carefully pipetted into each well. As a negative control, dilution buffer (pH 8.3) was added to a separate well, and rBPI$_{23}$ at concentrations of 5 μg/mL and 1 μg/mL were also added as positive controls. Each plate was incubated at 37° C. for 3 hours, and then 10 mL of molten overlayer agarose (at approximately 45° C.) was added into the level petri dish, allowed to harden and incubated overnight at 37° C. The next day, a clear zone was seen against the lawn of bacteria in those wells having bactericidal activity. In order to visually enhance this zone, a dilute Coomassie solution (consisting of 0.002% Coomassie Brilliant Blue, 27% methanol, 15% formaldehyde (37% stock solution) and water) was poured over the agar and allowed to stain for 24 hours. The bacterial zones were measured with a micrometer. The assay results for exemplary peptides (BPI.1 through BPI.169).are summarized in Table 33 for the Gram-negative bacteria *E. coli* J5 (rough) and *E. coli* 0113 (smooth). The bactericidal activities are expressed as the amount of peptide (pmol/well and μg/well) required to generate a 30 mm$^2$ bactericidal zone. Additional exemplary BPI peptides include BPI.221 through BPI.281. BPI peptides which retain antibacterial activity are expected to improve the therapeutic effectiveness of antibiotics when concurrently administered therewith. The peptides are screened for such activity in an in vivo model or according to in vitro tests, including models and tests described herein.

TABLE 33

| BPI Peptide | Sequence ID No. | Bactericidal Activity* | | | |
|---|---|---|---|---|---|
| | | *E. coli* J5 | | *E. coli* O111:B4 | |
| | | (pmol/well) | (μg/well) | (pmol/well) | (μg/well) |
| BPI.1 | 4 | —$^b$ | — | — | — |
| BPI.2 | 7 | >2733.5 | >5 | — | — |
| BPI.3 | 11 | 696 | 2.14 | — | — |
| BPI.4 | 3 | — | — | — | — |
| BPI.5 | 67 | 398 | 1.05 | >1904 | >5 |
| BPI.7 | 54 | 175 | 0.46 | >1890.6 | >5 |
| BPI.8 | 8 | >3797.1 | >5 | — | — |
| BPI.9 | 51 | 479 | 1.02 | >2345.9 | >5 |
| BPI.10 | | 102 | 0.41 | 697 | 2.76 |
| BPI.11 | 13 | 638 | 1.06 | — | — |
| BPI.12 | 14 | 525 | 1.78 | — | — |
| BPI.13 | 15 | 441 | 0.75 | >2923.9 | >5 |
| BPI.14 | 2 | — | — | — | — |
| BPI.15 | 16 | >2797.8 | >5 | — | — |
| BPI.16 | 17 | >2821.5 | >5 | — | — |
| BPI.17 | 18 | >2807.2 | >5 | — | — |
| BPI.18 | 19 | >2757.6 | >5 | — | — |
| BPI.19 | 20 | >2712.8 | >5 | — | — |
| BPI.20 | 21 | >2821.5 | >5 | — | — |
| BPI.21 | 22 | >2917 | >5 | — | — |
| BPI.22 | 23 | >2821.50 | >5 | — | — |
| BPI.23 | 24 | 1330 | 2.36 | >2821.15 | >5 |
| BPI.24 | 25 | 655 | 1.16 | >2821.50 | >5 |
| BPI.25 | 26 | >2866.8 | >5 | — | — |
| BPI.26 | 27 | >2852.1 | >5 | — | — |
| BPI.27 | 28 | >2797.8 | >5 | — | — |
| BPI.28 | 29 | >2821.5 | >5 | — | — |
| BPI.29 | 56 | 442 | 1.5 | >1469.2 | >5 |
| BPI.30 | 52 | 76 | 0.23 | 608 | 1.84 |
| BPI.31 | 33 | 938 | 1.55 | — | — |
| BPI.32 | 34 | 614 | 1.04 | — | — |
| BPI.33 | 35 | 575 | 0.95 | — | — |
| BPI.34 | 36 | 916 | 1.54 | — | — |
| BPI.35 | 37 | 263 | 0.45 | — | — |
| BPI.36 | 38 | 1652 | 2.64 | — | — |
| BPI.37 | 39 | 1284 | 2.14 | — | — |
| BPI.38 | 40 | 1698 | 2.83 | — | — |
| BPI.39 | 41 | 316 | 0.52 | — | — |
| BPI.40 | 42 | 1760 | 2.94 | — | — |
| BPI.41 | 43 | 2465 | 4.03 | — | — |
| BPI.42 | 44 | 265 | 0.44 | >3041.3 | >5 |
| BPI.43 | 45 | 729 | 1.21 | >3024.8 | >5 |
| BPI.44 | 46 | 481 | 0.8 | 2983 | 4.93 |
| BPI.45 | 31 | 1302 | 2.23 | >1696.7 | >5 |
| BPI.46 | 57 | 186 | 0.47 | >1811.2 | >5 |
| BPI.47 | 58 | 98 | 0.25 | 577 | 1.46 |
| BPI.48 | 59 | 42 | 0.1 | 254 | 0.61 |
| BPI.54 | 5 | — | — | — | — |
| BPI.55 | 61 | 299 | 0.75 | >1592.2 | >5 |
| BPI.56 | 47 | 1387 | 2.54 | — | — |
| BPI.57 | 99 | 514 | 1.05 | — | — |
| BPI.58 | 9 | 1050 | 2.03 | — | — |
| BPI.59 | 30 | >2312.3 | >5 | — | — |
| BPI.60 | 32 | >2136.5 | >5 | — | — |
| BPI.61 | 48 | >2093.5 | >5 | — | — |
| BPI.63 | 53 | 87 | 0.31 | 512 | 1.8 |
| BPI.65 oxidized | 10 | 895 | 1.82 | — | — |
| BPI.65 reduced | 68 | 1362 | 2.77 | — | — |
| BPI.66 | 49 | >3496.7 | >5 | — | — |
| BPI.67 | 50 | >1901.8 | >5 | — | — |
| BPI.69 | 60 | 57 | 0.21 | 244 | 0.88 |
| BPI.70 | 63 | — | — | — | — |
| BPI.71 | 64 | 2297 | 4.53 | — | — |
| BPI.72 | 66 | >1911.2 | >5 | — | — |
| BPI.73 | 62 | 57 | 0.11 | >1810.9 | >5 |
| BPI.74 | 70 | 732 | 2.21 | >2148.2 | >5 |
| BPI.75 | 100 | 2030.8 | 4.96 | — | — |
| BPI.76 | 71 | >3906.5 | >5 | — | — |
| BPI.77 | 72 | 455 | 0.85 | — | — |
| BPI.79 | 73 | >2282.9 | >5 | — | — |

TABLE 33-continued

Bactericidal Activity*

| BPI Peptide | Sequence ID No. | E. coli J5 (pmol/well) | (µg/well) | E. coli O111:B4 (pmol/well) | (µg/well) |
|---|---|---|---|---|---|
| BPI.80 | 74 | 655 | 1.24 | — | — |
| BPI.81 | 75 | 284 | 0.52 | >2344.9 | >5 |
| BPI.82 | 76 | 171 | 0.32 | >1197.8 | >5 |
| BPI.83 | 77 | 155 | 0.27 | >2033.5 | >5 |
| BPI.84 | 78 | 12 | 0.02 | >2016.9 | >5 |
| BPI.85 | 79 | 227 | 0.4 | >1881.2 | >5 |
| BPI.86 | 80 | 1520 | 2.58 | — | — |
| BPI.87 | 81 | 189 | 0.32 | >1535.8 | >5 |
| BPI.88 | 82 | 70.32 | 0.13 | 540.15 | 1 |
| BPI.89 | 84 | 229.09 | 0.43 | >1882.4 | >5 |
| BPI.90 | 85 | 83.11 | 0.16 | 1763 | 3.32 |
| BPI.91 | 86 | >3843.5 | >5 | — | — |
| BPI.92 | 87 | 331.8 | 0.57 | — | — |
| BPI.93 | 88 | 212.87 | 0.76 | >980.3 | >5 |
| BPI.94 | 89 | 922.54 | 1.59 | >922.5 | >5 |
| BPI.95 | 90 | 330.88 | 0.6 | >1397.6 | >5 |
| BPI.96 | 101 | 378.33 | 0.65 | >2048.5 | >5 |
| BPI.97 | 92 | 296.58 | 0.53 | — | — |
| BPI.98 | 83 | >1626.1 | >5 | >1626.1 | >5 |
| BPI.99 | 93 | 722.9 | 2.99 | >1064.1 | >5 |
| BPI.100 | 94 | 407.74 | 0.73 | >2655 | >5 |
| BPI.101 | 95 | 1329.3 | 4.79 | >1329.3 | >5 |
| BPI.102 | 96 | >2635.6 | >5 | >2635.6 | >5 |
| BPI.103 | 102 | 165.18 | 0.31 | 415.19 | 0.78 |
| BPI.104 | 103 | 385.85 | 0.64 | 1376.42 | 2.30 |
| BPI.105 | 104 | 65.35 | 0.12 | 206.98 | 0.39 |
| BPI.106 | 105 | 427.12 | 0.72 | >3413.80 | >5 |
| BPI.107 | 106 | 384.67 | 0.68 | >2795.70 | >5 |
| BPI.108 | 107 | 661.05 | 1.17 | >3219.02 | >5 |
| BPI.109 | 108 | 306.80 | 0.54 | >2822.90 | >5 |
| BPI.110 | 109 | 812.33 | 1.44 | >2950.15 | >5 |
| BPI.111 | 110 | 959.00 | 1.71 | >2808.69 | >5 |
| BPI.112 | 111 | 1485.92 | 2.84 | — | — |
| BPI.113 | 112 | 270.66 | 0.50 | >2950.15 | >5 |
| BPI.114 | 113 | 2329.68 | 3.10 | — | — |
| BPI.116 | 114 | 73.82 | 0.13 | >2788.19 | >5 |
| BPI.119 | 115 | 106.70 | 0.20 | 536.44 | 1.02 |
| BPI.120 | 116 | — | — | — | — |
| BPI.121 | 117 | 154.35 | 0.3 | 1856.40 | 3.55 |
| BPI.122 | 118 | 179.89 | 0.36 | 2123.57 | 4.2 |
| BPI.123 | 119 | 247.20 | 0.43 | >2865.02 | >5 |
| BPI.124 | 120 | 91.23 | 0.17 | >2580.12 | >5 |
| BPI.125 | 121 | 428.85 | 0.75 | >3149.74 | >5 |
| BPI.126 | 122 | 1979.97 | 3.39 | — | — |
| BPI.127 | 123 | 406.01 | 0.68 | — | — |
| BPI.128 | 124 | 2271.14 | 3.80 | — | — |
| BPI.129 | 125 | 1685.10 | 2.90 | — | — |
| BPI.130 | 126 | 325.75 | 0.68 | >2903.34 | >5 |
| BPI.131 | 127 | 1438.21 | 2.48 | — | — |
| BPI.132 | 128 | >2988.50 | >5 | — | — |
| BPI.133 | 129 | 2316.59 | 3.91 | — | — |
| BPI.134 | 130 | 162.5 | 0.30 | 580.11 | 1.05 |
| BPI.135 | 131 | 1052.02 | 1.74 | 3321.69 | >5 |
| BPI.136 | 132 | >3030.74 | >5 | — | — |
| BPI.137 | 133 | N.T. | N.T. | N.T. | N.T. |
| BPI.138 | 134 | 64.57 | 0.11 | 995.40 | 1.74 |
| BPI.139 | 135 | 1261.37 | 2.13 | 3793.91 | >5 |
| BPI.140 | 136 | 84.76 | 0.26 | 605.34 | 1.89 |
| BPI.141 | 137 | >2809.51 | >5 | — | — |
| BPI.142 | 138 | 922.21 | 1.76 | — | — |
| BPI.143 | 139 | >2838.99 | >5 | — | — |
| BPI.144 | 140 | 510.02 | 0.86 | — | — |
| BPI.145 | 141 | N.T. | N.T. | N.T. | N.T. |
| BPI.146 | 142 | — | — | — | — |
| BPI.147 | 143 | >2558.17 | >5 | — | — |
| BPI.148 | 144 | >2805.45 | >5 | — | — |
| BPI.149 | 147 | 44.00 | 0.57 | 391.00 | 5.00 |
| BPI.150 | 148 | 220.00 | 0.58 | >2380.67 | >5 |
| BPI.151 | | N.T. | N.T. | N.T. | N.T. |
| BPI.152 | | N.T. | N.T. | N.T. | N.T. |
| BPI.153 | 149 | N.T. | N.T. | N.T. | N.T. |
| BPI.154 | 150 | 197.00 | 0.55 | 2977.76 | >5 |
| BPI.155 | 151 | >1795.66 | >5 | >1795.66 | >5 |
| BPI.156 | 152 | N.T. | N.T. | N.T. | N.T. |
| BPI.157 | 153 | N.T. | N.T. | N.T. | N.T. |
| BPI.158 | 154 | N.T. | N.T. | N.T. | N.T. |
| BPI.159 | 155 | 765.43 | 2.41 | >1589.88 | >5 |
| BPI.160 | 156 | 288.78 | 0.81 | >1781.59 | >5 |
| BPI.161 | 157 | 1201.79 | 2.00 | — | — |
| BPI.162 | 158 | N.T. | N.T. | N.T. | N.T. |
| BPI.163 | 159 | N.T. | N.T. | N.T. | N.T. |
| BPI.164 | 160 | N.T. | N.T. | N.T. | N.T. |
| BPI.165 | 161 | N.T. | N.T. | N.T. | N.T. |
| BPI.166 | 162 | 514.00 | 0.83 | >3078.72 | >5 |
| BPI.167 | 163 | >4585.73 | >5 | — | — |
| BPI.168 | 164 | 1460.98 | 2.87 | >1948.48 | >5 |
| BPI.169 | 165 | 4893.83 | >5 | >4974.43 | >5 |
| BPI.170 | 227 | 3693.06 | >5 | — | — |
| MAP.1* | | 106 | 0.82 | 552.79 | 4.27 |
| MAP.2** | | >690.9 | >5 | >690.9 | >5 |

<sup>a</sup>Amount added to well to achieve a 30 mm² hole as determined by PROBIT analysis as described in Examples 15 and 16.
<sup>b</sup>No detectable activity up to 5 µg/well.
<sup>c</sup>N.T. = not tested
*MAP.1 = β-Ala-Nα,Nε-[Nα,Nε(BPI.2)Lys]Lys
**MAP.2 = β-Ala-Nα,Nε-[Nα,Nε(BPI.13)Lys]Lys

EXAMPLE 25

EFFECTS OF CONCURRENT ADMINISTRATION OF BPI PROTEIN PRODUCT AND TETRACYCLINE OR GENTAMICIN ON E. COLI 0111:B4

Additional MIC assays were performed to determine the sensitivity of E. coli 0111:B4 (as described in Example 1) to the effects of BPI protein products concurrently administered with the antibiotic tetracycline or with the antibiotic gentamicin.

For these experiments, organisms were grown overnight at 37° C. in 5 mL of Mueller-Hinton broth. This overnight culture was diluted 1:50 into 5 mL of fresh broth and incubated for an additional 3 hours at 37° C. to attain log-phase growth. Bacteria were pelleted for 5 minutes at 1500 ×g and resuspended in fresh broth to give a final concentration of $2 \times 10^6$ cells per mL.

$rBPI_{23}$ and antibiotic (either tetracycline or gentamicin) were diluted such that 100 µl bacterial suspension, 50 µl antibiotic and 50 Al diluted $rBPI_{23}$, gave concentrations in serial dilutions from 10 µg/mL tetracycline or 2.5 µg/mL gentamicin and from 30 µg/mL $rBPI_{23}$ with a fixed concentration of $10^6$ cells/mL. Incubation was carried out in flat bottom 96 well microtiter plates for 18 hours at 37° C., and the plates were read in an automatic plate reader (Titretek Multiscan) at 590 nm.

A 4–6 fold decrease in absorbance was observed with tetracycline or gentamicin with certain concentrations of BPI protein product. The MIC of tetracycline without $rBPI_{23}$ of 10 µg/mL and was reduced by $rBPI_{23}$ to 5 µg/mL. The MIC of gentamicin without $rBPI_{23}$ was 0.6 µg/mL and was reduced by $rBPI_{23}$ to 0.3 µg/mL.

A partial summary of the data described in the foregoing examples, grouped by general classes of antibiotics, appears below in Table 34 and is displayed as the effects of BPI protein products on the therapeutic effectiveness of antibiotics for various gram-negative organisms.

TABLE 34

| ANTIBIOTIC CLASS | EFFECTS OF BPI PROTEIN PRODUCT WHEN CONCURRENTLY ADMINISTERED WITH ANTIBIOTICS WITHIN CLASS |
|---|---|
| β-lactams: penicillins and cephalosporins | reversed resistance of Pseudomonas aeruginosa, other Pseudomonas, Xanthamonas, E. coli, Citrobacter, Klebsiella, Enterobacter, Serratia, Providencia, Acinetobacter increased susceptibility of Pseudomonas aeruginosa, other Pseudomonas, E. coli, Citrobacter, Klebsiella, Enterobacter, Serratia, Proteus, Providencia, Morganella, Acinetobacter enhanced early bactericidal effect for E. coli, Enterobacter in killing curves in vivo synergy shown for treatment of E. coli infection in mouse and rabbit models |
| β-lactams other than penicillins and cephalosporins: aztreonam and imipenem | aztreonam: reversed resistance of Pseudomonas aeruginosa, Acinetobacter increased susceptibility of Acinetobacter increased susceptibility of Pseudomonas aeruginosa, Citrobacter, Enterobacter imipenem: increased susceptibility of Pseudomonas aeruginosa, Proteus, Providencia, Acinetobacter |
| aminoglycosides | reversed resistance of Pseudomonas aeruginosa, Xanthamonas, Acinetobacter increased susceptibility of Pseudomonas aeruginosa, other Pseudomonas, E. coli, Citrobacter, Serratia, Proteus, Providencia, Morganella, Acinetobacter checkerboard synergy (FIC < 0.5) for E. coli, Salmonella, Klebsiella, Edwardsiella; greater than additive interaction (FIC ≦ 1.0) for Pseudomonas aeruginosa, Enterobacter |
| sulfonamides and trimethoprim | in vivo synergy shown for treatment of E. coli infection in mouse model reversed resistance of Pseudomonas aeruginosa, Xanthamonas, Klebsiella, Acinetobacter increased susceptibility of Enterobacter, Proteus, Acinetobacter enhanced early bactericidal effect for Klebsiella, Enterobacter in killing curves; slight early enhancement for E. coli |
| fluoroquinolones and quinolones | reversed resistance of Pseudomonas aeruginosa, Acinetobacter increased susceptibility of Pseudomonas aeruginosa, Xanthamonas, Enterobacter, Acinetobacter reversed resistance of Klebsiella in antibiotic killing curves |
| polymyxins | checkerboard synergy (FIC < 0.5) for Pseudomonas aeruginosa, E. coli, Providencia; additive interaction (FIC ≦ 1.0) for Enterobacter |
| chloramphenicol | reversed resistance and increased susceptibility for Acinetobacter |

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

What is claimed is:

1. In a method of enhancing the effect of antibiotic treatment of a patient infected with gram-negative bacteria by concurrently administering bactericidal/permeability-increasing (BPI) protein and an antibiotic, the improvement comprising concurrently administering BPI protein product and tetracycline in the treatment of a patient infected with an Eschenrichia gram-negative bacterial species.

2. In a method for treating a patient infected with a Klebsiella gram-negative bacterial species that is resistant to ciprofloxacin, the improvement comprising the step of concurrently administering the antibiotic and an amount of BPI protein product effective to reverse the resistance of the gram-negative bacterial species to the antibiotic.

3. The method of any one of claims 1 or 2 wherein the BPI protein product is an N-terminal fragment of BPI protein with a molecular weight of approximately 21 to 25 kD, or a dimeric form thereof.

4. The method of any one of claims 1 or 2 wherein the BPI protein product is $rBPI_{23}$, $rBPI_{21}$, or $rBPI_{50}$.

* * * * *

UNITED STATES PATENT AND TRADEMARK OFFICE
CERTIFICATE OF CORRECTION

PATENT NO. : 6,140,306
DATED : October 31, 2000
INVENTOR(S) : Lambert et al

Page 1 of 1

It is certified that error appears in the above-identified patent and that said Letters Patent is hereby corrected as shown below:

<u>Column 217</u>,
Line 33, in claim 1, "Eschenrichia" should be --Escherichia--.
Line 35, in claim 2, "Klebsiella" should be --Klebsiella--.

Signed and Sealed this

Twelfth Day of June, 2001

*Attest:*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,140,306 | Page 1 of 1 |
| DATED | : October 31, 2000 | |
| INVENTOR(S) | : Lambert et al | |

It is certified that error appears in the above-identified patent and that said Letters Patent is hereby corrected as shown below:

Column 217,
Line 33, in claim 1, "Eschenrichia" should be --*Escherichia*--.
Line 35, in claim 2, "Klebsiella" should be --*Klebsiella*--.

Signed and Sealed this

Twenty-sixth Day of June, 2001

*Attest:*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 227

(2) INFORMATION FOR SEQ ID NO:1:

(i) SEQUENCE CHARACTERISTICS:
      (A) LENGTH: 29 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "Domain I"

(xi) SEQUENCE DESCRIPTION: SEQ ID NO:1:

Ala Ser Gln Gln Gly Thr Ala Ala Leu Gln Lys Glu Leu Lys Arg Ile
1             5                   10               15

Lys Ile Pro Asp Tyr Ser Asp Ser Phe Lys Ile Lys His
           20                 25

(2) INFORMATION FOR SEQ ID NO:2:

(i) SEQUENCE CHARACTERISTICS:
      (A) LENGTH: 30 amino acids
      (B) TYPE: amino acid

```
            (D) TOPOLOGY: linear (ii) MOLECULE TYPE: peptide (ix) FEATURE:
            (A) NAME/KEY: misc_feature
            (D) OTHER INFORMATION: "BPI.14"

(xi) SEQUENCE DESCRIPTION: SEQ ID NO:2:

Gly Thr Ala Ala Leu Gln Lys Glu Leu Lys Arg Ile Lys Ile Pro Asp
1               5                  10                  15

Tyr Ser Asp Ser Phe Lys Ile Lys His Leu Gly Lys Gly His
            20                  25                  30

(2) INFORMATION FOR SEQ ID NO:3:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.4"

(xi) SEQUENCE DESCRIPTION: SEQ ID NO:3:

Leu Gln Lys Glu Leu Lys Arg Ile Lys Ile Pro Asp Tyr Ser Asp Ser
1               5                  10                  15

Phe Lys Ile Lys His Leu
            20

(2) INFORMATION FOR SEQ ID NO:4:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.1"

(xi) SEQUENCE DESCRIPTION: SEQ ID NO:4:

Gln Gln Gly Thr Ala Ala Leu Gln Lys Glu Leu Lys Arg Ile Lys
1               5                  10                  15

(2) INFORMATION FOR SEQ ID NO:5:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.54"

(xi) SEQUENCE DESCRIPTION: SEQ ID NO:5:

Gly Thr Ala Ala Leu Gln Lys Glu Leu Lys Arg Ile Lys Ile Pro
1               5                  10                  15

(2) INFORMATION FOR SEQ ID NO:6:
```

(i) SEQUENCE CHARACTERISTICS:
        (A) LENGTH: 35 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "Domain II"

(xi) SEQUENCE DESCRIPTION: SEQ ID NO:6:

Ser Ser Gln Ile Ser Met Val Pro Asn Val Gly Leu Lys Phe Ser Ile
1               5                   10                  15

Ser Asn Ala Asn Ile Lys Ile Ser Gly Lys Trp Lys Ala Gln Lys Arg
            20                  25                  30

Phe Leu Lys
        35

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.2"

(xi) SEQUENCE DESCRIPTION: SEQ ID NO:7:

Ile Lys Ile Ser Gly Lys Trp Lys Ala Gln Lys Arg Phe Leu Lys
1               5                   10                  15

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.8"

(xi) SEQUENCE DESCRIPTION: SEQ ID NO:8:

Lys Trp Lys Ala Gln Lys Arg Phe Leu Lys
1               5                   10

(2) INFORMATION FOR SEQ ID NO:9:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.58"

(xi) SEQUENCE DESCRIPTION: SEQ ID NO:9:

Cys Ile Lys Ile Ser Gly Lys Trp Lys Ala Gln Lys Arg Phe Leu Lys
1               5                   10                  15

```
(2) INFORMATION FOR SEQ ID NO:10:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.65 oxidized"

(xi) SEQUENCE DESCRIPTION: SEQ ID NO:10:

Cys Ile Lys Ile Ser Gly Lys Trp Lys Ala Gln Lys Arg Phe Leu Lys
1               5                   10                  15

Cys (2) INFORMATION FOR SEQ ID NO:11:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.3"

(xi) SEQUENCE DESCRIPTION: SEQ ID NO:11:

Asn Val Gly Leu Lys Phe Ser Ile Ser Asn Ala Asn Ile Lys Ile Ser
1               5                   10                  15

Gly Lys Trp Lys Ala Gln Lys Arg Phe Leu Lys
            20                  25

(2) INFORMATION FOR SEQ ID NO:12:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "Domain III"

(xi) SEQUENCE DESCRIPTION: SEQ ID NO:12:

Val His Val His Ile Ser Lys Ser Lys Val Gly Trp Leu Ile Gln Leu
1               5                   10                  15

Phe His Lys Lys Ile Glu Ser Ala Leu Arg Asn Lys
            20                  25

(2) INFORMATION FOR SEQ ID NO:13:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.11"
```

(xi) SEQUENCE DESCRIPTION: SEQ ID NO:13:

Lys Ser Lys Val Trp Leu Ile Gln Leu Phe His Lys Lys
1               5                   10

(2) INFORMATION FOR SEQ ID NO:14:

(i) SEQUENCE CHARACTERISTICS:
            (A) LENGTH: 29 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.12"

(xi) SEQUENCE DESCRIPTION: SEQ ID NO:14:

Ser Val His Val His Ile Ser Lys Ser Lys Val Gly Trp Leu Ile Gln
1               5                   10                  15

Leu Phe His Lys Lys Ile Glu Ser Ala Leu Arg Asn Lys
            20                  25

(2) INFORMATION FOR SEQ ID NO:15:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.13"

(xi) SEQUENCE DESCRIPTION: SEQ ID NO:15:

Lys Ser Lys Val Gly Trp Leu Ile Gln Leu Phe His Lys Lys
1               5                   10

(2) INFORMATION FOR SEQ ID NO:16:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.15"

(xi) SEQUENCE DESCRIPTION: SEQ ID NO:16:

Ala Lys Ile Ser Gly Lys Trp Lys Ala Gln Lys Arg Phe Leu Lys
1               5                   10                  15

(2) INFORMATION FOR SEQ ID NO:17:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.16"

```
       (xi) SEQUENCE DESCRIPTION: SEQ ID NO:17:

Ile Ala Ile Ser Gly Lys Trp Lys Ala Gln Lys Arg Phe Leu Lys
1               5                   10                  15

(2) INFORMATION FOR SEQ ID NO:18:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.17"

(xi) SEQUENCE DESCRIPTION: SEQ ID NO:18:

Ile Lys Ala Ser Gly Lys Trp Lys Ala Gln Lys Arg Phe Leu Lys
1               5                   10                  15

(2) INFORMATION FOR SEQ ID NO:19:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.18"

(xi) SEQUENCE DESCRIPTION: SEQ ID NO:19:

Ile Lys Ile Ala Gly Lys Trp Lys Ala Gln Lys Arg Phe Leu Lys
1               5                   10                  15

(2) INFORMATION FOR SEQ ID NO:20:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.19"

(xi) SEQUENCE DESCRIPTION: SEQ ID NO:20:

Ile Lys Ile Ser Ala Lys Trp Lys Ala Gln Lys Arg Phe Leu Lys
1               5                   10                  15

(2) INFORMATION FOR SEQ ID NO:21:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.20"

(xi) SEQUENCE DESCRIPTION: SEQ ID NO:21:

Ile Lys Ile Ser Gly Ala Trp Lys Ala Gln Lys Arg Phe Leu Lys
```

```
                1               5              10              15
```

(2) INFORMATION FOR SEQ ID NO:22:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.21"

(xi) SEQUENCE DESCRIPTION: SEQ ID NO:22:

```
Ile Lys Ile Ser Gly Lys Ala Lys Ala Gln Lys Arg Phe Leu Lys
1               5              10              15
```

(2) INFORMATION FOR SEQ ID NO:23:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.22"

(xi) SEQUENCE DESCRIPTION: SEQ ID NO:23:

```
Ile Lys Ile Ser Gly Lys Trp Ala Ala Gln Lys Arg Phe Leu Lys
1               5              10              15
```

(2) INFORMATION FOR SEQ ID NO:24:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.23"

(xi) SEQUENCE DESCRIPTION: SEQ ID NO:24:

```
Ile Lys Ile Ser Gly Lys Trp Lys Ala Ala Lys Arg Phe Leu Lys
1               5              10              15
```

(2) INFORMATION FOR SEQ ID NO:25:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.24"

(xi) SEQUENCE DESCRIPTION: SEQ ID NO:25:

```
Ile Lys Ile Ser Gly Lys Trp Lys Ala Gln Ala Arg Phe Leu Lys
1               5              10              15
```

```
(2) INFORMATION FOR SEQ ID NO:26:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.25"

(xi) SEQUENCE DESCRIPTION: SEQ ID NO:26:

Ile Lys Ile Ser Gly Lys Trp Lys Ala Gln Lys Ala Phe Leu Lys
1               5                   10                  15

(2) INFORMATION FOR SEQ ID NO:27:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.26"

(xi) SEQUENCE DESCRIPTION: SEQ ID NO:27:

Ile Lys Ile Ser Gly Lys Trp Lys Ala Gln Lys Arg Ala Leu Lys
1               5                   10                  15

(2) INFORMATION FOR SEQ ID NO:28:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.27"

(xi) SEQUENCE DESCRIPTION: SEQ ID NO:28:

Ile Lys Ile Ser Gly Lys Trp Lys Ala Gln Lys Arg Phe Ala Lys
1               5                   10                  15

(2) INFORMATION FOR SEQ ID NO:29:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.28"

(xi) SEQUENCE DESCRIPTION: SEQ ID NO:29:

Ile Lys Ile Ser Gly Lys Trp Lys Ala Gln Lys Arg Phe Leu Ala
1               5                   10                  15

(2) INFORMATION FOR SEQ ID NO:30:

(i) SEQUENCE CHARACTERISTICS:
```

(A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.59"

(xi) SEQUENCE DESCRIPTION: SEQ ID NO:30:

Ile Lys Ile Ser Gly Ala Trp Ala Ala Gln Lys Arg Phe Leu Lys
1               5                   10                  15

(2) INFORMATION FOR SEQ ID NO:31:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.45"

(xi) SEQUENCE DESCRIPTION: SEQ ID NO:31:

Ile Lys Ile Ser Gly Lys Trp Lys Ala Ala Arg Phe Leu Lys
1               5                   10                  15

(2) INFORMATION FOR SEQ ID NO:32:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.60"

(xi) SEQUENCE DESCRIPTION: SEQ ID NO:32:

Ile Ala Ile Ser Gly Lys Trp Lys Ala Gln Lys Arg Phe Leu Ala
1               5                   10                  15

(2) INFORMATION FOR SEQ ID NO:33:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.31"

(xi) SEQUENCE DESCRIPTION: SEQ ID NO:33:

Ala Ser Lys Val Gly Trp Leu Ile Gln Leu Phe His Lys Lys
1               5                   10

(2) INFORMATION FOR SEQ ID NO:34:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.32"

(xi) SEQUENCE DESCRIPTION: SEQ ID NO:34:

Lys Ala Lys Val Gly Trp Leu Ile Gln Leu Phe His Lys Lys
1               5                   10

(2) INFORMATION FOR SEQ ID NO:35:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.33"

(xi) SEQUENCE DESCRIPTION: SEQ ID NO:35:

Lys Ser Ala Val Gly Trp Leu Ile Gln Leu Phe His Lys Lys
1               5                   10

(2) INFORMATION FOR SEQ ID NO:36:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.34"

(xi) SEQUENCE DESCRIPTION: SEQ ID NO:36:

Lys Ser Lys Ala Gly Trp Leu Ile Gln Leu Phe His Lys Lys
1               5                   10

(2) INFORMATION FOR SEQ ID NO:37:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.35"

(xi) SEQUENCE DESCRIPTION: SEQ ID NO:37:

Lys Ser Lys Val Ala Trp Leu Ile Gln Leu Phe His Lys Lys
1               5                   10

(2) INFORMATION FOR SEQ ID NO:38:

(i) SEQUENCE CHARACTERISTICS:
            (A) LENGTH: 14 amino acids
            (B) TYPE: amino acid
            (D) TOPOLOGY: linear (ii) MOLECULE TYPE: peptide

```
         (ix) FEATURE:
               (A) NAME/KEY: misc_feature
               (D) OTHER INFORMATION: "BPI.36"

(xi) SEQUENCE DESCRIPTION: SEQ ID NO:38:

Lys Ser Lys Val Gly Ala Leu Ile Gln Leu Phe His Lys Lys
1               5                  10

(2) INFORMATION FOR SEQ ID NO:39:

(i) SEQUENCE CHARACTERISTICS:
               (A) LENGTH: 14 amino acids
               (B) TYPE: amino acid
               (D) TOPOLOGY: linear (ii) MOLECULE TYPE: peptide (ix) FEATURE:
               (A) NAME/KEY: misc_feature
               (D) OTHER INFORMATION: "BPI.37"

(xi) SEQUENCE DESCRIPTION: SEQ ID NO:39:

Lys Ser Lys Val Gly Trp Ala Ile Gln Leu Phe His Lys Lys
1               5                  10

(2) INFORMATION FOR SEQ ID NO:40:

(i) SEQUENCE CHARACTERISTICS:
               (A) LENGTH: 14 amino acids
               (B) TYPE: amino acid
               (D) TOPOLOGY: linear (ii) MOLECULE TYPE: peptide (ix) FEATURE:
               (A) NAME/KEY: misc_feature
               (D) OTHER INFORMATION: "BPI.38"

(xi) SEQUENCE DESCRIPTION: SEQ ID NO:40:

Lys Ser Lys Val Gly Trp Leu Ala Gln Leu Phe His Lys Lys
1               5                  10

(2) INFORMATION FOR SEQ ID NO:41:

(i) SEQUENCE CHARACTERISTICS:
               (A) LENGTH: 14 amino acids
               (B) TYPE: amino acid
               (D) TOPOLOGY: linear (ii) MOLECULE TYPE: peptide (ix) FEATURE:
               (A) NAME/KEY: misc_feature
               (D) OTHER INFORMATION: "BPI.39"

(xi) SEQUENCE DESCRIPTION: SEQ ID NO:41:

Lys Ser Lys Val Gly Trp Leu Ile Ala Leu Phe His Lys Lys
1               5                  10

(2) INFORMATION FOR SEQ ID NO:42:

(i) SEQUENCE CHARACTERISTICS:
               (A) LENGTH: 14 amino acids
               (B) TYPE: amino acid
               (D) TOPOLOGY: linear (ii) MOLECULE TYPE: peptide (ix) FEATURE:
               (A) NAME/KEY: misc_feature
               (D) OTHER INFORMATION: "BPI.40"
```

(xi) SEQUENCE DESCRIPTION: SEQ ID NO:42:

Lys Ser Lys Val Gly Trp Leu Ile Gln Ala Phe His Lys Lys
1               5                  10

(2) INFORMATION FOR SEQ ID NO:43:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.41"

(xi) SEQUENCE DESCRIPTION: SEQ ID NO:43:

Lys Ser Lys Val Gly Trp Leu Ile Gln Leu Ala His Lys Lys
1               5                  10

(2) INFORMATION FOR SEQ ID NO:44:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.42"

(xi) SEQUENCE DESCRIPTION: SEQ ID NO:44:

Lys Ser Lys Val Gly Trp Leu Ile Gln Leu Phe Ala Lys Lys
1               5                  10

(2) INFORMATION FOR SEQ ID NO:45:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.43"

(xi) SEQUENCE DESCRIPTION: SEQ ID NO:45:

Lys Ser Lys Val Gly Trp Leu Ile Gln Leu Phe His Ala Lys
1               5                  10

(2) INFORMATION FOR SEQ ID NO:46:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.44"

(xi) SEQUENCE DESCRIPTION: SEQ ID NO:46:

```
Lys Ser Lys Val Gly Trp Leu Ile Gln Leu Phe His Lys Ala
1               5                   10
```

(2) INFORMATION FOR SEQ ID NO:47:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.56"

(xi) SEQUENCE DESCRIPTION: SEQ ID NO:47:

```
Ile Lys Ile Ser Gly Lys Trp Lys Ala Lys Gln Arg Phe Leu Lys
1               5                   10                  15
```

(2) INFORMATION FOR SEQ ID NO:48:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.61"

(xi) SEQUENCE DESCRIPTION: SEQ ID NO:48:

```
Ile Lys Ile Ser Gly Lys Phe Lys Ala Gln Lys Arg Phe Leu Lys
1               5                   10                  15
```

(2) INFORMATION FOR SEQ ID NO:49:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.66"

(ix) FEATURE:
        (A) NAME/KEY: Modified-site
        (B) LOCATION: 7
        (D) OTHER INFORMATION: /label= D-Trp
            /note= "The amino acid at position 7 is
            D-tryptophan"

(xi) SEQUENCE DESCRIPTION: SEQ ID NO:49:

```
Ile Lys Ile Ser Gly Lys Trp Lys Ala Gln Lys Arg Phe Leu Lys
1               5                   10                  15
```

(2) INFORMATION FOR SEQ ID NO:50:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature (D) OTHER INFORMATION: "BPI.67"

(ix) FEATURE:
        (A) NAME/KEY: Modified-site
        (B) LOCATION: 6..8
        (D) OTHER INFORMATION: /label= Substituted-Ala
            /note= "The alanine at position 7 is
            beta-1-naphthyl-substituted"

(xi) SEQUENCE DESCRIPTION: SEQ ID NO:50:

Ile Lys Ile Ser Gly Lys Ala Lys Ala Gln Lys Arg Phe Leu Lys
1               5                   10                  15

(2) INFORMATION FOR SEQ ID NO:51:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.9"

(xi) SEQUENCE DESCRIPTION: SEQ ID NO:51:

Lys Arg Phe Leu Lys Lys Trp Lys Ala Gln Lys Arg Phe Leu Lys
1               5                   10                  15

(2) INFORMATION FOR SEQ ID NO:52:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.30"

(xi) SEQUENCE DESCRIPTION: SEQ ID NO:52:

Lys Trp Lys Ala Gln Lys Arg Phe Leu Lys Lys Ser Lys Val Gly Trp
1               5                   10                  15

Leu Ile Gln Leu Phe His Lys Lys
            20

(2) INFORMATION FOR SEQ ID NO:53:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.63"

(xi) SEQUENCE DESCRIPTION: SEQ ID NO:53:

Ile Lys Ile Ser Gly Lys Trp Lys Ala Gln Lys Arg Phe Leu Lys
1               5                   10                  15

Ser Lys Val Gly Trp Leu Ile Gln Leu Phe His Lys Lys
            20                  25

(2) INFORMATION FOR SEQ ID NO:54:

```
       (i) SEQUENCE CHARACTERISTICS:
           (A) LENGTH: 20 amino acids
           (B) TYPE: amino acid
           (D) TOPOLOGY: linear (ii) MOLECULE TYPE: peptide (ix) FEATURE:
           (A) NAME/KEY: misc_feature
           (D) OTHER INFORMATION: "BPI.7"

(xi) SEQUENCE DESCRIPTION: SEQ ID NO:54:

Lys Trp Lys Ala Gln Lys Arg Phe Leu Lys Trp Lys Ala Gln Lys
1               5                  10                  15

Arg Phe Leu Lys
            20

(2) INFORMATION FOR SEQ ID NO:55:

(i) SEQUENCE CHARACTERISTICS:
           (A) LENGTH: 25 amino acids
           (B) TYPE: amino acid
           (D) TOPOLOGY: linear (ii) MOLECULE TYPE: peptide (ix) FEATURE:
           (A) NAME/KEY: misc_feature
           (D) OTHER INFORMATION: "BPI.10.1"

(xi) SEQUENCE DESCRIPTION: SEQ ID NO:55:

Lys Arg Phe Leu Lys Lys Trp Lys Ala Gln Lys Arg Phe Leu Lys
1               5                  10                  15

Trp Lys Ala Gln Lys Arg Phe Leu Lys
            20                  25

(2) INFORMATION FOR SEQ ID NO:56:

(i) SEQUENCE CHARACTERISTICS:
           (A) LENGTH: 28 amino acids
           (B) TYPE: amino acid
           (D) TOPOLOGY: linear (ii) MOLECULE TYPE: peptide (ix) FEATURE:
           (A) NAME/KEY: misc_feature
           (D) OTHER INFORMATION: "BPI.29"

(xi) SEQUENCE DESCRIPTION: SEQ ID NO:56:

Lys Ser Lys Val Gly Trp Leu Ile Gln Leu Phe His Lys Lys Ser
1               5                  10                  15

Lys Val Gly Trp Leu Ile Gln Leu Phe His Lys Lys
            20                  25

(2) INFORMATION FOR SEQ ID NO:57:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (ix) FEATURE:
           (A) NAME/KEY: misc_feature
           (D) OTHER INFORMATION: "BPI.46"

(xi) SEQUENCE DESCRIPTION: SEQ ID NO:57:
```

```
Lys Trp Lys Ala Ala Ala Arg Phe Leu Lys Trp Lys Ala Gln Lys
1               5                   10                  15

Arg Phe Leu Lys
            20

(2) INFORMATION FOR SEQ ID NO:58:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.47"

(xi) SEQUENCE DESCRIPTION: SEQ ID NO:58:

Lys Trp Lys Ala Gln Lys Arg Phe Leu Lys Lys Trp Lys Ala Ala Ala
1               5                   10                  15

Arg Phe Leu Lys
            20

(2) INFORMATION FOR SEQ ID NO:59:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.48"

(xi) SEQUENCE DESCRIPTION: SEQ ID NO:59:

Lys Trp Lys Ala Ala Ala Arg Phe Leu Lys Lys Trp Lys Ala Ala Ala
1               5                   10                  15

Arg Phe Leu Lys
            20

(2) INFORMATION FOR SEQ ID NO:60:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.69"

(xi) SEQUENCE DESCRIPTION: SEQ ID NO:60:

Lys Trp Lys Ala Ala Ala Arg Phe Leu Lys Lys Trp Lys Ala Ala Ala
1               5                   10                  15

Arg Phe Leu Lys Lys Trp Lys Ala Ala Ala Arg Phe Leu Lys
            20                  25                  30

(2) INFORMATION FOR SEQ ID NO:61:

(i) SEQUENCE CHARACTERISTICS:
        (A) LENGTH: 21 amino acids
        (B) TYPE: amino acid
```

```
        (D) TOPOLOGY: linear (ii) MOLECULE TYPE: peptide (ix) FEATURE:
        (A) NAME/KEY: misc_feature
        (D) OTHER INFORMATION: "BPI.55"

(xi) SEQUENCE DESCRIPTION: SEQ ID NO:61:

Gly Trp Leu Ile Gln Leu Phe His Lys Lys Ile Glu Ser Ala Leu Arg
1               5                  10                  15

Asn Lys Met Asn Ser
            20

(2) INFORMATION FOR SEQ ID NO:62:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.73"

(xi) SEQUENCE DESCRIPTION: SEQ ID NO:62:

Ile Lys Ile Ser Gly Lys Trp Lys Ala Gln Phe Arg Phe Leu Lys
1               5                  10                  15

(2) INFORMATION FOR SEQ ID NO:63:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.70"

(ix) FEATURE:
        (A) NAME/KEY: Modified-site
        (B) LOCATION: 8..10
        (D) OTHER INFORMATION: /label= Substituted-Ala
            /note= "The alanine at position 7 is
            beta-3-pyridyl-substituted"

(xi) SEQUENCE DESCRIPTION: SEQ ID NO:63:

Ile Lys Ile Ser Gly Lys Ala Lys Ala Gln Lys Arg Phe Leu Lys
1               5                  10                  15

(2) INFORMATION FOR SEQ ID NO:64:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.71"

(ix) FEATURE:
        (A) NAME/KEY: Modified-site
        (B) LOCATION: 13..15
        (D) OTHER INFORMATION: /label= Substituted-Ala
```

```
       /note= "The alanine at position 13 is
       beta-3-pyridyl-substituted"

(xi) SEQUENCE DESCRIPTION: SEQ ID NO:64:

Ile Lys Ile Ser Gly Lys Trp Lys Ala Gln Lys Arg Ala Leu Lys
1               5                  10                  15
```

(2) INFORMATION FOR SEQ ID NO:65:

```
    (i) SEQUENCE CHARACTERISTICS:
        (A) LENGTH: 26 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.10.2"

(xi) SEQUENCE DESCRIPTION: SEQ ID NO:65:

Gln Lys Arg Phe Leu Lys Lys Trp Lys Ala Gln Lys Arg Phe Leu Lys
1               5                  10                  15

Lys Trp Lys Ala Gln Lys Arg Phe Leu Lys
                20                  25
```

(2) INFORMATION FOR SEQ ID NO:66:

```
    (i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.72"

(ix) FEATURE:
        (A) NAME/KEY: Modified-site
        (B) LOCATION: 1..3
        (D) OTHER INFORMATION: /label= D-alanine
            /note= "The position 1 and position 2 alanine
            residues are both D-alanine"

(xi) SEQUENCE DESCRIPTION: SEQ ID NO:66:

Ala Ala Ile Lys Ile Ser Gly Lys Trp Lys Ala Gln Lys Arg Phe Leu
1               5                  10                  15

Lys
```

(2) INFORMATION FOR SEQ ID NO:67:

```
    (i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.5"

(xi) SEQUENCE DESCRIPTION: SEQ ID NO:67:

Val His Val His Ile Ser Lys Ser Lys Val Gly Trp Leu Ile Gln Leu
1               5                  10                  15

Phe His Lys Lys Ile Glu
            20
```

(2) INFORMATION FOR SEQ ID NO:68:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.65 reduced"

(ix) FEATURE:
        (A) NAME/KEY: Disulfide-bond
        (B) LOCATION: 1..17

(xi) SEQUENCE DESCRIPTION: SEQ ID NO:68:

```
Cys Ile Lys Ile Ser Gly Lys Trp Lys Ala Gln Lys Arg Phe Leu Lys
 1               5                  10                  15

Cys
```

(2) INFORMATION FOR SEQ ID NO:69:

(i) SEQUENCE CHARACTERISTICS:
        (A) LENGTH: 487 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: "rBPI"

(xi) SEQUENCE DESCRIPTION: SEQ ID NO:69:

```
Met Arg Glu Asn Met Ala Arg Gly Pro Cys Asn Ala Pro Arg Trp Val
-31 -30              -25                 -20

Ser Leu Met Val Leu Val Ala Ile Gly Thr Ala Val Thr Ala Ala Val
-15             -10                  -5                       1

Asn Pro Gly Val Val Val Arg Ile Ser Gln Lys Gly Leu Asp Tyr Ala
                 5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
            35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
                 85                  90                  95

Leu Lys Met Ser Gly Asn Phe Asp Leu Ser Ile Glu Gly Met Ser Ile
                100                 105                 110

Ser Ala Asp Leu Lys Leu Gly Ser Asn Pro Thr Ser Gly Lys Pro Thr
                115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
```

```
                165                 170                 175
Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
            260                 265                 270

Gly Val Leu Lys Met Thr Leu Arg Asp Asp Met Ile Pro Lys Glu Ser
        275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
    355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
    435                 440                 445

Gly Ala Asp Val Val Tyr Lys
450                 455

(2) INFORMATION FOR SEQ ID NO:70:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.74"

(xi) SEQUENCE DESCRIPTION: SEQ ID NO:70:

Lys Ser Lys Val Gly Trp Leu Ile Gln Leu Phe His Lys Lys Trp
1               5                   10                  15

Lys Ala Gln Lys Arg Phe Leu Lys
            20
```

-continued (2) INFORMATION FOR SEQ ID NO:71:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.76"

(ix) FEATURE:
        (A) NAME/KEY: Modified-site
        (B) LOCATION: 10..12
        (D) OTHER INFORMATION: /label= D-Phe
            /note= "The amino acid at position 11 is
            D-phenylalanine"

(xi) SEQUENCE DESCRIPTION: SEQ ID NO:71:

Ile Lys Ile Ser Gly Lys Trp Lys Ala Gln Phe Arg Phe Leu Lys
1               5                   10                  15

(2) INFORMATION FOR SEQ ID NO:72:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.77"

(xi) SEQUENCE DESCRIPTION: SEQ ID NO:72:

Ile Lys Ile Ser Gly Lys Trp Lys Ala Gln Trp Arg Phe Leu Lys
1               5                   10                  15

(2) INFORMATION FOR SEQ ID NO:73:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.79"

(xi) SEQUENCE DESCRIPTION: SEQ ID NO:73:

Ile Lys Ile Ser Gly Lys Trp Lys Ala Lys Lys Arg Phe Leu Lys
1               5                   10                  15

(2) INFORMATION FOR SEQ ID NO:74:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.80"

(ix) FEATURE:
        (A) NAME/KEY: Modified-site (B) LOCATION: 10..12
            (D) OTHER INFORMATION: /label= Substituted-Ala
                /note= "The alanine at position 11 is
                beta-1-naphthyl-substituted"

(xi) SEQUENCE DESCRIPTION: SEQ ID NO:74:

Ile Lys Ile Ser Gly Lys Trp Lys Ala Gln Ala Arg Phe Leu Lys
1               5                   10                  15

(2) INFORMATION FOR SEQ ID NO:75:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.81"

(xi) SEQUENCE DESCRIPTION: SEQ ID NO:75:

Ile Lys Ile Ser Gly Lys Trp Lys Ala Phe Lys Arg Phe Leu Lys
1               5                   10                  15

(2) INFORMATION FOR SEQ ID NO:76:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.82"

(xi) SEQUENCE DESCRIPTION: SEQ ID NO:76:

Lys Ser Lys Val Gly Trp Leu Ile Gln Leu Trp His Lys Lys
1               5                   10

(2) INFORMATION FOR SEQ ID NO:77:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.83"

(ix) FEATURE:
        (A) NAME/KEY: Modified-site
        (B) LOCATION: 10..12
        (D) OTHER INFORMATION: /label= Substituted-Ala
            /note= "The alanine at position 6 is
            beta-1-naphthyl-substituted"

(xi) SEQUENCE DESCRIPTION: SEQ ID NO:77:

Lys Ser Lys Val Gly Ala Lys Ile Gln Leu Phe His Lys Lys
1               5                   10

(2) INFORMATION FOR SEQ ID NO:78:

(i) SEQUENCE CHARACTERISTICS:
        (A) LENGTH: 15 amino acids

```
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.84"

(ix) FEATURE:
          (A) NAME/KEY: Modified-site
          (B) LOCATION: 6..8
          (D) OTHER INFORMATION: /label= Substituted-Ala
              /note= "The alanine at position 7 is
              beta-1-naphthyl-substituted"

(xi) SEQUENCE DESCRIPTION: SEQ ID NO:78:

Ile Lys Ile Ser Gly Lys Ala Lys Ala Gln Phe Arg Phe Leu Lys
1               5                  10                  15

(2) INFORMATION FOR SEQ ID NO:79:

(i) SEQUENCE CHARACTERISTICS:
          (A) LENGTH: 14 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.85"

(xi) SEQUENCE DESCRIPTION: SEQ ID NO:79:

Lys Ser Lys Val Leu Trp Leu Ile Gln Leu Phe His Lys Lys
1               5                  10

(2) INFORMATION FOR SEQ ID NO:80:

(i) SEQUENCE CHARACTERISTICS:
          (A) LENGTH: 14 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.86"

(xi) SEQUENCE DESCRIPTION: SEQ ID NO:80:

Lys Ser Lys Val Gly Trp Leu Ile Leu Leu Phe His Lys Lys
1               5                  10

(2) INFORMATION FOR SEQ ID NO:81:

(i) SEQUENCE CHARACTERISTICS:
          (A) LENGTH: 14 amino acids
          (B) TYPE: amino acid
          (D) TOPOLOGY: linear (ii) MOLECULE TYPE: peptide (ix) FEATURE:
          (A) NAME/KEY: misc_feature
          (D) OTHER INFORMATION: "BPI.87"

(xi) SEQUENCE DESCRIPTION: SEQ ID NO:81:

Lys Ser Lys Val Gly Trp Leu Ile Gln Leu Phe Leu Lys Lys
1               5                  10
```

(2) INFORMATION FOR SEQ ID NO:82:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.88"

(xi) SEQUENCE DESCRIPTION: SEQ ID NO:82:

```
Ile Lys Ile Ser Gly Lys Trp Lys Ala Phe Phe Arg Phe Leu Lys
1               5                  10                  15
```

(2) INFORMATION FOR SEQ ID NO:83:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.98"

(ix) FEATURE:
        (A) NAME/KEY: Modified-site
        (B) LOCATION: 2
        (D) OTHER INFORMATION: /label= Substituted-Trp
            /note= "The alanine at position 2 is
            beta-1-naphthyl-substituted"

(xi) SEQUENCE DESCRIPTION: SEQ ID NO:83:

```
Lys Trp Lys Ala Gln Phe Arg Phe Leu Lys Lys Ser Lys Val Gly Trp
1               5                  10                  15

Leu Ile Phe Leu Phe His Lys Lys
                20
```

(2) INFORMATION FOR SEQ ID NO:84:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.89"

(ix) FEATURE:
        (A) NAME/KEY: Modified-site
        (B) LOCATION: 6..8
        (D) OTHER INFORMATION: /label= Substituted-Ala
            /note= "The alanine at position 7 is
            beta-1-naphthyl-substituted"

(xi) SEQUENCE DESCRIPTION: SEQ ID NO:84:

```
Ile Lys Ile Ser Gly Lys Ala Lys Ala Phe Lys Arg Phe Leu Lys
1               5                  10                  15
```

(2) INFORMATION FOR SEQ ID NO:85:

(i) SEQUENCE CHARACTERISTICS:
        (A) LENGTH: 15 amino acids
        (B) TYPE: amino acid -continued

```
        (D) TOPOLOGY: linear (ii) MOLECULE TYPE: peptide (ix) FEATURE:
        (A) NAME/KEY: misc_feature
        (D) OTHER INFORMATION: "BPI.90"

(ix) FEATURE:
        (A) NAME/KEY: Modified-site
        (B) LOCATION: 6..8
        (D) OTHER INFORMATION: /label= Substituted-Ala
            /note= "The alanine at position 7 is
            beta-1-naphthyl-substituted"

(xi) SEQUENCE DESCRIPTION: SEQ ID NO:85:

Ile Lys Ile Ser Gly Lys Ala Lys Ala Phe Phe Arg Phe Leu Lys
1               5                   10                  15

(2) INFORMATION FOR SEQ ID NO:86:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.91"

(xi) SEQUENCE DESCRIPTION: SEQ ID NO:86:

Lys Ser Lys Val Gly Trp Leu Ile Phe Leu Phe His Lys Lys
1               5                   10

(2) INFORMATION FOR SEQ ID NO:87:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.92"

(xi) SEQUENCE DESCRIPTION: SEQ ID NO:87:

Lys Ser Lys Val Gly Trp Leu Ile Lys Leu Phe His Lys Lys
1               5                   10

(2) INFORMATION FOR SEQ ID NO:88:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.93"

(ix) FEATURE:
        (A) NAME/KEY: Modified-site
        (B) LOCATION: 6..8
        (D) OTHER INFORMATION: /label= Substituted-Ala
            /note= "The alanine at position 7 is
            beta-1-naphthyl-substituted"
```

(xi) SEQUENCE DESCRIPTION: SEQ ID NO:88:

Ile Lys Ile Ser Gly Lys Ala Lys Ala Gln Phe Arg Phe Leu Lys Lys
1               5                   10                  15

Ser Lys Val Gly Trp Leu Ile Gln Leu Phe His Lys Lys
            20                  25

(2) INFORMATION FOR SEQ ID NO:89:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.94"

(xi) SEQUENCE DESCRIPTION: SEQ ID NO:89:

Lys Ser Lys Val Gly Trp Leu Ile Gln Leu Phe Phe Lys Lys
1               5                   10

(2) INFORMATION FOR SEQ ID NO:90:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.95"

(xi) SEQUENCE DESCRIPTION: SEQ ID NO:90:

Lys Ser Lys Val Phe Trp Leu Ile Gln Leu Phe His Lys Lys
1               5                   10

(2) INFORMATION FOR SEQ ID NO:91:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.96"

(xi) SEQUENCE DESCRIPTION: SEQ ID NO:91:

Lys Ser Lys Val Gly Trp Leu Ile Gln Leu Phe His Lys Phe
1               5                   10

(2) INFORMATION FOR SEQ ID NO:92:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.97"

(xi) SEQUENCE DESCRIPTION: SEQ ID NO:92:

Lys Ser Lys Val Lys Trp Leu Ile Gln Leu Phe His Lys Lys
1               5                  10

(2) INFORMATION FOR SEQ ID NO:93:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.99"

(xi) SEQUENCE DESCRIPTION: SEQ ID NO:93:

Lys Trp Lys Ala Gln Trp Arg Phe Leu Lys Lys Trp Lys Ala Gln Trp
1               5                  10                  15

Arg Phe Leu Lys Lys Trp Lys Ala Gln Trp Arg Phe Leu Lys
            20                  25                  30

(2) INFORMATION FOR SEQ ID NO:94:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.100"

(xi) SEQUENCE DESCRIPTION: SEQ ID NO:94:

Lys Ser Lys Val Lys Trp Leu Ile Lys Leu Phe His Lys Lys
1               5                  10

(2) INFORMATION FOR SEQ ID NO:95:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.101"

(xi) SEQUENCE DESCRIPTION: SEQ ID NO:95:

Lys Ser Lys Val Lys Trp Leu Ile Lys Leu Phe Phe Lys Phe Lys Ser
1               5                  10                  15

Lys Val Lys Trp Leu Ile Lys Leu Phe Phe Lys Phe
            20                  25

(2) INFORMATION FOR SEQ ID NO:96:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:

(A) NAME/KEY: misc_feature
(D) OTHER INFORMATION: "BPI.102"

(xi) SEQUENCE DESCRIPTION: SEQ ID NO:96:

Lys Trp Lys Ala Gln Phe Arg Phe Leu Lys Lys Ser Lys Val Gly Trp
1               5                   10                  15

Leu Ile Leu Leu Phe His Lys Lys
            20

(2) INFORMATION FOR SEQ ID NO:97:

(i) SEQUENCE CHARACTERISTICS:
      (A) LENGTH: 1443 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 1..1443

(ix) FEATURE:
      (A) NAME/KEY: mat_peptide
      (B) LOCATION: 76..1443

(ix) FEATURE:
      (A) NAME/KEY: misc_feature
      (D) OTHER INFORMATION: "rLBP"

(xi) SEQUENCE DESCRIPTION: SEQ ID NO:97:

```
ATG GGG GCC TTG GCC AGA GCC CTG CCG TCC ATA CTG CTG GCA TTG CTG        48
Met Gly Ala Leu Ala Arg Ala Leu Pro Ser Ile Leu Leu Ala Leu Leu
-25             -20                 -15                 -10

CTT ACG TCC ACC CCA GAG GCT CTG GGT GCC AAC CCC GGC TTG GTC GCC        96
Leu Thr Ser Thr Pro Glu Ala Leu Gly Ala Asn Pro Gly Leu Val Ala
            -5                  1                   5

AGG ATC ACC GAC AAG GGA CTG CAG TAT GCG GCC CAG GAG GGG CTA TTG       144
Arg Ile Thr Asp Lys Gly Leu Gln Tyr Ala Ala Gln Glu Gly Leu Leu
            10                  15                  20

GCT CTG CAG AGT GAG CTG CTC AGG ATC ACG CTG CCT GAC TTC ACC GGG       192
Ala Leu Gln Ser Glu Leu Leu Arg Ile Thr Leu Pro Asp Phe Thr Gly
        25                  30                  35

GAC TTG AGG ATC CCC CAC GTC GGC CGT GGG CGC TAT GAG TTC CAC AGC       240
Asp Leu Arg Ile Pro His Val Gly Arg Gly Arg Tyr Glu Phe His Ser
40                  45                  50                  55

CTG AAC ATC CAC AGC TGT GAG CTG CTT CAC TCT GCG CTG AGG CCT GTC       288
Leu Asn Ile His Ser Cys Glu Leu Leu His Ser Ala Leu Arg Pro Val
            60                  65                  70

CCT GGC CAG GGC CTG AGT CTC AGC ATC TCC GAC TCC TCC ATC CGG GTC       336
Pro Gly Gln Gly Leu Ser Leu Ser Ile Ser Asp Ser Ser Ile Arg Val
            75                  80                  85

CAG GGC AGG TGG AAG GTG CGC AAG TCA TTC TTC AAA CTA CAG GGC TCC       384
Gln Gly Arg Trp Lys Val Arg Lys Ser Phe Phe Lys Leu Gln Gly Ser
        90                  95                  100

TTT GAT GTC AGT GTC AAG GGC ATC AGC ATT TCG GTC AAC CTC CTG TTG       432
Phe Asp Val Ser Val Lys Gly Ile Ser Ile Ser Val Asn Leu Leu Leu
        105                 110                 115

GGC AGC GAG TCC TCC GGG AGG CCC ACA GTT ACT GCC TCC AGC TGC AGC       480
Gly Ser Glu Ser Ser Gly Arg Pro Thr Val Thr Ala Ser Ser Cys Ser
120                 125                 130                 135

AGT GAC ATC GCT GAC GTG GAG GTG GAC ATG TCG GGA GAC TTG GGG TGG       528
Ser Asp Ile Ala Asp Val Glu Val Asp Met Ser Gly Asp Leu Gly Trp
            140                 145                 150
```

```
CTG TTG AAC CTC TTC CAC AAC CAG ATT GAG TCC AAG TTC CAG AAA GTA      576
Leu Leu Asn Leu Phe His Asn Gln Ile Glu Ser Lys Phe Gln Lys Val
        155                 160                 165

CTG GAG AGC AGG ATT TGC GAA ATG ATC CAG AAA TCG GTG TCC TCC GAT      624
Leu Glu Ser Arg Ile Cys Glu Met Ile Gln Lys Ser Val Ser Ser Asp
        170                 175                 180

CTA CAG CCT TAT CTC CAA ACT CTG CCA GTT ACA ACA GAG ATT GAC AGT      672
Leu Gln Pro Tyr Leu Gln Thr Leu Pro Val Thr Thr Glu Ile Asp Ser
        185                 190                 195

TTC GCC GAC ATT GAT TAT AGC TTA GTG GAA GCC CCT CGG GCA ACA GCC      720
Phe Ala Asp Ile Asp Tyr Ser Leu Val Glu Ala Pro Arg Ala Thr Ala
200                 205                 210                 215

CAG ATG CTG GAG GTG ATG TTT AAG GGT GAA ATC TTT CAT CGT AAC CAC      768
Gln Met Leu Glu Val Met Phe Lys Gly Glu Ile Phe His Arg Asn His
                220                 225                 230

CGT TCT CCA GTT ACC CTC CTT GCT GCA GTC ATG AGC CTT CCT GAG GAA      816
Arg Ser Pro Val Thr Leu Leu Ala Ala Val Met Ser Leu Pro Glu Glu
                235                 240                 245

CAC AAC AAA ATG GTC TAC TTT GCC ATC TCG GAT TAT GTC TTC AAC ACG      864
His Asn Lys Met Val Tyr Phe Ala Ile Ser Asp Tyr Val Phe Asn Thr
            250                 255                 260

GCC AGC CTG GTT TAT CAT GAG GAA GGA TAT CTG AAC TTC TCC ATC ACA      912
Ala Ser Leu Val Tyr His Glu Glu Gly Tyr Leu Asn Phe Ser Ile Thr
        265                 270                 275

GAT GAG ATG ATA CCG CCT GAC TCT AAT ATC CGA CTG ACC ACC AAG TCC      960
Asp Glu Met Ile Pro Pro Asp Ser Asn Ile Arg Leu Thr Thr Lys Ser
280                 285                 290                 295

TTC CGA CCC TTC GTC CCA CGG TTA GCC AGG CTC TAC CCC AAC ATG AAC     1008
Phe Arg Pro Phe Val Pro Arg Leu Ala Arg Leu Tyr Pro Asn Met Asn
                300                 305                 310

CTG GAA CTC CAG GGA TCA GTG CCC TCT GCT CCG CTC CTG AAC TTC AGC     1056
Leu Glu Leu Gln Gly Ser Val Pro Ser Ala Pro Leu Leu Asn Phe Ser
                315                 320                 325

CCT GGG AAT CTG TCT GTG GAC CCC TAT ATG GAG ATA GAT GCC TTT GTG     1104
Pro Gly Asn Leu Ser Val Asp Pro Tyr Met Glu Ile Asp Ala Phe Val
            330                 335                 340

CTC CTG CCC AGC TCC AGC AAG GAG CCT GTC TTC CGG CTC AGT GTG GCC     1152
Leu Leu Pro Ser Ser Ser Lys Glu Pro Val Phe Arg Leu Ser Val Ala
        345                 350                 355

ACT AAT GTG TCC GCC ACC TTG ACC TTC AAT ACC AGC AAG ATC ACT GGG     1200
Thr Asn Val Ser Ala Thr Leu Thr Phe Asn Thr Ser Lys Ile Thr Gly
360                 365                 370                 375

TTC CTG AAG CCA GGA AAG GTA AAA GTG GAA CTG AAA GAA TCC AAA GTT     1248
Phe Leu Lys Pro Gly Lys Val Lys Val Glu Leu Lys Glu Ser Lys Val
                380                 385                 390

GGA CTA TTC AAT GCA GAG CTG TTG GAA GCG CTC CTC AAC TAT TAC ATC     1296
Gly Leu Phe Asn Ala Glu Leu Leu Glu Ala Leu Leu Asn Tyr Tyr Ile
            395                 400                 405

CTT AAC ACC TTC TAC CCC AAG TTC AAT GAT AAG TTG GCC GAA GGC TTC     1344
Leu Asn Thr Phe Tyr Pro Lys Phe Asn Asp Lys Leu Ala Glu Gly Phe
        410                 415                 420

CCC CTT CCT CTG CTG AAG CGT GTT CAG CTC TAC GAC CTT GGG CTG CAG     1392
Pro Leu Pro Leu Leu Lys Arg Val Gln Leu Tyr Asp Leu Gly Leu Gln
425                 430                 435

ATC CAT AAG GAC TTC CTG TTC TTG GGT GCC AAT GTC CAA TAC ATG AGA     1440
Ile His Lys Asp Phe Leu Phe Leu Gly Ala Asn Val Gln Tyr Met Arg
440                 445                 450                 455

GTT                                                                 1443
Val
```

(2) INFORMATION FOR SEQ ID NO:98:

(i) SEQUENCE CHARACTERISTICS:
        (A) LENGTH: 481 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: "rLBP"

(xi) SEQUENCE DESCRIPTION: SEQ ID NO:98:

```
Met Gly Ala Leu Ala Arg Ala Leu Pro Ser Ile Leu Ala Leu Leu
-25                 -20                 -15                 -10

Leu Thr Ser Thr Pro Glu Ala Leu Gly Ala Asn Pro Gly Leu Val Ala
                 -5                   1                   5

Arg Ile Thr Asp Lys Gly Leu Gln Tyr Ala Ala Gln Glu Gly Leu Leu
             10                  15                  20

Ala Leu Gln Ser Glu Leu Leu Arg Ile Thr Leu Pro Asp Phe Thr Gly
     25                  30                  35

Asp Leu Arg Ile Pro His Val Gly Arg Gly Arg Tyr Glu Phe His Ser
 40                  45                  50                  55

Leu Asn Ile His Ser Cys Glu Leu Leu His Ser Ala Leu Arg Pro Val
                 60                  65                  70

Pro Gly Gln Gly Leu Ser Leu Ser Ile Ser Asp Ser Ser Ile Arg Val
             75                  80                  85

Gln Gly Arg Trp Lys Val Arg Lys Ser Phe Phe Lys Leu Gln Gly Ser
     90                  95                 100

Phe Asp Val Ser Val Lys Gly Ile Ser Ile Ser Val Asn Leu Leu Leu
105                 110                 115

Gly Ser Glu Ser Ser Gly Arg Pro Thr Val Thr Ala Ser Ser Cys Ser
120                 125                 130                 135

Ser Asp Ile Ala Asp Val Glu Val Asp Met Ser Gly Asp Leu Gly Trp
             140                 145                 150

Leu Leu Asn Leu Phe His Asn Gln Ile Glu Ser Lys Phe Gln Lys Val
             155                 160                 165

Leu Glu Ser Arg Ile Cys Glu Met Ile Gln Lys Ser Val Ser Ser Asp
             170                 175                 180

Leu Gln Pro Tyr Leu Gln Thr Leu Pro Val Thr Thr Glu Ile Asp Ser
     185                 190                 195

Phe Ala Asp Ile Asp Tyr Ser Leu Val Glu Ala Pro Arg Ala Thr Ala
200                 205                 210                 215

Gln Met Leu Glu Val Met Phe Lys Gly Glu Ile Phe His Arg Asn His
                 220                 225                 230

Arg Ser Pro Val Thr Leu Leu Ala Ala Val Met Ser Leu Pro Glu Glu
             235                 240                 245

His Asn Lys Met Val Tyr Phe Ala Ile Ser Asp Tyr Val Phe Asn Thr
             250                 255                 260

Ala Ser Leu Val Tyr His Glu Glu Gly Tyr Leu Asn Phe Ser Ile Thr
265                 270                 275

Asp Glu Met Ile Pro Pro Asp Ser Asn Ile Arg Leu Thr Thr Lys Ser
280                 285                 290                 295

Phe Arg Pro Phe Val Pro Arg Leu Ala Arg Leu Tyr Pro Asn Met Asn
             300                 305                 310
```

Leu Glu Leu Gln Gly Ser Val Pro Ser Ala Pro Leu Leu Asn Phe Ser
            315                 320                 325

Pro Gly Asn Leu Ser Val Asp Pro Tyr Met Glu Ile Asp Ala Phe Val
            330                 335                 340

Leu Leu Pro Ser Ser Ser Lys Glu Pro Val Phe Arg Leu Ser Val Ala
            345                 350                 355

Thr Asn Val Ser Ala Thr Leu Thr Phe Asn Thr Ser Lys Ile Thr Gly
360                 365                 370                 375

Phe Leu Lys Pro Gly Lys Val Lys Val Glu Leu Lys Glu Ser Lys Val
            380                 385                 390

Gly Leu Phe Asn Ala Glu Leu Leu Glu Ala Leu Leu Asn Tyr Tyr Ile
            395                 400                 405

Leu Asn Thr Phe Tyr Pro Lys Phe Asn Asp Lys Leu Ala Glu Gly Phe
            410                 415                 420

Pro Leu Pro Leu Leu Lys Arg Val Gln Leu Tyr Asp Leu Gly Leu Gln
            425                 430                 435

Ile His Lys Asp Phe Leu Phe Leu Gly Ala Asn Val Gln Tyr Met Arg
440                 445                 450                 455

Val (2) INFORMATION FOR SEQ ID NO:99:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.57"

(xi) SEQUENCE DESCRIPTION: SEQ ID NO:99:

Cys Ile Lys Ile Ser Gly Lys Trp Lys Ala Gln Lys Arg Pro Leu Cys
1               5                   10                  15

(2) INFORMATION FOR SEQ ID NO:100:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.75"

(xi) SEQUENCE DESCRIPTION: SEQ ID NO:100:

Ile Lys Lys Arg Ala Ile Ser Phe Leu Gly Lys Lys Trp Gln Lys
1               5                   10                  15

(2) INFORMATION FOR SEQ ID NO:101:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:

(A) NAME/KEY: misc_feature
            (D) OTHER INFORMATION: "BPI.282"

(xi) SEQUENCE DESCRIPTION: SEQ ID NO:101:

Lys Trp Lys Ala Phe Phe Arg Phe Leu Lys Trp Lys Ala Phe Phe
1               5                  10                  15

Arg Phe Leu Lys
            20

(2) INFORMATION FOR SEQ ID NO:102:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.103"

(xi) SEQUENCE DESCRIPTION: SEQ ID NO:102:

Ile Lys Ile Ser Gly Lys Trp Lys Ala Trp Lys Arg Phe Leu Lys Lys
1               5                  10                  15

(2) INFORMATION FOR SEQ ID NO:103:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.104"

(xi) SEQUENCE DESCRIPTION: SEQ ID NO:103:

Lys Ser Lys Val Gly Trp Leu Ile Ser Leu Phe His Lys Lys
1               5                  10

(2) INFORMATION FOR SEQ ID NO:104:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.105"

(ix) FEATURE:
            (A) NAME/KEY: Modified-site
            (B) LOCATION: 13
            (C) OTHER INFORMATION: /label= Substituted-Ala
                /note= "The alanine at position 13 is beta-1-
                naphthyl-substituted."

(xi) SEQUENCE DESCRIPTION: SEQ ID NO:104:

Ile Lys Ile Ser Gly Lys Trp Lys Ala Trp Lys Arg Ala Leu Lys Lys
1               5                  10                  15

(2) INFORMATION FOR SEQ ID NO:105:

(i) SEQUENCE CHARACTERISTICS:

```
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.106"

(xi) SEQUENCE DESCRIPTION: SEQ ID NO:105:

Lys Ser Lys Val Gly Trp Leu Ile Thr Leu Phe His Lys Lys
1               5                   10

(2) INFORMATION FOR SEQ ID NO:106:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.107"

(xi) SEQUENCE DESCRIPTION: SEQ ID NO:106:

Lys Ser Lys Val Gly Trp Leu Ile Gln Leu Phe Trp Lys Lys
1               5                   10

(2) INFORMATION FOR SEQ ID NO:107:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.108"

(xi) SEQUENCE DESCRIPTION: SEQ ID NO:107:

Lys Ser Lys Val Gly Trp Leu Ile Gln Leu Phe His Lys Trp
1               5                   10

(2) INFORMATION FOR SEQ ID NO:108:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.109"

(ix) FEATURE:
        (A) NAME/KEY: Modified-site
        (B) LOCATION: 11
        (C) OTHER INFORMATION: /label= Substituted-Ala
            /note= "The alanine at position 11 is beta-1-
            naphthyl-substituted."

(xi) SEQUENCE DESCRIPTION: SEQ ID NO:108:

Lys Ser Lys Val Gly Trp Leu Ile Gln Leu Ala His Lys Lys
1               5                   10
```

(2) INFORMATION FOR SEQ ID NO:109:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.110"

(ix) FEATURE:
        (A) NAME/KEY: Modified-site
        (B) LOCATION: 12
        (C) OTHER INFORMATION: /label= Substituted-Ala
            /note= "The alanine at position 12 is beta-1-
            naphthyl-substituted."

(xi) SEQUENCE DESCRIPTION: SEQ ID NO:109:

Lys Ser Lys Val Gly Trp Leu Ile Gln Leu Phe Ala Lys Lys
1            5                    10

(2) INFORMATION FOR SEQ ID NO:110:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.111"

(ix) FEATURE:
        (A) NAME/KEY: Modified-site
        (B) LOCATION: 14
        (C) OTHER INFORMATION: /label= Substituted-Ala
            /note= "The alanine at position 14 is beta-1-
            naphthyl-substituted."

(xi) SEQUENCE DESCRIPTION: SEQ ID NO:110:

Lys Ser Lys Val Gly Trp Leu Ile Gln Leu Phe His Lys Ala
1            5                    10

(2) INFORMATION FOR SEQ ID NO:111:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.112"

(ix) FEATURE:
        (A) NAME/KEY: Modified-site
        (B) LOCATION: 7
        (C) OTHER INFORMATION: /label= Substituted-Ala
            /note= "The alanine at position 7 is beta-1-
            naphthyl-substituted."

(ix) FEATURE:
        (A) NAME/KEY: Modified-site
        (B) LOCATION: 11
        (C) OTHER INFORMATION: /label= Substituted-Ala
            /note= "The alanine at position 11 is beta-1-
            naphthyl-substituted."

(xi) SEQUENCE DESCRIPTION: SEQ ID NO:111:

Ile Lys Ile Ser Gly Lys Ala Lys Ala Gln Ala Arg Phe Leu Lys
1               5                   10                  15

(2) INFORMATION FOR SEQ ID NO:112:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.113"

(xi) SEQUENCE DESCRIPTION: SEQ ID NO:112:

Lys Ser Lys Val Gly Trp Leu Ile Gln Phe Phe His Lys Lys
1               5                   10

(2) INFORMATION FOR SEQ ID NO:113:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.114"

(xi) SEQUENCE DESCRIPTION: SEQ ID NO:113:

Lys Trp Gln Leu Arg Ser Lys Gly Lys Ile Lys Ile Phe Lys Ala
1               5                   10                  15

(2) INFORMATION FOR SEQ ID NO:114:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.116"

(ix) FEATURE:
        (A) NAME/KEY: Modified-site
        (B) LOCATION: 6
        (C) OTHER INFORMATION: /label= Substituted-Ala
            /note= "The alanine at position 6 is beta-1-
            naphthyl-substituted."

(xi) SEQUENCE DESCRIPTION: SEQ ID NO:114:

Lys Ser Lys Val Lys Ala Leu Ile Gln Leu Phe His Lys Lys
1               5                   10

(2) INFORMATION FOR SEQ ID NO:115:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.119"

(ix) FEATURE:
        (A) NAME/KEY: Modified-site
        (B) LOCATION: 7
        (C) OTHER INFORMATION: /label= Substituted-Ala
            /note= "The alanine at position 7 is beta-1-
            naphthyl-substituted."

(ix) FEATURE:
        (A) NAME/KEY: Modified-site
        (B) LOCATION: 10
        (C) OTHER INFORMATION: /label= Substituted-Ala
            /note= "The alanine at position 10 is beta-1-
            naphthyl-substituted."

(xi) SEQUENCE DESCRIPTION: SEQ ID NO:115:

Ile Lys Ile Ser Gly Lys Ala Lys Ala Ala Lys Arg Phe Leu Lys
1               5                   10                  15

(2) INFORMATION FOR SEQ ID NO:116:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.120"

(xi) SEQUENCE DESCRIPTION: SEQ ID NO:116:

Ile Lys Ile Ser Gly Lys Trp Lys Ala Gln Lys Arg Lys Leu Lys
1               5                   10                  15

(2) INFORMATION FOR SEQ ID NO:117:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.121"

(ix) FEATURE:
        (A) NAME/KEY: Modified-site
        (B) LOCATION: 10
        (C) OTHER INFORMATION: /label= Substituted-Ala
            /note= "The alanine at position 10 is beta-1-
            naphthyl-substituted."

(ix) FEATURE:
        (A) NAME/KEY: Modified-site
        (B) LOCATION: 11
        (C) OTHER INFORMATION: /label= Substituted-Ala
            /note= "The alanine at position 11 is beta-1-
            naphthyl-substituted."

(xi) SEQUENCE DESCRIPTION: SEQ ID NO:117:

Ile Lys Ile Ser Gly Lys Trp Lys Ala Ala Ala Arg Phe Leu Lys
1               5                   10                  15

(2) INFORMATION FOR SEQ ID NO:118:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.122"

(ix) FEATURE:
            (A) NAME/KEY: Modified-site
            (B) LOCATION: 7
            (C) OTHER INFORMATION: /label= Substituted-Ala
                /note= "The alanine at position 7 is beta-1-
                naphthyl-substituted."

(ix) FEATURE:
            (A) NAME/KEY: Modified-site
            (B) LOCATION: 10
            (C) OTHER INFORMATION: /label= Substituted-Ala
                /note= "The alanine at position 10 is beta-1-
                naphthyl-substituted."

(ix) FEATURE:
            (A) NAME/KEY: Modified-site
            (B) LOCATION: 11
            (C) OTHER INFORMATION: /label= Substituted-Ala
                /note= "The alanine at position 11 is beta-1-
                naphthyl-substituted."

(xi) SEQUENCE DESCRIPTION: SEQ ID NO:118:

Ile Lys Ile Ser Gly Lys Ala Lys Ala Ala Ala Arg Phe Leu Lys
1               5                   10                  15

(2) INFORMATION FOR SEQ ID NO:119:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.123"

(ix) FEATURE:
            (A) NAME/KEY: Modified-site
            (B) LOCATION: 9
            (C) OTHER INFORMATION: /label= Substituted-Phe
                /note= "The phenylalanine at position 9 is
                p-amino-substituted."

(xi) SEQUENCE DESCRIPTION: SEQ ID NO:119:

Lys Ser Lys Val Gly Trp Leu Ile Phe Leu Phe His Lys Lys
1               5                   10

(2) INFORMATION FOR SEQ ID NO:120:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.124"

(xi) SEQUENCE DESCRIPTION: SEQ ID NO:120:

Lys Ser Lys Val Lys Trp Leu Ile Gln Leu Trp His Lys Lys
1               5                   10

(2) INFORMATION FOR SEQ ID NO:121:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.125"

(xi) SEQUENCE DESCRIPTION: SEQ ID NO:121:

Lys Ser Lys Val Gly Trp Leu Ile Tyr Leu Phe His Lys Lys
1               5                   10

(2) INFORMATION FOR SEQ ID NO:122:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.126"

FEATURE:
        (A) NAME/KEY: Modified-site
    (B) LOCATION: 6
    (C) OTHER INFORMATION: /label= D-Trp
            /note= "The amino acid at position 6 is
            D-tryptophan."

(xi) SEQUENCE DESCRIPTION: SEQ ID NO:122:

Lys Ser Lys Val Gly Trp Leu Ile Gln Leu Phe His Lys Lys
1               5                   10

(2) INFORMATION FOR SEQ ID NO:123:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.127"

(xi) SEQUENCE DESCRIPTION: SEQ ID NO:123:

Lys Ser Lys Val Gly Phe Leu Ile Gln Leu Phe His Lys Lys
1               5                   10

(2) INFORMATION FOR SEQ ID NO:124:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature (D) OTHER INFORMATION: "BPI.128"

(ix) FEATURE:
         (A) NAME/KEY: Modified-site
         (B) LOCATION: 6
         (C) OTHER INFORMATION: /label= D-Phe
             /note= "The amino acid at position 6 is
             D-phenylalanine."

(xi) SEQUENCE DESCRIPTION: SEQ ID NO:124:

Lys Ser Lys Val Gly Phe Leu Ile Gln Leu Pro His Lys Lys
1               5                   10

(2) INFORMATION FOR SEQ ID NO:125:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.129"

(ix) FEATURE:
         (A) NAME/KEY: Modified-site
         (B) LOCATION: 6
         (C) OTHER INFORMATION: /label= Substituted-Ala
             /note= "The alanine at position 6 is
             D-1-beta-1-naphthyl-
             substituted."

(xi) SEQUENCE DESCRIPTION: SEQ ID NO:125:

Lys Ser Lys Val Gly Ala Leu Ile Gln Leu Phe His Lys Lys
1               5                   10

(2) INFORMATION FOR SEQ ID NO:126:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "BPI.130"

(ix) FEATURE:
         (A) NAME/KEY: Modified-site
         (B) LOCATION: 6
         (C) OTHER INFORMATION: /label= Substituted-Ala
             /note= "The alanine at position 6 is
             2-beta-1-naphthyl-
             substituted."

(xi) SEQUENCE DESCRIPTION: SEQ ID NO:126:

Lys Ser Lys Val Gly Ala Leu Ile Gln Leu Phe His Lys Lys
1               5                   10

(2) INFORMATION FOR SEQ ID NO:127:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:

(A) NAME/KEY: misc_feature
        (D) OTHER INFORMATION: "BPI.131"

(ix) FEATURE:
        (A) NAME/KEY: Modified-site
        (B) LOCATION: 6
        (C) OTHER INFORMATION: /label= Substituted-Ala
            /note= "The alanine at position 6 is
            D-2-beta-1-naphthyl-
            substituted."

(xi) SEQUENCE DESCRIPTION: SEQ ID NO:127:

Lys Ser Lys Val Gly Ala Leu Ile Gln Leu Phe His Lys Lys
1               5                   10

(2) INFORMATION FOR SEQ ID NO:128:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.132"

(ix) FEATURE:
        (A) NAME/KEY: Modified-site
        (B) LOCATION: 6
        (C) OTHER INFORMATION: /label= Substituted-Ala
            /note= "The alanine at position 6 is
            pyridyl-substituted."

(xi) SEQUENCE DESCRIPTION: SEQ ID NO:128:

Lys Ser Lys Val Gly Ala Leu Ile Gln Leu Phe His Lys Lys
1               5                   10

(2) INFORMATION FOR SEQ ID NO:129:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.133"

(ix) FEATURE:
        (A) NAME/KEY: Modified-site
        (B) LOCATION: 6
        (C) OTHER INFORMATION: /label= Substituted-Phe
            /note= "The phenylalanine at position 6 is
            para-amino-
            substituted."

(xi) SEQUENCE DESCRIPTION: SEQ ID NO:129:

Lys Ser Lys Val Gly Phe Leu Ile Gln Leu Phe His Lys Lys
1               5                   10

(2) INFORMATION FOR SEQ ID NO:130:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
            (A) NAME/KEY: misc_feature
            (D) OTHER INFORMATION: "BPI.134"

(ix) FEATURE:
            (A) NAME/KEY: Modified-site
            (B) LOCATION: 5
            (C) OTHER INFORMATION: /label= Substituted-Phe
                /note= "The phenylalanine at position 5 is
                para-amino-substituted."

(xi) SEQUENCE DESCRIPTION: SEQ ID NO:130:

Lys Ser Lys Val Phe Trp Leu Ile Gln Leu Phe His Lys Lys
1               5                   10

(2) INFORMATION FOR SEQ ID NO:131:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.135"

(xi) SEQUENCE DESCRIPTION: SEQ ID NO:131:

Lys Ser Lys Val Gly Lys Leu Ile Gln Leu Pro His Lys Lys
1               5                   10

(2) INFORMATION FOR SEQ ID NO:132:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.136"

(xi) SEQUENCE DESCRIPTION: SEQ ID NO:132:

Ile Lys Ile Ser Gly Lys Trp Lys Ala Gln Glu Arg Phe Leu Lys
1               5                   10                  15

(2) INFORMATION FOR SEQ ID NO:133:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.137"

(xi) SEQUENCE DESCRIPTION: SEQ ID NO:133:

Cys Lys Ser Lys Val Gly Trp Leu Ile Gln Leu Phe His Lys Lys Cys
1               5                   10                  15

(2) INFORMATION FOR SEQ ID NO:134:

(i) SEQUENCE CHARACTERISTICS:
            (A) LENGTH: 14 amino acids
            (B) TYPE: amino acid (D) TOPOLOGY: linear (ii) MOLECULE TYPE: peptide (ix) FEATURE:
        (A) NAME/KEY: misc_feature
        (D) OTHER INFORMATION: "BPI.138"

(xi) SEQUENCE DESCRIPTION: SEQ ID NO:134:

Lys Ser Lys Val Lys Phe Leu Ile Gln Leu Phe His Lys Lys
1               5                   10

(2) INFORMATION FOR SEQ ID NO:135:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.139"

(xi) SEQUENCE DESCRIPTION: SEQ ID NO:135:

Lys Ser Lys Val Gly Tyr Leu Ile Gln Leu Phe His Lys Lys
1               5                   10

(2) INFORMATION FOR SEQ ID NO:136:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.140"

(ix) FEATURE:
        (A) NAME/KEY: Modified-site
        (B) LOCATION: 1
        (C) OTHER INFORMATION: /label= Substituted-Ala
            /note= "The alanine at position 1 is
            beta-1-naphthyl-substituted."

(ix) FEATURE:
        (A) NAME/KEY: Modified-site
        (B) LOCATION: 2
        (C) OTHER INFORMATION: /label= Substituted-Ala
            /note= "The alanine at position 2 is
            beta-1-naphthyl-substituted."

(xi) SEQUENCE DESCRIPTION: SEQ ID NO:136:

Ala Ala Arg Phe Leu Lys Phe
1               5

(2) INFORMATION FOR SEQ ID NO:137:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.141"

(xi) SEQUENCE DESCRIPTION: SEQ ID NO:137:

Ile Lys Ile Ser Gly Lys Trp Lys Ala Gln Lys Arg Trp Leu Lys
1               5                   10                  15

(2) INFORMATION FOR SEQ ID NO:138:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.142"

(xi) SEQUENCE DESCRIPTION: SEQ ID NO:138:

Lys Ser Lys Val Gly Trp Leu Ile Gln Trp Phe His Lys Lys
1               5                   10

(2) INFORMATION FOR SEQ ID NO:139:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.143"

(ix) FEATURE:
        (A) NAME/KEY: Modified-site
        (B) LOCATION: 10
        (C) OTHER INFORMATION: /label= Substituted-Ala
            /note= "The alanine at position 10 is
            beta-1-naphthyl-substituted."

(xi) SEQUENCE DESCRIPTION: SEQ ID NO:139:

Lys Ser Lys Val Gly Trp Leu Ile Gln Ala Phe His Lys Lys
1               5                   10

(2) INFORMATION FOR SEQ ID NO:140:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.144"

(ix) FEATURE:
        (A) NAME/KEY: Modified-site
        (B) LOCATION: 6
        (C) OTHER INFORMATION: /label= Substituted-Ala
            /note= "The alanine at position 6 is
            cyclohexyl-substituted."

(xi) SEQUENCE DESCRIPTION: SEQ ID NO:140:

Lys Ser Lys Val Gly Ala Leu Ile Gln Leu Phe His Lys Lys
1               5                   10

(2) INFORMATION FOR SEQ ID NO:141:

(i) SEQUENCE CHARACTERISTICS:
    (A) LENGTH: 24 amino acids
    (B) TYPE: amino acid
    (D) TOPOLOGY: linear (ii) MOLECULE TYPE: peptide (ix) FEATURE:
    (A) NAME/KEY: misc_feature
    (D) OTHER INFORMATION: "BPI.145"

(xi) SEQUENCE DESCRIPTION: SEQ ID NO:141:

Lys Trp Lys Ala Ala Ala Arg Phe Leu Lys Lys Ser Lys Val Gly Trp
1               5                   10                  15

Leu Ile Gln Leu Phe His Lys Lys
            20

(2) INFORMATION FOR SEQ ID NO:142:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.146"

(ix) FEATURE:
        (A) NAME/KEY: Modified-site
        (B) LOCATION: 12
        (C) OTHER INFORMATION: /label= Substituted-Ala
            /note= "The alanine at position 12 is
            beta-1-naphthyl-substituted."

(ix) FEATURE:
        (A) NAME/KEY: Modified-site
        (B) LOCATION: 14
        (C) OTHER INFORMATION: /label= Substituted-Ala
            /note= "The alanine at position 14 is
            beta-1-naphthyl-substituted."

(xi) SEQUENCE DESCRIPTION: SEQ ID NO:142:

Lys Ser Lys Val Gly Trp Leu Ile Gln Leu Phe Ala Lys Ala
1               5                   10

(2) INFORMATION FOR SEQ ID NO:143:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.147"

(xi) SEQUENCE DESCRIPTION: SEQ ID NO:143:

Ile Lys Ile Ser Gly Lys Trp Lys Ala Glu Lys Lys Phe Leu Lys
1               5                   10                  15

(2) INFORMATION FOR SEQ ID NO:144:

(i) SEQUENCE CHARACTERISTICS:
        (A) LENGTH: 14 amino acids
        (B) TYPE: amino acid
        (D) TOPOLOGY: linear

```
    (ii) MOLECULE TYPE: peptide (ix) FEATURE:
         (A) NAME/KEY: misc_feature
         (D) OTHER INFORMATION: "BPI.148"

(ix) FEATURE:
         (A) NAME/KEY: Modified-site
         (B) LOCATION: 6
         (C) OTHER INFORMATION: /label= Substituted-Ala
             /note= "The alanine at position 6 is
             beta-1-naphthyl-substituted."

(ix) FEATURE:
         (A) NAME/KEY: Modified-site
         (B) LOCATION: 12
         (C) OTHER INFORMATION: /label= Substituted-Ala
             /note= "The alanine at position 12 is
             beta-1-naphthyl-substituted."

(xi) SEQUENCE DESCRIPTION: SEQ ID NO:144:

Lys Ser Lys Val Gly Ala Leu Ile Gln Leu Phe Ala Lys Lys
1               5                   10

(2) INFORMATION FOR SEQ ID NO:145:

(i) SEQUENCE CHARACTERISTICS:
        (A) LENGTH: 1813 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 31..1491

(ix) FEATURE:
         (A) NAME/KEY: mat_peptide
         (B) LOCATION: 124..1491

(ix) FEATURE:
         (A) NAME/KEY: misc_feature
         (D) OTHER INFORMATION: "rBPI"

(xi) SEQUENCE DESCRIPTION: SEQ ID NO:145:

CAGGCCTTGA GGTTTTGGCA GCTCTGGAGG ATG AGA GAG AAC ATG GCC AGG GGC         54
                                Met Arg Glu Asn Met Ala Arg Gly
                                -31 -30                 -25

CCT TGC AAC GCG CCG AGA TGG GTG TCC CTG ATG GTG CTC GTC GCC ATA        102
Pro Cys Asn Ala Pro Arg Trp Val Ser Leu Met Val Leu Val Ala Ile
            -20             -15                 -10

GGC ACC GCC GTG ACA GCG GCC GTC AAC CCT GGC GTC GTG GTC AGG ATC        150
Gly Thr Ala Val Thr Ala Ala Val Asn Pro Gly Val Val Val Arg Ile
        -5                  1               5

TCC CAG AAG GGC CTG GAC TAC GCC AGC CAG CAG GGG ACG GCC GCT CTG        198
Ser Gln Lys Gly Leu Asp Tyr Ala Ser Gln Gln Gly Thr Ala Ala Leu
10              15                  20                  25

CAG AAG GAG CTG AAG AGG ATC AAG ATT CCT GAC TAC TCA GAC AGC TTT        246
Gln Lys Glu Leu Lys Arg Ile Lys Ile Pro Asp Tyr Ser Asp Ser Phe
            30                  35                  40

AAG ATC AAG CAT CTT GGG AAG GGG CAT TAT AGC TTC TAC AGC ATG GAC        294
Lys Ile Lys His Leu Gly Lys Gly His Tyr Ser Phe Tyr Ser Met Asp
                45                  50                  55

ATC CGT GAA TTC CAG CTT CCC AGT TCC CAG ATA AGC ATG GTG CCC AAT        342
Ile Arg Glu Phe Gln Leu Pro Ser Ser Gln Ile Ser Met Val Pro Asn
        60                  65                  70

GTG GGC CTT AAG TTC TCC ATC AGC AAC GCC AAT ATC AAG ATC AGC GGG        390
```

```
Val Gly Leu Lys Phe Ser Ile Ser Asn Ala Asn Ile Lys Ile Ser Gly
     75                  80                  85

AAA TGG AAG GCA CAA AAG AGA TTC TTA AAA ATG AGC GGC AAT TTT GAC        438
Lys Trp Lys Ala Gln Lys Arg Phe Leu Lys Met Ser Gly Asn Phe Asp
 90                  95                 100                 105

CTG AGC ATA GAA GGC ATG TCC ATT TCG GCT GAT CTG AAG CTG GGC AGT        486
Leu Ser Ile Glu Gly Met Ser Ile Ser Ala Asp Leu Lys Leu Gly Ser
                    110                 115                 120

AAC CCC ACG TCA GGC AAG CCC ACC ATC ACC TGC TCC AGC TGC AGC AGC        534
Asn Pro Thr Ser Gly Lys Pro Thr Ile Thr Cys Ser Ser Cys Ser Ser
                125                 130                 135

CAC ATC AAC AGT GTC CAC GTG CAC ATC TCA AAG AGC AAA GTC GGG TGG        582
His Ile Asn Ser Val His Val His Ile Ser Lys Ser Lys Val Gly Trp
            140                 145                 150

CTG ATC CAA CTC TTC CAC AAA AAA ATT GAG TCT GCG CTT CGA AAC AAG        630
Leu Ile Gln Leu Phe His Lys Lys Ile Glu Ser Ala Leu Arg Asn Lys
        155                 160                 165

ATG AAC AGC CAG GTC TGC GAG AAA GTG ACC AAT TCT GTA TCC TCC AAG        678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT        726
Leu Gln Pro Tyr Phe Gln Thr Leu Pro Val Met Thr Lys Ile Asp Ser
                190                 195                 200

GTG GCT GGA ATC AAC TAT GGT CTG GTG GCA CCT CCA GCA ACC ACG GCT        774
Val Ala Gly Ile Asn Tyr Gly Leu Val Ala Pro Pro Ala Thr Thr Ala
            205                 210                 215

GAG ACC CTG GAT GTA CAG ATG AAG GGG GAG TTT TAC AGT GAG AAC CAC        822
Glu Thr Leu Asp Val Gln Met Lys Gly Glu Phe Tyr Ser Glu Asn His
        220                 225                 230

CAC AAT CCA CCT CCC TTT GCT CCA CCA GTG ATG GAG TTT CCC GCT GCC        870
His Asn Pro Pro Pro Phe Ala Pro Pro Val Met Glu Phe Pro Ala Ala
235                 240                 245

CAT GAC CGC ATG GTA TAC CTG GGC CTC TCA GAC TAC TTC TTC AAC ACA        918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA        966
Ala Gly Leu Val Tyr Gln Glu Ala Gly Val Leu Lys Met Thr Leu Arg
                270                 275                 280

GAT GAC ATG ATT CCA AAG GAG TCC AAA TTT CGA CTG ACA ACC AAG TTC       1014
Asp Asp Met Ile Pro Lys Glu Ser Lys Phe Arg Leu Thr Thr Lys Phe
            285                 290                 295

TTT GGA ACC TTC CTA CCT GAG GTG GCC AAG AAG TTT CCC AAC ATG AAG       1062
Phe Gly Thr Phe Leu Pro Glu Val Ala Lys Lys Phe Pro Asn Met Lys
        300                 305                 310

ATA CAG ATC CAT GTC TCA GCC TCC ACC CCG CCA CAC CTG TCT GTG CAG       1110
Ile Gln Ile His Val Ser Ala Ser Thr Pro Pro His Leu Ser Val Gln
315                 320                 325

CCC ACC GGC CTT ACC TTC TAC CCT GCC GTG GAT GTC CAG GCC TTT GCC       1158
Pro Thr Gly Leu Thr Phe Tyr Pro Ala Val Asp Val Gln Ala Phe Ala
330                 335                 340                 345

GTC CTC CCC AAC TCC TCC CTG GCT TCC CTC TTC CTG ATT GGC ATG CAC       1206
Val Leu Pro Asn Ser Ser Leu Ala Ser Leu Phe Leu Ile Gly Met His
                350                 355                 360

ACA ACT GGT TCC ATG GAG GTC AGC GCC GAG TCC AAC AGG CTT GTT GGA       1254
Thr Thr Gly Ser Met Glu Val Ser Ala Glu Ser Asn Arg Leu Val Gly
            365                 370                 375

GAG CTC AAG CTG GAT AGG CTG CTC CTG GAA CTG AAG CAC TCA AAT ATT       1302
Glu Leu Lys Leu Asp Arg Leu Leu Leu Glu Leu Lys His Ser Asn Ile
        380                 385                 390
```

```
GGC CCC TTC CCG GTT GAA TTG CTG CAG GAT ATC ATG AAC TAC ATT GTA              1350
Gly Pro Phe Pro Val Glu Leu Leu Gln Asp Ile Met Asn Tyr Ile Val
    395                 400                 405

CCC ATT CTT GTG CTG CCC AGG GTT AAC GAG AAA CTA CAG AAA GGC TTC              1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG              1446
Pro Leu Pro Thr Pro Ala Arg Val Gln Leu Tyr Asn Val Val Leu Gln
                430                 435                 440

CCT CAC CAG AAC TTC CTG CTG TTC GGT GCA GAC GTT GTC TAT AAA                  1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC            1551

ACCGGCTGCC TTTCCCCAGG GAATCCTCTC CAGATCTTAA CCAAGAGCCC CTTGCAAACT            1611

TCTTCGACTC AGATTCAGAA ATGATCTAAA CACGAGGAAA CATTATTCAT TGGAAAAGTG            1671

CATGGTGTGT ATTTTAGGGA TTATGAGCTT CTTTCAAGGG CTAAGGCTGC AGAGATATTT            1731

CCTCCAGGAA TCGTGTTTCA ATTGTAACCA AGAAATTTCC ATTTGTGCTT CATGAAAAAA            1791

AACTTCTGGT TTTTTTCATG TG                                                     1813
```

(2) INFORMATION FOR SEQ ID NO:146:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO:146:

```
Met Arg Glu Asn Met Ala Arg Gly Pro Cys Asn Ala Pro Arg Trp Val
-31 -30             -25                 -20

Ser Leu Met Val Leu Val Ala Ile Gly Thr Ala Val Thr Ala Ala Val
-15             -10                  -5                   1

Asn Pro Gly Val Val Val Arg Ile Ser Gln Lys Gly Leu Asp Tyr Ala
             5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
            35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                70                  75                  80

Asn Ala Asn Ile Lys Ile Ser Gly Lys Trp Lys Ala Gln Lys Arg Phe
                85                  90                  95

Leu Lys Met Ser Gly Asn Phe Asp Leu Ser Ile Glu Gly Met Ser Ile
               100                 105                 110

Ser Ala Asp Leu Lys Leu Gly Ser Asn Pro Thr Ser Gly Lys Pro Thr
               115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
                165                 170                 175
```

```
Val Thr Asn Ser Val Ser Lys Leu Gln Pro Tyr Phe Gln Thr Leu
            180             185                 190

Pro Val Met Thr Lys Ile Asp Ser Val Ala Gly Ile Asn Tyr Gly Leu
    195             200             205

Val Ala Pro Pro Ala Thr Thr Ala Glu Thr Leu Asp Val Gln Met Lys
210             215             220                     225

Gly Glu Phe Tyr Ser Glu Asn His His Asn Pro Pro Phe Ala Pro
                230             235             240

Pro Val Met Glu Phe Pro Ala Ala His Asp Arg Met Val Tyr Leu Gly
            245             250             255

Leu Ser Asp Tyr Phe Phe Asn Thr Ala Gly Leu Val Tyr Gln Glu Ala
            260             265             270

Gly Val Leu Lys Met Thr Leu Arg Asp Asp Met Ile Pro Lys Glu  Ser
    275             280             285

Lys Phe Arg Leu Thr Thr Lys Phe Phe Gly Thr Phe Leu Pro Glu Val
290             295             300                     305

Ala Lys Lys Phe Pro Asn Met Lys Ile Gln Ile His Val Ser Ala Ser
            310             315             320

Thr Pro Pro His Leu Ser Val Gln Pro Thr Gly Leu Thr Phe Tyr Pro
            325             330             335

Ala Val Asp Val Gln Ala Phe Ala Val Leu Pro Asn Ser Ser Leu Ala
            340             345             350

Ser Leu Phe Leu Ile Gly Met His Thr Thr Gly Ser Met Glu Val Ser
    355             360             365

Ala Glu Ser Asn Arg Leu Val Gly Glu Leu Lys Leu Asp Arg Leu Leu
370             375             380                     385

Leu Glu Leu Lys His Ser Asn Ile Gly Pro Phe Pro Val Glu Leu Leu
            390             395                     400

Gln Asp Ile Met Asn Tyr Ile Val Pro Ile Leu Val Leu Pro Arg Val
            405             410             415

Asn Glu Lys Leu Gln Lys Gly Phe Pro Leu Pro Thr Pro Ala Arg Val
            420             425             430

Gln Leu Tyr Asn Val Val Leu Gln Pro His Gln Asn Phe Leu Leu Phe
    435             440             445

Gly Ala Asp Val Val Tyr Lys
450             455

(2) INFORMATION FOR SEQ ID NO:147:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.149"

(xi) SEQUENCE DESCRIPTION: SEQ ID NO:147:

Lys Trp Lys Val Phe Lys Lys Ile Glu Lys Lys Ser Lys Val Gly Trp
1               5                   10                  15

Leu Ile Gln Leu Phe His Lys Lys
            20

(2) INFORMATION FOR SEQ ID NO:148:
```

```
    (i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.150"

(xi) SEQUENCE DESCRIPTION: SEQ ID NO:148:

Lys Trp Ala Phe Ala Lys Lys Gln Lys Lys Arg Leu Lys Arg Gln Trp
 1               5                  10                  15

Leu Lys Lys Phe
            20

(2) INFORMATION FOR SEQ ID NO:149:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.153"

(xi) SEQUENCE DESCRIPTION: SEQ ID NO:149:

Lys Trp Lys Ala Gln Lys Arg Phe Leu Lys Lys Trp Lys Ala Gln Lys
 1               5                  10                  15

Arg Phe Leu Lys Lys Trp Lys Ala Gln Lys Arg Phe Leu Lys
            20                  25                  30

(2) INFORMATION FOR SEQ ID NO:150:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.154"

(ix) FEATURE:
        (A) NAME/KEY: Modified-site
        (B) LOCATION: 5
        (C) OTHER INFORMATION: /label= Substituted-Ala
            /note= "Position 5 is
            beta-1-naphthyl-substituted."

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(xi) SEQUENCE DESCRIPTION: SEQ ID NO:150:

Lys Trp Lys Ala Ala Ala Arg Phe Leu Lys Lys Trp Lys Ala Gln Lys
 1               5                  10                  15

Arg Phe Leu Lys
            20

(2) INFORMATION FOR SEQ ID NO:151:
```

(i) SEQUENCE CHARACTERISTICS:
            (A) LENGTH: 20 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.155"

(ix) FEATURE:
            (A) NAME/KEY: Modified-site
            (B) LOCATION: 15
            (C) OTHER INFORMATION: /label= Substituted-Ala
                /note= "Position 15 is
                beta-1-naphthyl-substituted."

(ix) FEATURE:
            (A) NAME/KEY: Modified-site
            (B) LOCATION: 16
            (C) OTHER INFORMATION: /label= Substituted-Ala
                /note= "Position 16 is
                beta-1-naphthyl-substituted."

(xi) SEQUENCE DESCRIPTION: SEQ ID NO:151:

Lys Trp Lys Ala Gln Lys Arg Phe Leu Lys Lys Trp Lys Ala Ala Ala
1               5                   10                  15

Arg Phe Leu Lys
            20

(2) INFORMATION FOR SEQ ID NO:152:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.156"

(ix) FEATURE:
            (A) NAME/KEY: Modified-site
            (B) LOCATION: 5
            (C) OTHER INFORMATION: /label= Substituted-Ala
                /note= "Position 5 is
                beta-1-naphthyl-substituted."

(ix) FEATURE:
            (A) NAME/KEY: Modified-site
            (B) LOCATION: 6
            (C) OTHER INFORMATION: /label= Substituted-Ala
                /note= "Position 6 is
                beta-1-naphthyl-substituted."

(ix) FEATURE:
            (A) NAME/KEY: Modified-site
            (B) LOCATION: 15
            (C) OTHER INFORMATION: /label= Substituted-Ala
                /note= "Position 15 is
                beta-1-naphthyl-substituted."

(ix) FEATURE:
            (A) NAME/KEY: Modified-site
            (B) LOCATION: 16
            (C) OTHER INFORMATION: /label= Substituted-Ala
                /note= "Position 16 is
                beta-1-naphthyl-substituted."

(xi) SEQUENCE DESCRIPTION: SEQ ID NO:152:

Lys Trp Lys Ala Ala Ala Arg Phe Leu Lys Lys Trp Lys Ala Ala Ala

```
 1               5                  10                  15
Arg Phe Leu Lys
            20

(2) INFORMATION FOR SEQ ID NO:153:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.157"

(ix) FEATURE:
        (A) NAME/KEY: Modified-site
        (B) LOCATION: 5
        (C) OTHER INFORMATION: /label= Substituted-Ala
            /note= "Position 5 is
            beta-1-naphthyl-substituted."

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(ix) FEATURE:
        (A) NAME/KEY: Modified-site
        (B) LOCATION: 15
        (C) OTHER INFORMATION: /label= Substituted-Ala
            /note= "Position 15 is
            beta-1-naphthyl-substituted."

(ix) FEATURE:
        (A) NAME/KEY: Modified-site
        (B) LOCATION: 16
        (C) OTHER INFORMATION: /label= Substituted-Ala
            /note= "Position 16 is
            beta-1-naphthyl-substituted."

(ix) FEATURE:
        (A) NAME/KEY: Modified-site
        (B) LOCATION: 25
        (C) OTHER INFORMATION: /label= Substituted-Ala
            /note= "Position 25 is
            beta-1-naphthyl-substituted."

(ix) FEATURE:
        (A) NAME/KEY: Modified-site
        (B) LOCATION: 26
        (C) OTHER INFORMATION: /label= Substituted-Ala
            /note= "Position 26 is
            beta-1-naphthyl-substituted."

(xi) SEQUENCE DESCRIPTION: SEQ ID NO:153:

Lys Trp Lys Ala Ala Ala Arg Phe Leu Lys Trp Lys Ala Ala Ala
 1               5                  10                  15

Arg Phe Leu Lys Lys Trp Lys Ala Ala Ala Arg Phe Leu Lys
                20                  25                  30

(2) INFORMATION FOR SEQ ID NO:154:

(i) SEQUENCE CHARACTERISTICS:
        (A) LENGTH: 29 amino acids
        (B) TYPE: amino acid
        (D) TOPOLOGY: linear (ii) MOLECULE TYPE: peptide
```

(ix) FEATURE:
            (A) NAME/KEY: misc_feature
            (D) OTHER INFORMATION: "BPI.158"

(ix) FEATURE:
            (A) NAME/KEY: Modified-site
            (B) LOCATION: 10
            (C) OTHER INFORMATION: /label= Substituted-Ala
                /note= "Position 10 is
                beta-1-naphthyl-substituted."

(ix) FEATURE:
            (A) NAME/KEY: Modified-site
            (B) LOCATION: 11
            (C) OTHER INFORMATION: /label= Substituted-Ala
                /note= "Position 11 is
                beta-1-naphthyl-substituted."

(xi) SEQUENCE DESCRIPTION: SEQ ID NO:154:

Ile Lys Ile Ser Gly Lys Trp Lys Ala Ala Ala Arg Phe Leu Lys Lys
1               5                   10                  15

Ser Lys Val Gly Trp Leu Ile Gln Leu Phe His Lys Lys
            20                  25

(2) INFORMATION FOR SEQ ID NO:155:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.159"

(ix) FEATURE:
        (A) NAME/KEY: Modified-site
        (B) LOCATION: 2
        (C) OTHER INFORMATION: /label= Substituted-Ala
            /note= "Position 2 is
            beta-1-naphthyl-substituted."

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(xi) SEQUENCE DESCRIPTION: SEQ ID NO:155:

Lys Ala Lys Ala Gln Ala Arg Phe Leu Lys Lys Ser Lys Val Gly Trp
1               5                   10                  15

Leu Ile Gln Leu Trp His Lys Lys
            20

(2) INFORMATION FOR SEQ ID NO:156:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.160"

(ix) FEATURE:
        (A) NAME/KEY: Modified-site
        (B) LOCATION: 2

(C) OTHER INFORMATION: /label= Substituted-Ala
                /note= "Position 2 is
                beta-1-naphthyl-substituted."

(ix) FEATURE:
         (A) NAME/KEY: Modified-site
         (B) LOCATION: 6
         (C) OTHER INFORMATION: /label= Substituted-Ala
                /note= "Position 6 is
                beta-1-naphthyl-substituted."

(ix) FEATURE:
         (A) NAME/KEY: Modified-site
         (B) LOCATION: 12
         (C) OTHER INFORMATION: /label= Substituted-Ala
                /note= "Position 12 is
                beta-1-naphthyl-substituted."

(ix) FEATURE:
         (A) NAME/KEY: Modified-site
         (B) LOCATION: 16
         (C) OTHER INFORMATION: /label= Substituted-Ala
                /note= "Position 16 is
                beta-1-naphthyl-substituted."

(xi) SEQUENCE DESCRIPTION: SEQ ID NO:156:

Lys Ala Lys Ala Gln Ala Arg Phe Leu Lys Lys Ala Lys Ala Gln Ala
1               5                   10                  15

Arg Phe Leu Lys
            20

(2) INFORMATION FOR SEQ ID NO:157:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.161"

(xi) SEQUENCE DESCRIPTION: SEQ ID NO:157:

Lys Ser Lys Val Lys Ala Leu Ile Gln Leu Phe His Lys Lys
1               5                   10

(2) INFORMATION FOR SEQ ID NO:158:

(i) SEQUENCE CHARACTERISTICS:
         (A) LENGTH: 24 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.162"

(xi) SEQUENCE DESCRIPTION: SEQ ID NO:158:

Lys Trp Lys Ala Gln Trp Arg Phe Leu Lys Lys Ser Lys Val Gly Trp
1               5                   10                  15

Leu Ile Gln Leu Phe His Lys Lys
            20

(2) INFORMATION FOR SEQ ID NO:159:

(i) SEQUENCE CHARACTERISTICS:
         (A) LENGTH: 20 amino acids

```
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.163"

(xi) SEQUENCE DESCRIPTION: SEQ ID NO:159:

Lys Trp Lys Ala Gln Trp Arg Phe Leu Lys Lys Trp Lys Ala Gln Trp
1               5                   10                  15

Arg Phe Leu Lys
            20

(2) INFORMATION FOR SEQ ID NO:160:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.164"

(ix) FEATURE:
            (A) NAME/KEY: Modified-site
            (B) LOCATION: 5
            (C) OTHER INFORMATION: /label= Substituted-Ala
                /note= "Position 5 is
                beta-1-naphthyl-substituted."

(ix) FEATURE:
            (A) NAME/KEY: Modified-site
            (B) LOCATION: 15
            (C) OTHER INFORMATION: /label= Substituted-Ala
                /note= "Position 15 is
                beta-1-naphthyl-substituted."

(xi) SEQUENCE DESCRIPTION: SEQ ID NO:160:

Lys Trp Lys Ala Ala Lys Arg Phe Leu Lys Lys Trp Lys Ala Ala Lys
1               5                   10                  15

Arg Phe Leu Lys
            20

(2) INFORMATION FOR SEQ ID NO:161:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.165"

(ix) FEATURE:
            (A) NAME/KEY: Modified-site
            (B) LOCATION: 2
            (C) OTHER INFORMATION: /label= Substituted-Ala
                /note= "Position 2 is
                beta-1-naphthyl-substituted."

(ix) FEATURE:
            (A) NAME/KEY: Modified-site
            (B) LOCATION: 12
            (C) OTHER INFORMATION: /label= Substituted-Ala
                /note= "Position 12 is
```

-continued beta-1-naphthyl-substituted."

(xi) SEQUENCE DESCRIPTION: SEQ ID NO:161:

```
Lys Ala Lys Ala Gln Phe Arg Phe Leu Lys Lys Ala Lys Ala Gln Phe
1               5                   10                  15
Arg Phe Leu Lys
            20
```

(2) INFORMATION FOR SEQ ID NO:162:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.166"

(xi) SEQUENCE DESCRIPTION: SEQ ID NO:162:

```
Lys Ser Lys Val Gly Val Leu Ile Gln Leu Phe His Lys Lys
1               5                   10
```

(2) INFORMATION FOR SEQ ID NO:163:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.167"

(xi) SEQUENCE DESCRIPTION: SEQ ID NO:163:

```
Lys Trp Lys Ala Gln Lys Arg Phe
1               5
```

(2) INFORMATION FOR SEQ ID NO:164:

(i) SEQUENCE CHARACTERISTICS:
        (A) LENGTH: 14 amino acids
        (B) TYPE: amino acid
        (D) TOPOLOGY: circular (ii) MOLECULE TYPE: peptide (ix) FEATURE:
        (A) NAME/KEY: misc_feature
        (D) OTHER INFORMATION: "BPI.168"

(xi) SEQUENCE DESCRIPTION: SEQ ID NO:164:

```
Cys Lys Trp Lys Ala Gln Lys Arg Phe Leu Lys Met Ser Cys
1               5                   10
```

(2) INFORMATION FOR SEQ ID NO:165:

(i) SEQUENCE CHARACTERISTICS:
        (A) LENGTH: 10 amino acids
        (B) TYPE: amino acid
        (D) TOPOLOGY: circular (ii) MOLECULE TYPE: peptide (ix) FEATURE:
        (A) NAME/KEY: misc_feature (D) OTHER INFORMATION: "BPI.169"

(xi) SEQUENCE DESCRIPTION: SEQ ID NO:165:

Cys Lys Trp Lys Ala Gln Lys Arg Phe Cys
1               5                   10

(2) INFORMATION FOR SEQ ID NO:166:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.221"

(ix) FEATURE:
        (A) NAME/KEY: Modified-site
        (B) LOCATION: 13
        (C) OTHER INFORMATION: /label= Substituted-Ala
            /note= "Position 13 is
            beta-1-naphthyl-substituted."

(xi) SEQUENCE DESCRIPTION: SEQ ID NO:166:

Ile Lys Ile Ser Gly Lys Trp Lys Ala Gln Lys Arg Ala Leu Lys
1               5                   10                  15

(2) INFORMATION FOR SEQ ID NO:167:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.222"

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(ix) FEATURE:
        (A) NAME/KEY: Modified-site
        (B) LOCATION: 14
        (C) OTHER INFORMATION: /label= Substituted-Ala
            /note= "Position 14 is
            beta-1-naphthyl-substituted."

(xi) SEQUENCE DESCRIPTION: SEQ ID NO:167:

Lys Ser Lys Val Gly Ala Leu Ile Gln Leu Phe His Lys Ala
1               5                   10

(2) INFORMATION FOR SEQ ID NO:168:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.223"

-continued

```
        (ix) FEATURE:
             (A) NAME/KEY: Modified-site
             (B) LOCATION: 6
             (C) OTHER INFORMATION: /label= Substituted-Ala
                 /note= "Position 6 is
                 beta-1-naphthyl-substituted."

(ix) FEATURE:
             (A) NAME/KEY: Modified-site
             (B) LOCATION: 10
             (C) OTHER INFORMATION: /label= Substituted-Ala
                 /note= "Position 10 is
                 beta-1-naphthyl-substituted."

(xi) SEQUENCE DESCRIPTION: SEQ ID NO:168:

Lys Ser Lys Val Gly Ala Leu Ile Gln Ala Phe His Lys Lys
1               5                   10

(2) INFORMATION FOR SEQ ID NO:169:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "BPI.224"

(ix) FEATURE:
             (A) NAME/KEY: Modified-site
             (B) LOCATION: 6
             (C) OTHER INFORMATION: /label= Substituted-Ala
                 /note= "Position 6 is
                 beta-1-naphthyl-substituted."

(ix) FEATURE:
             (A) NAME/KEY: Modified-site
             (B) LOCATION: 9
             (C) OTHER INFORMATION: /label= Substituted-Phe
                 /note= "Position 9 is
                 para-amino-substituted."

(xi) SEQUENCE DESCRIPTION: SEQ ID NO:169:

Lys Ser Lys Val Gly Ala Leu Ile Phe Leu Phe His Lys Lys
1               5                   10

(2) INFORMATION FOR SEQ ID NO:170:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "BPI.225"

(ix) FEATURE:
             (A) NAME/KEY: Modified-site
             (B) LOCATION: 6
             (C) OTHER INFORMATION: /label= Substituted-Ala
                 /note= "Position 6 is
                 beta-1-naphthyl-substituted."

(ix) FEATURE:
             (A) NAME/KEY: Modified-site
             (B) LOCATION: 5
             (C) OTHER INFORMATION: /label= Substituted-Phe
                 /note= "Position 5 is
``` para-amino-substituted."

(xi) SEQUENCE DESCRIPTION: SEQ ID NO:170:

Lys Ser Lys Val Phe Ala Leu Ile Gln Leu Phe His Lys Lys
1               5                  10

(2) INFORMATION FOR SEQ ID NO:171:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.226"

(ix) FEATURE:
        (A) NAME/KEY: Modified-site
        (B) LOCATION: 6
        (C) OTHER INFORMATION: /label= Substituted-Ala
            /note= "Position 6 is
            beta-1-naphthyl-substituted."

(xi) SEQUENCE DESCRIPTION: SEQ ID NO:171:

Lys Ser Lys Val Gly Ala Leu Ile Gln Leu Trp His Lys Lys
1               5                  10

(2) INFORMATION FOR SEQ ID NO:172:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.227"

(ix) FEATURE:
        (A) NAME/KEY: Modified-site
        (B) LOCATION: 10
        (C) OTHER INFORMATION: /label= Substituted-Ala
            /note= "Position 10 is
            beta-1-naphthyl-substituted."

(ix) FEATURE:
        (A) NAME/KEY: Modified-site
        (B) LOCATION: 14
        (C) OTHER INFORMATION: /label= Substituted-Ala
            /note= "Position 14 is
            beta-1-naphthyl-substituted."

(xi) SEQUENCE DESCRIPTION: SEQ ID NO:172:

Lys Ser Lys Val Gly Trp Leu Ile Gln Ala Phe His Lys Ala
1               5                  10

(2) INFORMATION FOR SEQ ID NO:173:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.228"

```
    (ix) FEATURE:
         (A) NAME/KEY: Modified-site
         (B) LOCATION: 9
         (C) OTHER INFORMATION: /label= Substituted-Phe
             /note= "Position 9 is
             para-amino-substituted."

(ix) FEATURE:
         (A) NAME/KEY: Modified-site
         (B) LOCATION: 14
         (C) OTHER INFORMATION: /label= Substituted-Ala
             /note= "Position 14 is
             beta-1-naphthyl-substituted."

(xi) SEQUENCE DESCRIPTION: SEQ ID NO:173:

Lys Ser Lys Val Gly Trp Leu Ile Phe Leu Phe His Lys Ala
1               5                   10

(2) INFORMATION FOR SEQ ID NO:174:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.229"

(ix) FEATURE:
         (A) NAME/KEY: Modified-site
         (B) LOCATION: 5
         (C) OTHER INFORMATION: /label= Substituted-Ala
             /note= "Position 5 is
             para-amino-substituted."

(ix) FEATURE:
         (A) NAME/KEY: Modified-site
         (B) LOCATION: 14
         (C) OTHER INFORMATION: /label= Substituted-Ala
             /note= "Position 14 is
             beta-1-naphthyl-substituted."

(xi) SEQUENCE DESCRIPTION: SEQ ID NO:174:

Lys Ser Lys Val Phe Trp Leu Ile Gln Leu Phe His Lys Ala
1               5                   10

(2) INFORMATION FOR SEQ ID NO:175:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.230"

(ix) FEATURE:
         (A) NAME/KEY: Modified-site
         (B) LOCATION: 14
         (C) OTHER INFORMATION: /label= Substituted-Ala
             /note= "Position 14 is
             beta-1-naphthyl-substituted."

(xi) SEQUENCE DESCRIPTION: SEQ ID NO:175:

Lys Ser Lys Val Gly Trp Leu Ile Gln Leu Trp His Lys Ala
1               5                   10
```

(2) INFORMATION FOR SEQ ID NO:176:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.231"

(ix) FEATURE:
        (A) NAME/KEY: Modified-site
        (B) LOCATION: 10
        (C) OTHER INFORMATION: /label= Substituted-Ala
            /note= "Position 10 is
            beta-1-naphthyl-substituted."

(ix) FEATURE:
        (A) NAME/KEY: Modified-site
        (B) LOCATION: 12
        (C) OTHER INFORMATION: /label= Substituted-Ala
            /note= "Position 12 is
            beta-1-naphthyl-substituted."

(xi) SEQUENCE DESCRIPTION: SEQ ID NO:176:

```
Lys Ser Lys Val Gly Trp Leu Ile Gln Ala Phe Ala Lys Lys
1               5                   10
```

(2) INFORMATION FOR SEQ ID NO:177:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.232"

(ix) FEATURE:
        (A) NAME/KEY: Modified-site
        (B) LOCATION: 9
        (C) OTHER INFORMATION: /label= Substituted-Phe
            /note= "Position 9 is
            para-amino-substituted."

(ix) FEATURE:
        (A) NAME/KEY: Modified-site
        (B) LOCATION: 12
        (C) OTHER INFORMATION: /label= Substituted-Ala
            /note= "Position 12 is
            beta-1-naphthyl-substituted."

(xi) SEQUENCE DESCRIPTION: SEQ ID NO:177:

```
Lys Ser Lys Val Gly Trp Leu Ile Phe Leu Phe Ala Lys Lys
1               5                   10
```

(2) INFORMATION FOR SEQ ID NO:178:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.233"

```
        (ix) FEATURE:
             (A) NAME/KEY: Modified-site
             (B) LOCATION: 5
             (C) OTHER INFORMATION: /label= Substituted-Phe
                   /note= "Position 5 is
                   para-amino-substituted."

(ix) FEATURE:
             (A) NAME/KEY: Modified-site
             (B) LOCATION: 12
             (C) OTHER INFORMATION: /label= Substituted-Ala
                   /note= "Position 12 is
                   beta-1-naphthyl-substituted."

(xi) SEQUENCE DESCRIPTION: SEQ ID NO:178:

Lys Ser Lys Val Phe Trp Leu Ile Gln Leu Phe Ala Lys Lys
1               5                   10

(2) INFORMATION FOR SEQ ID NO:179:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "BPI.234"

(ix) FEATURE:
             (A) NAME/KEY: Modified-site
             (B) LOCATION: 12
             (C) OTHER INFORMATION: /label= Substituted-Ala
                   /note= "Position 12 is
                   beta-1-naphthyl-substituted."

(xi) SEQUENCE DESCRIPTION: SEQ ID NO:179:

Lys Ser Lys Val Gly Trp Leu Ile Gln Leu Trp Ala Lys Lys
1               5                   10

(2) INFORMATION FOR SEQ ID NO:180:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "BPI.235"

(ix) FEATURE:
             (A) NAME/KEY: Modified-site
             (B) LOCATION: 9
             (C) OTHER INFORMATION: /label= Substituted-Phe
                   /note= "Position 9 is
                   para-amino-substituted."

(ix) FEATURE:
             (A) NAME/KEY: Modified-site
             (B) LOCATION: 10
             (C) OTHER INFORMATION: /label= Substituted-Ala
                   /note= "Position 10 is
                   beta-1-naphthyl-substituted."

(xi) SEQUENCE DESCRIPTION: SEQ ID NO:180:

Lys Ser Lys Val Gly Trp Leu Ile Phe Ala Phe His Lys Lys
1               5                   10
```

(2) INFORMATION FOR SEQ ID NO:181:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.236"

(ix) FEATURE:
        (A) NAME/KEY: Modified-site
        (B) LOCATION: 5
        (C) OTHER INFORMATION: /label= Substituted-Phe
            /note= "Position 5 is
            para-amino-substituted."

(ix) FEATURE:
        (A) NAME/KEY: Modified-site
        (B) LOCATION: 10
        (C) OTHER INFORMATION: /label= Substituted-Ala
            /note= "Position 10 is
            beta-1-naphthyl-substituted."

(xi) SEQUENCE DESCRIPTION: SEQ ID NO:181:

Lys Ser Lys Val Phe Trp Leu Ile Gln Ala Phe His Lys Lys
1             5                    10

(2) INFORMATION FOR SEQ ID NO:182:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.237"

(ix) FEATURE:
        (A) NAME/KEY: Modified-site
        (B) LOCATION: 10
        (C) OTHER INFORMATION: /label= Substituted-Ala
            /note= "Position 10 is
            beta-1-naphthyl-substituted."

(xi) SEQUENCE DESCRIPTION: SEQ ID NO:182:

Lys Ser Lys Val Gly Trp Leu Ile Gln Ala Trp His Lys Lys
1             5                    10

(2) INFORMATION FOR SEQ ID NO:183:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.238"

(ix) FEATURE:
        (A) NAME/KEY: Modified-site
        (B) LOCATION: 5
        (C) OTHER INFORMATION: /label= Substituted-Phe
            /note= "Position 5 is
            para-amino-substituted."

```
    (ix) FEATURE:
         (A) NAME/KEY: Modified-site
         (B) LOCATION: 9
         (C) OTHER INFORMATION: /label= Substituted-Phe
             /note= "Position 9 is
             para-amino-substituted."

(xi) SEQUENCE DESCRIPTION: SEQ ID NO:183:

Lys Ser Lys Val Phe Trp Leu Ile Phe Leu Phe His Lys Lys
1               5                   10

(2) INFORMATION FOR SEQ ID NO:184:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.239"

(ix) FEATURE:
         (A) NAME/KEY: Modified-site
         (B) LOCATION: 9
         (C) OTHER INFORMATION: /label= Substituted-Phe
             /note= "Position 9 is
             para-amino-substituted."

(xi) SEQUENCE DESCRIPTION: SEQ ID NO:184:

Lys Ser Lys Val Gly Trp Leu Ile Phe Leu Trp His Lys Lys
1               5                   10

(2) INFORMATION FOR SEQ ID NO:185:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.240"

(ix) FEATURE:
         (A) NAME/KEY: Modified-site
         (B) LOCATION: 5
         (C) OTHER INFORMATION: /label= Substituted-Phe
             /note= "Position 5 is
             para-amino-substituted."

(xi) SEQUENCE DESCRIPTION: SEQ ID NO:185:

Lys Ser Lys Val Phe Trp Leu Ile Gln Leu Trp His Lys Lys
1               5                   10

(2) INFORMATION FOR SEQ ID NO:186:

(i) SEQUENCE CHARACTERISTICS:
         (A) LENGTH: 24 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.247"
```

```
        (ix) FEATURE:
              (A) NAME/KEY: Modified-site
              (B) LOCATION: 2
              (C) OTHER INFORMATION: /label= Substituted-Ala
                  /note= "Position 2 is
                  beta-1-naphthyl-substituted."

(ix) FEATURE:
              (A) NAME/KEY: Modified-site
              (B) LOCATION: 6
              (C) OTHER INFORMATION: /label= Substituted-Ala
                  /note= "Position 6 is
                  beta-1-naphthyl-substituted."

(xi) SEQUENCE DESCRIPTION: SEQ ID NO:186:

Lys Ala Lys Ala Gln Ala Arg Phe Leu Lys Lys Ser Lys Val Gly Trp
1               5                   10                  15

Leu Ile Leu Leu Phe His Lys Lys
                    20

(2) INFORMATION FOR SEQ ID NO:187:

(i) SEQUENCE CHARACTERISTICS:
              (A) LENGTH: 24 amino acids
              (B) TYPE: amino acid
              (D) TOPOLOGY: linear (ii) MOLECULE TYPE: peptide (ix) FEATURE:
              (A) NAME/KEY: misc_feature
              (D) OTHER INFORMATION: "BPI.245"

(xi) SEQUENCE DESCRIPTION: SEQ ID NO:187:

Lys Trp Lys Ala Gln Phe Arg Phe Leu Lys Lys Ser Lys Val Gly Trp
1               5                   10                  15

Leu Ile Gln Leu Trp His Lys Lys
                20

(2) INFORMATION FOR SEQ ID NO:188:

(i) SEQUENCE CHARACTERISTICS:
              (A) LENGTH: 24 amino acids
              (B) TYPE: amino acid
              (D) TOPOLOGY: linear (ii) MOLECULE TYPE: peptide (ix) FEATURE:
              (A) NAME/KEY: misc_feature
              (D) OTHER INFORMATION: "BPI.246"

(ix) FEATURE:
              (A) NAME/KEY: Modified-site
              (B) LOCATION: 16
              (C) OTHER INFORMATION: /label= Substituted-Ala
                  /note= "Position 16 is
                  D-beta-2-naphthyl-substituted."

(xi) SEQUENCE DESCRIPTION: SEQ ID NO:188:

Lys Trp Lys Ala Gln Phe Arg Phe Leu Lys Lys Ser Lys Val Gly Ala
1               5                   10                  15

Leu Ile Gln Leu Phe His Lys Lys
                20

(2) INFORMATION FOR SEQ ID NO:189:

(i) SEQUENCE CHARACTERISTICS:
              (A) LENGTH: 24 amino acids
              (B) TYPE: amino acid
```

```
          (D) TOPOLOGY: linear (ii) MOLECULE TYPE: peptide (ix) FEATURE:
         (A) NAME/KEY: misc_feature
         (D) OTHER INFORMATION: "BPI.248"

(ix) FEATURE:
         (A) NAME/KEY: Modified-site
         (B) LOCATION: 2
         (C) OTHER INFORMATION: /label= Substituted-Ala
             /note= "Position 2 is
             beta-1-naphthyl-substituted."

(ix) FEATURE:
         (A) NAME/KEY: Modified-site
         (B) LOCATION: 6
         (C) OTHER INFORMATION: /label= Substituted-Ala
             /note= "Position 6 is
             beta-1-naphthyl-substituted."

(ix) FEATURE:
         (A) NAME/KEY: Modified-site
         (B) LOCATION: 16
         (C) OTHER INFORMATION: /label= Substituted-Ala
             /note= "Position 16 is
             D-beta-2-naphthyl-substituted."

(xi) SEQUENCE DESCRIPTION: SEQ ID NO:189:

Lys Ala Lys Ala Gln Ala Arg Phe Leu Lys Lys Ser Lys Val Gly Ala
1               5                   10                  15
Leu Ile Gln Leu Phe His Lys Lys
            20

(2) INFORMATION FOR SEQ ID NO:190:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.242"

(ix) FEATURE:
         (A) NAME/KEY: Modified-site
         (B) LOCATION: 6
         (C) OTHER INFORMATION: /label= Substituted-Ala
             /note= "Position 6 is
             D-beta-2-naphthyl-substituted."

(xi) SEQUENCE DESCRIPTION: SEQ ID NO:190:

Lys Ser Lys Val Gly Ala Leu Ile Leu Leu Phe His Lys Lys
1               5                   10

(2) INFORMATION FOR SEQ ID NO:191:

(i) SEQUENCE CHARACTERISTICS:
         (A) LENGTH: 28 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.272"

(xi) SEQUENCE DESCRIPTION: SEQ ID NO:191:
```

```
Lys Ser Lys Val Gly Trp Leu Ile Leu Leu Phe His Lys Lys Lys Ser
1               5                   10                  15

Lys Val Gly Trp Leu Ile Leu Leu Phe His Lys Lys
            20                  25

(2) INFORMATION FOR SEQ ID NO:192:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.275"

(xi) SEQUENCE DESCRIPTION: SEQ ID NO:192:

Lys Ser Lys Val Gly Trp Leu Ile Phe Leu Phe His Lys Lys Lys Ser
1               5                   10                  15

Lys Val Gly Trp Leu Ile Phe Leu Phe His Lys Lys
            20                  25

(2) INFORMATION FOR SEQ ID NO:193:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.270"

(xi) SEQUENCE DESCRIPTION: SEQ ID NO:193:

Lys Ser Lys Val Gly Trp Leu Ile Leu Leu Phe His Lys Lys Lys Ser
1               5                   10                  15

Lys Val Gly Trp Leu Ile Gln Leu Phe His Lys Lys
            20                  25

(2) INFORMATION FOR SEQ ID NO:194:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.271"

(xi) SEQUENCE DESCRIPTION: SEQ ID NO:194:

Lys Ser Lys Val Gly Trp Leu Ile Gln Leu Phe His Lys Lys Lys Ser
1               5                   10                  15

Lys Val Gly Trp Leu Ile Leu Leu Phe His Lys Lys
            20                  25

(2) INFORMATION FOR SEQ ID NO:195:

(i) SEQUENCE CHARACTERISTICS:
        (A) LENGTH: 28 amino acids
        (B) TYPE: amino acid
        (D) TOPOLOGY: linear
```

```
    (ii) MOLECULE TYPE: peptide (ix) FEATURE:
         (A) NAME/KEY: misc_feature
         (D) OTHER INFORMATION: "BPI.273"

(xi) SEQUENCE DESCRIPTION: SEQ ID NO:195:

Lys Ser Lys Val Gly Trp Leu Ile Phe Leu Phe His Lys Lys Lys Ser
1               5                   10                  15

Lys Val Gly Trp Leu Ile Gln Leu Phe His Lys Lys
            20                  25

(2) INFORMATION FOR SEQ ID NO:196:

(i) SEQUENCE CHARACTERISTICS:
         (A) LENGTH: 28 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.274"

(xi) SEQUENCE DESCRIPTION: SEQ ID NO:196:

Lys Ser Lys Val Gly Trp Leu Ile Gln Leu Phe His Lys Lys Lys Ser
1               5                   10                  15

Lys Val Gly Trp Leu Ile Phe Leu Phe His Lys Lys
            20                  25

(2) INFORMATION FOR SEQ ID NO:197:

(i) SEQUENCE CHARACTERISTICS:
         (A) LENGTH: 24 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.276"

(xi) SEQUENCE DESCRIPTION: SEQ ID NO:197:

Lys Trp Lys Ala Gln Phe Arg Phe Leu Lys Lys Ser Lys Val Gly Trp
1               5                   10                  15

Leu Ile Phe Leu Phe His Lys Lys
            20

(2) INFORMATION FOR SEQ ID NO:198:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.241"

(xi) SEQUENCE DESCRIPTION: SEQ ID NO:198:

Lys Ser Lys Val Gly Trp Leu Ile Leu Leu Trp His Lys Lys
1               5                   10
```

(2) INFORMATION FOR SEQ ID NO:199:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.243"

(ix) FEATURE:
        (A) NAME/KEY: Modified-site
        (B) LOCATION: 6
        (C) OTHER INFORMATION: /label= Substituted-Ala
            /note= "Position 6 is
            D-beta-2-naphthyl-substituted."

(xi) SEQUENCE DESCRIPTION: SEQ ID NO:199:

Lys Ser Lys Val Gly Ala Leu Ile Gln Leu Trp His Lys Lys
1               5                   10

(2) INFORMATION FOR SEQ ID NO:200:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.244"

(ix) FEATURE:
        (A) NAME/KEY: Modified-site
        (B) LOCATION: 6
        (C) OTHER INFORMATION: /label= Substituted-Ala
            /note= "Position 6 is
            D-beta-2-naphthyl-substituted."

(xi) SEQUENCE DESCRIPTION: SEQ ID NO:200:

Lys Ser Lys Val Gly Ala Leu Ile Leu Leu Trp His Lys Lys
1               5                   10

(2) INFORMATION FOR SEQ ID NO:201:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.249"

(xi) SEQUENCE DESCRIPTION: SEQ ID NO:201:

Lys Ser Lys Val Gly Gly Leu Ile Gln Leu Phe His Lys Lys
1               5                   10

(2) INFORMATION FOR SEQ ID NO:202:

(i) SEQUENCE CHARACTERISTICS:
        (A) LENGTH: 14 amino acids
        (B) TYPE: amino acid
        (D) TOPOLOGY: linear (ii) MOLECULE TYPE: peptide

```
    (ix) FEATURE:
         (A) NAME/KEY: misc_feature
         (D) OTHER INFORMATION: "BPI.250"

(xi) SEQUENCE DESCRIPTION: SEQ ID NO:202:

Lys Ser Lys Val Gly Leu Leu Ile Gln Leu Phe His Lys Lys
1               5                   10

(2) INFORMATION FOR SEQ ID NO:203:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.251"

(xi) SEQUENCE DESCRIPTION: SEQ ID NO:203:

Lys Ser Lys Val Gly Ile Leu Ile Gln Leu Phe His Lys Lys
1               5                   10

(2) INFORMATION FOR SEQ ID NO:204:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.252"

(ix) FEATURE:
         (A) NAME/KEY: Modified-site
         (B) LOCATION: 6
         (D) OTHER INFORMATION: /label= D-Ala
             /note= "The amino acid at position 6 is
             D-alanine"

(xi) SEQUENCE DESCRIPTION: SEQ ID NO:204:

Lys Ser Lys Val Gly Ala Leu Ile Gln Leu Phe His Lys Lys
1               5                   10

(2) INFORMATION FOR SEQ ID NO:205:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "BPI.253"

(ix) FEATURE:
         (A) NAME/KEY: Modified-site
         (B) LOCATION: 6
         (D) OTHER INFORMATION: /label= D-Val
             /note= "The amino acid at position 6 is
             D-valine"

(xi) SEQUENCE DESCRIPTION: SEQ ID NO:205:

Lys Ser Lys Val Gly Val Leu Ile Gln Leu Phe His Lys Lys
```

(2) INFORMATION FOR SEQ ID NO:206:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.254"

(ix) FEATURE:
        (A) NAME/KEY: Modified-site
        (B) LOCATION: 6
        (D) OTHER INFORMATION: /label= beta-Ala
            /note= "The amino acid at position 6 is
            beta-alanine"

(xi) SEQUENCE DESCRIPTION: SEQ ID NO:206:

Lys Ser Lys Val Gly Ala Leu Ile Gln Leu Phe His Lys Lys
1               5                   10

(2) INFORMATION FOR SEQ ID NO:207:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.255"

(ix) FEATURE:
        (A) NAME/KEY: Modified-site
        (B) LOCATION: 6
        (D) OTHER INFORMATION: /label= delta-aba
            /note= "The amino acid at position 6 is
            delta-aminobutyric acid"

(xi) SEQUENCE DESCRIPTION: SEQ ID NO:207:

Lys Ser Lys Val Gly Xaa Leu Ile Gln Leu Phe His Lys Lys
1               5                   10

(2) INFORMATION FOR SEQ ID NO:208:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.256"

(ix) FEATURE:
        (A) NAME/KEY: Modified-site
        (B) LOCATION: 6
        (D) OTHER INFORMATION: /label= gaba
            /note= "The amino acid at position 6 is
            gamma-aminobutyric acid"

(xi) SEQUENCE DESCRIPTION: SEQ ID NO:208:

Lys Ser Lys Val Gly Xaa Leu Ile Gln Leu Phe His Lys Lys
1               5                   10

(2) INFORMATION FOR SEQ ID NO:209:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.257"

(ix) FEATURE:
        (A) NAME/KEY: Modified-site
        (B) LOCATION: 6
        (D) OTHER INFORMATION: /label= d-methyl-A
            /note= "The amino acid at position 6 is
            delta-Methyl-alanine"

(xi) SEQUENCE DESCRIPTION: SEQ ID NO:209:

Lys Ser Lys Val Gly Ala Leu Ile Gln Leu Phe His Lys Lys
1               5                10

(2) INFORMATION FOR SEQ ID NO:210:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.258"

(ix) FEATURE:
        (A) NAME/KEY: Modified-site
        (B) LOCATION: 6
        (D) OTHER INFORMATION: /label= t-butyl-G
            /note= "The amino acid at position 6 is
            tert-butyl-glycine"

(xi) SEQUENCE DESCRIPTION: SEQ ID NO:210:

Lys Ser Lys Val Gly Gly Leu Ile Gln Leu Phe His Lys Lys
1               5                10

(2) INFORMATION FOR SEQ ID NO:211:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.259"

(ix) FEATURE:
        (A) NAME/KEY: Modified-site
        (B) LOCATION: 6
        (D) OTHER INFORMATION: /label= N-methyl-G
            /note= "The amino acid at position 6 is
            N-Methyl-glycine"

(xi) SEQUENCE DESCRIPTION: SEQ ID NO:211:

Lys Ser Lys Val Gly Gly Leu Ile Gln Leu Phe His Lys Lys
1               5                10

(2) INFORMATION FOR SEQ ID NO:212:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.260"

(ix) FEATURE:
        (A) NAME/KEY: Modified-site
        (B) LOCATION: 6
        (D) OTHER INFORMATION: /label= N-methyl-V
            /note= "The amino acid at position 6 is
            N-Methyl-valine"

(xi) SEQUENCE DESCRIPTION: SEQ ID NO:212:

```
Lys Ser Lys Val Gly Val Leu Ile Gln Leu Phe His Lys Lys
1               5                   10
```

(2) INFORMATION FOR SEQ ID NO:213:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.261"

(ix) FEATURE:
        (A) NAME/KEY: Modified-site
        (B) LOCATION: 6
        (D) OTHER INFORMATION: /label= N-methyl-L
            /note= "The amino acid at position 6 is
            N-Methyl-leucine"

(xi) SEQUENCE DESCRIPTION: SEQ ID NO:213:

```
Lys Ser Lys Val Gly Leu Leu Ile Gln Leu Phe His Lys Lys
1               5                   10
```

(2) INFORMATION FOR SEQ ID NO:214:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.262"

(xi) SEQUENCE DESCRIPTION: SEQ ID NO:214:

```
Lys Ser Lys Val Gly Trp Leu Ile Asn Leu Phe His Lys Lys
1               5                   10
```

(2) INFORMATION FOR SEQ ID NO:215:

(i) SEQUENCE CHARACTERISTICS:
        (A) LENGTH: 14 amino acids
        (B) TYPE: amino acid
        (D) TOPOLOGY: linear

```
        (ii) MOLECULE TYPE: peptide (ix) FEATURE:
            (A) NAME/KEY: misc_feature
            (D) OTHER INFORMATION: "BPI.263"

(xi) SEQUENCE DESCRIPTION: SEQ ID NO:215:

Lys Ser Lys Val Gly Trp Leu Ile Glu Leu Phe His Lys Lys
1               5                  10

(2) INFORMATION FOR SEQ ID NO:216:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.264"

(xi) SEQUENCE DESCRIPTION: SEQ ID NO:216:

Lys Ser Lys Val Gly Trp Leu Ile Asp Leu Phe His Lys Lys
1               5                  10

(2) INFORMATION FOR SEQ ID NO:217:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.265"

(xi) SEQUENCE DESCRIPTION: SEQ ID NO:217:

Lys Ser Lys Val Gly Trp Leu Ile Lys Leu Phe His Lys Lys
1               5                  10

(2) INFORMATION FOR SEQ ID NO:218:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "BPI.266"

(xi) SEQUENCE DESCRIPTION: SEQ ID NO:218:

Lys Ser Lys Val Lys Val Leu Ile Gln Leu Phe His Lys Lys
1               5                  10

(2) INFORMATION FOR SEQ ID NO:219:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
```

(A) NAME/KEY: misc_feature
        (D) OTHER INFORMATION: "BPI.267"

(xi) SEQUENCE DESCRIPTION: SEQ ID NO:219:

Lys Ser Lys Val Lys Trp Ala Ile Gln Leu Phe His Lys Lys
1               5                   10

(2) INFORMATION FOR SEQ ID NO:220:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.268"

(xi) SEQUENCE DESCRIPTION: SEQ ID NO:220:

Lys Ser Lys Val Gly Val Ala Ile Gln Leu Phe His Lys Lys
1               5                   10

(2) INFORMATION FOR SEQ ID NO:221:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.269"

(xi) SEQUENCE DESCRIPTION: SEQ ID NO:221:

Lys Ser Lys Val Lys Val Ala Ile Gln Leu Phe His Lys Lys
1               5                   10

(2) INFORMATION FOR SEQ ID NO:222:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.277"

(ix) FEATURE:
        (A) NAME/KEY: Modified-site
        (B) LOCATION: 2
        (C) OTHER INFORMATION: /label= Substituted-Ala
            /note= "The alanine at position 2 is
            beta-1-naphthyl-substituted."

(xi) SEQUENCE DESCRIPTION: SEQ ID NO:222:

Lys Ala Lys Ala Gln Phe Arg Phe Leu Lys Lys Ser Lys Val Gly Trp
1               5                   10                  15

Leu Ile Leu Leu Phe His Lys Lys
                20

(2) INFORMATION FOR SEQ ID NO:223:

(i) SEQUENCE CHARACTERISTICS:

(A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.278"

(xi) SEQUENCE DESCRIPTION: SEQ ID NO:223:

Ile Lys Ile Ser Gly Lys Trp Lys Ala Ala Trp Arg Phe Leu Lys
1               5                   10                  15

(2) INFORMATION FOR SEQ ID NO:224:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.279"

(ix) FEATURE:
        (A) NAME/KEY: Modified-site
        (B) LOCATION: 10
        (C) OTHER INFORMATION: /label= Substituted-Ala
            /note= "The alanine at position 10 is
            beta-1-naphthyl-substituted."

(xi) SEQUENCE DESCRIPTION: SEQ ID NO:224:

Ile Lys Ile Ser Gly Lys Trp Lys Ala Ala Phe Arg Phe Leu Lys
1               5                   10                  15

(2) INFORMATION FOR SEQ ID NO:225:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.280"

(xi) SEQUENCE DESCRIPTION: SEQ ID NO:225:

Ile Lys Ile Ser Gly Lys Trp Lys Ala Ala Phe Arg Phe Leu Lys
1               5                   10                  15

(2) INFORMATION FOR SEQ ID NO:226:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.281"

(ix) FEATURE:
        (A) NAME/KEY: Modified-site
        (B) LOCATION: 10
        (C) OTHER INFORMATION: /label= Substituted-Ala
            /note= "The alanine at position 10 is -continued

```
               beta-1-naphthyl-substituted."

(xi) SEQUENCE DESCRIPTION: SEQ ID NO:226:

Ile Lys Ile Ser Gly Lys Trp Lys Ala Ala Ala Arg Phe Leu Lys
1               5                   10                  15

(2) INFORMATION FOR SEQ ID NO:227:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.170"

(xi) SEQUENCE DESCRIPTION: SEQ ID NO:227:

Lys Trp Lys Ala Gln Lys Arg Phe Leu Lys Met Ser
1               5                   10
```